(12) United States Patent
Yeh et al.

(10) Patent No.: US 12,220,589 B2
(45) Date of Patent: Feb. 11, 2025

(54) WIRELESS IMPLANTABLE DEVICE POSITION VALIDATION IN SITU

(71) Applicant: NeuSpera Medical Inc., San Jose, CA (US)

(72) Inventors: Alexander Yeh, Los Altos Hills, CA (US); Timothy A. Fayram, Gilroy, CA (US); Brad Holinski, Newark, CA (US); Thomas Burpee Ellsworth, III, San Jose, CA (US); Shivkumar Sabesan, South San Francisco, CA (US); Stephen James Schellenberg, Aptos, CA (US); Milton M. Morris, Houston, TX (US); Elia Junco, Palo Alto, CA (US)

(73) Assignee: NEUSPERA MEDICAL, INC, San Jose, CA (US)

( * ) Notice: Subject to any disclaimer, the term of this patent is extended or adjusted under 35 U.S.C. 154(b) by 432 days.

(21) Appl. No.: 17/597,069

(22) PCT Filed: Jun. 25, 2020

(86) PCT No.: PCT/US2020/039545
§ 371 (c)(1),
(2) Date: Dec. 23, 2021

(87) PCT Pub. No.: WO2020/264108
PCT Pub. Date: Dec. 30, 2020

(65) Prior Publication Data
US 2022/0314008 A1 Oct. 6, 2022

Related U.S. Application Data

(60) Provisional application No. 63/017,235, filed on Apr. 29, 2020, provisional application No. 62/951,285, (Continued)

(51) Int. Cl.
*A61N 1/37* (2006.01)
*A61B 17/04* (2006.01)
(Continued)

(52) U.S. Cl.
CPC ...... *A61N 1/37241* (2013.01); *A61B 17/0469* (2013.01); *A61B 17/3468* (2013.01);
(Continued)

(58) Field of Classification Search
CPC .............. A61N 1/0558; A61N 1/37241; A61B 17/3468
See application file for complete search history.

(56) References Cited

U.S. PATENT DOCUMENTS 5,578,009 A * 11/1996 Kraus ................ A61M 25/104
604/95.04
7,270,669 B1 9/2007 Sra
(Continued)

FOREIGN PATENT DOCUMENTS

WO WO-2020264108 A1 12/2020

OTHER PUBLICATIONS

"International Application Serial No. PCT/US2020/039545, International Search Report mailed Nov. 20, 2020", 5 pgs.
(Continued)

*Primary Examiner* — Eric D. Bertram
(74) *Attorney, Agent, or Firm* — SCHWEGMAN LUNDBERG & WOESSNER, P.A.

(57) ABSTRACT

Systems, devices, and methods discussed herein can be for validating a position of a wirelessly powered electrostimulation device while the device is implanted in body tissue. A method can include situating the electrostimulation device in tissue and before an affixation mechanism of the electrostimulation device is deployed to maintain an implanted position of the electrostimulation device, and while elec-
(Continued)

trodes of the device are in contact with the tissue, performing electrical testing of the electrostimulation device to determine whether the electrostimulation from the electrostimulation device evokes a specified response from the body that contains the tissue.

15 Claims, 58 Drawing Sheets

Related U.S. Application Data filed on Dec. 20, 2019, provisional application No. 62/949,915, filed on Dec. 18, 2019, provisional application No. 62/940,679, filed on Nov. 26, 2019, provisional application No. 62/925,356, filed on Oct. 24, 2019, provisional application No. 62/900,478, filed on Sep. 14, 2019, provisional application No. 62/866,419, filed on Jun. 25, 2019.

(51) Int. Cl.
    *A61B 17/34*     (2006.01)
    *A61N 1/05*     (2006.01)
    *A61N 1/372*     (2006.01)
    *A61N 1/378*     (2006.01)
    *A61M 25/01*     (2006.01)

(52) U.S. Cl.
    CPC ......... *A61N 1/0558* (2013.01); *A61N 1/3787* (2013.01); *A61M 25/0102* (2013.01); *A61M 2205/02* (2013.01)

(56) References Cited

U.S. PATENT DOCUMENTS

| | | | |
|---|---|---|---|
| 8,543,222 B1* | 9/2013 | Sochor | A61B 90/11 607/116 |
| 2003/0023262 A1* | 1/2003 | Welch | A61F 2/011 606/194 |
| 2006/0085041 A1 | 4/2006 | Hastings et al. | |
| 2007/0265582 A1* | 11/2007 | Kaplan | A61M 37/0069 604/260 |
| 2011/0160557 A1 | 6/2011 | Cinbis et al. | |
| 2016/0250467 A1 | 9/2016 | Pari | |
| 2017/0189679 A1 | 7/2017 | Jiang et al. | |
| 2017/0265941 A1 | 9/2017 | Brannan et al. | |
| 2018/0071539 A1* | 3/2018 | Hastings | A61N 1/37512 |
| 2018/0099138 A1* | 4/2018 | Bonner | A61N 1/059 |
| 2018/0256906 A1 | 9/2018 | Pivonka et al. | |
| 2019/0022394 A1* | 1/2019 | Fayram | H02J 50/20 |
| 2019/0060642 A1 | 2/2019 | Boggs, II et al. | |

OTHER PUBLICATIONS

"International Application Serial No. PCT/US2020/039545, Invitation to Pay Additional Fees mailed Sep. 8, 2020", 2 pgs.
"International Application Serial No. PCT/US2020/039545, Written Opinion mailed Nov. 20, 2020", 19 pgs.
Lee, Jungpyo, et al., "A MEMS ultrasound stimulation system for modulation of neural circuits with high spatial resolution in vitro", Microsystems & Nanoengineering (2019) 5:28 Microsystems & Nanoengineering https://doi.org/10.1038/s41378-019-0070-5, https://www.nature.com/articles/s41378-019-0070-5.pdf.
"International Application Serial No. PCT US2020 039545, International Preliminary Report on Patentability mailed Jan. 6, 2022", 21 pages.

\* cited by examiner

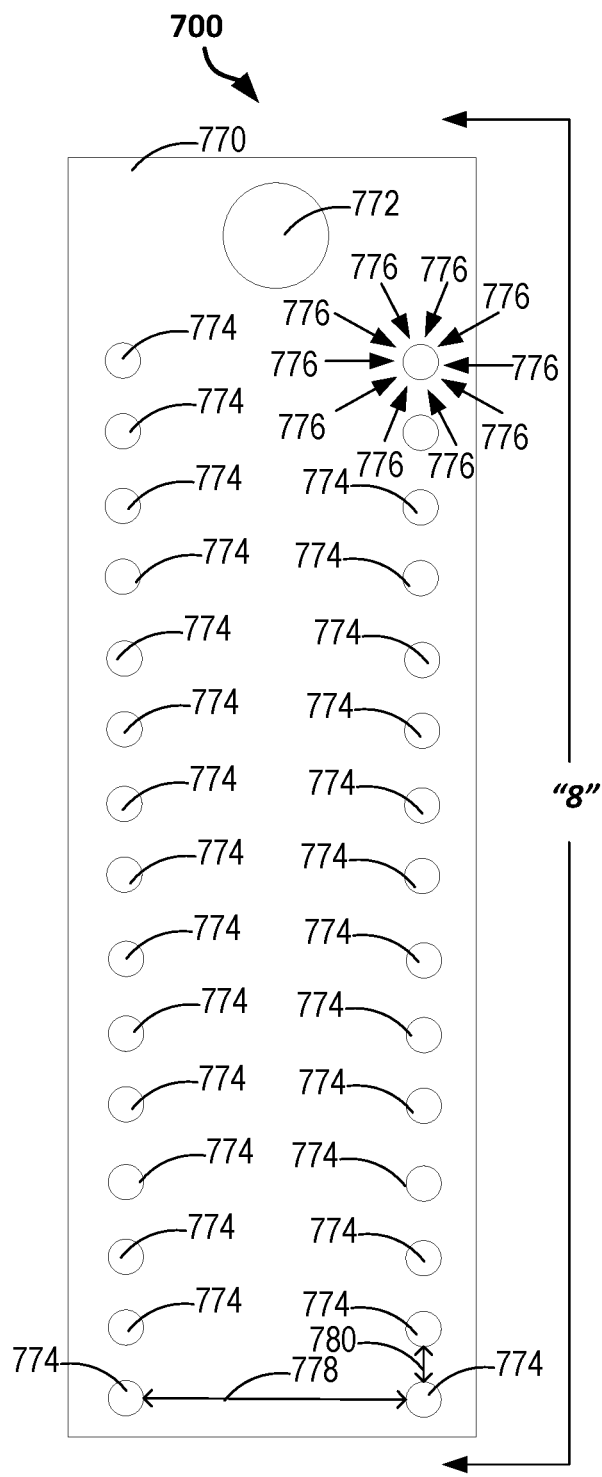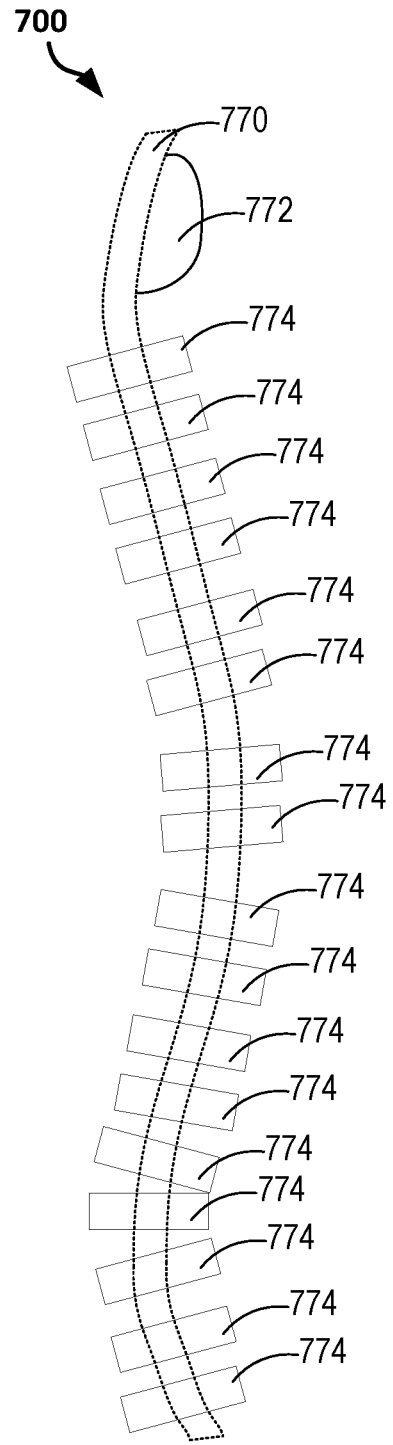
FIG. 7
FIG. 8

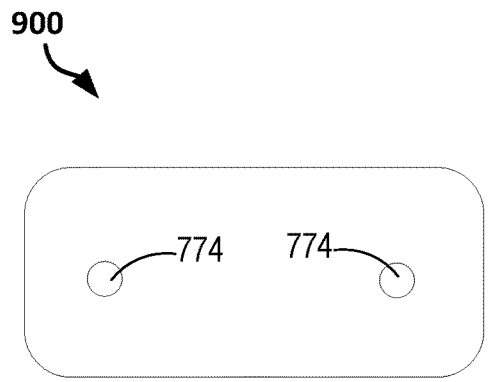
FIG. 9
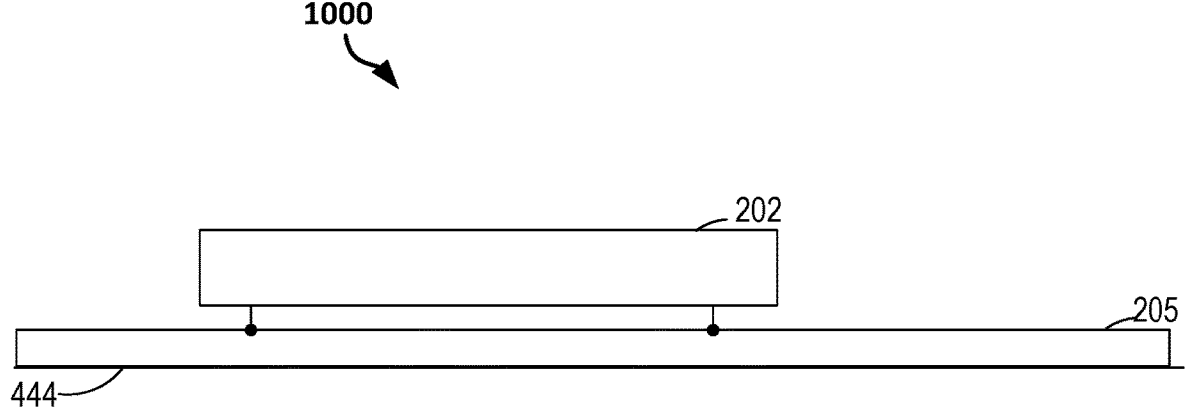
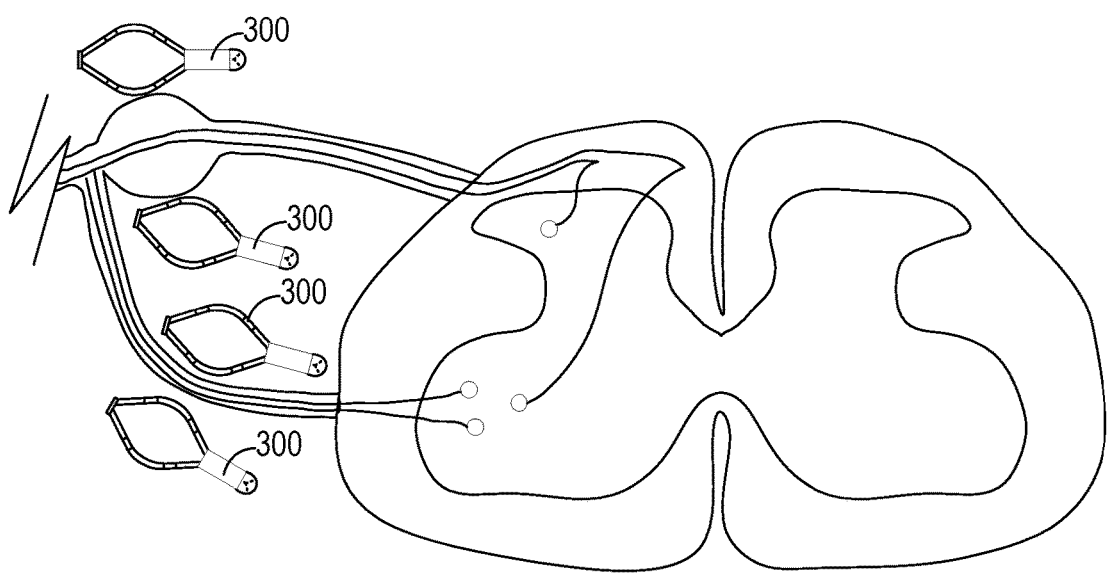
FIG. 10

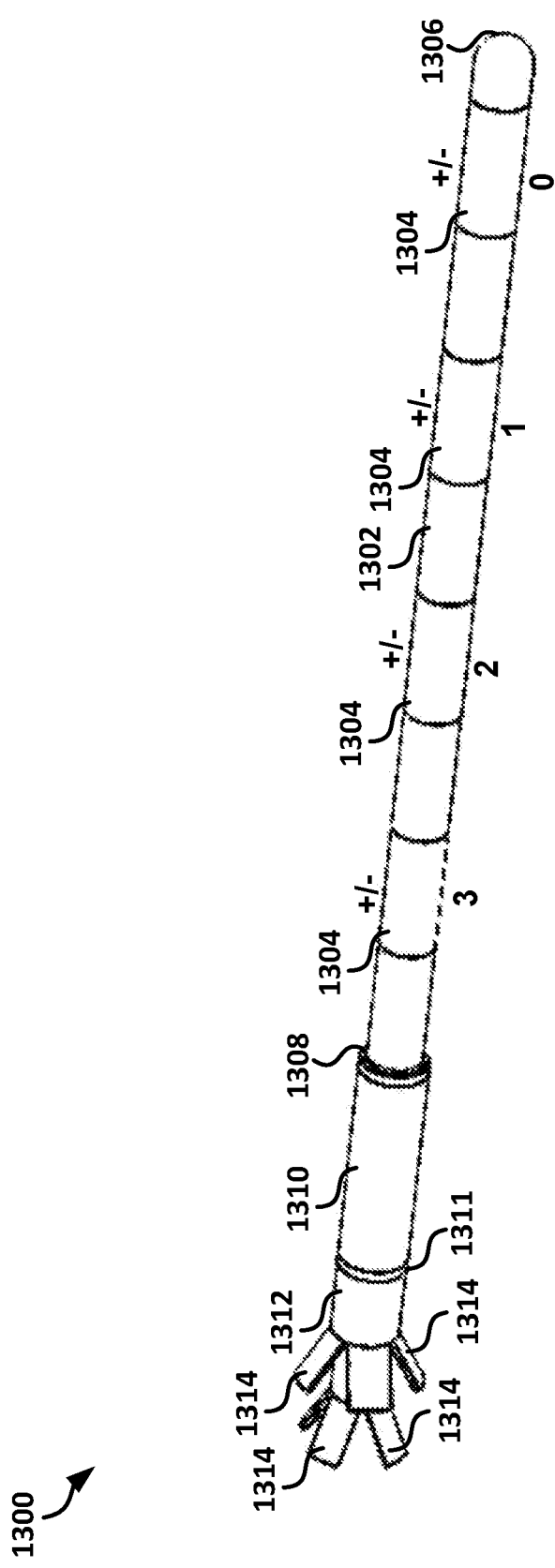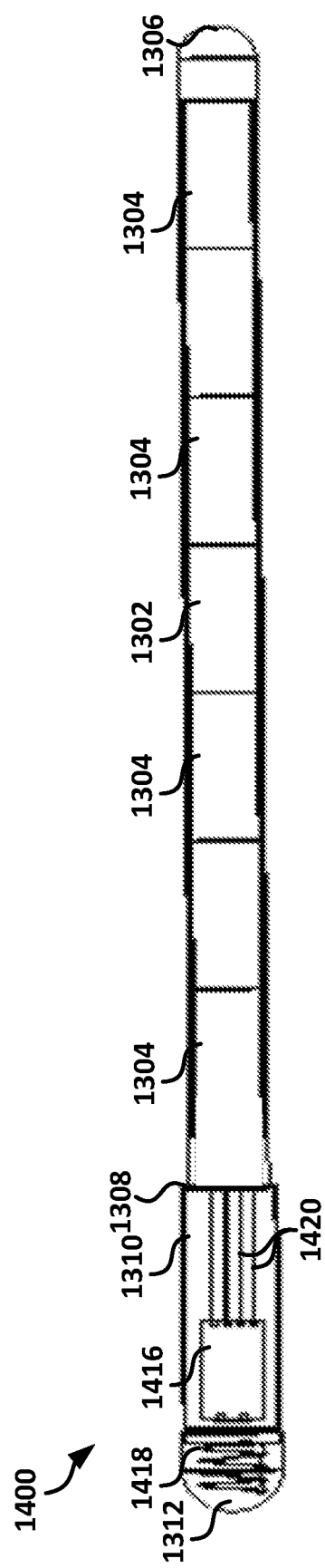
FIG. 13
FIG. 14

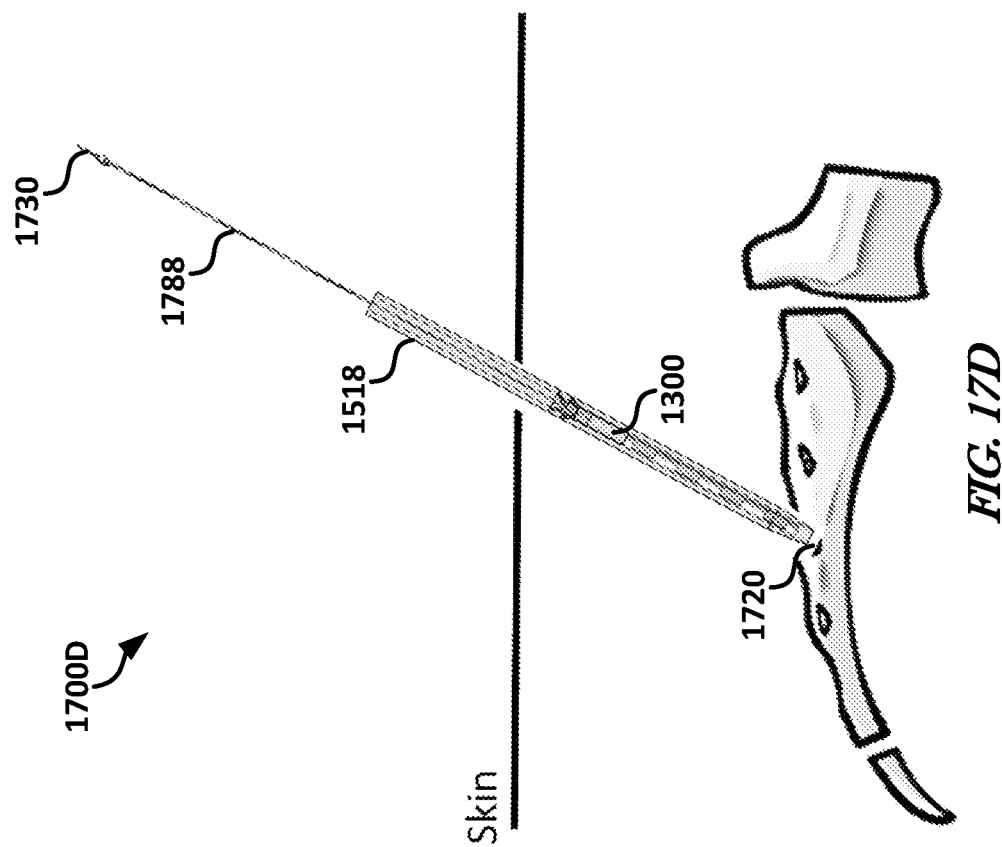
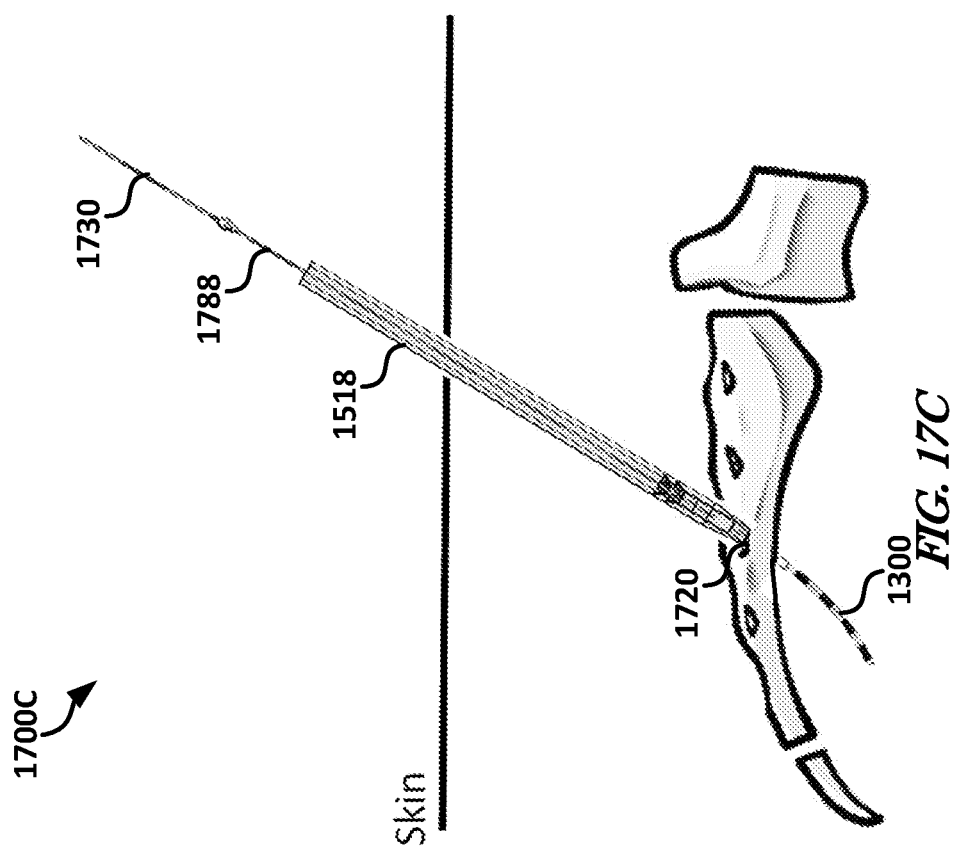

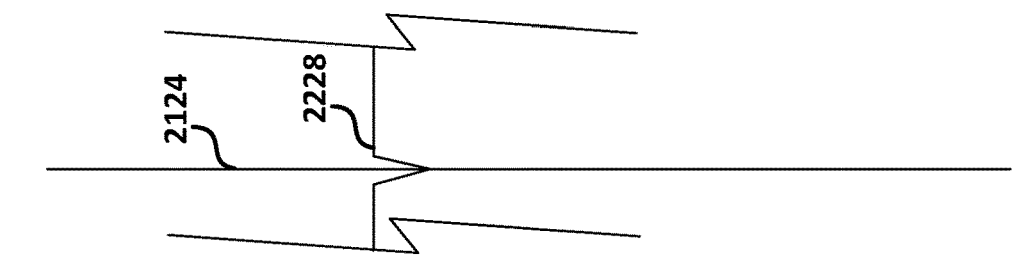
FIG. 24
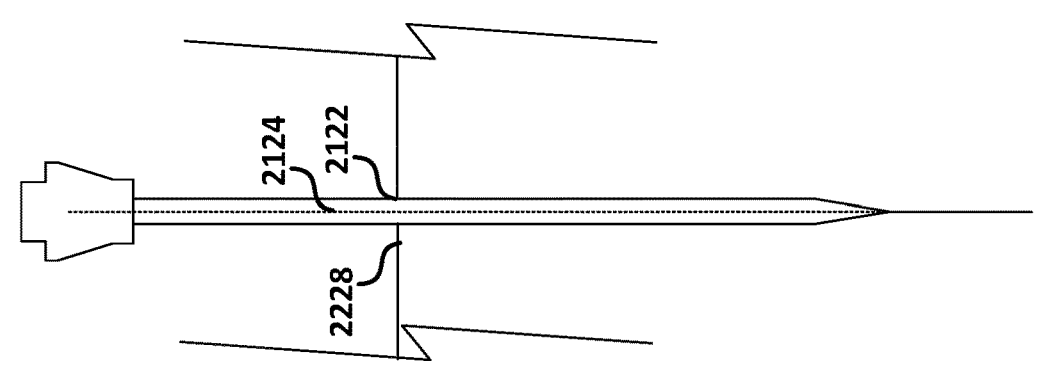
FIG. 23
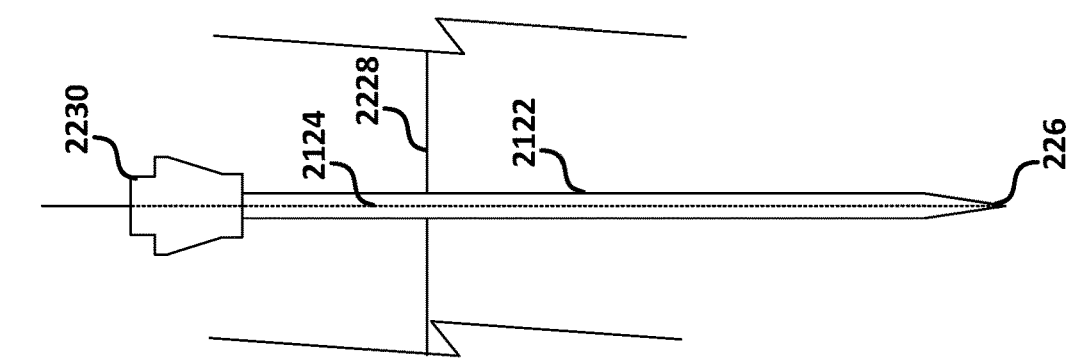
FIG. 22
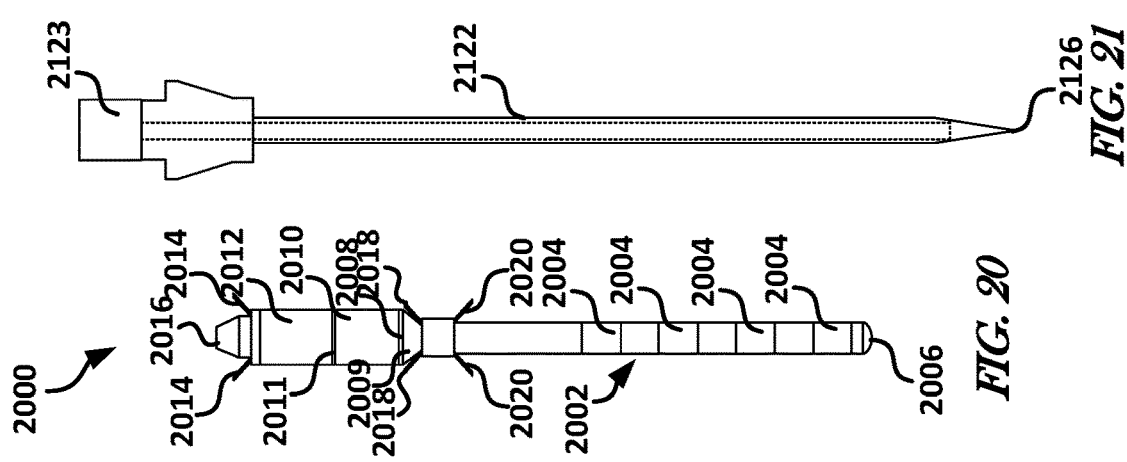
FIG. 21
FIG. 20

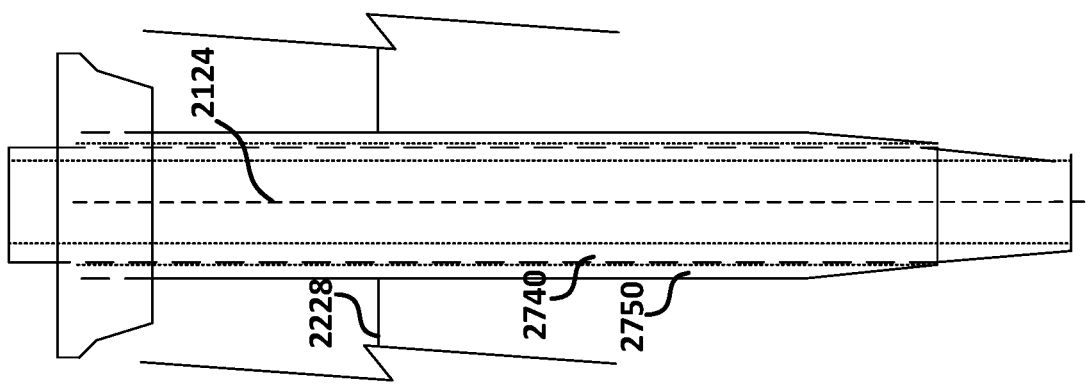
FIG. 28
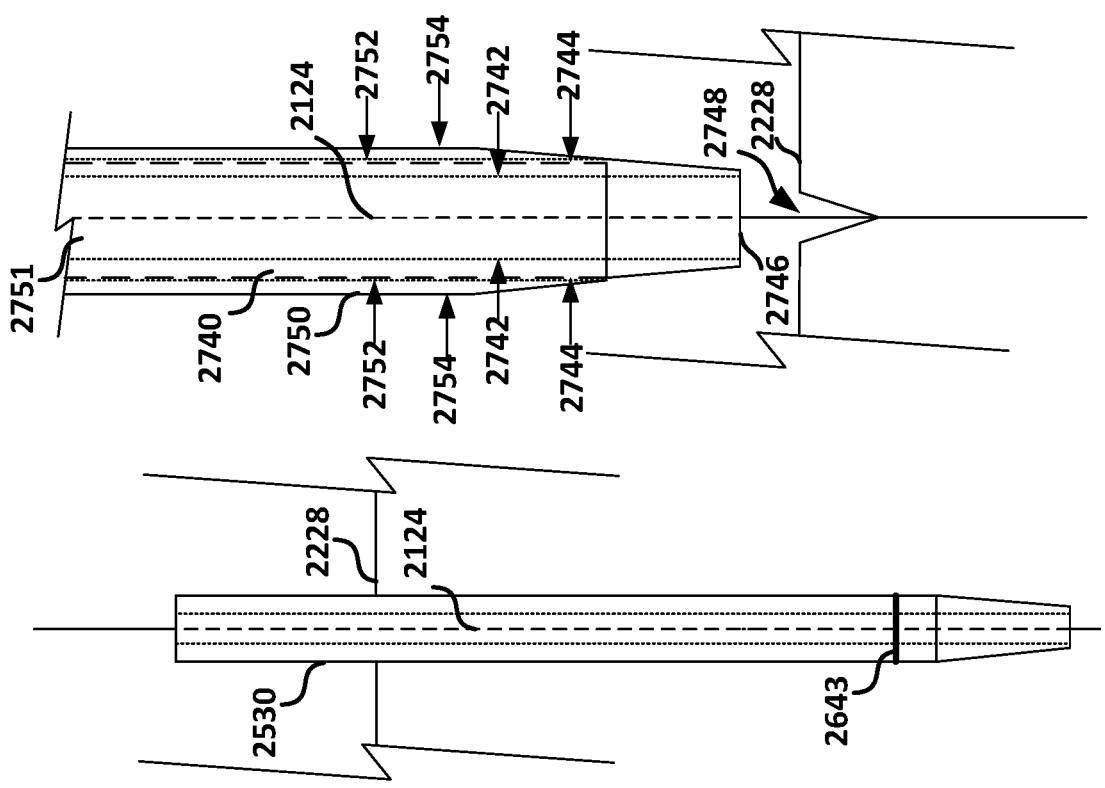
FIG. 27
FIG. 26
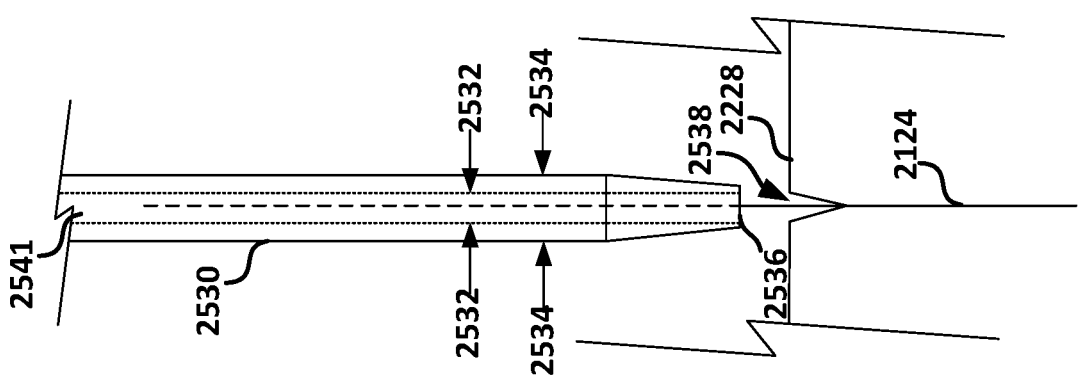
FIG. 25

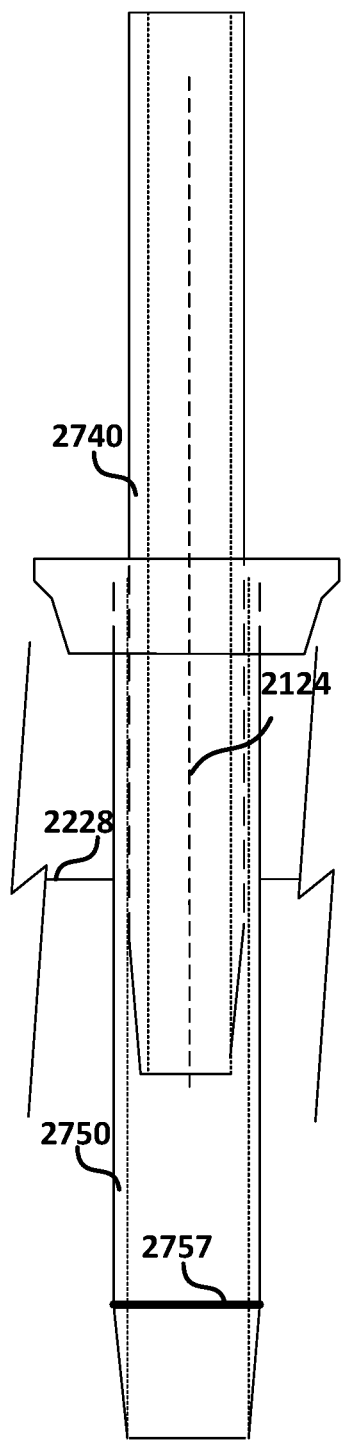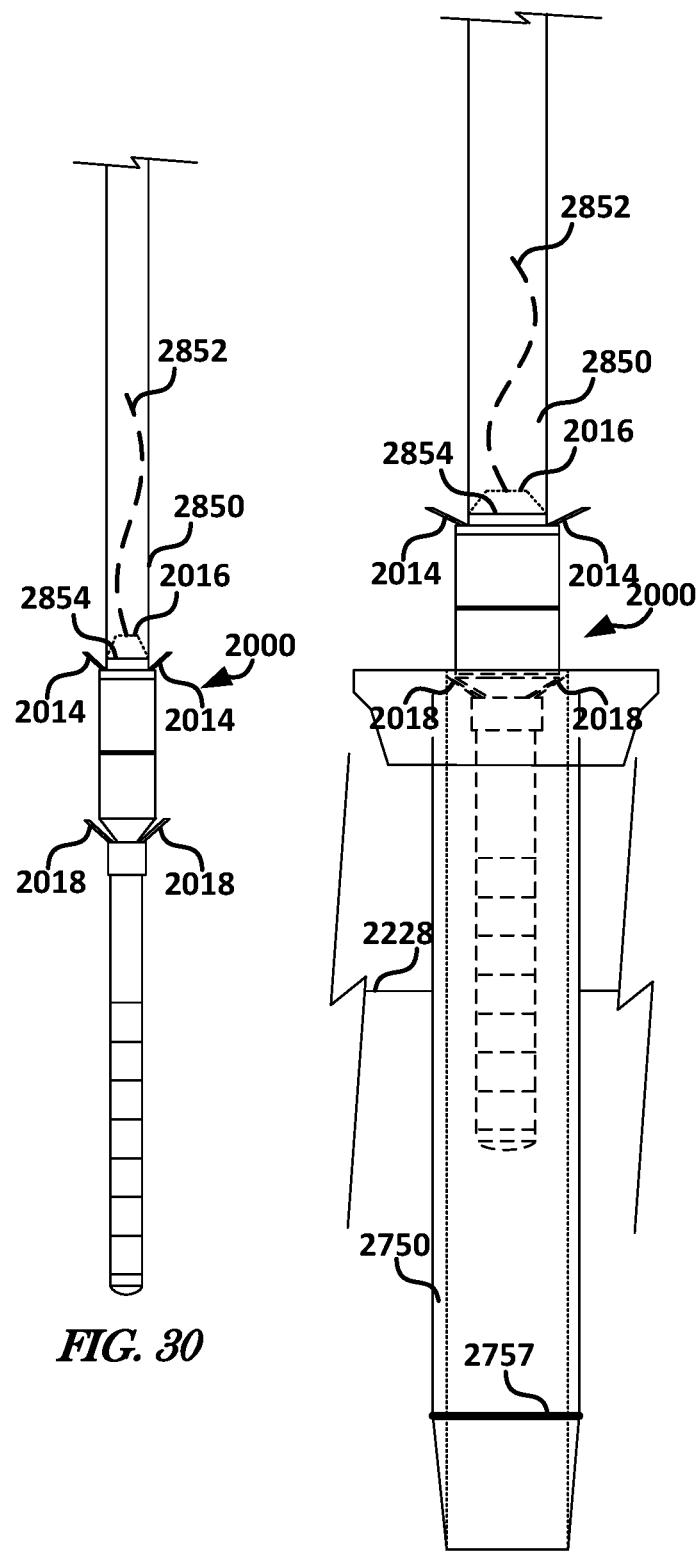
FIG. 30
FIG. 29
FIG. 31

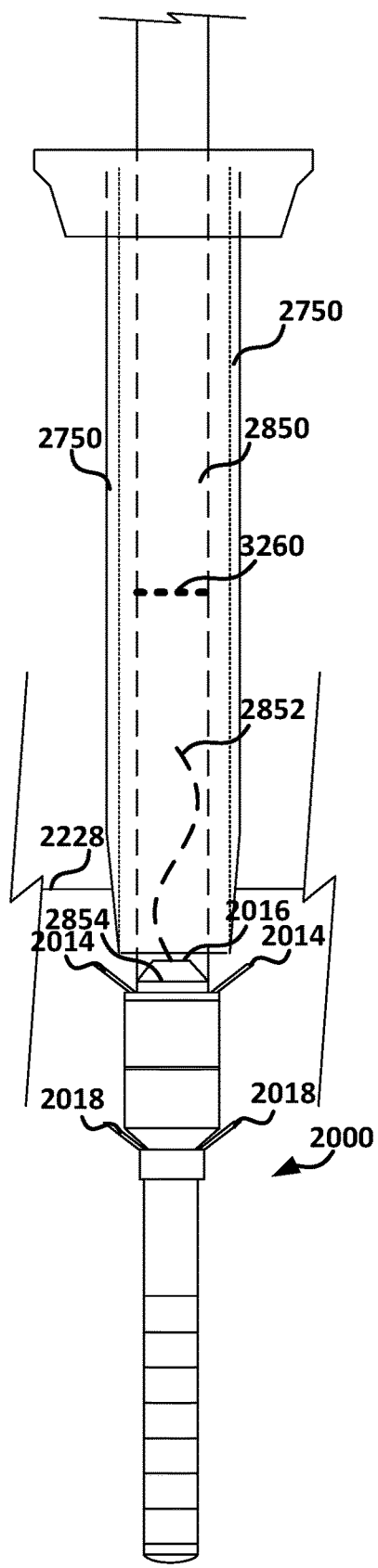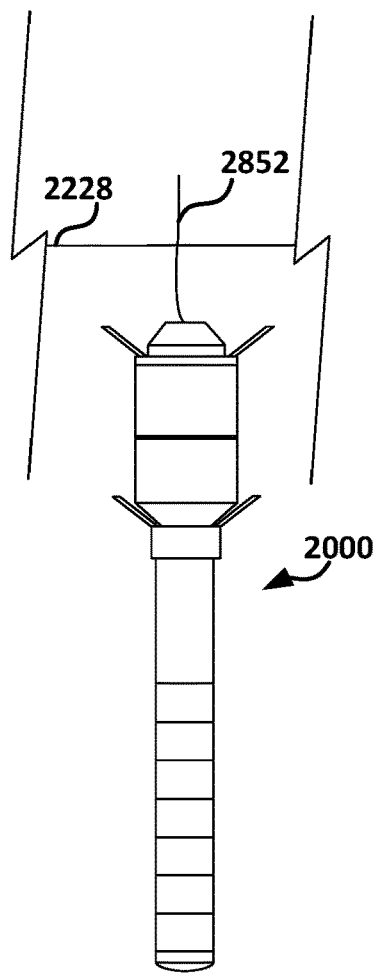
FIG. 32
FIG. 33

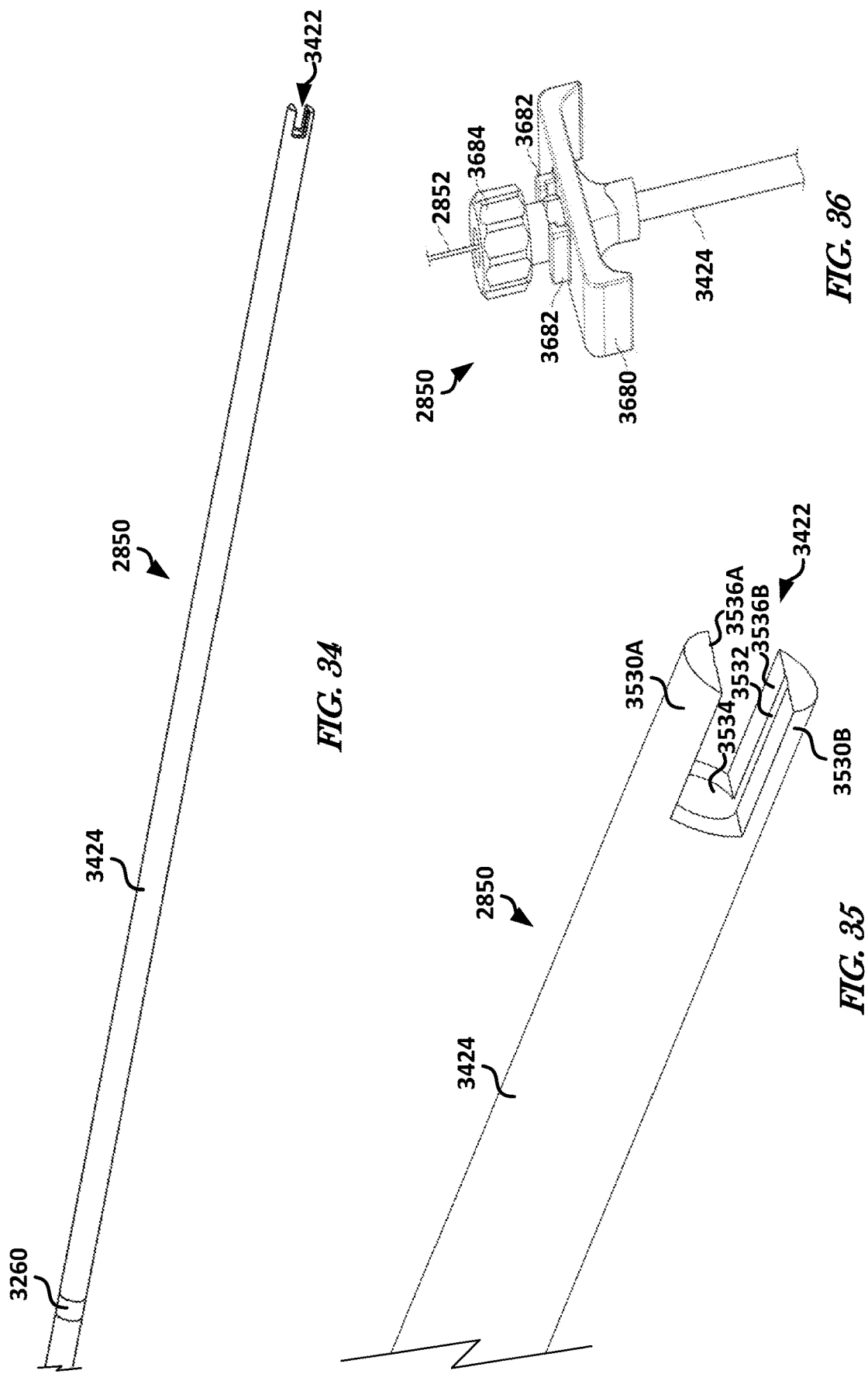

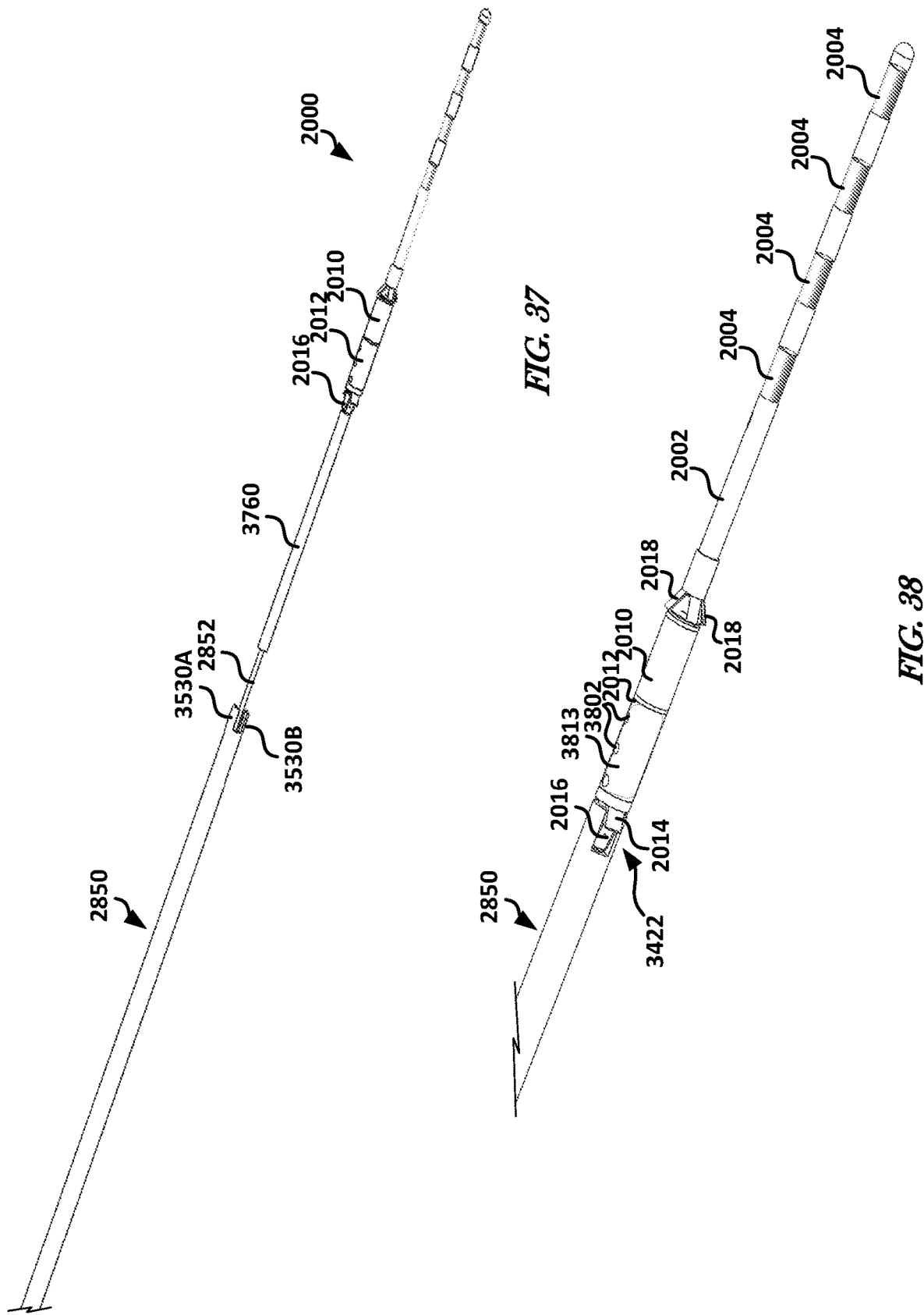

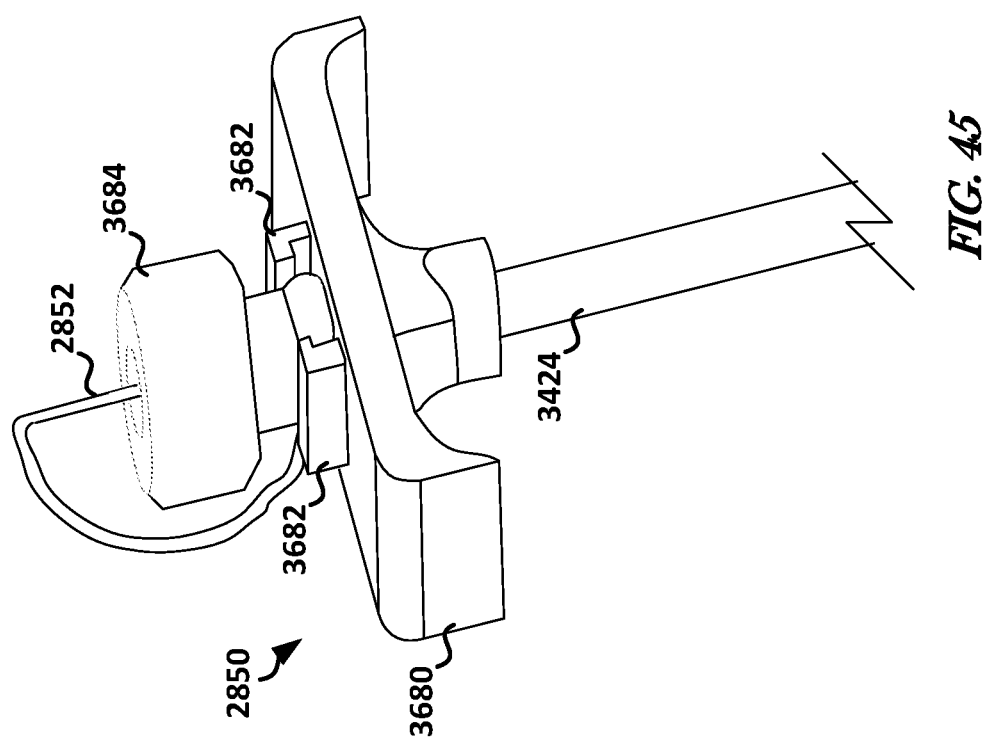

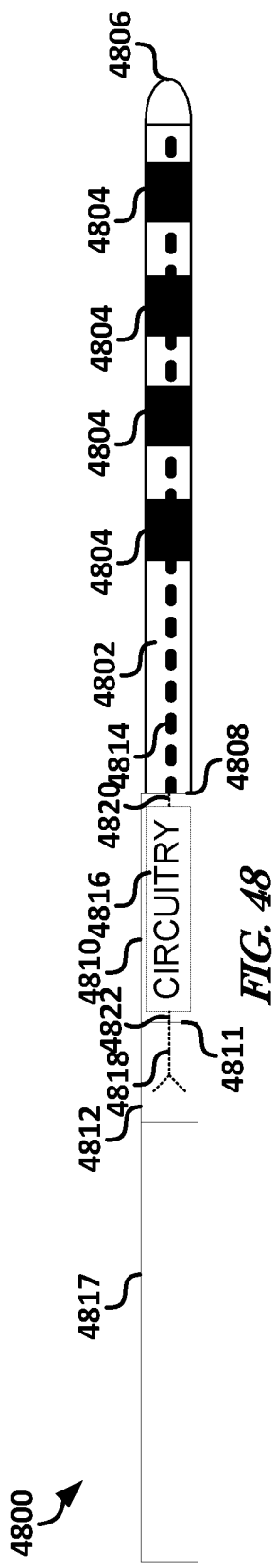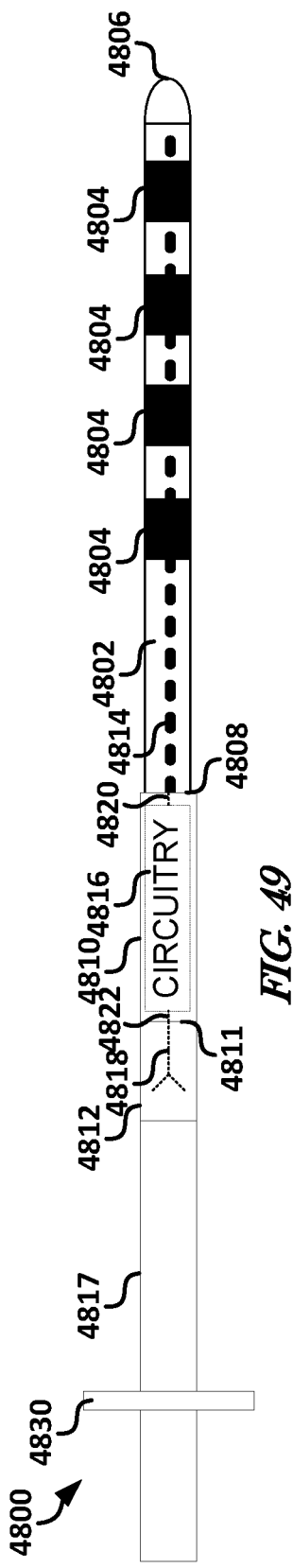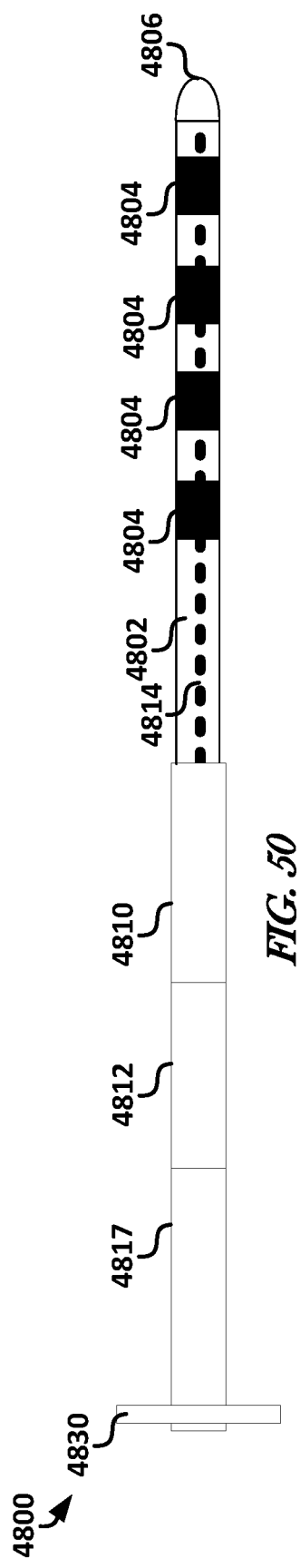

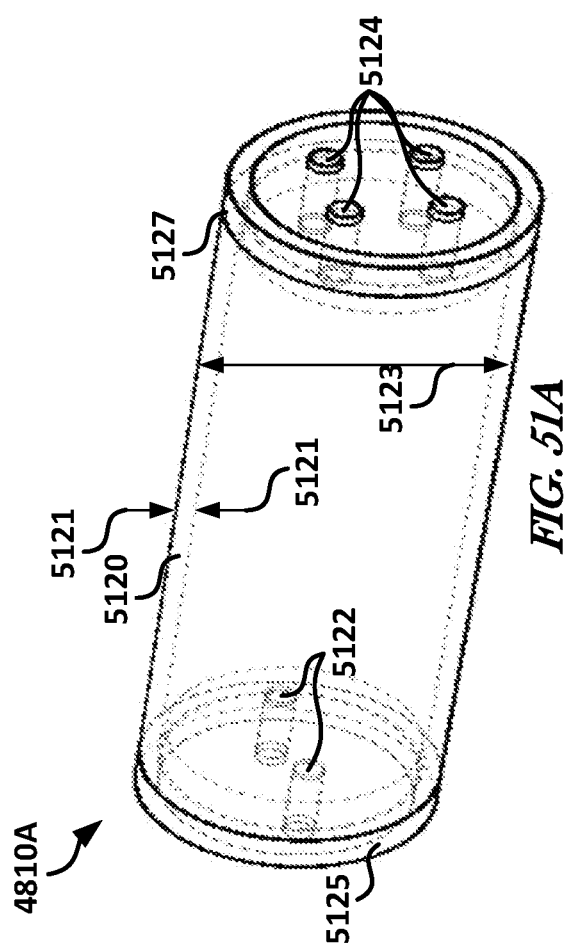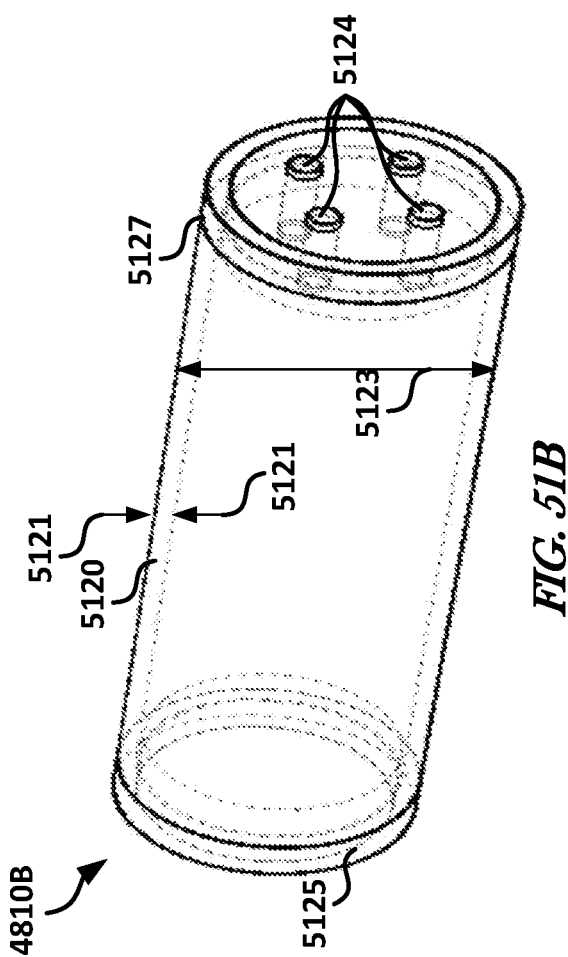

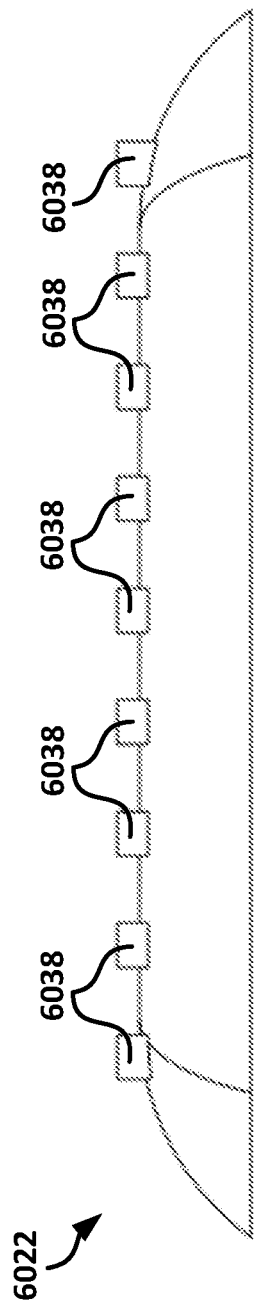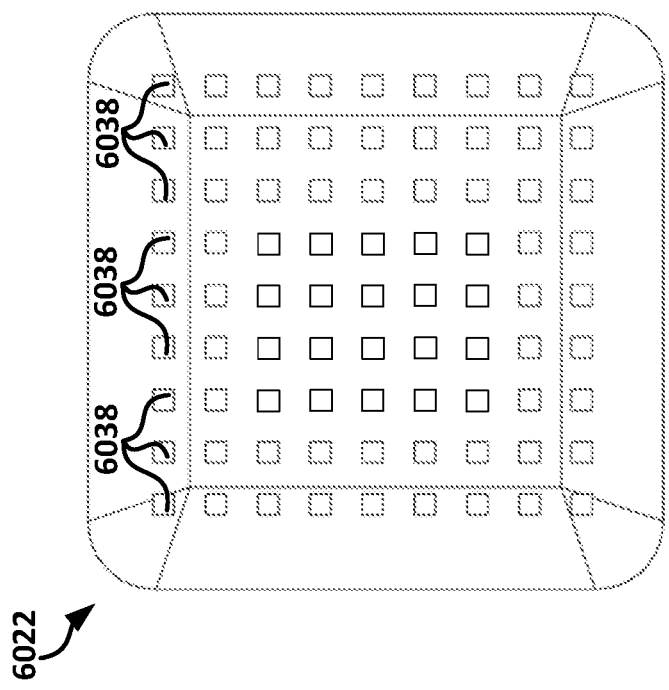

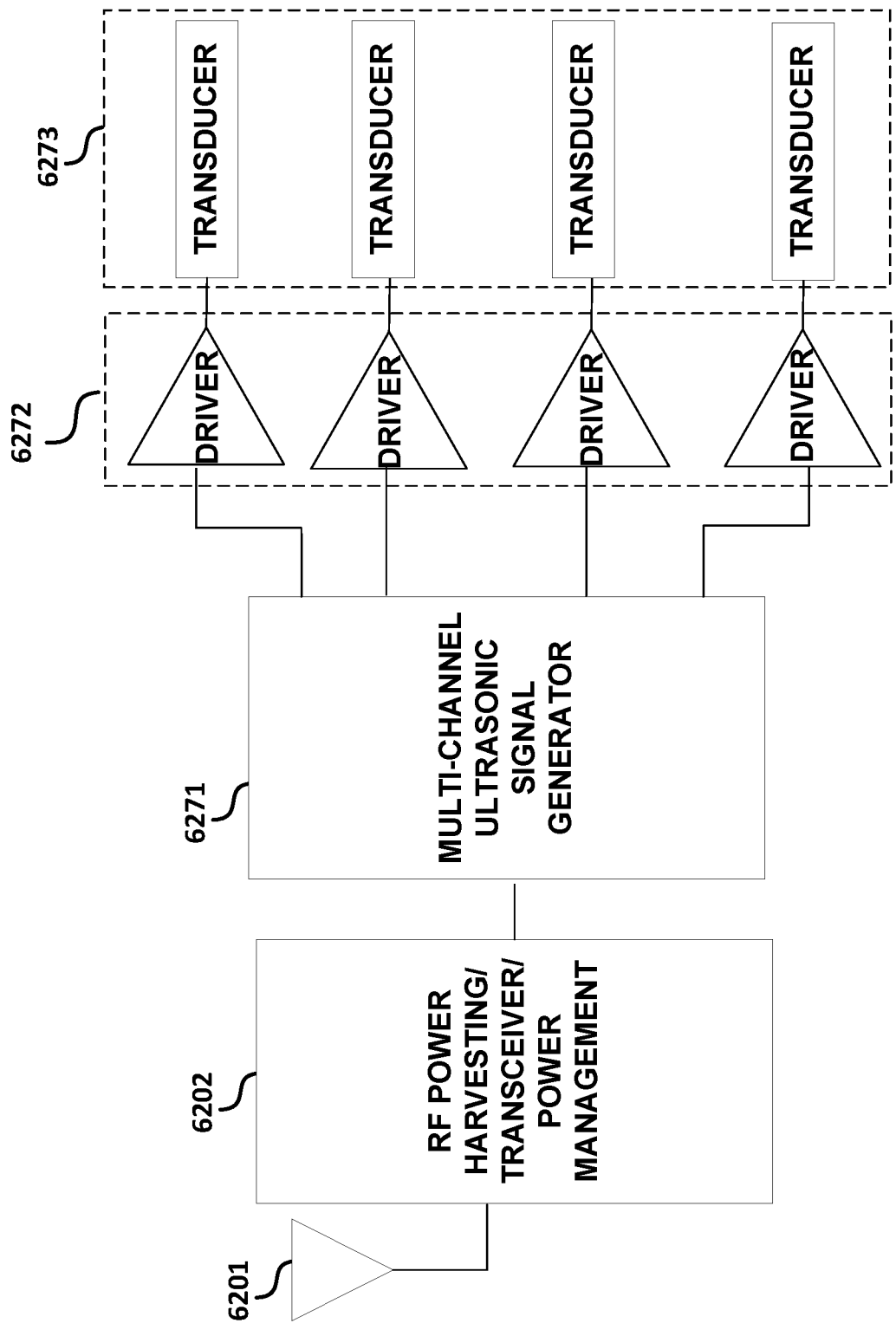

WIRELESS IMPLANTABLE DEVICE POSITION VALIDATION IN SITU

CLAIM OF PRIORITY

This patent application is a U.S. National Stage filing under 35 U.S.C. § 371 of PCT Patent Application No. PCT/US2020/039545, filed on Jun. 25, 2020, which claims the benefit of priority to U.S. Provisional Patent Application No. 62/866,419, filed Jun. 25, 2019; U.S. Provisional Patent Application No. 62/900,478, filed Sep. 14, 2019; U.S. Provisional Patent Application No. 62/925,356; U.S. Provisional Patent Application No. 62/940,679, filed Nov. 26, 2019; U.S. Provisional Patent Application No. 62/951,285, filed Dec. 20, 2019; U.S. Provisional Patent Application No. 62/949,915, filed Dec. 18, 2019; U.S. Provisional Patent Application No. 63/017,235, filed Apr. 29, 2020, all of which are hereby incorporated herein by reference in their entirety.

BACKGROUND

Various wireless powering methods for implantable electronics are based on nearfield or farfield coupling. These and other methods suffer from several disadvantages. For example, using nearfield or farfield techniques, a power harvesting structure in an implanted device can typically be large (e.g., typically on the order of a centimeter or larger) and therefore can be difficult to implant or use in some areas of the body. In nearfield communications, coils external to the body can similarly be large, bulky and oftentimes inflexible. Such constraints present difficulties in incorporation of an external device into a patient's daily life. Furthermore, the intrinsic exponential decay of nearfield signals limits miniaturization of an implanted device beyond superficial depths, for example, at depths greater than 1 centimeter. On the other hand, the radiative nature of farfield signals can limit energy transfer efficiency.

Wireless midfield technology can be used to provide signals from an external source to an implanted sensor or therapy-delivery device. Midfield-based devices can have various advantages over conventional nearfield or farfield devices. For example, a midfield device may not require a relatively large implanted pulse generator and one or more leads that electrically connect the pulse generator to stimulation electrodes. A midfield device can have a relatively small receiver antenna and can therefore provide a simpler implant procedure relative to larger devices. Simpler implant procedures can correspond to lower cost and a lower risk of infection or other complications related to implant or explant.

Another advantage of using midfield powering technology includes a battery or power source that can be provided externally to a patient, and thus circuit requirements for battery-powered implantable devices, such as low power consumption and high efficiency, can be relaxed. Another advantage of using midfield powering technology can include an implanted device that can be physically smaller than a battery-powered device. Thus, midfield powering technology can help enable better patient tolerance and comfort along with potentially lower manufacturing and implantation costs.

SUMMARY

Although considerable progress has been made in the realm of medical device therapy, a need exists for improved implantable device position validation, testing, or the like, that reduces time required for implantation, damage to tissue, or the like. A need further exists for improved treatment that not only treats an immediate condition, but also aids in treating a side effect of the condition, such as inflammation. A need further exists for improved brain stimulation. A need further exists for improved intravascular stimulation of a therapy target. The present inventors have recognized that a problem to be solved can include This Summary is intended to provide an overview of subject matter of the present application. It is not intended to provide an exclusive or exhaustive explanation of the invention or inventions discussed herein. The detailed description is included to provide further information about the present patent application.

In some embodiments, a method of validating a position of a wirelessly powered electrostimulation device (e.g., a midfield powered electrostimulation device) while the device is implanted in body tissue is provided. The method can comprise or consist essentially of situating the electrostimulation device in tissue and before an affixation mechanism of the electrostimulation device is deployed to maintain an implanted position of the electrostimulation device, and while electrodes of the device are in contact with the tissue, testing the electrostimulation device by delivering a test stimulus to the tissue to determine whether the test stimulus from the electrostimulation device evokes a specified response from the body that contains the tissue.

The method can include, wherein situating the electrostimulation device in tissue includes using a catheter and a push rod configured to travel inside the catheter. Testing of the electrostimulation device can occur while the affixation mechanism (e.g., a tine) of the device is situated in the catheter and the catheter is at least partially inside the tissue.

The catheter and/or push rod can comprise a radio transparent material. Testing the electrical stimulation device can occur while the push rod is engaged with a push rod interface of the electrostimulation device. In some embodiments, such as embodiments in which the push rod does not comprise radio transparent material, the method can further comprise pulling the push rod away from the electrostimulation device before delivering the test stimulus to the tissue, and while the electrodes of the device are in contact with the tissue.

Situating the electrostimulation device in the tissue can include translating the device axially inside the catheter while the catheter is partially in the tissue so the electrodes extend out of the catheter into the tissue and the affixation mechanism remains in the catheter.

The method can further comprise pulling the push rod away from the electrostimulation device while maintaining a suture in a lumen of the push rod, the suture extending through the lumen of the push rod and mechanically connected to a proximal portion of the electrostimulation device. Maintaining the suture in the lumen can include securing a proximal portion of the suture wrapped at least partially around a thread of the push rod. Securing the thread can further include tightening a luer cap around the thread of the push rod. The thread can be one of a plurality of threads. The proximal portion of the suture can include a first wrapping of a first portion of the suture around a first thread of the plurality of threads. The method can further include securing a different second portion of the suture wrapped at least partially around a second thread of the plurality of threads, such that rotating the luer cap is configured to release the first portion of the suture while retaining the different second portion of the suture.

Maintaining the suture in the lumen can additionally or alternatively include situating a retention mechanism on the suture, the retention mechanism configured such that it cannot travel through the lumen. The implanted position of the electrostimulation device can be proximate to a dorsal root ganglion (DRG) or a ventral root.

Performing the testing can include performing operations by an external device in wireless communication with the electrostimulation device. The operations can comprise providing a first configuration signal to the electrostimulation device to cause the electrostimulation device to have a first configuration wherein a particular first one of its electrodes is configured for use as an anode electrode and a particular second one of its electrodes is configured for use as a cathode electrode. The operations can comprise providing one or more first operation signals to the electrostimulation device to cause the electrostimulation device to provide, as a portion of the test stimulus, a first electrostimulation output at a specified first voltage or current level. The operations can further comprise, in response to a determination that the first electrostimulation output did not evoke the specified response, providing one or more second operation signals to the electrostimulation device to cause the electrostimulation device to provide, as a subsequent portion of the test stimulus, a second electrostimulation output at a specified second voltage or current level that is greater than the first voltage or current level. The operations can further comprise, in response to the first or the second electrostimulation output evoking the specified response from the patient, recording information about the first configuration and about the specified second voltage or current level that caused the response.

The method can further comprise in response to a determination that the second voltage or current level is at or above a specified threshold, providing a second configuration signal to the electrostimulation device that cause the testing to use a different electrode configuration. The method can further include determining whether the specified response is evoked using information from an electromyography sensor situated on the patient. The method can further include determining whether the specified response is evoked using information from an accelerometer sensor situated on the patient.

The method can further include alerting an operator to adjust a position of the electrostimulation device within the patient when the first or second voltage or current level meets or exceeds a specified threshold level. Alerting the operator to adjust the position of the electrostimulation device can include providing instructions to re-position the electrostimulation device without requiring removal of the electrostimulation device from a deployment catheter.

In some embodiments a system for validating a position of a wirelessly powered electrostimulation device in body tissue is provided. The system can be used for validating an efficacy of electrostimulation provided to the body tissue using the electrostimulation device in the validated position. The system can include an implantable electrostimulation device including electrodes and an affixation mechanism, wherein the affixation mechanism is configured to be deployed to maintain an implanted position of the electrostimulation in tissue. The system can include at least one device situated external to a patient, the at least one device including a display device, an antenna, and processing circuitry configured to, before deployment of the affixation mechanism and while the electrodes of the device are in contact with the tissue, deliver a test stimulus to the body tissue to determine whether the test stimulus from the electrostimulation device evokes a specified response from the body tissue.

The system can further include a catheter situated at least partially in the tissue and including the electrostimulation device situated only partially therein. The system can further include a push rod configured to travel inside the catheter and to advance the electrostimulation device through at least a portion of the catheter. The electrostimulation device can be configured to deliver the test stimulus to the body tissue while the affixation mechanism of the electrostimulation device is situated in the catheter and the catheter is at least partially in the body tissue. The catheter can comprise a radio transparent material. The push rod can comprise a radio transparent material.

The electrostimulation device can be configured to deliver the test stimulus to the body tissue while the push rod is engaged with a push rod interface of the electrostimulation device. The electrostimulation device can be configured to deliver the test stimulus to the body tissue when electrodes of the electrostimulation device are provided outside of the catheter and in the body tissue and the affixation mechanism is disposed inside of the catheter.

The system can further include a suture extending through a lumen of the push rod and mechanically connected to a proximal portion of the electrostimulation device. The test stimulus can be generated while the push rod is decoupled from the electrostimulation device and the suture is disposed in the lumen of the push rod. The push rod can include a thread and a proximal portion of the suture can be situated around and secured to the thread of the push rod. The system can further include a luer cap configured to secure the suture to the thread of the push rod. The thread can be one of a plurality of threads. The proximal portion of the suture can be situated around and secured to a first thread of the plurality of threads. A different portion of the suture can be situated around and secured to a second thread of the plurality of threads. Rotation of the cap can be configured to release the proximal portion of the suture while retaining the different portion of the suture.

The system can further include a retention mechanism provided at a fixed position on the suture. The retention mechanism can be configured such that it cannot travel through the lumen. The implantable electrostimulation device can be configured to be implanted proximate to a dorsal root ganglion (DRG) or a ventral root in the body tissue.

The system can further include an external device in wireless communication with the electrostimulation device. The external device can include processing circuitry configured to control delivery of the test stimulus. Controlled delivery of the test stimulus can include providing a first configuration signal to the electrostimulation device to cause the electrostimulation device to have a first configuration wherein a particular first one of its electrodes is configured for use as an anode electrode and a particular second one of its electrodes is configured for use as a cathode electrode. Controlled delivery of the test stimulus can further include providing one or more first operation signals to the electrostimulation device to cause the electrostimulation device to provide, as a portion of the test stimulus, a first electrostimulation output at a specified first voltage or current level.

Controlled delivery of the test stimulus can further include, in response to a determination that the first electrostimulation output did not evoke the specified response from the patient, providing one or more second operation signals to the electrostimulation device to cause the electrostimulation device to provide, as a subsequent portion of the test stimulus, a second electrostimulation output at a specified second voltage or current level that is greater than the first voltage or current level. Controlled delivery of the test stimulus can further include, in response to the second electrostimulation output evoking the specified response from the patient, configuring the electrostimulation device to use the first configuration and the specified second voltage or current level to deliver a subsequent therapy to the body tissue.

The processing circuitry can be further configured to, in response to a determination that a stimulus voltage or current level is at or above a specified threshold, provide one or more signals to the electrostimulation device that cause the electrode configuration to change. The system can further include an electromyography sensor configured to provide information to the external device about whether the test stimulus produced a response. The processor circuitry can be further configured to use the information from the electromyography sensor to determine whether the first electrostimulation output evoked the specified response.

The system can further include an accelerometer configured to provide information to the external device about whether the test stimulus produced a response. The processor circuitry can be configured to use the information from the accelerometer to determine whether the first electrostimulation output evoked the specified response. The processing circuitry can be further configured to cause an interface device to alert an operator to adjust a position of the electrostimulation device within the patient when the first or second voltage or current level meets or exceeds a specified threshold level. The electrostimulation device can be a midfield electrostimulation device.

In some embodiments, a system can include an external wireless transmitter configured to communicate power and/or data to an electrostimulation device when the electrostimulation device is implanted in body tissue. The system can further include a radio transparent push rod assembly configured to be coupled with the electrostimulation device during implantation and during in-situ testing of the electrostimulation device. The system can further include the electrostimulation device, wherein the electrostimulation device comprises a tissue affixation mechanism. The system can further include a catheter configured to receive at least a portion of the electrostimulation device and to maintain the tissue affixation mechanism in an undeployed configuration until the electrostimulation is released from the catheter using the push rod assembly. The catheter can include a radio transparent material.

In some embodiments, a system can include an external wireless transmitter configured to communicate power and/or data to an electrostimulation device when the device is implanted in body tissue. The system can further include a push rod assembly configured to advance the electrostimulation device into the body tissue during an implantation procedure, the push rod assembly further configured to be disposed inside the body tissue and spaced apart from the electrostimulation device during in-situ testing of the electrostimulation device. The system can further include a suture mechanically connected to the electrostimulation device and situated at least partially inside a lumen of the push rod assembly, the push rod assembly further configured to de-couple from and re-couple with the electrostimulation device without being removed from the body tissue. The suture can be configured to move inside the lumen of the push rod assembly toward an operator to advance the electrostimulation device toward the push rod assembly.

In some embodiments, a system can include a catheter. The system can further include at least one of an electromyography sensor or accelerometer sensor configured to be disposed on a patient body. The system can further include a neurostimulation device comprising one or more tines, the neurostimulation device provided in the catheter and the catheter configured to inhibit deployment of the tines. The system can further include an external device communicatively coupled to the electromyography or accelerometer sensor. The external device can further include processing circuitry. The external device can further include a memory including instructions stored thereon that, when executed by the processing circuitry, cause the processing circuitry to perform operations for threshold testing.

The operations can further include providing one or more signals to the neurostimulation device that causes the neurostimulation device to configure the electrodes including configuring a first electrode as an anode and a second electrode as a cathode. The operations can further include providing one or more signals to the neurostimulation device that cause the neurostimulation device to produce first electrostimulation at a specified first voltage or current level. The operations can further include using information from the electromyography sensor or the accelerometer, determining that the first electrostimulation did not evoke a specified response from the patient, and providing one or more signals to the neurostimulation device that cause the device to produce second electrostimulation at a specified second voltage or current level that is greater than the first voltage or current level. The operations can further include using information from the electromyography sensor or the accelerometer, determining that one of the first or the second electrostimulation did evoke the specified response from the patient and providing one or more other signals to the neurostimulation device to cause the electrode configuration to change and the electrode configuration to be recorded along with the voltage or current level that caused the response. The operations can further include providing one or more signals to the neurostimulation device that cause the neurostimulation device to produce third electrostimulation at the voltage or current level at which the first or the second electrostimulation produced a response.

The operations can further include, in response to a determination that voltage or current is at or above a specified threshold, providing one or more other signals to the neurostimulation device to change the electrode configuration. The operations can further include providing instructions to an operator to change a position of the neurostimulation device within the patient in response to a determination that the recorded voltage or current level is at or greater than a threshold voltage or current level. The operations can further include providing one or more signals to the neurostimulation device that causes the device to configure the first electrode configured as the anode and the second electrode as the cathode. The operations can further include providing one or more signals to the neurostimulation device that cause the neurostimulation device to produce subsequent electrostimulation at the specified first voltage or current level. The instructions to the operator to change the position of the neurostimulation device include instructions for re-positioning the neurostimulation device without requiring completely removing the device from a catheter or deploying the tines of the device.

The neurostimulation device can be configured to receive power and/or data from the external device using a wireless midfield signal. The neurostimulation device can be situated to stimulate a dorsal root ganglion (DRG) or a ventral root of the patient.

In some embodiments, an elongate implantable device can include a body portion comprising one or more addressable electrodes. The implantable device can include a circuitry housing comprising drive circuitry coupled to the one or more addressable electrodes. The implantable device can include a severable extension structure coupled to the circuitry housing, the extension structure configured to receive an installation force to drive the device into body tissue. The implantable device can further include a retaining structure configured to mate with the severable extension structure. The body tissue can include mammal brain tissue.

In some embodiments, an electrostimulation device for implantation in a brain can include a wireless power receiver. The electrostimulation device can further include an electrostimulation signal generator configured to generate electrostimulation signals using power received from the wireless power receiver. The electrostimulation device can further include electrodes configured to deliver, to brain tissue, electrostimulation signals from the electrostimulation signal generator. The electrostimulation device can further include an extension structure configured to position the electrodes at a first depth inside of the brain, and wherein at least a portion of the extension structure is configured to be removed following implantation of the device in the brain. The electrostimulation device can further include an external retaining structure mated with the severable extension structure.

In some embodiments, a method can include wirelessly receiving, from a midfield source originating external to a patient body, a power signal at a receiver circuit of an implantable device implanted in a patient brain. The method can further include providing electrostimulation therapy to brain tissue of the patient brain using the received power signal. The method can further include removing at least a portion of a severable extension structure extending beyond a cranium of the patient body. The method can further include inserting a retention structure around a proximal portion of the implantable device at a location outside the patient brain to retain the implantable device in an implanted position.

In some embodiment a method can include providing, by a source external to a patient, a first stimulation command to a neurostimulation device implanted in the patient, the first stimulation command configured to cause the neurostimulation device to generate first electrical stimulation with first electrical stimulation parameters. The method can further include, following a first blanking period, providing, by the source, a second stimulation command to the neurostimulation device, the second stimulation command configured to cause the neurostimulation device to generate second electrical stimulation with second, different electrical stimulation parameters. The first blanking period can include a first specified or first random duration of time.

The blanking period can include a non-zero and fixed duration of time. The blanking period can include a non-zero duration of time that is determined at least in part using a pseudorandom number generator. The method can further include providing, by the source, a power signal to the neurostimulation device, wherein providing the power signal includes after providing the first stimulation command and before the first blanking period. The method can further include providing a second blanking period following the second stimulation command, wherein the first and second blanking periods have different durations. The duration of the second blanking period can be determined at least in part by a duration of the first blanking period. The first electrical stimulation parameters are for a tonic, pain treatment stimulation and the second electrical stimulation parameters are for inflammation treatment. The first and second stimulations can have different frequencies. A frequency of the second stimulation can be greater than a frequency of the first stimulation. The second electrical stimulation can be provided during an inter-stimulation rest of the tonic, pain treatment stimulation.

In some embodiments, an external source device can include a midfield antenna. The external source device can further include processing circuitry coupled to the midfield antenna. The external source device can further include a memory including instructions that, when executed by the processing circuitry, cause the processing circuitry to perform operations. The operations can include providing, by the midfield antenna, a first stimulation command to a neurostimulation device implanted in the patient that causes the neurostimulation device to generate first electrical stimulation with first electrical stimulation parameters. The operations can further include resting for a first random or specified duration of time. The operations can further include, in response to expiration of the first duration of time, providing by the midfield antenna, a second stimulation command to the neurostimulation device that cause the neurostimulation device to generate second electrical stimulation with second, different electrical stimulation parameters. The first specified duration of time can be static. The first specified duration of time can be determined based on a pseudorandom number generator.

The operations can further include, after providing the first stimulation command and before resting, providing by the midfield antenna, a power communication to the neurostimulation device. The operations can further include, after the neurostimulation device generates the second electrical stimulation, resting by the external source, for a second, different specified duration of time. The second, different specified duration of time can be determined based on the first specified duration of time. The first electrical stimulation parameters can be for a tonic, pain treatment stimulation and the second electrical stimulation parameters are for inflammation treatment. The second stimulation can be a different frequency from the first stimulation. The frequency of the second stimulation can be greater than the frequency of the first stimulation. The second electrical stimulation can be provided during an inter-stimulation rest of the tonic stimulation.

In some embodiments, a wireless power unit can include a case. The power unit can further include an antenna in the case, the antenna comprising multiple transmission ports. The power unit can further include circuitry in the case, the circuitry configured to electrically stimulate the ports so as to cause the ports to produce respective electromagnetic waves that give rise to propagating waves in tissue. The power unit can further include a phase change material inside the case and in thermal communication with the circuitry. The phase change material can be coupled with or provided adjacent to at least a portion of the circuitry that undergoes a temperature change during operation of the wireless power unit. The phase change material can include a formulated paraffin wax, a hydrated salt, or a combination thereof.

The power unit can further include a circuit board in the case, wherein the antenna and the phase change material are provided on opposite sides of the circuit board. The circuitry can include a phase change sensor to provide information about an amount of the phase change material that is in a particular phase. The circuitry can be configured to use information from the phase change sensor to determine an amount of thermal energy that can be dissipated by the power unit. The phase change sensor can include a resistivity sensor, a capacitance sensor, a temperature sensor, an optical sensor, or a combination thereof. A volume or a mass of the phase change material can be selected for use with the power unit based on a power capacity of a battery of the power unit or a continuous duration of therapy to be provided to a patient using the power unit.

The case can include a cover wall with fins extending from internal to the case and in contact with the phase change material through the cover wall of the case. The circuitry can be configured to use information from the phase change sensor to determine whether or when to turn off one or more functions of the power unit.

In some embodiments an ultrasonic therapy delivery system for implantation inside of a blood vessel of a patient is provided. The system can include a wireless receiver circuit configured to wirelessly receive power and/or data from a source device external to the patient. The system can include an expandable and contractible support structure having a first contracted configuration inside of a delivery cannula and having a second expanded configuration outside of the delivery cannula, wherein the support structure is coupled to the wireless receiver circuit. The system can further include one or more ultrasound transducers configured to use the wirelessly received power and/or data from the source device to provide an ultrasound therapy signal to a neural target in the patient. The support structure can include one or more fixation elements configured to couple at least a portion of the system to a blood vessel wall. The system can include an electrostimulation drive circuit coupled to one or more electrodes, wherein the one or more electrodes are configured to penetrate a wall of the blood vessel.

The system can include a drive circuit coupled to the one or more transducers, wherein the one or more transducers are configured to face or touch an inner wall of the blood vessel when the system is implanted inside the vessel. The system can further include at least two transducers that are spaced apart and coupled to different portions of a biocompatible mesh structure that is configured to interface with a vessel wall. The mesh structure can include a honeycomb structure that integrates with the vessel wall. The support structure can include a substantially cylindrical stent. The support structure can include a coiled biocompatible wire. The wireless receiver circuit can be configured to receive a midfield power signal.

In some embodiments, an electrostimulation or sensor system for implantation inside of a blood vessel of a patient is provided. The system can include a wireless receiver circuit configured to wirelessly receive power and/or data from a source device external to the patient. The system can further include a control circuit coupled to the wireless receiver circuit. The system can further include one or more ultrasound transducers coupled to the control circuit and configured to provide an ultrasound therapy to a neural target in the patient. The system can further include an expandable and contractible support structure having a first contracted configuration inside of a delivery catheter and having a second expanded configuration outside of the delivery catheter. The support structure can be coupled to and configured to locate, with respect to inner walls of the blood vessel, the wireless receiver circuit, the control circuit, and the one or more transducers such that blood flow is not occluded when the system is deployed inside the blood vessel.

In some embodiment a method for deploying a midfield-powered device inside of a blood vessel is provided. The method can include inserting a cannula into a patient blood vessel, the cannula comprising an ultrasound transducer configured to be deployed inside the vessel, the device comprising a support structure having a first contracted configuration inside of the cannula and having a second expanded configuration outside of the cannula. The method can further include using a push rod or other deployment feature, sliding the device relative to the cannula sheath to deposit the device inside the vessel. The method can further include expanding the support structure from the first contracted configuration to the second expanded configuration, including using a portion of the support structure to bring the ultrasound transducer into contact an inner wall of the blood vessel to thereby retain the device in a specified location relative to the blood vessel.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

FIGS. 7 and 8 illustrate, by way of example, respective diagrams of an embodiment of an implanting aid.

FIG. 9 illustrates, by way of example, a diagram of an embodiment of another implanting aid.

FIG. 10 illustrates, by way of example, a diagram of an embodiment of a system of implantable devices.

FIG. 13 illustrates, by way of example, a perspective view diagram of an embodiment of an implantable device.

FIG. 14 illustrates, by way of example, a diagram of another embodiment of an implantable device that shows internal circuitry and an antenna internal to the device.

FIGS. 17A, 17B, 17C, and 17D illustrate, by way of example, perspective view diagrams of an embodiment of an implantable device extraction system.

FIG. 20 illustrates, by way of example, a diagram of an embodiment of an implantable device.

FIGS. 21-33 illustrate, by way of example, diagrams of respective portions of a process of implanting an implantable device.

FIG. 34 illustrates, by way of example, a perspective view diagram of an embodiment of a push rod.

FIG. 35 illustrates, by way of example, an embodiment of an implantable device interface of a push rod.

FIG. 36 illustrates, by way of example, a diagram of an embodiment of a proximal portion of a push rod.

FIG. 37 illustrates, by way of example, a perspective view diagram of an embodiment of a push rod with a suture situated partially in a lumen.

FIG. 38 illustrates, by way of example, a perspective view diagram of an embodiment of a push rod interface engaged with an implantable device interface.

FIG. 45 illustrates, by way of example, a diagram of an embodiment of a push rod with a suture secured thereto.

FIG. 48 illustrates generally an example of an implantable device, such as can be configured to deliver electrostimulation signals to a brain.

FIG. 49 illustrates generally an example of the implantable device of FIG. 48 with a retention structure.

FIG. 50 illustrates generally an example of the implantable device of FIG. 49 with a portion of an extension structure of the device removed.

FIGS. 51A, 51B, and 52 illustrate generally examples of circuitry housings such as for use with an implantable device.

FIGS. 60 and 61 illustrate, by way of example, side and top view diagrams of an embodiment of a top cover of a power unit with fins.

FIG. 62A illustrates generally a schematic example of a portion of an implantable device that includes one or more ultrasound transducers.

DETAILED DESCRIPTION

Figure 1:
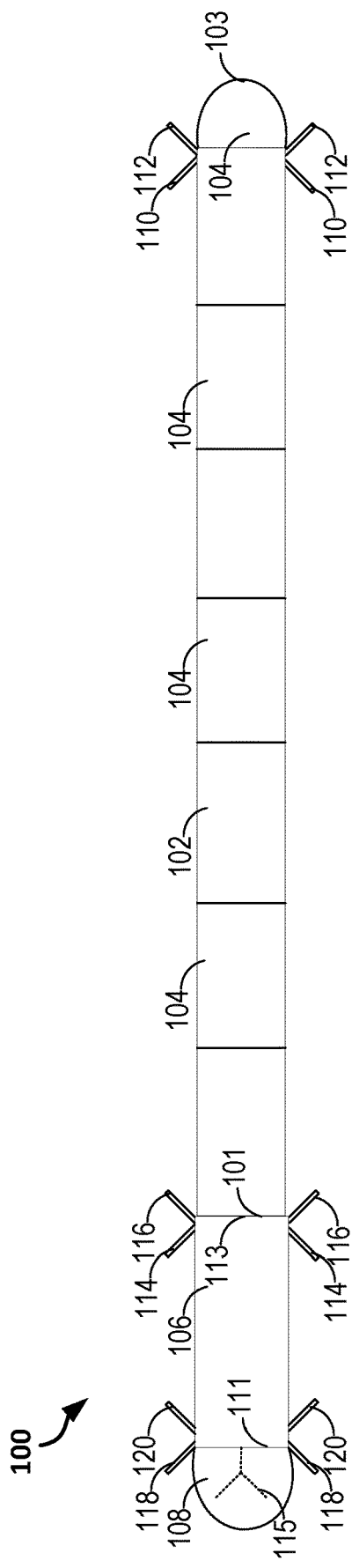
FIG. 1 illustrates, by way of example, a perspective view diagram of an embodiment of an implantable device.

In the following description that includes examples of different nerve-electrode interfaces and peripheral devices, reference is made to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. The present inventors contemplate examples using any combination or permutation of those elements shown or described (or one or more aspects thereof), either with respect to a particular example (or one or more aspects thereof), or with respect to other examples (or one or more aspects thereof) shown or described herein. Generally discussed herein are implantable devices and methods of assembling the implantable devices.

Midfield powering technology can be used to provide power to one or more deeply implanted electrostimulation devices from one or more external power sources located on or near a tissue surface, such as at an external surface of a user's skin. The user can be a clinical patient or other user. Devices that include or use midfield powering technology can have one or more advantages over conventional implantable pulse generators such as may have one or more relatively large, implanted batteries and/or one or more lead systems. Midfield devices, in contrast, can include relatively small battery cells that can be configured to receive and store relatively small amounts of power. A midfield device can include one or more electrodes integrated in a unitary implantable package. Thus, in some examples, a midfield-powered device can provide a simpler implant procedure over other conventional devices, which can lead to a lower cost and a lower risk of infection or other implant complications. Another advantage of midfield-powered devices can include an amount of power that can be transferred to the implanted device. The ability to focus energy from an external midfield source device to particular locations inside the body can allow for an increase in an amount of power transferred to a particular implanted device.

An advantage of using midfield powering technology can include a main battery or power source being provided externally to the patient, and thus low power consumption and high efficiency circuitry requirements of conventional battery-powered implantable devices can be relaxed. Another advantage of using midfield powering technology can include an implanted device that can be physically smaller than a battery-powered device. Midfield powering technology can thus help enable better patient tolerance and comfort along with potentially lower costs to manufacture and/or to implant in patient tissue.

In one or more examples, multiple devices can be implanted in patient tissue and can be configured to deliver a therapy and/or sense physiologic information about a patient and/or about the therapy. The multiple implanted devices can be configured to communicate with one or more external devices. In one or more examples, the one or more external devices are configured to provide power and/or data signals to the multiple implanted devices, such as concurrently or in a time-multiplexed (e.g., "round-robin") fashion. The provided power and/or data signals can be steered or directed by an external device to transfer the signals to an implant efficiently. Although the present disclosure may refer to a power signal or data signal specifically, such references are to be generally understood as optionally including one or both of power and data signals.

Several embodiments described herein can be advantageous because they include one, several, or all of the following benefits, which are believed to satisfy various previously-unmet needs. Advantages of embodiments can include one or more of: an implantable midfield powered stimulator that is consistently positioned at the proper angle and depth relative to a target DRG or other nerve structure for effective therapeutic response; an implantable midfield powered stimulator that is intuitively easier for neurosurgeons to implant relative to the existing implantable DRG stimulation systems; shortening procedure times, increasing responder rate, and reducing complications and revisions; an implantable midfield powered stimulator system that allows for simple implantation of multiple neurostimulators that are precisely located and powered by a single external source; a larger mechanical fixture or a smaller fixture guided by a laser projection system to precisely locate the position for introduction of the implant tools; a fixture that could be adapted for use with conventional DRG Stimulation systems providing similar procedural benefits.

Various embodiments herein can be advantageous because they provide an ability to test whether an implantable device is properly situated to provide sufficient stimulation to treat a condition. They can also provide the ability to identify an electrode configuration, as well as a frequency and amplitude configuration (or other electrical waveform configuration) that evokes a response from a patient.

Various embodiments herein can be advantageous because they provide an ability to situate and secure a wireless implantable device in a brain. They can also provide an ability to improve an implantation process through a hard, dense structure, such as the cranium. They can also help ensure that an implanted device does not travel while implanted.

Some embodiments herein can be advantageous because they can aid in thermal management of an external power source. The external power source can become hot or otherwise reach a temperature that is uncomfortable to the patient. Improved temperature management of the external power source is provided by embodiments.

Various embodiments herein can be advantageous because they help reduce inflammation and ultimately aid recovery of the patient. These embodiments can perform an inflammation stimulation, distinct from a therapy stimulation that treats a different condition of the patient. Both of these stimulations can be provided by a same implantable device. Some embodiments herein can be advantageous because they provide an additional or alternative stimulation, other than electrical stimulation, for a nerve target. Such embodiments can be intravascular or outside the vasculature, such as to reach different therapy targets.

In one or more examples, one or more of these benefits and others can be realized using, at least partially, a system for manipulating an evanescent field at or near an external tissue surface to transmit power and/or data wirelessly to one or more target devices implanted in the tissue. In one or more examples, one or more of these benefits can be realized using a device or devices implanted in a body or capable of being implanted in a body and as described herein. In one or more examples, one or more of these benefits can be realized using a midfield powering and/or communication device (e.g., a transmitter device and/or a receiver device or a transceiver device).

A system can include a signal generator system adapted to provide multiple different sets of signals (e.g., RF signals). Each set can include two or more separate signals in some embodiments. The system can also include a midfield transmitter including multiple excitation ports, the midfield transmitter coupled to the RF signal generator system, and the midfield transmitter being adapted to transmit the multiple different sets of RF signals at respective different times via the excitation ports. The excitation ports can be adapted to receive respective ones of the separate signals from each set of RF signals. Each of the transmitted sets of RF signals can include a non-negligible magnetic field (H-field) component that is substantially parallel to the external tissue surface. In one or more examples, each set of transmitted RF signals is adapted or selected to differently manipulate an evanescent field at or near the tissue surface to transmit a power and/or data signal to one or more target devices implanted in the tissue via a midfield signal, such as instead of via inductive nearfield coupling or radiative far-field transmission.

In one or more examples, one or more of the above-mentioned benefits, among others, can be realized, at least in part, using an implantable therapy delivery device (e.g., a device configured to provide neural stimulation) that includes receiver circuitry including an antenna (e.g., an electric field or magnetic field based antenna) configured to receive a midfield power signal from an external source device, such as when the receiver circuitry is implanted within tissue. The implantable therapy delivery device can include therapy delivery circuitry. The therapy delivery circuitry can be coupled to the receiver circuitry. The therapy delivery circuitry can be configured to provide signal pulses to one or more energy delivery members (e.g., electrostimulation electrodes), which may be integrally coupled to a body of the therapy delivery device or positioned separately from (e.g., not located on) the body of the therapy delivery device, such as by using a portion of the received midfield power signal from the external source device (e.g., sometimes referred to herein as an external device, an external source, an external midfield device, a midfield transmitter device, a midfield coupler, a midfield powering device, a powering device, or the like, depending on the configuration and/or usage context of the device). The signal pulses can include one or more electrostimulation therapy pulses and/or data pulses. In one or more examples, one or more of the above-mentioned benefits, among others, can be realized, at least in part, using an external transmitter and/or receiver (e.g., transceiver) device that includes an electrode pair configured to be disposed at an external tissue surface, and the electrode pair is configured to receive an electrical signal via the tissue. The electrical signal can correspond to an electrostimulation therapy delivered to the tissue by the therapy delivery device. A demodulator circuit can be coupled to the electrode pair and can be configured to demodulate a portion of the received electrical signal, such as to recover a data signal originated by the therapy delivery device or by another implanted device.

In one or more examples that include using a midfield wireless coupler, tissue can act as a dielectric to tunnel energy. Coherent interference of propagating modes can confine a field at a focal plane to less than a corresponding vacuum wavelength, for example, with a spot size subject to a diffraction limit in a high-index material. In one or more examples, a receiver (e.g., a device implanted in tissue) positioned at such a high energy density region can be one or more orders of magnitude smaller than a conventional nearfield implantable receiver or can be implanted more deeply in tissue (e.g., greater than 1 cm in depth). In one or more examples, a transmitter source described herein can be configured to provide electromagnetic energy to various target locations, including for example to one or more deeply implanted devices. In an example, the energy can be provided to a location with greater than about a few millimeters of positioning accuracy. That is, a transmitted power or energy signal can be directed or focused to a target location that is within about one wavelength of the signal in tissue. Such energy focusing is substantially more accurate than the focusing available via traditional inductive means and is sufficient to provide adequate power to a receiver. In other wireless powering approaches using nearfield coupling (inductive coupling and its resonant enhanced derivatives), evanescent components outside tissue (e.g., near the source) remain evanescent inside tissue, which does not allow for effective depth penetration. Unlike nearfield coupling, energy from a midfield source is primarily carried in propagating modes and, as a result, an energy transport depth is limited by environmental losses rather than by intrinsic decay of the nearfield. Energy transfer implemented with these characteristics can be at least two to three orders of magnitude more efficient than nearfield systems.

Midfield Stimulation of Dorsal Root Ganglion

Section headings herein, like the one above ("MIDFIELD STIMULATION OF DORSAL ROOT GANGLION"), are provided to guide a reader generally to material corresponding to the topic indicated by the heading. However, discussions under a particular heading are not to be construed as applying only to configurations of a single type; instead, the various features discussed in the various sections or subsections herein can be combined in various ways and permutations. For example, the disclosures in "WIRELESS THRESHOLD TESTING IN NEUROMODULATION" and "TESTING AND VERIFICATION OF IMPLANTABLE STIMULATION DEVICES" are processes and systems that can be used individually or together. Further, these sections can be used in combination with a method, device, or system discussed in "MIDFIELD STIMULATION OF DORSAL ROOT GANGLION". "IMPROVED THERMAL MANAGEMENT IN WIRELESS POWER UNIT" can be combined with a method, system, or device of any other section herein as this disclosure improves the external power unit and such an external power unit can be used to power any of the implantable neurostimulation devices or communicate with an external device or component discussed. Similarly, "NEUROMODULATION FOR PAIN AND INFLAMMATION" can be combined with a method, system, or device of any other section herein as this disclosure improves therapy using an electrostimulation device (sometimes called an implantable device or a neuromodulation device) by improvements to the external power source and such a device can be used with technology disclosed in any other section. Further, "INTRAVENOUS ULTRASOUND NEUROMODULATION SYSTEMS AND METHODS" can be combined with a method, system, or device of any other section herein as this disclosure improves therapy using an electrostimulation device by improvements to the implantable device and retaining the implantable device in a vascular structure and such a device can be used with technology disclosed in any other section.

Generally discussed herein are embodiments of devices, methods, and systems for dorsal root ganglion (DRG) stimulation and/or a corresponding ventral root (VR) stimulation. A DRG includes sensory neurons that provide electrical signals (information) from a body periphery to the spinal cord. Dorsal root ganglia reside in openings known as the intervertebral foramina. DRG neurons emerge from the dorsal root of the spinal nerves, carrying sensory messages from various receptors, such as including those for pain or temperature, towards the central nervous system for response. While the DRG provides signals to the brain, the VR sends signals to peripheral body parts, such as parts of legs, arms, torso, or the like.

The DRG lie in the intervertebral foramina. The DRG are considered to be in, or comprise a portion of, the peripheral nervous system because they are situated outside the spinal cord. The DRG can be an active participant in peripheral processes including platelet activating factor (PAF), inflammation, and neuropathic pain. Many of the human body's peripheral features are electrically coupled to the spinal cord (and the brain) through respective DRG. For example, nerves that terminate in the leg, back, arm, foot, hand, left side of body to lower sympathetic nerve activity, such as to lower blood pressure for treatment of hypertension, or that terminate in some other peripheral body part, a T12 DRG (e.g., to modulate an endogenous opioid system of the body and reduce back pain), lower or upper extremity, low back, groin, buttock, hip, thigh, knee, lower leg, ankle, testicle, pelvis, and perineum are coupled to the central nervous system such as through the DRG. Applications of DRG stimulation can include treatment of complex regional pain syndrome, diabetic peripheral neuropathy, idiopathic peripheral neuropathy, chemotherapy-induced peripheral neuropathy, HIV related neuropathy, postsurgical pain, pelvic pain, groin pain, phantom limb or stump pain, or postherpetic neuralgia, among others. In an example, DRG stimulation is superior to spinal cord stimulation for reducing neuropathic pain in a focused location where the regional afferent nerves are connected at a particular DRG.

The DRG are responsible for the transmission of sensory messages from receptors such as thermoreceptors, nociceptor, proprioceptors, and chemoreceptors, to the CNS. The DRG includes, or acts as a pathway for, many of the human sensory neurons. These neurons relay sensory neural messages from the periphery to the CNS (e.g., to the brain and spinal cord).

Stimulation of the DRG can help control a sensation of perception of pain (nociception), temperature, or hunger, and can influence muscle contraction or relaxation, or the like. The DRG can be affected by damage to the brain, spine, or surrounding structures. Stimulation of a DRG can help a defective or faulty DRG or portion thereof to reduce neuropathic pain signals from a connected peripheral nerve system to provide signal regulation. Embodiments discussed herein provide implantable devices, implantation techniques, and systems for DRG, VR, or other nerve stimulation.

FIG. 1 illustrates, by way of example, a perspective view diagram of an embodiment of an implantable device 100. The device 100 can be used for DRG, VR, or other nerve stimulation in some embodiments. The device 100 as illustrated includes a body portion 102, a plurality of electrodes 104, a circuitry housing 106, an antenna housing 108, an affixation mechanism in the form of distal tines 110, 112 and proximal tines 114, 116, 118, and 120. Some but not all tines 110, 112, 114, 116, 118, 120 may be used in some embodiments, and some embodiments may omit tines. Other affixation mechanisms include coils, spikes, knurled surface, rough surface, divots, bumps, barbs, or the like.

The body portion 102 can be made of a flexible or rigid material. In one or more embodiments, the body portion 102 can include a bio-compatible material. The body portion 102 can include platinum, iridium, titanium, ceramic, zirconia, alumina, glass, polyurethane, silicone, epoxy, and/or a combination thereof among others.

The body portion 102 includes electrodes 104 thereon or at least partially therein. The electrodes 104, as illustrated, are ring electrodes however other kinds or configurations of electrodes can similarly be used. The electrodes 104 as illustrated are about evenly distributed along the body portion (e.g., with about an equal space between directly adjacent pairs of electrodes).

The body portion 102 includes a circuitry housing 106 coupled thereto at a first end 101 of the body portion 102. The first end 101 (more proximal end) of the body portion 102 is opposite a second end 103 (more distal end) of the body portion 102. The second end 103 can be situated closer to a particular DRG target than the first end 101 while implanted.

The circuitry housing 106 can provide a hermetic enclosure for electric and/or electronic components and interconnects housed therein. The electrodes 104 can be respectively electrically connected to circuitry in the circuitry housing 106 using one or more feedthroughs and one or more conductors.

The antenna housing 108 can be attached to the circuitry housing 106 at a first end 111 (more proximal end) of the circuitry housing 106. The first end 111 is opposite a second end 113 (more distal end) of the circuitry housing 106. The second end 113 is the end through which the electrodes 104 are electrically connected. An antenna 115 within the antenna housing 108 can be used for powering and communication to and/or from the device 100.

The antenna housing 108 can be brazed or otherwise coupled to the circuitry housing 106. The antenna housing 108 can include an epoxy, tecothane, or other radio frequency (RF) transparent (e.g., at the frequency used to communicate to/from the implant) and protective material.

In one or more embodiments, the antenna housing 108 can include a ceramic material such as zirconia or alumina. The dielectric constant of zirconia is close to that of muscle. This matching of dielectric characteristics allows for stabilization for the circuit impedance of the antenna 115 and decreases the change in impedance when the antenna 115 is surrounded by different tissue types. The power transfer efficiency while the antenna 115 is surrounded by a lower permittivity tissue is increased when using a ceramic housing. In this case, the antenna can be composed as a single ceramic structure with the feedthrough.

In operation, the implantable device 100 can be situated in tissue such that one or more of the electrodes 104 are proximate a nerve, such as a target portion of a DRG or a VR. Embodiments of devices for situating the implantable device 100 in a proper location for nerve stimulation are provided elsewhere herein. Proximate means close enough that electrostimulation produced by the implantable device is incident the object to which the implantable is proximate.

In an example, electrostimulation therapy is provided using the implantable device 100. Midfield powering technology can provide power to a deeply implanted electrostimulation device, such as the implantable device 100, from an external power source (e.g., external source 202, see FIG. 2) located on or near a tissue surface, such as at an external surface of a patient's skin. The external power source can be external to the body in which the device 100 is implanted. The external power source and the device 100 can communicate using wireless transmissions therebetween. For example, the external power source can provide electrical energy to the device 100. The device 100 can use the electrical energy for powering components in the circuitry housing 106 and for providing electrical stimulation through the electrodes 104.

Several embodiments described herein are particularly advantageous because they include one, several, or all of the following benefits: (i) a dynamically configurable, active midfield transceiver that is configured to provide RF signals to modulate an evanescent field at a tissue surface and thereby generate a propagating field within tissue, such as to transmit power and/or data signals to an implanted target device, (ii) a dynamically configurable, substantially passive midfield transceiver or lens that is configured to receive remote RF signals and in response provide RF signals to modulate an evanescent field at a tissue surface and thereby generate a propagating field within tissue, such as to transmit power and/or data signals to an implanted target device, (iii) an implantable device with multiple electrode configurations to provide flexibility in stimulation location and allow for some variance in implant location, (iv) an implant position aid to help situate the implant device near a nerve target or adjust for changes in posture in body orientation, (v) implantable device retention mechanisms (e.g., tines) to help retain the implantable device near the target, (vi) multiple receivers that simulate DRGs bilaterally (being powered by a single external powering unit), (vii) does not require a sharp bend of the lead in an epidural space to the DRG exiting the spinal foramen (this avoids the leading cause of failure of a current system for DRG stimulation), (vii) a trans-foramonal delivery technique is less invasive and easier to perform than prior delivery techniques, among others.

The external source can provide an electromagnetic wave that is incident on the antenna 115. The antenna 115 can transduce the electromagnetic wave to electrical signals that provide power to the implantable device 100. The components in the circuitry housing 106 can include an energy storage component that additionally, or alternatively, can be charged to provide power to circuitry of the implantable device 100.

The tines 110, 112, 114, 116, 118, 120 aid retention of the device 100 at an implant location near a nerve. The tines 110, 114, 118 can extend from the body of the implantable device 100. A portion of the tines 110, 114, 118 further away from the body of the implantable device 100 can be closer to the antenna housing 108. A portion of the tines 110, 114, 118 closer to the implantable device 100 can be closer to the end 103 opposite the antenna housing 108. The tines 112, 116, 120 can extend from the body of the implantable device 100. A portion of the tine 112, 116, 120 further away from the body of the implantable device 100 can be closer to the end 103. A portion of the tine 112, 116, 120 closer to the body of the implantable device 100 can be closer to the antenna housing 108.

Tines 118, 120 can be attached at a proximal portion of the circuitry housing 106. Tines 114, 116 can be attached at distal portion of the circuitry housing 106. Tines 110, 112 can be attached near the end 103 of the implantable device 100. The tines 110, 112, 114, 116, 118, 120 can be configured to affix the implantable device 100 to or near a specific anatomical structure. Not all tines 110, 112, 114, 116, 118, 120 are required in all embodiments. Some embodiments can include one set of opposing tines. Opposing tines are tines that extend away from the implantable device 100 in opposite directions. The tines 110, 112, 114, 116, 118, 120 can be made of a polymer or other semi-flexible material, such as can include silicone, polyurethane, epoxy, or like materials. The tines 110, 112, 114, 116, 118, 120 can flare away from a central axis of the implantable device 100 such that a distal portion of a given tine 110, 112, 114, 116, 118, 120 is closer to the central axis than a more proximal portion of the given tine 110, 112, 114, 116, 118, 120, such as is shown in FIG. 1.

Embodiments can include generating an electric field-based stimulation pattern proximate a DRG and/or a VR structure. In an example, the same or other stimulation can be provided at one or more target locations along the spinal column.

In an example, DRG stimulation can be used for regularizing (e.g., normalizing) neurologic signal behavior for an afferent nerve structure in a particular target location. The corresponding VR is in close proximity and the associated efferent nerve structure could be stimulated as well. In some examples, however, it can be desirable to avoid stimulation of the corresponding VR to a particular DRG target.

In an example, neurostimulation of a particular DRG location can be used to: treat neuropathic pain in a particular body area; reestablish normal circulatory perfusion in a particular body area; access the Autonomic Nervous System (ANS) such as to help drive a normal balance between sympathetic and parasympathetic response, such as to help regularize blood pressure or to mitigate an inflammatory response; or to provide a motor signal to a nearby VR.

The ANS includes two main divisions, the sympathetic and the parasympathetic nervous systems. The sympathetic nervous system is primarily involved in "fight or flight" type responses, such as increasing heart rate or blood pressure or constricting blood vessels in the skin or dilating vessels in muscles. The parasympathetic nervous system is involved in energy conservation functions and, for example, increases gastrointestinal motility and secretion, or increases bladder contractility. There are some areas in which blood vessels are under competing sympathetic and parasympathetic control, such as in the nose or erectile tissues. In some areas, there can be a competitive balance between sympathetic tone and parasympathetic tone, for example, in controlling heart rate or pupil dilation.

Figure 2:
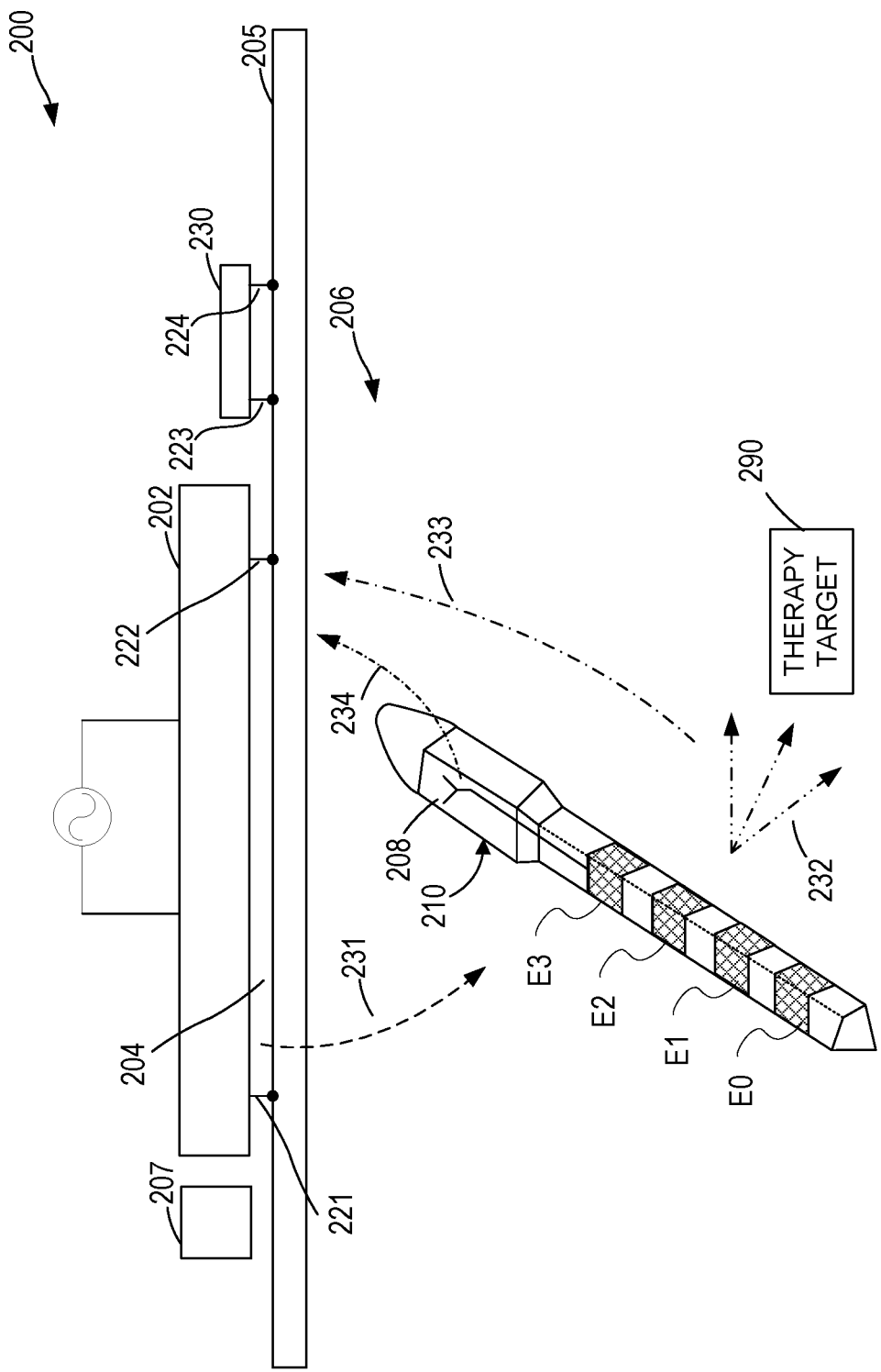
FIG. 2 illustrates, by way of example, an embodiment of an implantable device, such as can include a multi-polar therapy delivery device.

FIG. 2 illustrates, by way of example, a schematic of an embodiment of a system 200 using wireless communication paths. The system 200 includes an example of an external source 202, such as a midfield transmitter source, sometimes referred to as a midfield coupler, located at or above an interface 205 between air 204 and a higher-index material 206, such as body tissue. The external source 202 can produce a source current (e.g., an in-plane source current). The source current (e.g., in-plane source current) can generate an electric field and a magnetic field. The magnetic field can include a non-negligible component that is parallel to the surface of the source 202 and/or to a surface of the higher-index material 206 (e.g., a surface of the higher-index material 206 that faces the external source 202).

The external source 202 can include at least a pair of outwardly facing electrodes 221 and 222. The electrodes 221 and 222 can be configured to contact a tissue surface, for example, at the interface 205. In one or more embodiments, the external source 202 is configured for use with a sleeve, pocket, or other garment or accessory that maintains the external source 202 adjacent to the higher-index material 206, and that optionally maintains the electrodes 221 and 222 in physical contact with a tissue surface. In one or more embodiments, the sleeve, pocket, or other garment or accessory can include or use a conductive fiber or fabric, and the electrodes 221 and 222 can be in physical contact with the tissue surface via the conductive fiber or fabric.

In one or more embodiments, more than two outwardly facing electrodes can be used and processor circuitry onboard or auxiliary to the source 202 can be configured to select an optimal pair or group of electrodes to use to sense far field signal information (e.g., signal information corresponding to a delivered therapy signal or to a nearfield signal). In such embodiments, the electrodes can operate as antennas. In one or more embodiments, the source 202 includes three outwardly facing electrodes arranged as a triangle, or four outwardly facing electrodes arranged as a rectangle, and any two or more of the electrodes can be selected for sensing and/or can be electrically grouped or coupled together for sensing or diagnostics. In one or more embodiments, the processor circuitry can be configured to test multiple different electrode combination selections to identify an optimal configuration for sensing a far field signal.

FIG. 2 illustrates an embodiment of an implantable device 210, such as can include a multi-polar therapy delivery device configured to be implanted in the higher-index material 206. The implantable device 210 can include similar or same components as the implantable device 100. In one or more embodiments, the implantable device 210 is implanted in tissue below the tissue-air interface 205. In FIG. 2, the implantable device 210 includes an elongate body and multiple electrodes E0, E1, E2, and E3 that are axially spaced apart along a portion of the elongate body. The implantable device 210 includes receiver and/or transmitter circuitry (not shown in FIG. 2) that can enable communication between the implantable device 210 and the external source 202.

The various electrodes E0-E3 can be configured to deliver electrostimulation therapy to patient tissue, such as at or near a neural or muscle target. In one or more embodiments, at least one electrode can be selected for use as an anode and at least one other electrode can be selected for use as a cathode to define an electrostimulation vector. In one or more embodiments, electrode E1 is selected for use as an anode and electrode E2 is selected for use as a cathode. Together, the E1-E2 combination defines an electrostimulation vector V12. Various vectors can be configured independently to provide a neural electrostimulation therapy to the same or different tissue target, such as concurrently or at different times.

In one or more embodiments, the source 202 includes an antenna and the implantable device 210 includes an antenna 208 (e.g., an electric field-based or magnetic field-based antenna). The antennas can be configured (e.g., in length, width, shape, material, etc.) to transmit and receive signals at substantially the same frequency. The implantable device 210 can be configured to transmit power and/or data signals through the antenna 208 to the external source 202 and can receive power and/or data signals transmitted by the external source 202. The external source 202 and implantable device 210 can be used for transmission and/or reception of RF signals. A transmit/receive (T/R) switch can be used to switch each RF port of the external source 202 from a transmit (transmit data or power) mode to a receive (receive data) mode. A T/R switch can similarly be used to switch the implantable device 210 between transmit and receive modes.

In one or more embodiments, a receive terminal on the external source 202 can be connected to one or more components that detect a phase and/or amplitude of a received signal from the implantable device 210. The phase and amplitude information can be used to program a phase of the transmit signal, such as to be substantially the same relative phase as a signal received from the implantable device 210. To help achieve this, the external source 202 can include or use a phase-matching and/or amplitude-matching network. The phase-matching and/or amplitude matching network can be configured for use with a midfield antenna that includes multiple ports.

The implantable device 210 can be configured to receive a midfield signal 231 from the external source 202. The midfield signal 231 can include power and/or data signal components. In some embodiments, a power signal component can include one or more data components embedded therein. In one or more embodiments, the midfield signal 231 includes configuration data for use by the implantable device 210. The configuration data can define, among other things, therapy signal parameters, such as a therapy signal frequency, pulse width, amplitude, or other signal waveform parameters. In one or more embodiments, the implantable device 210 can be configured to deliver an electrostimulation therapy to a therapy target 290, such as can include a neural target (e.g., a nerve, a portion of a DRG, etc.), a muscle target, or other tissue target. An electrostimulation therapy delivered to the therapy target 290 can be provided using a portion of a power signal received from the external source 202. Examples of the therapy target 290 can include nerve tissue or neural targets, for example including nerve tissue or neural targets at or near cervical, thoracic, lumbar, or sacral regions of the spine, brain tissue, muscle tissue, abnormal tissue (e.g., tumor or cancerous tissue), targets corresponding to sympathetic or parasympathetic nerve systems, targets at or near peripheral nerve bundles or fibers, at or near other targets selected to treat incontinence, urinary urge, overactive bladder, fecal incontinence, constipation, pain, neuralgia, pelvic pain, movement disorders or other diseases or disorders, deep brain stimulation (DBS) therapy targets or any other condition, disease or disorder (such as those other conditions, diseases, or disorders identified herein).

Delivering the electrostimulation therapy can include using a portion of a power signal received via the midfield signal 231 and providing a current signal to an electrode or an electrode pair (e.g., two or more of E0-E3), coupled to the implantable device 210, to stimulate the therapy target 290. As a result of the current signal provided to the electrode(s), a nearfield signal 232 can be generated. An electric potential difference resulting from the nearfield signal 232 can be detected remotely from the therapy delivery location. Various factors can influence where and whether the potential difference can be detected, including, among other things, characteristics of the therapy signal, a type or arrangement of the therapy delivery electrodes, and characteristics of any surrounding biologic tissue. Such a remotely detected electric potential difference can be considered a far field signal 233. The far field signal 233 can represent an attenuated portion of the nearfield signal 232. That is, the nearfield signal 232 and the far field signal 233 can originate from the same signal or field, such as with the nearfield signal 232 considered to be associated with a region at or near the implantable device 210 and the therapy target 290, and with the far field signal 233 considered to be associated with other regions more distal from the implantable device 210 and the therapy target 290. In one or more embodiments, information about the implantable device 210, or about a previously-provided or future planned therapy provided by the implantable device 210, can be encoded in a therapy signal and detected and decoded by the external source 202 by way of the far field signal 233.

In one or more embodiments, the device 210 can be configured to provide a series of electrostimulation pulses to a tissue target (e.g., neural target). For example, the device 210 can provide multiple electrostimulation pulses separated in time, such as using the same or different electrostimulation vectors, to provide a therapy. In one or more embodiments, a therapy comprising multiple signals can be provided to multiple different vectors in parallel or can be provided in sequence such as to provide a series or sequence of electrostimulation pulses to the same neural target. Thus, even if one vector is more optimal than the others for eliciting a patient response, the therapy as a whole can be more effective than stimulating only the known-optimal vector because (1) the target may experience a rest period during periods of non-stimulation, and/or (2) stimulating the areas nearby and/or adjacent to the optimal target can elicit some patient benefit.

The system 200 can include a sensor 207 at or near the interface 205 between air 204 and the higher-index material 206. The sensor 207 can include, among other things, one or more electrodes, an optical sensor, an accelerometer, a temperature sensor, a force sensor, a pressure sensor, or a surface electromyography (EMG) device. The sensor 207 may comprise multiple sensors (e.g., two, three, four or more than four sensors). Depending on the type of sensor(s) used, the sensor 207 can be configured to monitor electrical, muscle, or other activity near the device 210 and/or near the source 202. For example, the sensor 207 can be configured to monitor muscle activity at a tissue surface. If muscle activity greater than a specified threshold activity level is detected, then a power level of the source 202 and/or of the device 210 can be adjusted. In one or more embodiments, the sensor 207 can be coupled to or integrated with the source 202, and in other examples, the sensor 207 can be separate from, and in data communication with (e.g., using a wired or wireless electrical coupling or connection), the source 202 and/or the device 210.

The system 200 can include a far field sensor device 230 that can be separate from, or communicatively coupled with, one or more of the source 202 and the sensor 207. The far field sensor device 230 can include two or more electrodes and can be configured to sense a far field signal, such as the far field signal 233 corresponding to a therapy delivered by the device 210. The far field sensor device 230 can include at least one pair of outwardly facing electrodes 223 and 224 configured to contact a tissue surface, for example, at the interface 205. In one or more embodiments, three or more electrodes can be used, and processor circuitry on-board or auxiliary to the far field sensor device 230 can select various combinations of two or more of the electrodes for use in sensing the far field signal 233. In one or more embodiments, the far field sensor device 230 can be configured for use with a sleeve, pocket, or other garment or accessory that maintains the far field sensor device 230 adjacent to the higher-index material 206, and that optionally maintains the electrodes 223 and 224 in physical contact with a tissue surface. In one or more embodiments, the sleeve, pocket, or other garment or accessory can include or use a conductive fiber or fabric, and the electrodes 223 and 224 can be in physical contact with the tissue surface via the conductive fiber or fabric. In an example, the sensor device 230 can include or comprise a portion of the sensor 1802 (see the discussion of FIG. 18, below), such as can include or use an EMG sensor.

In one or more embodiments, the external source 202 provides a midfield signal 231 including power and/or data signals to the implantable device 210. The midfield signal 231 includes a signal (e.g., an RF signal) having various or adjustable amplitude, frequency, phase, and/or other signal characteristics. The implantable device 210 can include an antenna, such as described below, that can receive the midfield signal 231 and, based on characteristics of receiver circuitry in the implantable device 210, can modulate the received signal at the antenna to thereby generate a backscatter signal. In one or more embodiments, the implantable device 210 can encode information in the backscatter signal 212, such as information about a characteristic of the implantable device 210 itself, about a received portion of the midfield signal 231, about a therapy provided by the implantable device 210, and/or other information. The backscatter signal 212 can be received by an antenna at the external source 202 and/or the far field sensor device 230 or can be received by another device. In one or more embodiments, a biological signal can be sensed by a sensor of the implantable device 210, such as a glucose sensor, an electropotential (e.g., an electromyography (EMG) sensor, electrocardiograph (ECG) sensor, resistance, or other electrical sensor), a light sensor, a temperature, a pressure sensor, an oxygen sensor, a motion sensor, or the like. A signal representative of the detected biological signal can be modulated onto the backscatter signal 212. In such embodiments, the sensor 207 can include a corresponding monitor device, such as a glucose, temperature, ECG, EMG, oxygen, or other monitor, such as to receive, demodulate, interpret, and/or store data modulated onto the backscatter signal.

In one or more embodiments, the external source 202 and/or the implantable device 210 can include an optical transceiver configured to facilitate communication between the external source 202 and the implantable device 210. The external source 202 can include a light source, such as a photo laser diode or LED, or can include a photo detector, or can include both of a light source and a photo detector. The implantable device 210 can include a light source, such as a photo laser diode or LED, or can include a photo detector, or can include both of a light source and a photo detector. In an embodiment, the external source 202 and/or implantable device 210 can include a window, such as made of quartz, glass, or other translucent material, adjacent to its light source or photo detector.

In an embodiment, optical communications can be separate from or supplemental to an electromagnetic coupling between the external source 202 and the implantable device 210. Optical communication can be provided using light pulses modulated according to various protocols, such as using pulse position modulation (PPM). In an embodiment, a light source and/or photo detector on-board the implantable device 210 can be powered by a power signal received at least in part via midfield coupling with the external source 202.

In an embodiment, a light source at the external source 202 can send a communication signal through skin, into subcutaneous tissue, and through an optical window (e.g., quartz window) in the implantable device 210. The communication signal can be received at a photo detector on-board the implantable device 210. Various measurement information, therapy information, or other information from or about the implantable device can be encoded and transmitted from the implantable device 210 using a light source provided at the implantable device 210. The light signal emitted from the implantable device 210 can travel through the same optical window, subcutaneous tissue, and skin tissue, and can be received at photo detector on-board the external source 202. In an example, the light sources and/or photo detectors can be configured to emit and/or receive, respectively, electromagnetic waves in the visible or infrared ranges, such as in a range of about 670-910 nm wavelength (e.g., 670 nm-800 nm, 700 nm760 nm, 670 nm870 nm, 740 nm850 nm, 800 nm-910 nm, overlapping ranges thereof, or any value within the recited ranges).

The external source 202 can be positioned near the surface of the skin above the implantable device 210. This can help to efficiently transmit Radio Frequency (RF) wireless signals from the external source 202 to the implantable device 210. Typically, a use will wear a custom garment, belt or harness to retain the external source 202 in an advantageous transmission position above the implantable device 210. This can help retain the external source 202 in a secure position during ambulatory conditions.

Figure 3:
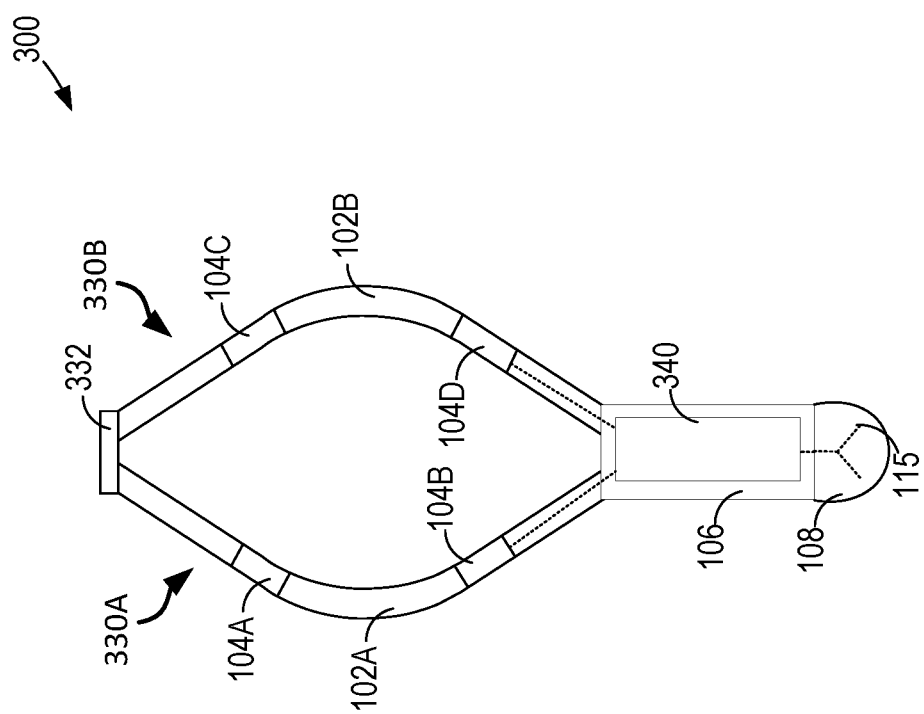
FIG. 3 illustrates, by way of example, a diagram of an embodiment of an implantable device with multiple elongated extensions.

FIG. 3 illustrates, by way of example, a diagram of an embodiment of an implantable device 300 with multiple elongated extensions 330A, 330B. Each of the elongated extensions 330A, 330B can include a respective body portion 102A, 102B that is similarly configured to the body portion 102 of the implantable device 100 from the example of FIG. 1. The elongated extensions 330A, 330B can each include zero, one, or more electrodes situated thereon and electrically connected to circuitry in the circuitry housing 106. For example, the first elongated extension 330A can include first and second electrodes 104A and 104B. The second elongated extension 330B can include one or more other electrodes, such as third and fourth electrodes 104C, 104D situated thereon and electrically connected to circuitry in the circuitry housing 106. The body portions 102A, 102B can be formed of a material that can be shaped or formed. The shape or form can allow the elongated extensions 330A, 300B to be situated such that an electromagnetic field generated between two or more of the electrodes 104A-104E can be incident on a stimulation target, such as a nerve target, such as a DRG or VR, or another target.

Any of the electrodes 104A-104D can be independently configured as an anode or a cathode, or groups of the electrodes can be configured together as an anode or a cathode. Such a configuration can provide a single device that can generate a variety of electromagnetic field patterns that affect a range of locations. Further, more or fewer electrodes can be present on one or more of the elongated extensions 330A, 330B. Similarly, one elongated extension or more than two elongated extensions can be included in the implantable device 300.

The elongated extensions 330A, 330B can be connected together, such as by a retainer 332. The retainer 332 can have various shapes, such as a semi-ellipse, a box, a cone, a pyramid, a cone, an irregular shape or the like. The retainer 332, in some embodiments, can be tapered so as to be thinner on an end facing away from the circuitry housing 106 than an end attached to the elongated extensions 330A, 330B.

The elongated extensions 330A, 330B can be affixed to the retainer 332. The elongated extensions 330A, 330B can be affixed using an interference fit into the retainer 332, using adhesive to connect to the retainer 332, using an over-molded epoxy structure, or the like. The retainer 332 can include a polymer, metal, ceramic, or other biocompatible material.

The circuitry 340 in the circuitry housing 106 can be electrically coupled or connected to the antenna 115. The circuitry 340 can be electrically connected to each of the electrodes 104A-104D. The circuitry 340 can include one or more electrical or electronic components configured to transduce electromagnetic energy incident on the antenna 115 to electrical power to be provided to the electrodes 104A-104D. The electrical or electronic components can include one or more transistors, resistors, capacitors, inductors, diodes, power supplies, rectifiers, buck or boost converters, switches, multiplexers, oscillators, logic gates (e.g., AND, OR, XOR, negate, buffer, or the like), modulators, demodulators, amplifiers, phase shifters, central processing units (CPUs), application specific integrated circuits (ASICs), field programmable gate arrays (FPGAs), or the like.

The circuitry 340 can be configured to connect one or more of the electrodes 104A-104D to electrical ground and another one or more of the electrodes 104A-104D to electrical power. Such a configuration can cause an electromagnetic field to be generated between two of the electrodes 104A-104D. An electromagnetic field can thus be generated between electrodes 104A and 104B, 104A and 104C, 104A and 104D, 104B and 104C, 104B and 104D, or 104C and 104D. With more electrodes 104, more configurations are possible.

Figure 4:
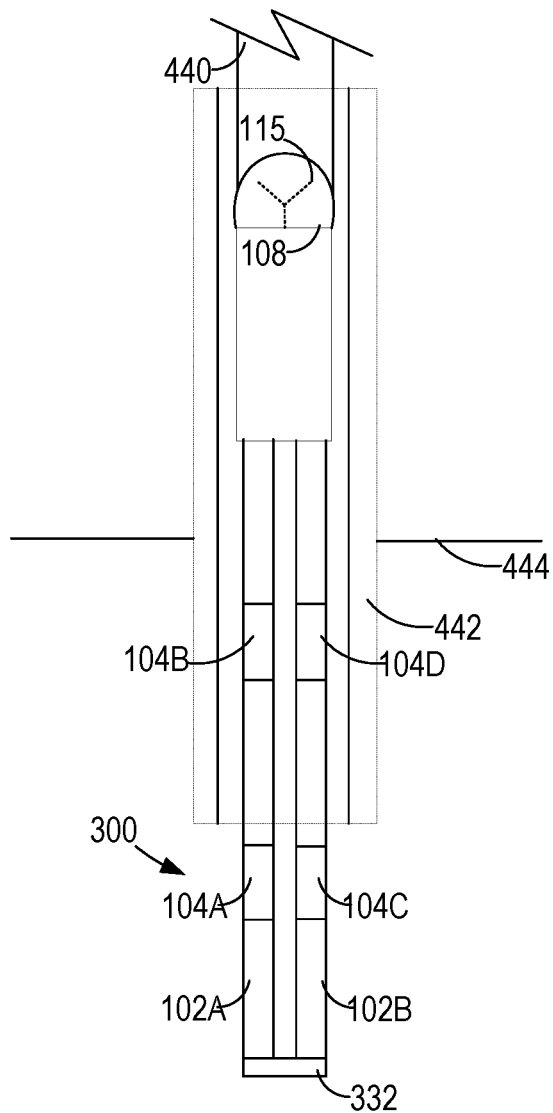
FIG. 4 illustrates, by way of example, a diagram of an embodiment of the implantable device being implanted in tissue.

FIG. 4 illustrates, by way of example, a diagram of an embodiment of the implantable device 100 being implanted in tissue 444. A catheter 442 can puncture tissue 444 near a site of implantation. The site of implantation can be near a nerve, such as a DRG or VR. The catheter 442 can guide the implantable device 100 to a location in the tissue 444. A push rod 440 can be manually manipulated to push the implantable device 300 into the tissue 444, such as through the catheter 442.

Figure 5:
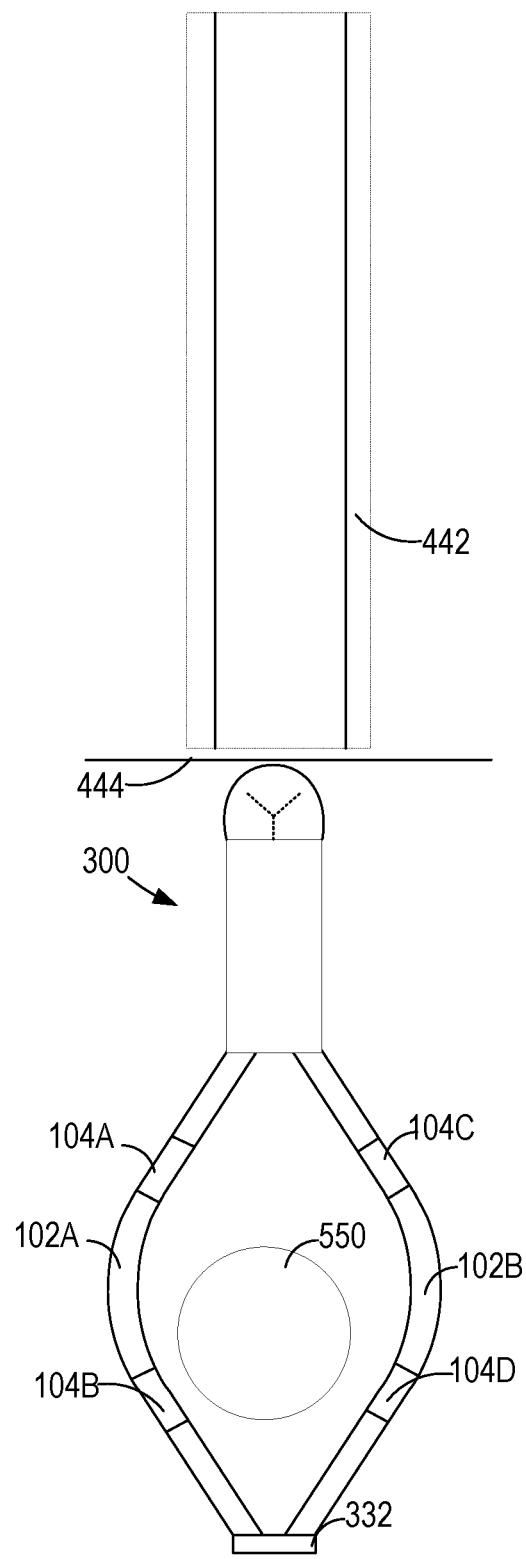
FIG. 5 illustrates, by way of example, a diagram of an embodiment of the implantable device of FIG. 4 after the implantable device is situated near a stimulation target.

FIG. 5 illustrates, by way of example, a diagram of an embodiment of the implantable device 300 of FIG. 3 after the implantable device 300 is situated near a stimulation target 550. In FIG. 5, the push rod 440 and the catheter 442 have been removed from the tissue 444. The implantable device 300 can be situated such that the electrodes 104A-104D are sufficiently proximate the target 550. Sufficiently proximate means that, in at least one configuration of anode and cathode of the electrodes 104A-104D, electrical stimulation is incident on the target 550 (e.g., a portion of a nerve, such as a DRG or VR a muscle, tendon, or other structure accessible through the tissue 444).

As the implantable device 300 extends out of the catheter 442, the elongated extensions 102A, 102B can alter shape, such as to bow as shown in FIG. 5 or otherwise deform to some desired shape. The shape can be achieved by using a shape-memory material, a semi-rigid pre-formed material, or the like in the elongated extensions 102A, 102B. A semi-rigid pre-formed material is formed as a desired shape, but can be temporarily collapsed, such as to be in the shape shown in FIG. 4, such as for purposes of implantation or delivery to an implate site.

Figure 6:
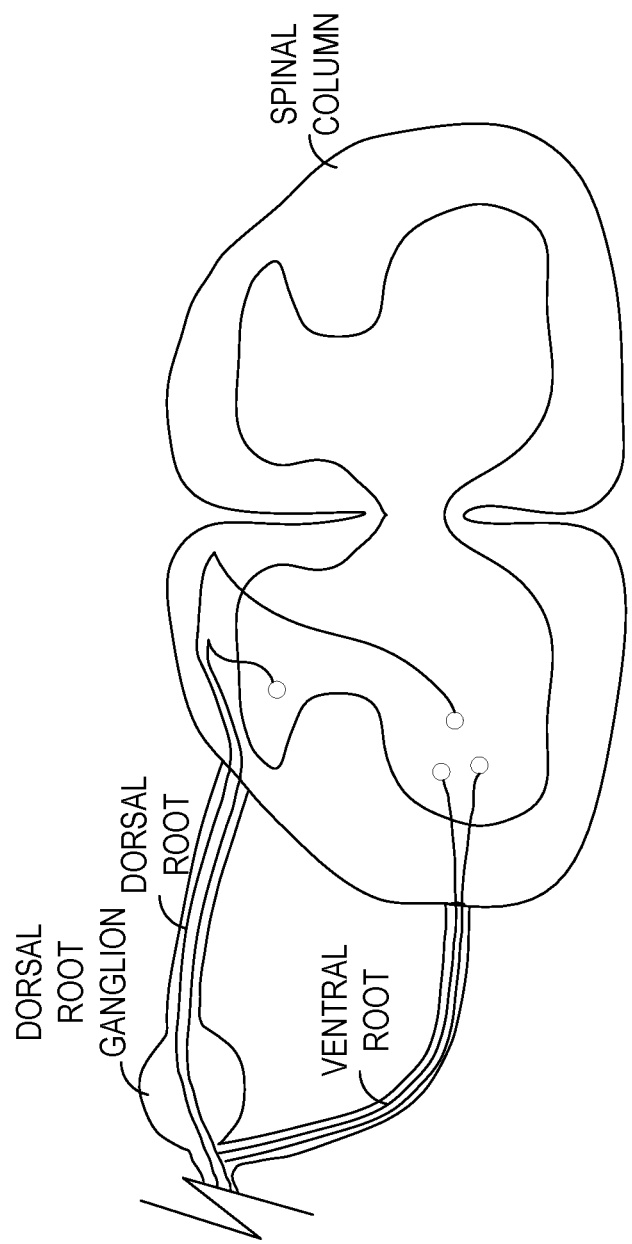
FIG. 6 illustrates, by way of example a diagram of an intervertebral foramina between spinal vertebrae.

FIG. 6 illustrates, by way of example a diagram of an intervertebral foramina between spinal vertebrae. Along the spinal column, at individual vertebrae locations, there are respective DRG and VR structures. The network of DRG and VR structures provide access to a peripheral nervous system. The DRG and VR lie in the interverbral foramina. The DRG receive afferent (sensory) signals and the VR transmits efferent (motor) signals. The signals at the DRG and VR combine to control information like pain and temperature sensations. They are part of the peripheral nervous system as they are situated outside the spinal cord.

FIGS. 7 and 8 illustrate, by way of example, respective diagrams of an embodiment of an implanting aid 700. FIG. 8 illustrates a section view diagram of the implanting aid 700 of FIG. 7 from the direction indicated by arrows labeled "8". The implanting aid 700 can help locate an implant site for the target 550. The implanting aid 700 as illustrated includes a substrate 770, a location register 772, and one or more conduits 774. The substrate 770 can include a flexible material that can conform to a surface on which it is situated. The substrate 770 can conform to a surface of a back, for example.

The location register 772, when placed properly, can register the conduits 774 on the tissue relative to the location register 772. The relative positions of the conduits 774 can allow for access to respective targets 550, such as the DRG or VR in a vertebral foramina. The location register 772 can be situated above or around a specific vertebrae, such as a C7 vertebrae at a base of a neck. The location register 772 can be situated in a depression above the C7 vertebrae (closer to the head).

The conduits 774 can be situated and oriented such that, when an implantable device is inserted through the conduit 774 and into tissue 444, the implantable device 100, 210, 300 is near a specified target 550. In the embodiment illustrated, the conduits 774 are situated and oriented to provide access to a nerve along a spinal column of a human.

Arrows 776 indicate different, possible orientations of the conduits 774. Each orientation has a different angle relative to a longitudinal axis of the spinal column or the target 550. The angle can be configured such that a longitudinal axis of the conduit intersects or is proximate to the target 550. The conduits 774 thus provide a wide range of orientation and location variability in implantable device 100, 300 insert locations.

A distance between conduits 774 (indicated by arrows 778, 780) can be determined based on an anatomy covered by the tissue 444. For example, an x-ray at or near a target can be reviewed to determine the locations and orientations of the conduits 774 relative to the register location 772. An amount of adipose tissue and natural body variation can affect the distance between the surface of the tissue 444 and the vertebrae can affect an implant depth.

The implant aid 700 allows for consistent introduction and positioning of the implantable device 100, 210, 300 in close proximity to the target 550. The implant aid 700 provides a reference access point for implant tool introduction. In an example, one or more size or orientation characteristics of the implant aid 700 or the various features thereof can be adjusted or changed to accommodate a particular patient's anatomy.

An example procedure for using the implant aid 700 in an implant procedure can include: select a version of implant aid 700 that is sized appropriately for a patient, locate the implant aid 700 so it is laterally centered along a patient's spine and vertically located on landmark vertebrae C3 near the top of the spinal column, identify target 550 for stimulation and precisely locate the desired conduits 774, introduce a guidewire through an introduction tube, introduce a dilator over the guidewire, pull back on the guidewire, introduce a sheath over the dilator, pull back on the dilator, introduce the implantable device 100, 210, 300 connected on a proximal end to a push rod 440 and implant the device to a target depth within the sheath, separate the push rod from the device, test stimulation with (e.g., sterile draped) the external source 202, ask the patient if they feel a response such as stimulation or paresthesia and, if the patient does not report a response, then try a different electrode configuration, and if the patient still does not report a response, then adjust an axial position of the device using the push rod (distal) or suture (proximal), and when the patient reports a desired response, then remove the sheath, set distal fixation, and close the implant site in tissue.

The implant aid 700 helps locate an introduction point using the introduction conduits 774 above the target 550 to be stimulated. The implant aid 700 can precisely align an angle of implant and serve as a registration for the depth of implant.

The implant aid 700 can be made of materials with pre-set plastic lumen inserts that serve as introduction conduits 774 for the implantable device 100, 210, 300. The conduits 774 can be connected together or over molded with a heavy gel so that the fixture does not move and remains in a fixed position during the implant procedure. Other metallic, thermoplastic elastomer, or other materials can be used in the implant aid 700 construction. The fixture could be designed for one time use or it could be reused.

Human subjects come in different shapes and sizes, such as with different heights, different body mass indexes, or the like, so there is not a one-size-fits-all implant aid 700. The implant aid 700 can be designed to be used for a range of heights. The spacing of the introduction tubes can be customized based on patient anatomical landmarks. The spacing of the introduction conduits 774 can be at a regular pitch or interval (e.g., 1 to 5 millimeter or another interval) center to center pattern. The implant aid 700 can be positioned based on a major longitudinal landmark, such as C7.

While the implant aid 700 is designed for use with the implantable device 100, 210, 300 with precise location of the conduits 774 above the respective target 550, it could be adapted for conventional stimulation systems with a lead that requires tunneling to a pulse generator. The conduits 774 can be designed with outboard slide slots to separate the lead body from the fixture once the electrode array is implanted. Each individual conduit 774 can include a radial slot of about 120 to 180 degrees that allows for the side exit of the lead body after the electrodes 104A-104D are correctly situated.

To determine whether the implantable device 100, 210, 300 is situated sufficiently proximate the target 550, the implantable device 100, 210, 300 can generate stimulation pulses while implanted. If it is desired to stimulate the DRG (e.g., without stimulating the VR), then a very quick, physical response (e.g., in the single milliseconds range) means that the implantable device 100, 210, 300 is improperly located or that an incorrect or ineffective configuration of the electrodes is currently active. If it is closer to the DRG, the signal will take more time to get the desired physical response (e.g., in the tens of milliseconds range). This is because the signal from the DRG goes to the brain, then to the VR, and then to an extremity that performs the physical response. A signal on the VR goes directly to the periphery of the body.

FIG. 9 illustrates, by way of example, a diagram of an embodiment of another implanting aid 900. The implanting aid 900 is similar to the implanting aid 700, but with only two conduits 774. The implanting aid 900 can be configured to mark implant sites on opposite sides of a vertebrae. The angle of the conduits 774 and the distance between the conduits 774 can be customized to accommodate different body shapes. Consider that vertebral foramina on opposite sides of the spinal column can be spaced differently between different people. The conduits 774 can be angled and spaced to accommodate these different body types and situations. Although the examples of FIGS. 7 and 9 show implanting aids with 30 and 2 conduits respectively, different implanting aid embodiments can have additional or fewer conduits.

FIG. 10 illustrates, by way of example, a diagram of an embodiment of a system 1000 of implantable devices 300. Multiple implantable devices 300 can be implanted near one or more targets. All of the implantable devices 300 can be powered by a single external source 202. The external source 202 can guide electromagnetic transmissions to different implantable devices 300, such as by altering transmission mechanisms (sometimes called ports), or by altering a phase of a transmission on a transmission mechanism, or the like. In this way, the external source 202 can provide power to multiple implantable devices 300 situated in the body.

Wireless Threshold Testing in Neuromodulation

This section generally relates to testing or verifying placement of a neuromodulation device. Conventional devices and methods used for nerve stimulation can have drawbacks such as not allowing for testing of the implant electrodes or not establishing "bellows" response thresholds before removal of the implant tools. This makes the testing and verification procedure more tedious and damaging because an incorrectly placed implant may need to be pulled out (e.g., with a string) and then re-inserted to make an adjustment to the implant location (other than slight outward adjustments that can be done by pulling the string).

In an example that includes a conventional neuromodulation implant, testing can be performed after implantation or delivery of the electrodes to a target. This testing usually includes fluoroscopy. The testing procedure for the such neuromodulation implants further includes manual connection of an opposite end of a lead with testing equipment, manual dialing of electrode amplitudes, and manual adjustment of electrode settings. Embodiments discussed herein provide improvements to these lead-based stimulation devices and to improvements in testing. In an example, embodiments herein allow for implant device testing and verification procedures to be performed with electrode placement or implantation, that is, substantially in real-time. The verification and testing procedure can be used with a leadless or a lead-based device.

Midfield powering technology can provide power to an implanted electrostimulation device from an external power source located on or near a tissue surface, such as at an external surface of a user's skin. The user can be a clinical patient or other user. The midfield powering technology can have one or more advantages over implantable pulse generators. For example, a pulse generator can have one or more relatively large, implanted batteries and/or one or more lead systems. Midfield devices, in contrast, can include relatively small battery cells that can be configured to receive and store relatively small amounts of power. A midfield device can include one or more electrodes integrated in a unitary implantable package. In some examples, a midfield-powered device can provide a simpler implant procedure over other conventional devices, which can lead to a lower cost and a lower risk of infection or other implant complications. One or more of the advantages can be realized due to an efficiency or an amount of power transferred to the implanted device. The ability to focus the energy from the midfield device can allow for an increase in the amount of power transferred to the implanted device. Implant procedures discussed herein can be used with lead-based devices, leadless devices, near field stimulation devices, far field stimulation devices, or midfield stimulation devices.

Figure 11A:
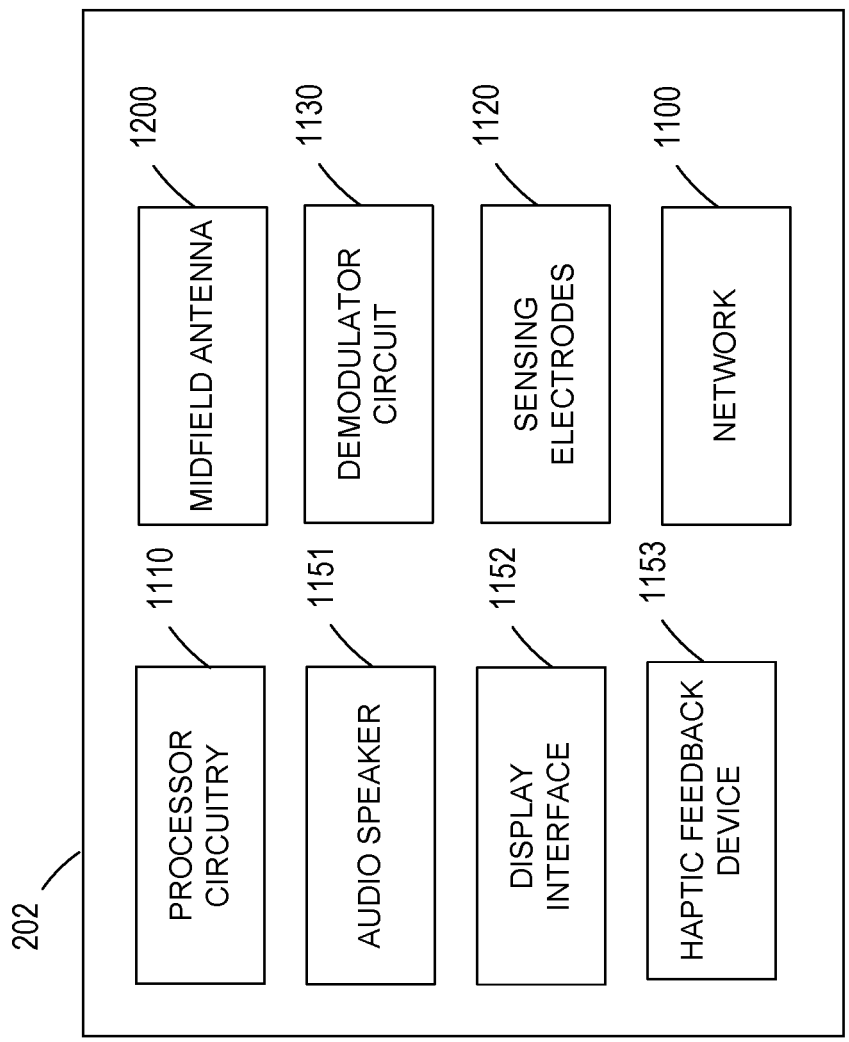
FIG. 11A illustrates, by way of example, a block diagram of an embodiment of a midfield source device.

FIG. 11A illustrates, by way of example, a block diagram of an embodiment of a midfield source device, such as the external source 202. The external source 202 can include various components, circuitry, or functional elements that are in data communication with one another. In the example of FIG. 11A, the external source 202 includes components, such as processor circuitry 1110, one or more sensing electrodes 1120 (e.g., including the electrodes 221 and 222), a demodulator circuitry 1130, a phase-matching or amplitude-matching network circuitry 1100, a midfield antenna 1200, and/or one or more feedback devices, such as can include or use an audio speaker 1151, a display interface 1152, and/or a haptic feedback device 1153. The midfield antenna 1200 is further described below in the embodiment of FIG. 12. The processor circuitry 1110 can be configured to coordinate the various functions and activities of the components, circuitry, and/or functional elements of the external source 202.

The midfield antenna 1200 can be configured to provide a midfield excitation signal, such as can include RF signals having a non-negligible H-field component that is substantially parallel to an external tissue surface. In one or more embodiments, the RF signals can be adapted or selected to manipulate an evanescent field at or near a tissue surface, such as to transmit a power and/or data signal to respective different target devices (e.g., the implantable device 210) implanted in tissue. The midfield antenna 1200 can be further configured to receive backscatter or another wireless signal information that can be demodulated by the demodulator circuitry 1130. The demodulated signals can be interpreted by the processor circuitry 1110. The midfield antenna 1200 can include a dipole antenna, a loop antenna, a coil antenna, a slot or strip antenna, or another antenna. The antenna 1200 can be shaped and sized to receive signals in a range of between about 400 MHz and about 4 GHz (e.g., between 400 MHz and 1 GHz, between 400 MHz and 3

GHz, between 500 MHz and 2 GHz, between 1 GHz and 3 GHz, between 500 MHz and 1.5 GHz, between 1 GHz and 2 GHz, between 2 GHz and 3 GHz, overlapping ranges thereof, or any value within the recited ranges). For embodiments incorporating a dipole antenna, the midfield antenna 1200 may comprise a straight dipole with two substantially straight conductors, a folded dipole, a short dipole, a cage dipole, a bow-tie dipole or batwing dipole.

The demodulator circuitry 1130 can be coupled to the sensing electrodes 1120. In one or more embodiments, the sensing electrodes 1120 can be configured to receive the farfield signal 233, such as based on a therapy provided by the implantable device 210, such as can be delivered to the therapy target 290. The therapy can include an embedded or intermittent data signal component that can be extracted from the farfield signal 233 by the demodulator circuitry 1130. For example, the data signal component can include an amplitude-modulated or phase-modulated signal component that can be discerned from background noise or other signals and processed by the demodulator circuitry 1130 to yield an information signal that can be interpreted by the processor circuitry 1110. Based on the content of the information signal, the processor circuitry 1110 can instruct one of the feedback devices to alert a patient, caregiver, or other system or individual. For example, in response to the information signal indicating successful delivery of a specified therapy, the processor circuitry 1110 can instruct the audio speaker 1151 to provide audible feedback to a patient, can instruct the display interface 1152 to provide visual or graphical information to a patient, and/or can instruct the haptic feedback device 1153 to provide a haptic stimulus to a patient. In one or more embodiments, the haptic feedback device 1153 includes a transducer configured to vibrate or to provide another mechanical signal.

Figure 11B:
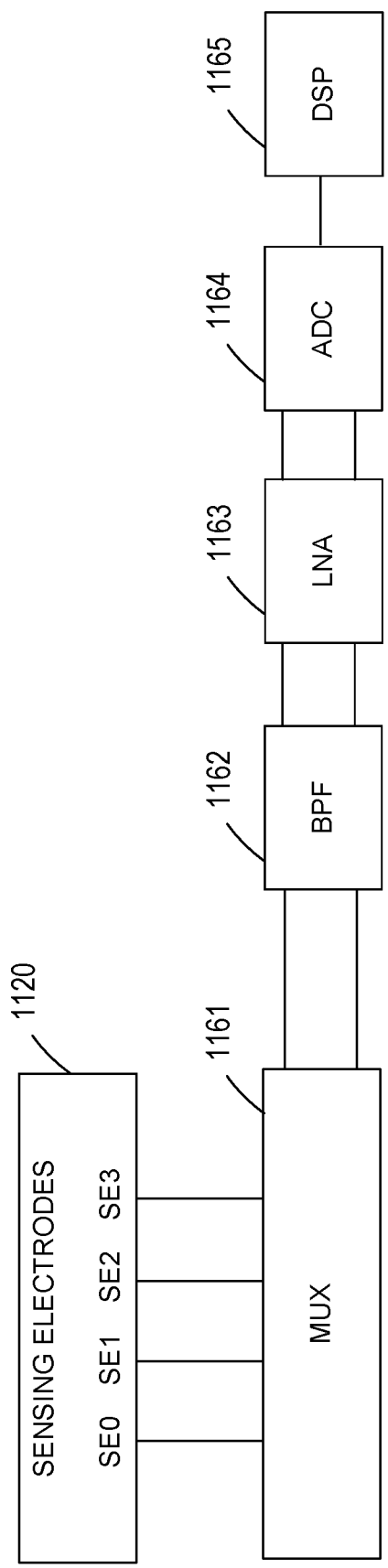
FIG. 11B illustrates, by way of example, a block diagram of an embodiment of a portion of a system configured to receive a signal.

FIG. 11B illustrates generally a block diagram of a portion of a system configured to receive a farfield signal 233. The system can include the sensing electrodes 1120, such as can include the electrodes 221 and 222 of the source 202, or the electrodes 223 and 224 of the farfield sensor device 230. In the example of FIG. 11B, there are at least four sensing electrodes represented collectively as the sensing electrodes 1120, and individually as SE0, SE1, SE2, and SE3; however, other numbers of sensing electrodes 1120 may also be used The sensing electrodes 1120 can be communicatively coupled to a multiplexer circuitry 1161. The multiplexer circuitry 1161 can select pairs of the electrodes, or electrode groups, for use in sensing farfield signal information. In one or more embodiments, the multiplexer circuitry 1161 selects an electrode pair or grouping based on a detected highest signal to noise ratio of a received signal, or based on another relative indicator of signal quality, such as amplitude, frequency content, and/or other signal characteristic.

Sensed electrical signals from the multiplexer circuitry 1161 can undergo various processing to extract information from the signals. For example, analog signals from the multiplexer circuitry 1161 can be filtered by a band pass filter 1162. The band pass filter 1162 can be centered on a known or expected modulation frequency of a sensed signal of interest. A band pass filtered signal can then be amplified by a low-noise amplifier 1163. The amplified signal can be converted to a digital signal by an analog-to-digital converter circuitry (ADC) 1164. The digital signal can be further processed by various digital signal processors 1165, as further described herein, such as to retrieve or extract an information signal communicated by the implantable device 210.

Figure 12:
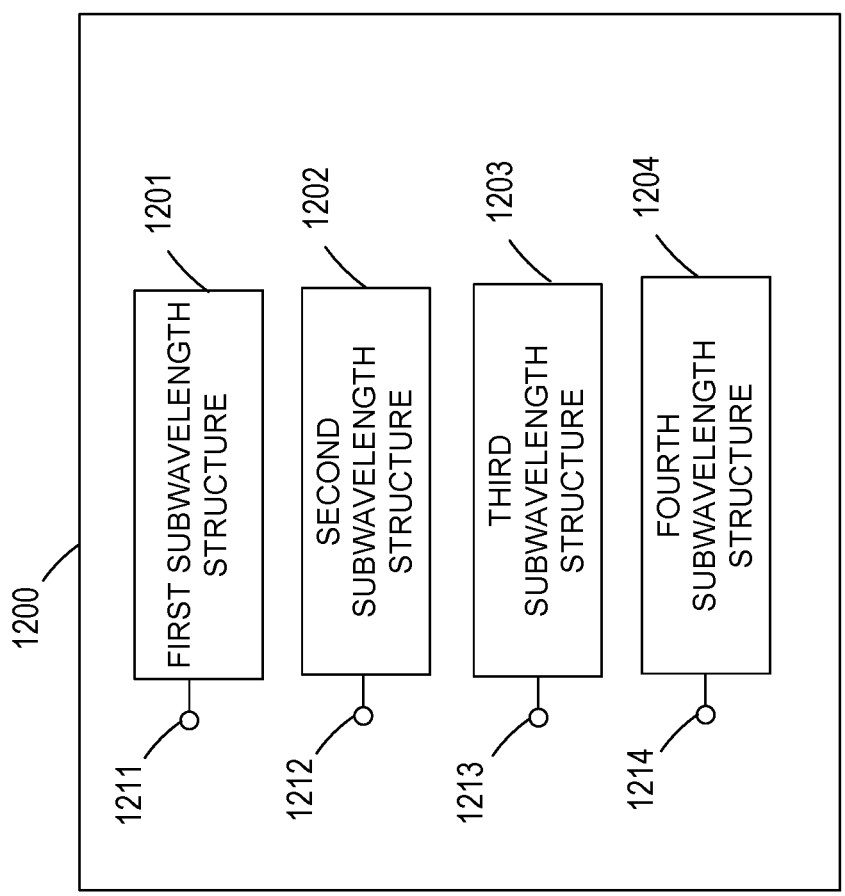
FIG. 12 illustrates, by way of example, a schematic view of an embodiment of a midfield antenna with multiple subwavelength structures.

FIG. 12 illustrates, by way of example, a schematic view of an embodiment of a midfield antenna 1200 with multiple subwavelength structures 1201, 1202, 1203, and 1204. The midfield antenna 1200 can include a midfield plate structure with a planar surface. The one or more subwavelength structures 1201-204 can be formed in the plate structure. In the example of FIG. 12, the antenna 1200 includes a first subwavelength structure 1201, a second subwavelength structure 1202, a third subwavelength structure 1203, and a fourth subwavelength structure 1204. Fewer or additional subwavelength structures can be used. The subwavelength structures can be excited individually or selectively by one or more RF ports (e.g., first through fourth RF ports 1211, 1212, 1213, and 1214) respectively coupled thereto. A "subwavelength structure" can include a hardware structure with dimensions defined relative to a wavelength of a field that is rendered and/or received by the external source 202. For example, for a given $\lambda_0$ corresponding to a signal wavelength in air, a source structure that includes one or more dimensions less than $\lambda_0$ can be considered to be a subwavelength structure. Various designs or configurations of subwavelength structures can be used. Some examples of a subwavelength structure can include a slot in a planar structure, or a strip or patch of a conductive sheet of substantially planar material.

FIG. 13 illustrates, by way of example, a perspective view diagram of an embodiment of an implantable device 1300. The implantable device 210 can include one or more features of other implantable devices, such as the implantable device 1300, discussed herein. The implantable device 1300, as illustrated, includes an elongated, distal body portion 1302. The body portion 1302 includes a plurality of electrodes 1304 embedded at least partially therein and/or affixed thereto. The body portion 1302 includes a distal end 1306 and a proximal end 1308. The proximal end 1308 is affixed to a circuitry housing 1310. The circuitry housing 1310 is affixed to an antenna housing 1312. The antenna housing 1312, as illustrated, includes a plurality of tines 1314 affixed thereto.

The body portion 1302, electrodes 1304, circuitry housing 1310, and antenna housing 1312 are illustrated as being generally cylindrical. The implantable device 1300 is configured to be powered wirelessly (e.g., through electromagnetic waves incident on the implantable device 1300 and external to the body in which the implantable device 1300 is implanted). The implantable device 1300 is configured to provide stimulation (e.g., neurostimulation, muscle stimulation, other electrostimulation) or other forms of modulation (e.g., denervation) to a therapy site within a patient (e.g., a human or other animal patient). The implantable device 1300 can be situated within a patient using one or more catheters.

The body portion 1302 can include a flexible material. In one or more embodiments, the flexible material can include polyurethane, silicone, epoxy and/or any other flexible material. In one or more embodiments, the body portion 1302 can include a shape memory polymer. The flexible material can provide the ability to shape the body portion 1302, such as while the body portion 1302 is internal to the patient.

The electrodes 1304 illustrated include an electrode array of four stimulation electrodes 1304 along the body portion 1302. The electrodes 1304, in one or more embodiments, include platinum, iridium, stainless steel, titanium, titanium nitride, or other conductive material. In one or more embodiments, the electrodes include a platinum and iridium alloy, such as a combination that is 90% platinum and 10% iridium. Other combinations are possible (e.g., 85% platinum and 15% iridium, 95% platinum and 5% iridium, 80% platinum and 20% iridium). In one or more embodiments, the electrodes can include a coating, such as with a material that can improve electrical performance in a specified medium, such as a body. In one or more embodiments, the electrodes 1304 are electrically separated from one another, such as by one or more electrical switches. In one or more embodiments, the electrodes 1304 are about one to ten millimeters (e.g., one to three, two to five, two to eight, three to six, four to nine, five to seven, six to ten, two to four, overlapping ranges thereof, or any value within the recited ranges, such as three millimeters) in width (along the elongated dimension of the body portion 1302). In one or more embodiments, the electrodes 1304 are separated by about one to ten millimeters (e.g., one to three, two to five, two to eight, three to six, four to nine, five to seven, six to ten, two to four, overlapping ranges thereof, or any value within the recited ranges, such as three mm). In one or more embodiments, the diameter of the electrodes is about one to five millimeters (e.g., one to two, one to three, two to four, three to five, overlapping ranges thereof, or any value within the recited ranges, such as 1.1 mm. 1.2 mm, 1.3 mm, 1.4 mm, 1.5 mm, 1.6 mm, 1.7 mm, 1.8 mm, 1.9 mm, 2.0 mm). The electrodes 1304 are, respectively, electrically connected to circuitry 1416 (see FIG. 14) and hermetically enclosed in the circuitry housing 1310. The circuitry housing 1310 can provide a hermetic enclosure for the circuitry 1416.

The circuitry housing 1310 can include titanium (e.g., commercially pure, 6Al/4V or another alloy), platinum, stainless steel, or a ceramic material (such as zirconia or alumina, for example), or other hermetic, biocompatible material. The circuitry housing 1310 provides an airtight space for the circuitry 1416. If a metallic material is used for the circuitry housing 1310, the circuitry housing 1310 can be used as part of the electrode array, such as can effectively increase the number of selectable electrodes 1304 for stimulation or other modulation.

An antenna housing 1312 can be located at a proximal end 1311 of the circuitry housing 1310. An antenna 1418 within the antenna housing 1312 can be used for powering and communication to and/or from the implantable device 1300, such as from a device external to the patient or subject.

Rather than being hermetic, the circuitry housing 1310 can be backfilled to prevent ingress of moisture therein. The backfill material can include a non-conductive, waterproof material, such as an epoxy, parylene, Tecothane® material, a copy thereof, or another material.

In one or more embodiments, tines 1314 can be attached at a proximal portion of the antenna housing 1312. The tines 1314 can provide the ability to affix (e.g., attach or couple) the implantable device 1300 at a specific location within the patient. The tines 1314 can be configured to affix the implantable device 1300 to a specific anatomical structure. The tines 1314 can be made of a polymer or other flexible or semi-flexible material, such as can include silicone, polyurethane, epoxy, or like materials. The tines 1314 can flare away from a central axis of the antenna housing 1312 such that a distal portion of a given tine 1314 is closer to the central axis than a more proximal portion of the given tine 1314, such as is shown in FIG. 13.

FIG. 14 illustrates, by way of example, a diagram of another embodiment of an implantable device 1400 that shows internal circuitry 1416 and an antenna 1418. The circuitry housing 1310 and the antenna housing 1312 are shown as transparent so as to not obscure the view of the items internal thereto.

The circuitry 1416 is configured to provide a programmable control for each electrode 1304 in the electrode array. Any of the electrodes along the array can be programmed, using or based on signals from the source 202 received at the circuitry 1416, as a current source or sink. Each of the electrodes 1304 can be independently addressed for current or voltage amplitude in generally the same manner. For example, to reach further into the patient, the electrode labelled "0" can be programmed as a current source. Any one or more of the other electrodes, in this example, can be programmed as a current sink.

The circuitry 1416 is shown housed within the circuitry housing 1310. The circuitry 1416 is electrically connected to the electrode array, such as at the distal portion of the circuitry housing 1310 by respective electrical connections 1420. The circuitry 1416 is electrically coupled to the antenna 1418, such as through an inductive coupling or a wired connection. The antenna 1418 and/or electrodes 1304 can be encapsulated in a non-hermetic material and connected to the circuitry 1416, such as by using one or more feedthrough connections.

Figure 15:
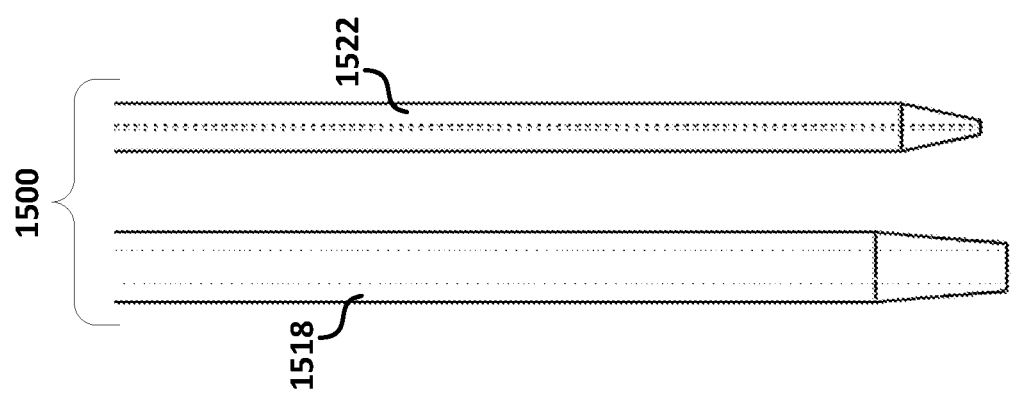
FIG. 15 illustrates, by way of example, an embodiment of a catheter and dilator for creating a path for or to an implantable device within a body.

FIG. 15 illustrates, by way of example, a perspective view diagram of an embodiment of a system 1500 including a catheter 1518 and dilator 1522 for situating the implantable device 1300 within a body. In one or more embodiments, access to the target nerve can be initially performed using a hollow needle (not shown in the figures), such as under imaging guidance (e.g., fluoroscopy, ultrasound, or the like). The needle can include radio-opaque markers thereon to aid in positioning. The physician my send electrical current through the needle to test for a proper physiologic response and help ensure that the needle is in a proper location. After sufficient placement of the needle is established, a guidewire can be inserted through the needle to a distal tip of the needle. The needle can then be retracted while the guidewire is held in place. Next, the hollow dilator 1522 is placed inside a catheter 1518. The catheter 1518 and dilator 1522 combination can then be placed over the guidewire and used to create a dilated channel to the target anatomy. The dilator 1522 and guidewire can then be removed. The remaining catheter 1518 creates a tunnel to access the target anatomy through which the implantable device 1300 can be situated, oriented, or otherwise placed at the proper location.

Figure 16:
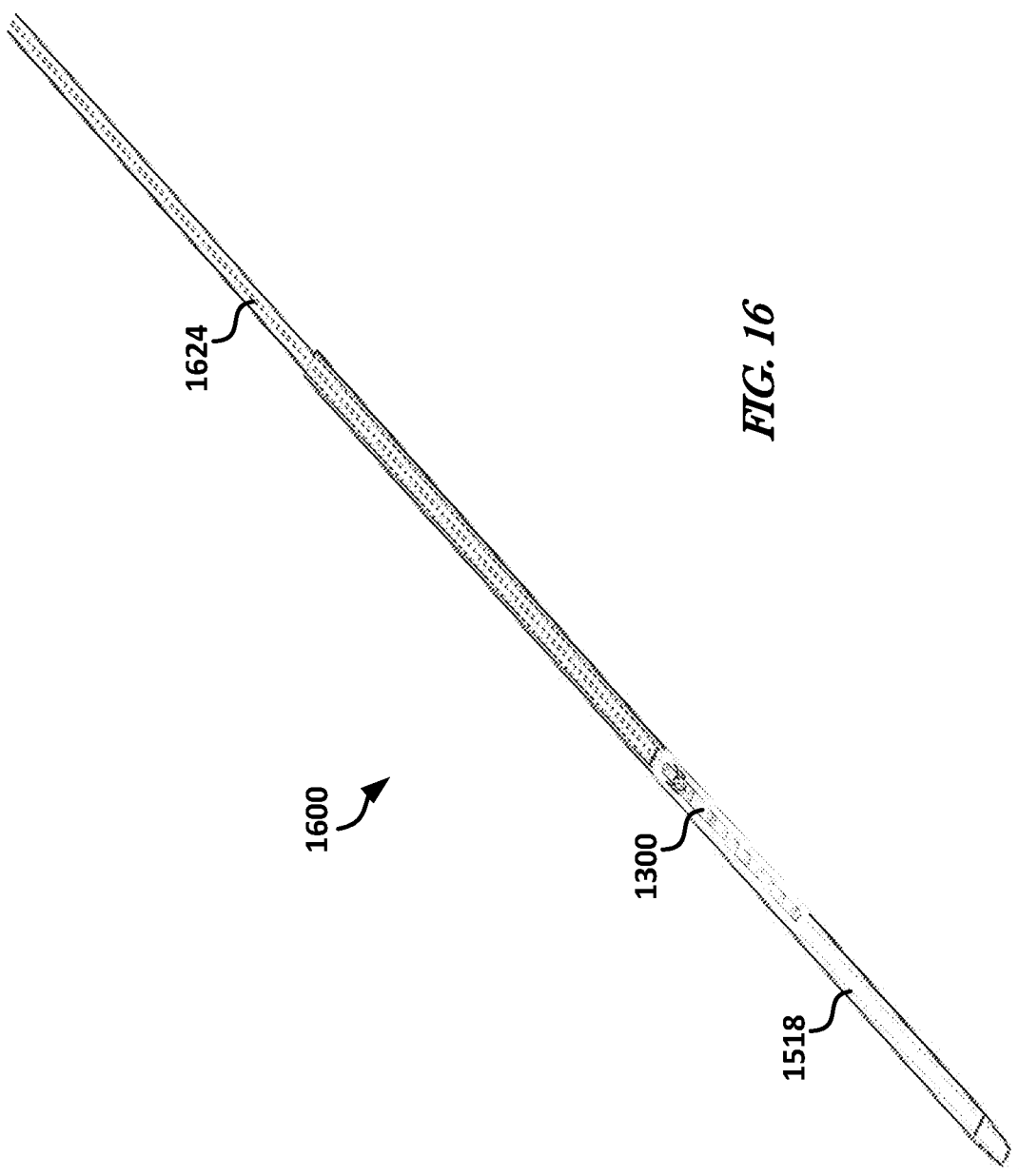
FIG. 16 illustrates, by way of example, a perspective view diagram of an embodiment of another system for situating a pushrod and sheath within a body.

FIG. 16 illustrates, by way of example, a perspective view diagram of an embodiment of another system 1600 for situating an implantable device 1300 within a body. A pushrod 1624 can be used to push the implantable device 1300 through the catheter 1518 to the target anatomy. The pushrod 1624 can be hollow, such as to allow a suture connected to the implantable device to pass through the pushrod 1624. The proximal end of the suture can remain above the skin surface of the patient. The implantable device 1300 is placed into the catheter 1518 and can have its proximal end connected to the pushrod 1624. The pushrod 1624, in one or more embodiments, includes a socket driving mechanism as previously discussed. Force is applied to the proximal end of the pushrod 1624 to guide the implantable device 1300 to an anatomical location. The pushrod 1624 can then be used to hold the implantable device 1300 at a set location while the physician pulls on the catheter 1518 to remove it. This action, in one or more embodiments, deploys the tines 1314 which expand when exposed. The pushrod 1624 can be removed, leaving the implantable device 1300 in place. The resistance to movement provided by the tines 1314 can be adequate to separate the implantable device 1300 from the pushrod 1624, or a release mechanism, such as a button and bearing or a button and connector device, can be used to release the pushrod 1624 from the implantable device 1300. In some embodiments, a second pushrod can be inserted into the pushrod 1624, such as to separate the implantable device 1300 from the pushrod 1624.

Figure 17B:
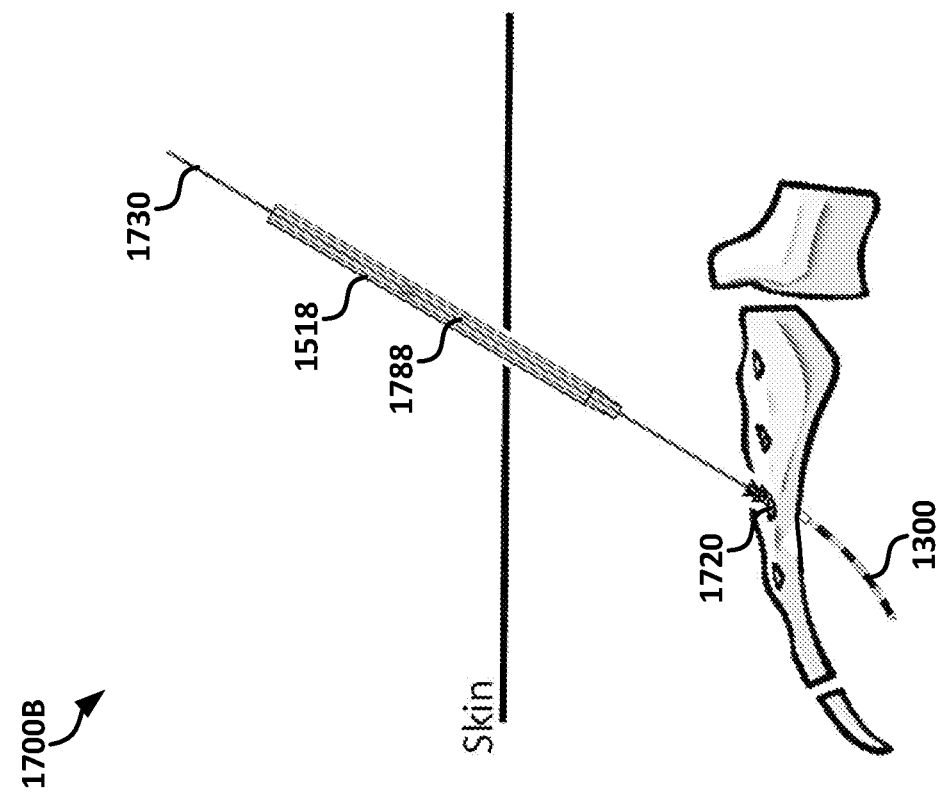
Figure 17A:
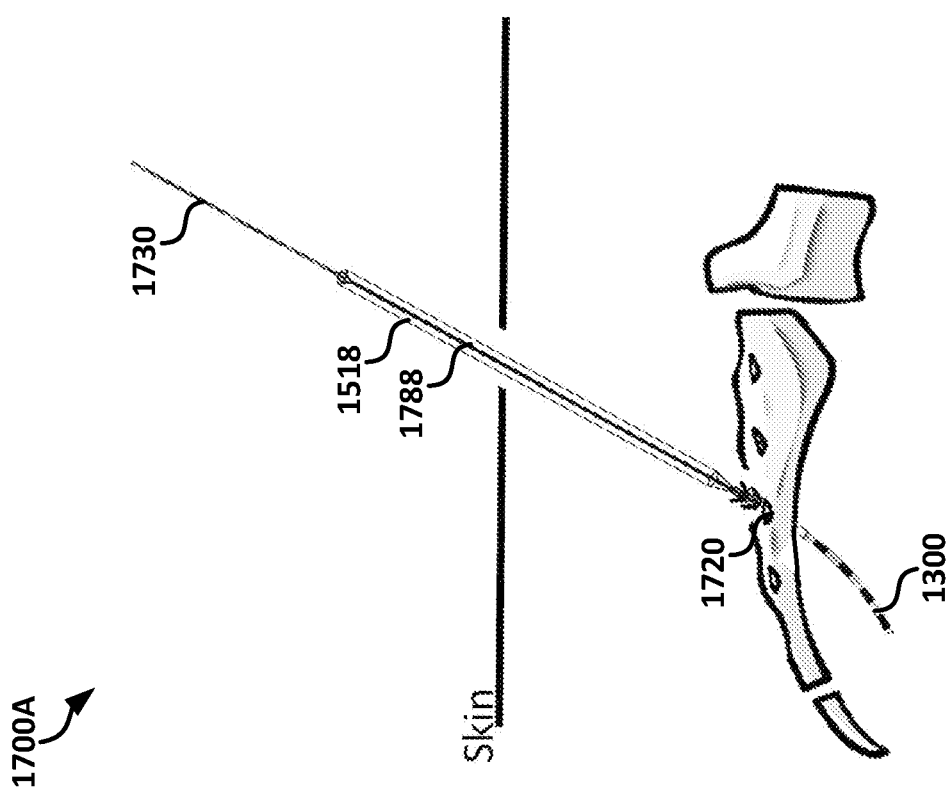

FIGS. 17A, 17B, 17C, and 17D illustrate, by way of example, perspective view diagrams of respective embodiments of implantable device extraction systems 1700A, 1700B, 1700C, and 1700D. The system 1700A includes a proximal end of a suture 1788 attached to an extension suture 1730. In the embodiments of FIGS. 17A-17C, the extension suture 1730 can be pre-tunneled through a needle 1522 (not shown in FIGS. 17A-17D). However, the needle 1522 can be extended over the extension suture 1730 after the extension suture 1730 is coupled to the suture 1788.

After the sutures 1730 and 1788 are securely connected, the physician (or other operating personnel) can pull the connected sutures until they are taut. The needle 1522 can then be inserted while maintaining the suture 1788 taut. The suture 1788 can be used as a guide to the implantable device 1300. FIG. 17A illustrates an embodiment after this procedure has been accomplished.

The needle 1522 can be removed and replaced with a dilator 1518, such as is shown in FIG. 17A. The dilator 1518 can be placed over the needle 1522 and then the needle 1522 can be removed and the dilator 1518 placed through skin, such as while keeping the suture 1788 taut. The needle 1522 includes an outer diameter that is less than an inner diameter of the dilator 1518.

Tissue can be dilated using larger dilators until a dilator 1518 with an inner diameter larger than a largest diameter of the implantable device 1300 can be inserted into the patient. In some embodiments that include the tines 1314, the tines 1314 are the portion of the implantable device 1300 with the largest diameter. In such embodiments, the inner diameter of the dilator 1518 should be larger than the effective diameter of the tines 1314. FIG. 17C illustrates the dilator 1518 over a portion of the implantable device 1300 and the suture 1788.

The dilator 1518 can be held in place, such as to help ensure the dilator 1518 does not retract. Pulling force can be applied to the suture 1730 and/or 1788 in order to allow the implantable device 1300 to be extracted from the body through the dilator 1518. FIG. 17D illustrates the implantable device 1300 within the dilator 1518 as it is being extracted from the body. The dilator 1518 can then be removed from the body.

The procedure discussed regarding FIGS. 17A-17D, or similar removal procedure, can be used in a case where an implant is improperly located. In such cases of improper location, the implantable device 1300 can be removed and re-implanted to a new location to get the implantable device 1300 more proximate to a therapy target 290. Such removal of the implantable device 1300 can be damaging to the patient, as more tissue is penetrated. Further, it is typically not known whether the implantable device 1300 is situated sufficiently close to the therapy target until after the dilator 1518, push rod 1624, or other implant/explant tool is removed from the patient or the implantable device 1300. Further yet, some implant procedures use fluoroscopy, and not actual electrical testing, to determine whether the implantable device 1300 is sufficiently located. While fluoroscopy can help identify a position of the implantable device 1300 relative to the therapy target, the electrical variation between implantable devices 1300 can cause the implantable device 1300, situated in a proper location, to be insufficient for getting a therapeutic response from the patient. These same problems exist whether the implantable device 1300 is leadless, like the implantable devices 210, 1300, or leaded.

Figure 18:
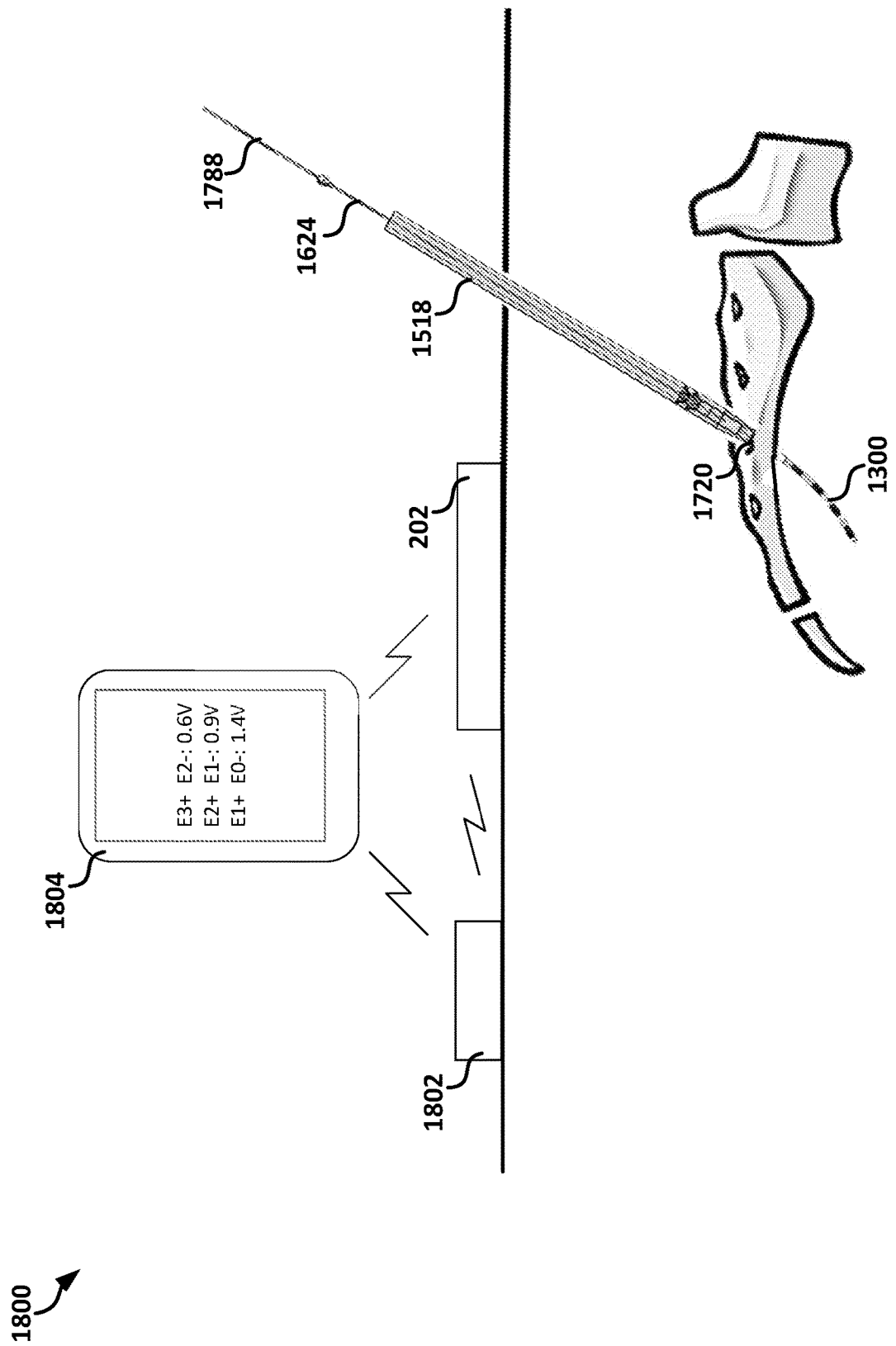
FIG. 18 illustrates, by way of example, a diagram of an embodiment of a system for testing and verification of an implantable device.

FIG. 18 illustrates, by way of example, a diagram of an embodiment of a system 1800 for testing and verification of implantable device placement and voltage or current threshold. The system 1800 as illustrated includes a display device 1804 communicatively coupled to a sensor 1802. The display device 1804 can provide a physician or other personnel that implant or test the implantable device 1300 with an indication of a voltage (or current) and a corresponding electrode configuration that resulted in a therapeutic response from a patient.

The sensor 1802 can include an accelerometer, electromyography (EMG) sensor, or the like. The sensor 1802 can include one more devices situated on the patient who is receiving the implantable device 1300. An EMG sensor provides signals that are used to generate an electromyogram. An electromyograph indicates electric potential generated by muscle cells. The electromyograph can help determine a biomechanical response of a human or animal. For example, an electromyograph of a buttock region can indicate glute flexion, a "bellows" reflex (a contraction of the pelvic floor), or the like. In another example, an electromyograph of a toe can indicate toe flexion. Generally, a toe flexion requires a larger stimulus (a higher amplitude voltage or current) than a glute flexion or a bellows reflex.

The sensor 1802 can be communicatively coupled to the display device 1804 and/or the external source 202. The display device 1804 can be communicatively coupled to the external source 202 and the sensor 1802. A communicative coupling can include a wired or wireless channel over which data can be communicated. Examples of communicative couplings include Bluetooth, Wi-Fi, Cellular, near field, far field, midfield, Zigbee, Universal Serial Bus (USB), firewire, optical waveguide couplings, inter integrated circuit (i2c), serial peripheral interface (SPI), universal asynchronous receiver-transmitter (UART), controller area network (CAN), or the like.

In some embodiments, the sensor 1802 can provide electromyograph data to either of the display device 1804 or the external source 202. In other embodiments, the sensor 1802 can analyze electromyograph data and provide a signal indicative of a response from the patient. The display device 1804 or the external source 202 can analyze the data from the sensor 1802 to determine whether a response was detected. If a response (e.g., a toe flexion, glute flexion, bellows response, or the like) is detected, the external source 202 can provide data to the display device 1804 indicating the current electrode configuration and the voltage or current level used to generate the response. The electrode configuration can include an indication of which electrode (E0, E1, E2, E3, etc.) of the implantable device 1300 is the anode and which electrode is the cathode.

The procedure discussed regarding FIG. 18 can be performed while the implantable device 1300 is still inserted in the dilator 1518, such as before tines 1314 of the implantable device 1300 are deployed. By performing the procedure under these conditions, re-locating the implantable device 1300 can be easier. The procedure can help indicate whether re-locating the implantable device 1300 is beneficial, such as when a minimum voltage to get a response is above a threshold value (e.g., under 2 Volts, under 1 Volt, a greater Voltage or a Voltage therebetween, such as for all electrode configurations along the therapy target 290). The re-location of the device 1300 is then easier to perform and less destructive to the patient as the tines are not deployed and the implantable device 1300 can be moved from its current position by pushing the push rod 1624, rotating the push rod 1624, or pulling on the suture 1788. Note that the implantable device 210 can be substituted for the implantable device 1300 and vice versa.

In some embodiments, the dilator 1518 and the push rod 1624 can be made of a radio transparent material. The radio transparent material does not interfere with the signal from the external source 202 to the antenna of the implantable device 1300. In other terms, a radio transparent material does not exhibit a thermal response to incident RF wave. Examples of radio transparent materials include, but are not limited to, polyether ether ketone (PEEK), Teflon, polyvinyl chloride (PVC), acrylonitrile butadiene styrene (ABS), high purity quartz, or the like.

There can be a delay between producing a stimulation pulse and receiving an indication from the sensor 1802 that a response was detected. To accurately record the electrode configuration and the corresponding voltage or current level that produced the response, some synchronization between the source 202 and the sensor 1802 can help. The source 202 can be programmed to compensate for the time delay in one or more of (1) issuing signals to the device that cause an electrode configuration change and the actual electrode configuration change occurring, (2) issuing signals to the device that cause an electrostimulation pulse to be generated and the actual electrostimulation pulse being generated, (3) the time it takes for the patient to generate a response, (4) the time it takes for the sensor 1802 or the source 202 or the display device to determine whether a response was detected, and (5) the time it takes for the sensor 1802 to relay data indicating that a response was detected and the data being received at the source 202.

Figure 19:
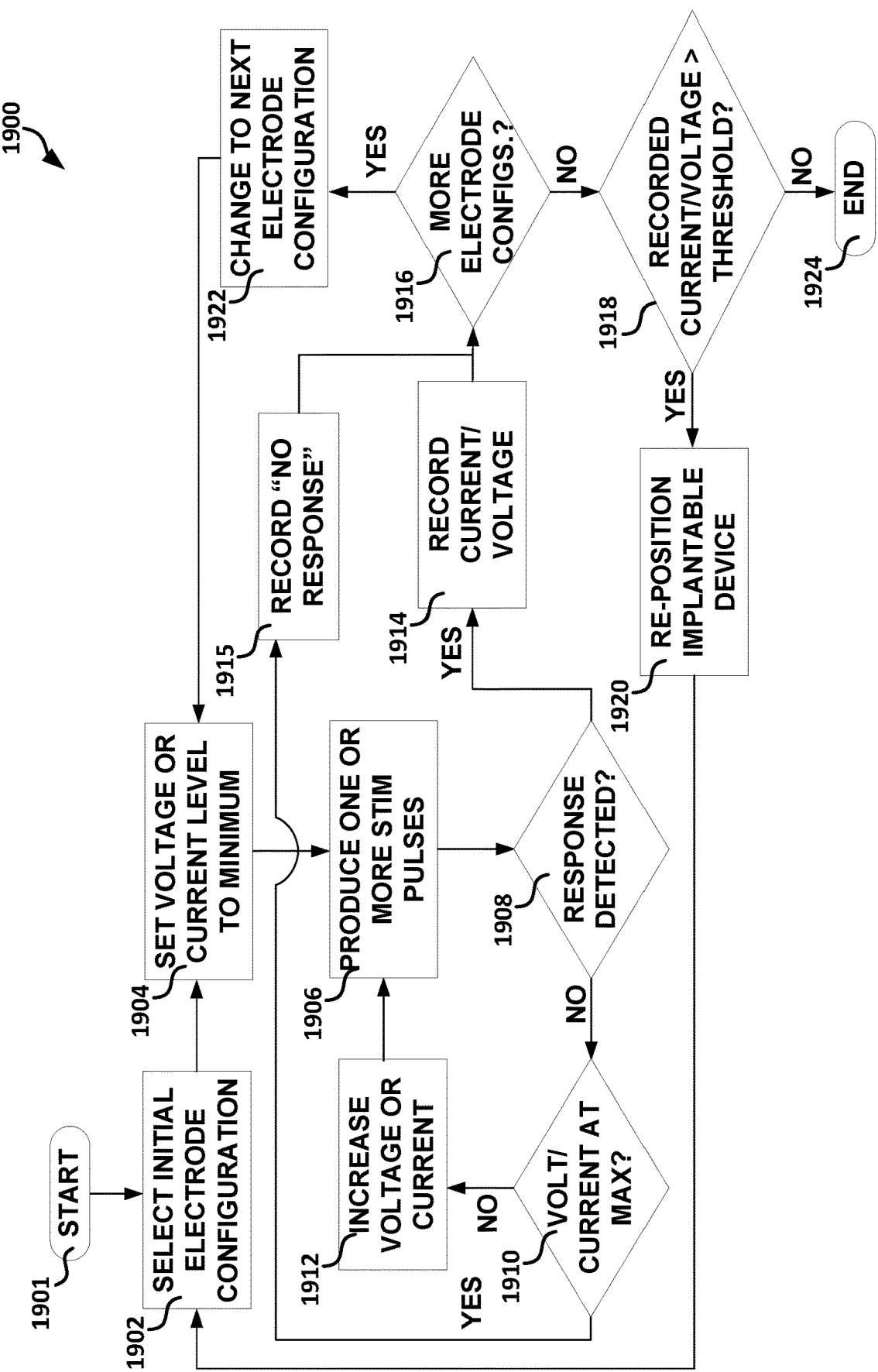
FIG. 19 illustrates, by way of example, a diagram of an embodiment of a method for testing and verification of an implantable device.

FIG. 19 illustrates, by way of example, a diagram of an embodiment of a method 1900 for threshold testing and placement verification of an implantable device, such as the implantable device 100, 210, 300, 1300. The method 1900 as illustrated includes starting at operation 1901. At operation 1902, an initial electrode configuration of the implantable device 210, 1300 can be selected. The selected configuration can be programmed into the implantable device 210, 1300 from the source 202. A voltage or current level at which the implantable device 210, 1300 can be set to a minimum value, at operation 1904. At operation 1906, the source 202 can cause the implantable device 210, 1300 to generate one or more stimulation pulses at the set voltage or current level. It can be determined whether the sensor 1802 detected a response, at operation 1908. If no response is detected, it can be determined whether the voltage or current level is currently at a maximum, at operation 1910. If a response is detected at operation 1908, the current or voltage level of the implantable device 210, 1300 can be recorded, at operation 1914. The operation 1914 can include providing the electrode configuration and the voltage or current level to the display device 1804.

If, at operation 1910, it is determined that the present current or voltage level set at the implantable device 210, 1300 is at a maximum value, "no response" entry can be recorded, at operation 1915. The operation 1915 can include providing the electrode configuration and a phrase or symbol indicating that no response was detected for this electrode configuration to the display device 1804. If, at operation 1910, it is determined that the present current or voltage level set at the implantable device 210, 1300 is not at a maximum value, the voltage or current level at the implantable device 210, 1300 can be increased at operation 1912. Then operation 1906 can be performed.

At operation 1916, it can be determined whether more electrode configurations are to be tested. In embodiments, all or a proper subset of all possible combinations of electrodes can be tested. Testing all combinations of electrodes can help indicate whether the implantable device 210, 1300 is situated such that the electrodes are situated along (e.g., parallel with) to the therapy target 290. Consider an implantable device 210, 1300 with four electrodes (E0, E1, E2, E3). All possible combinations includes using one member of each of the following pairs as an anode and the other member as a cathode {[E0, E1], [E0, E2], [E0, E3], [E1, E2], [E1, E3], [E2, E3]}. If each of the possible combinations records a same or similar current or voltage level, then the implantable device 210, 1300 is likely positioned along the therapy target 290.

If, at operation 1916, it is determined that there are more electrode configurations to test, then the source 202 can cause the implantable device 210, 1300 to operate at a next electrode configuration at operation 1922. Then operation 1904 can be performed. If, at operation 1916, it is determined that there are no more electrode configurations to test, then it can be determined whether one or more of the recorded current or voltage is greater than a threshold (or whether one or more of the recorded configurations is a "no response", or the like), at operation 1918. The threshold can be, for example, about 1 Volt, about 2 Volts, or some greater value or a value therebetween. If, at operation 1918, it is determined that one or more of the recorded voltage or current values is greater than the threshold, the implantable device 210, 1300 can be re-positioned at operation 1920. Then operation 1902 can be performed. The operation 1920 is easier and less invasive before the tines or other securing mechanism thereof are deployed. Re-positioning of the implantable device 210, 1300 is discussed further regarding FIGS. 17A-17D. If, at operation 1918, it is determined that the recorded current or voltage value is not greater than the threshold (and is not a "no response" or the like), the method 1900 can end at operation 1924.

The recorded voltage or current thresholds can be recorded at the source 202 or the implantable device 210, 1300. Future operation of the implantable device 210, 1300 can include using the recorded electrode configurations and corresponding current or voltage at which a response was detected.

Testing and Verification of Implantable Stimulation Devices

This section generally relates to electro-stimulation therapy devices and testing that the implantable device is implanted in a desired position. Although considerable progress has been made in the realm of medical device therapy, there still exists a need for therapy devices that provide stimulation to specific positions (e.g., locations, orientations, or the like) within the body. Further improvements to testing and verification of the implant position are desired. Generally discussed in this section are implantable devices and systems, devices, and methods for implantable device insertion, affixation, test and verification, and reposition.

FIG. 20 illustrates, by way of example, a diagram of an embodiment of an implantable device 2000. The implantable device 2000, as illustrated, includes an elongated, distal body portion 2002. The body portion 2002 includes a plurality of electrodes 2004 embedded at least partially therein or affixed thereto. The body portion 2002 includes a distal end 2006 and a proximal end 2008. The proximal end 2008 is affixed to a circuitry housing 2010. The circuitry housing 2010 is affixed to an antenna housing 2012. The antenna housing 2012, as illustrated, includes a plurality of tines 2014 affixed thereto. The implantable device 2000 includes other tines 2018 and 2020 affixed thereto near the proximal end 2008.

The body portion 2002, electrodes 2004, circuitry housing 2010, and antenna housing 2012 are illustrated, only by way of example, as being generally cylindrical. The implantable device 2000 is configured to be powered wirelessly (e.g., through electromagnetic waves incident on the implantable device 2000 from external to the tissue in which the implantable device 2000 is implanted). The implantable device 2000 is configured to provide electrical stimulation to a therapy site within a patient (e.g., a human or other animal patient). The implantable device 2000 can be situated within a patient using the method discussed regarding FIGS. 21-33.

The body portion 2002 can include a flexible material. The flexible material can include polyurethane, silicone, or epoxy. The flexible material can provide the ability to shape the body portion 2002, such as while the body portion is internal to the patient.

The electrodes 2004 illustrated include an electrode array of four stimulation electrodes 2004 along the body portion 2002. The electrodes 2004, in one or more embodiments, include platinum, iridium, stainless steel, titanium, titanium nitride, or other biocompatible, conductive material. In one or more embodiments, the electrodes include a platinum and iridium alloy, such as a combination that is 90% platinum and 10% iridium. In one or more embodiments, the electrodes 2004 are electrically separated from one another, such as by one or more electrical switches. The electrodes 2004 are respectively, electrically connected to a circuit hermetically enclosed in the circuitry housing 2010.

The circuitry housing 2010 can provide a hermetic enclosure for the circuitry therein. The circuitry housing 2010 can include titanium (e.g., commercially pure, 6Al/4V or another alloy), stainless steel, or a ceramic material (such as zirconia or alumina, for example), or other hermetic, biocompatible material. The circuitry housing 2010 provides an airtight space for the circuitry. If a metallic material is used for the circuitry housing 2010, the circuitry housing 2010 can be used as part of the electrode array, effectively increasing the number of selectable electrodes 2004 for stimulation.

The antenna housing 2012 can be attached at a proximal end 2011 of the circuitry housing 2010. An antenna within the antenna housing 2012 can be used for powering and communication to and/or from the implantable device 2000, such as from a device external to the medium in which the implantable device 2000 is situated.

Tines 2014 can be attached at a proximal portion of the antenna housing 2012 (e.g., a portion of the antenna housing 2012 that faces a surface of the tissue 2228 (see FIG. 22) after implantation). The tines 2014 can provide the ability to affix the implantable device 2000 at a specific position within the tissue. The tines 2014 can be configured to affix the implantable device 2000 to or near a specific anatomical structure. The tines 2014 can be made of a polymer or other flexible or semi-flexible material, such as can include silicone, polyurethane, epoxy, or like materials. The tines 2014 can flare away from a central axis of the antenna housing 2012 such that a distal portion of a given tine 2014 is closer to the central axis than a more proximal portion of the given tine 2014, such as is shown in FIG. 20, among other FIGS. An end of the tines 2014 that is not attached to the antenna housing 2012 (the free end of the tines 2014) can be closer to a tissue surface (after implantation) than an end of the tines 2014 attached to the antenna housing 2012. Such a configuration can help ensure that the implantable device 2000 does not wander towards the tissue surface.

Tines 2018 and 2020 can be attached near a proximal end of the body portion 2002. The tines 2018 and 2020 are similar to the tines with a different attachment point. The tines 2018 and 2020 can be attached to the device 2000 near the proximal end 2008. An end of the tines 2018 that is not attached to the body portion 2002 (the free end of the tines 2018) can be closer to a tissue surface than an end of the tines 2018 attached to the body portion 2002. Such a configuration can help ensure that the implantable device 2000 does not wander towards the tissue surface. An end of the tines 2020 that is not attached to the body portion 2002 (the free end of the tines 2020) can be further from a tissue surface than an end of the tines 2020 attached to the body portion 2002. Such a configuration can help ensure that the implantable device 2000 does not wander further into the tissue than the implant depth.

A push rod interface 2016 can be situated on a proximal end of the implantable device 2000. The push rod interface 2016 can be sized and shaped to mate with a push rod. More details regarding embodiments of some of the components of the implantable device 2000 are provided regarding other FIGS. and elsewhere herein.

FIGS. 21-33 illustrate, by way of example, perspective view diagrams of respective portions of a process of implanting an implantable device, such as the implantable device 2000, or one of the other implantable devices discussed herein, such as the implantable device 100, 300, etc. FIG. 21 illustrates, by way of example, a perspective view diagram of an embodiment of a needle 2122 and stylet 2123. The needle 2122 includes a hollow point 2126 to pierce through tissue and allow a guidewire 2124 to slide therethrough. The needle 2122 can be made of metal, such as can include a biocompatible metal, such as platinum, titanium, iridium, nitinol, or the like. The needle 2122 includes a lumen (e.g., a tubular structure) through which the guidewire 2124 can be situated.

The stylet 2123 is a structure that fills a lumen of the needle 2122. The stylet 2123, when inserted in the needle 2122, can help prevent material from getting into the lumen of the needle 2122 as the needle 2122 is advanced through tissue.

FIG. 22 illustrates, by way of example, a perspective view diagram of the needle 2122 and the guidewire 2124 partially situated in tissue 2228 after the stylet 2123 is removed. The needle 2122 can pierce the surface of the tissue 2228 and tissue 2228 below the surface thereof. The needle 2122 can be pushed, generally by a handle 2230, until the point 2126 is near an implant site for the implantable device 2000. The needle 2122 can be situated in a desired position (e.g., location, orientation, or the like) in the tissue 2228. The guidewire 2124 can be pushed through the needle 2122 until it is at or near the point 2126.

The guidewire 2124 provides a structure over or around which other tools can be inserted into an implant site. The guidewire 2124 can be inserted, using the needle 2122, to a position near which the implantable device 2000 is to be implanted. The guidewire 2124 can be made of a biocompatible metal material, such as can include platinum, titanium, iridium, nitinol, or the like.

FIG. 23 illustrates, by way of example, a perspective view diagram of an embodiment of the needle 2122 partially removed from the tissue 2228. The guidewire 2124 can be left in the tissue 2228 after removal of the needle 2122, as illustrated in FIG. 24. The guidewire 2124 can provide a path to the implant site for other implantation tools or the implantable device 2000.

FIG. 25 illustrates, by way of example, a perspective view diagram of an embodiment of a dilator 2530 situated over a portion of the guidewire 2124. The dilator 2530 includes a lumen 2541 through which the guidewire 2124 can travel. The lumen 2541 includes a diameter (indicated by arrows 2532) sufficient to accommodate the guidewire 2124. The dilator 2530 can be tapered at a distal end 2536. The taper can make it easier to insert the dilator 2530 in a hole 2538 in the tissue 2228, as compared to dilators without the taper. The taper can make it easier to widen the hole 2538, as compared to dilators without the taper. The dilator 2530 can be pushed into the hole 2538 in the tissue 2228 formed by the needle 2122. The dilator 2530 can widen the hole 2538 to the outer diameter (indicated by arrows 2534). The dilator 2530 can include a metal or other rigid structure. The rigid material can prevent kinking, crushing, and buckling of the dilator 2530 due to force from the fascia or bone.

FIG. 26 illustrates, by way of example, a perspective view diagram of an embodiment of the dilator 2530 pushed through the surface of the tissue 2228 and into the hole 2538. The end 2536 can be situated near the implant site. The dilator 2530 can include a radiopaque marker 2643. The radiopaque marker 2643, such as under fluoroscopy, can help guide the dilator 2530 to the implant site. The radiopaque marker 2643 can be near the end 2536 of the dilator 2530, such as to be located near the tapered portion of the dilator 2530.

FIG. 27 illustrates, by way of example, a perspective view diagram of an embodiment of the dilator 2530 removed from the tissue, and another dilator 2740 situated in a catheter 2750 and directed towards the surface of the tissue 2228. The dilator 2740 includes a lumen 2751 through which the guidewire 2124 can travel. The lumen 2751 includes a diameter (indicated by arrows 2742) sufficient to accommodate the guidewire 2124. The dilator 2740 can be tapered at a distal end 2746. The taper can make it easier to insert the dilator 2740 in the widened hole 2748 produced by the dilator 2530, as compared to dilators without the taper. The dilator 2740 can be pushed into the hole 2748 in the tissue 2228 formed by the dilator 2530. The dilator 2740 can widen the hole 2748 to the outer diameter (indicated by arrows 2744). The dilator 2740 can include a metal or other rigid material. The rigid material can prevent kinking, crushing, and buckling of the dilator 2740 due to force from the fascia or bone.

The dilator 2740 can widen the hole 2748 produced by pushing the dilator 2530 through the tissue 2228. For example, the dilator 2530 can widen the hole to about 5 French (e.g., about 1.6667 mm) and the dilator 2740 can widen the hole further, to about 7 French (e.g., about 2.3333 mm). These dimensions are merely examples and can be varied for the application.

The catheter 2750 can include a lumen through which the dilator 2740 can pass. The inner diameter of the catheter 2750 can be sufficient to accommodate a maximum width of the implantable device 2000. The maximum width of the implantable device 2000 is the greatest length perpendicular to the length (the longest dimension) of the implantable device 2000. In the example of the implantable device 2000 of FIG. 20, the maximum width is the width of the circuitry housing 2010 or the antenna housing 2012. Since the tines 2014, 2018, and 2020 are flexible, they do not need to be considered in the width determination. The catheter 2750 can include an inner diameter (indicated by arrows 2752) and an outer diameter (indicated by arrows 2754). The catheter 2750 with the dilator 2740 inserted therein, can be pushed (e.g., manually) towards and into the hole 2748. The catheter 2750 can include a metal or other rigid material. The rigid material can prevent kinking, crushing, and buckling of the catheter 2750 due to force from the fascia or bone.

The catheter 2750 can include a radiopaque marker 2757 situated near a distal end thereof. The radiopaque marker 2757, under fluoroscopy, can help an entity visualize a position or the radiopaque marker 2757. In embodiments in which the implantable device 2000 is to be situated near a sacral nerve, the radiopaque marker 2757 can be located in an opening in bone known as the S3 foramen.

FIG. 28 illustrates, by way of example, a perspective view diagram of an embodiment of the dilator 2740 and catheter 2750 inserted into position in the tissue. FIG. 29 illustrates, by way of example, a perspective view diagram of an embodiment of the dilator 2740 and guidewire 2124 being removed, leaving the catheter 2750 in the tissue. In some embodiments, the guidewire 2124 may be removed before or after the dilator 2740 or the guidewire 2124 may be removed simultaneously with the dilator 2740.

FIG. 30 illustrates, by way of example, a diagram of an embodiment of the implantable device 2000 mating with a push rod 2850. The implantable device 2000 may include a suture 2852 extending from a proximal end thereof. The suture 2852 may extend beyond the surface of the tissue 2228 (after implantation), to be external to the entity in which the implantable device 2000 is situated after the implantation. The suture 2852 may provide a structure that may be pulled, such as to extract the implantable device 2000 from the tissue.

The push rod 2850 includes a distal interface 2854 configured to mate with the push rod interface 2016 of the implantable device 2000.

FIG. 31 illustrates, by way of example, a diagram of an embodiment of the implantable device 2000 being pushed into the catheter 2750 by the push rod 2850. The tines 2014 and 2018 (or other tines) can be collapsed against the inner wall of the catheter 2750 as they are inserted into the catheter 2750. Note that other tines, such as the tines 2020, are not illustrated, but can be included in the implantable device 2000.

FIG. 32 illustrates, by way of example, a diagram of an embodiment of the implantable device 2000 pushed into position in the tissue 2228 and through the catheter 2750, and the catheter 2750 pulled out to deploy the tines 2014 and 2018. The implantable device 2000 may be situated such that the suture 2852 is partially internal to the tissue 2228 and partially external to the tissue 2228 in which the implantable device 2000 is situated.

The push rod 2850 can include a mark 3260 indicating how far to push the push rod 2850 into the tissue 2228. An entity performing the implantation can know that the implantable device 2000 is in the proper position when the mark 1360 is at or near a proximal end 2270 of the catheter 2750 or a surface of the tissue 2228.

The mark 3260 on the pushrod 2850 can be situated such that the electrodes 2004 are at the right positions when the mark 3260 is aligned with the proximal end of the catheter 2750. The mark 3260 is visible to the naked eye. At this point, the tines 2014 and 2018 (or other tines) are still within the catheter 2750 and not yet deployed. After the entity performing the implantation is confident of the electrode placement (e.g., through x-ray (fluoroscope)), the entity can pull the catheter 850 towards the surface of the tissue 2228, releasing the tines 2014 and 2018. Confirmation with fluoroscopy can be done to confirm that the implantable device 2000 remains properly situated.

FIG. 33 illustrates, by way of example, a diagram of an embodiment that includes the push rod 2850 and catheter 2750 removed from the tissue, leaving the implantable device 2000 implanted in the tissue.

An example implant procedure consistent with FIGS. 21-33 is provided regarding implanting the implantable device 2000 near a sacral nerve through an S3 foramen. An entity can palpate the sciatic notches to landmark S3 and S4. A sterile surgical marker can be used to identify the boney landmarks. A fluoroscopy device can be maneuvered into position to provide fluoroscopic mapping of the S3 sacral region to allow for location of various landmarks such as a sacral midline, sacroiliac (SI) joints, sciatic notches, medial foraminal borders and the sacral foramena (C-Arm fluoroscopy can be used during device insertion).

The foramen needle 2122 can be situated approximately 2 cm cephalad to the sacroiliac joints and 2 cm lateral to sacral midline. An implanting physician can identify foraminal margins by touch, such as until the S3 foramen is identified and penetrated. If necessary, the physician can adjust positioning by removing the needle 2122 and reinserting. Using fluoroscopy, the physician can insert the insulated foramen needle 2122 into the foramen at an angle (e.g., about 60-degrees relative to the skin or surface of the tissue 2228. The needle 2122 can enter the foraminal canal perpendicular to the bony surface, such as to position the needle 2122 parallel to the sacral nerve. The physician can confirm the location, orientation, and depth of the needle 2122 fluoroscopically and, if necessary, adjust positioning by removing the needle and reinserting. Fluoroscopic imagery can be saved throughout for reference.

The stylet 2123 can be removed from the needle 2122 and discarded. The guidewire 2124 can be fed through the needle until a mark (not shown in FIG. 21) on the guidewire 2124 reaches the top of the needle 2122. The foramen needle 2122 can be withdrawn over the guidewire 2124, such as without removing or perturbing the guidewire 2124. The needle 2122 can then be discarded.

A stab incision can be made along the guidewire 2124 prior to inserting the dilator 2530. The dilator 2530 can be inserted using or over the guidewire 2124 and advanced into the tissue 2228 until the distal tip 2536 of the dilator 2530 is at an anterior surface of the sacrum. If required, the physician can rotate the dilator 2530 to help advance it into the tissue. The dilator 2530 can be withdrawn while keeping the guidewire 2124 stable. The dilator 2530 can then be discarded.

The combined dilator 2740 and catheter 2750 can be advanced over the guidewire 2124 into the tissue 2228 until the radiopaque marker 2757 is approximately midway between the anterior and posterior surfaces of the sacrum. If required, the physician can rotate the dilator 2740 and catheter 2750 to help advance it into the tissue 2228. At this point, the guidewire 2124 can be removed while the dilator 2740 and catheter 2750 can remain in position. The guidewire 2124 can then be discarded.

The dilator 2740 can then be removed, leaving the catheter 2750 in position. The dilator 2740 can then be discarded. The implantable device 2000 and the push rod 2850 can be connected, such as by mating the push rod interface 2016 with an implantable device interface 3422, to create a push rod assembly. The push rod assembly can be advanced into the catheter 2750, distal tip of the implantable device 2000 first. The assembly can be advanced until the marker 3260 on the push rod 2850 reaches the top of the catheter 2750. The push rod 2850 can be rotated to position the implantable device 2000.

Using fluoroscopy, positioning or orientation of the implantable device 2000 can be confirmed. In an example, a most proximal electrode 2004 from the distal tip 2006 can be aligned with a fiducial, such as the radiopaque marker 2757 on the sheath. An image of the implantable device 2000 under fluoroscopy can be saved. The position of the implantable device 2000 can be adjusted if required (and confirmed with fluoroscopy).

Firmly keeping the push rod 2850 in place with one hand, the physician can use the other hand to partially withdraw the catheter 2750 until it meets a handle of the push rod 2850 and cannot be withdrawn further. With the catheter withdrawn, the tines on the implantable device 2000 can be exposed. In an example, the length of the push rod 2850 can be sufficient to insert the implantable device 2000 into the catheter 2750 and allow the catheter 2750 to be withdrawn to expose the tines 2014, etc.

Following release of the tines by movement of the catheter 2750, fluoroscopic imaging can be used to confirm that the implantable device 2000 has not moved away from its intended position. The position of the implantable device 2000 can be adjusted, if necessary. After the position of the implantable device 2000 is confirmed, a luer cap (see FIG. 36) can be removed from the push rod 2850. The push rod 2850 can be removed about a quarter to about halfway out of the catheter 2750. Using fluoroscopy, it can again be confirmed the implantable device 2000 remains in the intended position. If the implantable device 2000 is properly positioned, then the push rod 2850 can be removed over the suture 2852 attached to the proximal end of the implantable device 2000. The radial tines 2014, 2018, or 2020 on the implantable device 2000 should maintain the axial position of the device. The push rod 2850 can then be discarded. If the implantable device 2000 has moved away from its intended position, adjustments can be made. For example, while holding the suture 2852 taut, the physician can re-insert the push rod 2850 to properly position the implantable device. After the implantable device 2000 is in the desired position, then the physician can repeat the aforementioned push rod 2850 removal steps. Using fluoroscopy, the physician can ensure that the implantable device 2000 has not moved away from the intended position. The catheter 2750 can then be partially removed. Using fluoroscopy, the position of the implantable device 2000 can be confirmed. If the implantable device 2000 has not moved away from its intended position, then the physician can continue to remove the catheter 2750 and can discard the catheter 2750. The physician can use fluoroscopy to visualize the position of the implantable device 2000. If necessary, the physician can further adjust a position of the implantable device 2000 by pulling on the suture 2852.

FIG. 34 illustrates, by way of example, a perspective view diagram of an embodiment of the push rod 2850. The push rod 2850 can include an elongated body portion 3424. The elongated body portion 3424 can be hollow in a distal portion thereof, such as to allow the suture 2852 or sheath 3760 (see FIG. 37) to pass therethrough. The elongated body portion 3424 can include a metal, plastic, stainless steel, polyvinyl chloride (PVC), polytetrafluoroethylene (PTFE) or the like.

The push rod 2850 can include the marker 3260 that indicates the position of the marker 3260 relative to the catheter 2750. In use, an entity performing the implant procedure can push the push rod 2850 until the marker 3260 is at or near a most proximal end of the catheter 2750. The push rod 2850 can include an implantable device interface 3422. The implantable device interface 3422 is configured to mate with the push rod interface 2016.

FIG. 35 illustrates, by way of example, an exploded view diagram of an embodiment of the implantable device interface 3422 of the push rod 2850. The implantable device interface 3422 includes opposing legs 3530A, 3530B extending from the body portion 3424. The opposing legs 3530A, 3530B can be partial cylinders, partial ellipsoids, partial hypercubes, other polygonal shape, or the like. The legs 3530A, 3530B can include respective opposing faces 3536A, 3536B facing each other. The opposing faces 3536A, 3536B can be generally flat, or otherwise complement a shape of the push rod interface 2016. The opposing faces 3536A, 3536B can include a divot 3532 therein, such as to accommodate the shape of the suture 2852 or the sheath 3760. The divot 3532 can be arcuate. The body portion 3424 can be hollow such as to include a lumen 3534 (e.g., a tubular structure) extending therethrough. The lumen 3534 can include a shape that allows the suture 2852 or the sheath 3760 to pass therethrough. Such a configuration can allow the implantable device interface 3422 to engage the push rod interface 2016 with the suture 2852 or sheath 3760 at least partially in the lumen 3534.

FIG. 36 illustrates, by way of example, a diagram of an embodiment of a proximal portion of the push rod 2850. The pushrod 2850 as illustrated includes an elongated, hollow rod portion 3524, a handle 3680, detents 3682, a luer cap 3684, and a suture 2852. The pushrod 2850 can be used as described elsewhere herein. The luer cap 3684 can be removably attached to the handle 3680 by a mating luer thread (not shown as it is occluded by the luer cap 3684). As the luer cap 3684 is screwed onto the luer thread a tapered opening of the luer thread puts pressure on the suture 2852 to retain it in place. To remove the push rod 2850 from the suture 2852, the luer cap 3684 can be unthreaded from the luer thread and advanced along the suture 2852. After the suture 2852 is no longer in the luer cap 3684, the push rod 2850 can be advanced over the suture 2852 and removed from the implantable device 2000.

FIG. 37 illustrates, by way of example, a perspective view diagram of an embodiment of the push rod 2850 with the suture 2852 situated partially in the lumen 3534. FIG. 38 illustrates, by way of example, a perspective view diagram of an embodiment of the push rod interface 2016 engaged with the implantable device interface 3422. The sheath 3760 and the suture 2852 are situated in the lumen 3534 of the push rod 2850. The faces 3536A, 3536B are engaged with corresponding faces of the push rod interface 2016.

In an example, the implantable device 2000 can be situated in tissue 2228 and electrically tested, such as after the push rod 2850 and the catheter 2750 are removed from the tissue 2228. An example of a state of the implantable device 2000 for testing is illustrated in FIG. 33. A problem exists, however, with testing after the push rod 2850 and the catheter 2750 are removed because adjustment of a location or position or orientation of the implantable device 2000 can be limited. For example, a position adjustment of the implantable device 2000 in FIG. 33 can be limited to movement of the device towards a surface of the tissue 2228 in the direction of the suture 2852. That is, the suture 2852 can be pulled to move the implantable device 2000 towards the tissue 2228. In an example, if electrical testing fails, the implantable device 2000 can be extracted from the tissue 2228, re-implanted, and re-tested. Such implantation and re-implantation can lead to tissue bruising and may increase a duration of the overall implantation procedure. Further, subsequent implantation attempts may also be prone to error. Therefore, systems and techniques are desired for in-situ electrical testing and position verification of an implantable device, such as with flexibility to adjust a position (e.g., location, depth, or orientation) of the implantable device 2000 in tissue 2228 without extracting the implantable device 2000.

Figure 39:
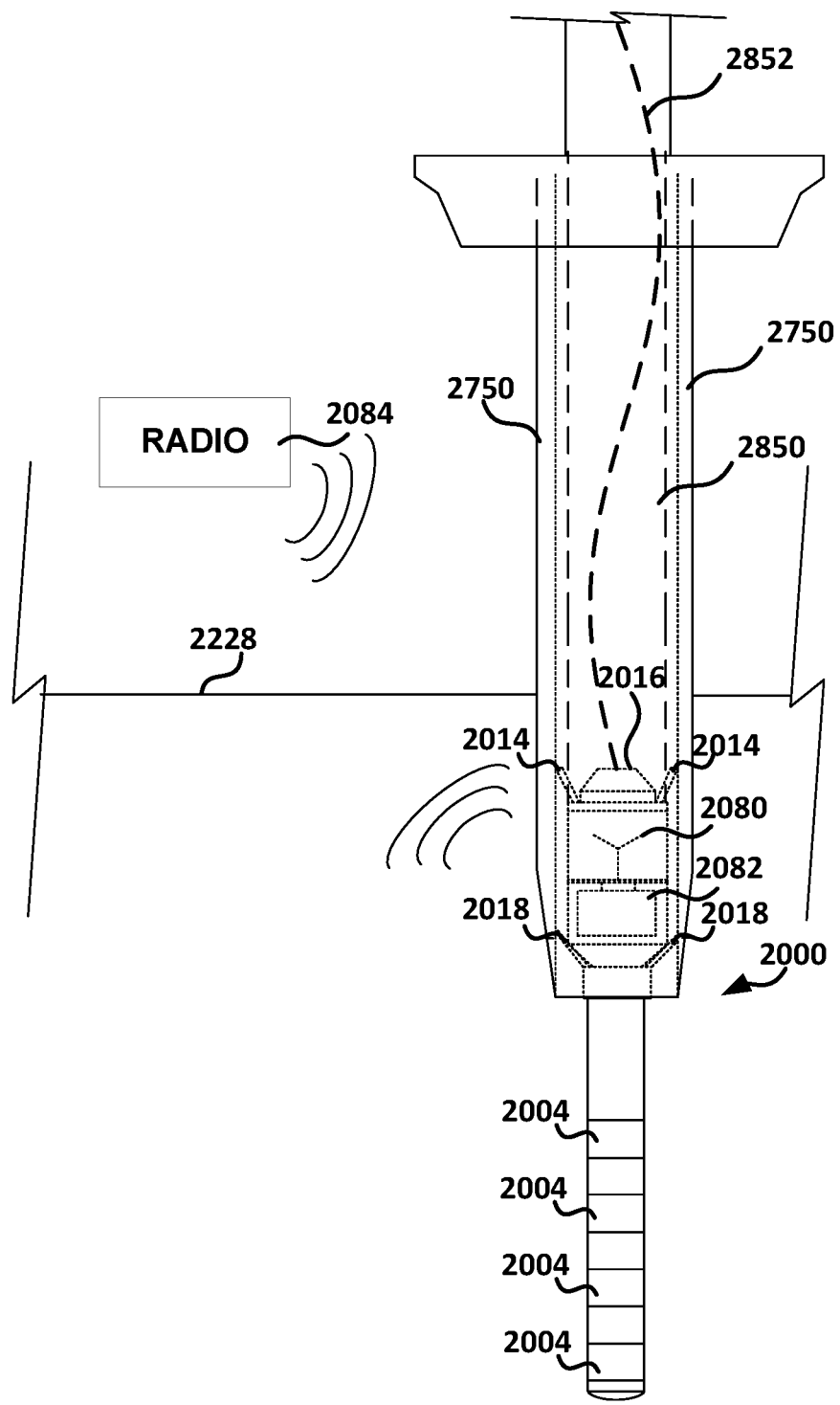
FIG. 39 illustrates, by way of example, a diagram of an embodiment of a system for electrical testing and position verification of an implanted device.

FIG. 39 illustrates, by way of example, a diagram of an embodiment of a system or electrical testing and position verification of the implantable device 2000. The system as illustrated includes the implantable device 2000 implanted in tissue 2228, such as by using the process discussed regarding FIGS. 21-33 or another implantation process. The system further includes a radio 2084 to transmit and/or receive data from the implantable device 2000.

The implantable device 100 in FIG. 39 includes an antenna 2080 and circuitry 2082. The antenna 2080 (e.g., an electric field-based or magnetic field-based antenna, such as a loop, helical, dipole, monopole, or other antenna) can be configured (e.g., in length, width, shape, material, etc.) to transmit and receive signals at substantially a same or different frequency. The implantable device 2000 can be configured to transmit power and/or data signals through the antenna 2080 to a radio 2084 and can receive power and/or data signals transmitted by the radio 2084. The radio 2084 or antenna 2080 of the implantable device 2000 can be used for transmission and/or reception of RF signals. In an example, the radio 2084 can be provided externally to the tissue 2228.

The circuitry 2082 is configured to provide a programmable control for each electrode 2004 in the electrode array. Any of the electrodes 2004 along the array can be programmed, using or based on signals from the radio 2084 received at the circuitry 2082, as a current source or sink. Each of the electrodes 2004 can be independently addressed for current or voltage amplitude in generally the same manner. For example, for an electrostimulation signal to reach furthest into the tissue 2228, a distal electrode can be programmed as a current source, and one or more of the other, more proximal, electrodes can be programmed as a current sink. Other electrode combinations can similarly be used.

The circuitry 2082 is shown housed within the circuitry housing 2010. The circuitry 2082 is electrically connected to the electrode array, such as at the distal portion of the circuitry housing 2010 by respective electrical connections. The circuitry 2082 is electrically coupled to the antenna 2080, such as through an inductive coupling or a wired connection. The antenna 2080 and/or electrodes 2004 can be encapsulated in a non-hermetic material and connected to the circuitry 2082, such as by using one or more feedthrough connections. The circuitry 2082 can include electrical or electronic components configured to perform operations of the implantable device 2000, such as receiving data from the radio 2084, via the antenna 2080, providing therapy to a patient via one or more of the electrodes 2004, sensing electrical signals within the patient, or providing data to the radio 2084. The electrical or electronic components can include a transistor, resistor, capacitor, diode, inductor, central processing unit (CPU), field programmable gate array (FPGA), application specific integrated circuit (ASIC), graphics processing unit (GPU), switch, multiplexer, logic gate (e.g., AND, OR, XOR, negate, buffer, or the like), power supply, regulator, modulator, demodulator, amplifier, phase locked loop, buck converter, boost converter, analog to digital converter (ADC), digital to analog converter (DAC), surface acoustic wave (SAW) device, or the like.

To test the implantable device 2000, such as while retaining an ability to alter an implant position of the device 2000, the implantable device 2000 can be situated at an implant position and tested, such as while the push rod 2850 is coupled to the implantable device 2000, the catheter 2750 is inside the tissue 2228, and the tines 2014, 2018 are not deployed. However, in some examples, the catheter 2750 or the push rod 2850 can interfere with communication between the radio 2084 and the implantable device 2000.

One solution to the interference issue includes using radiotransparent materials in forming the catheter 2750 and the push rod 2850. This can help reduce any interference caused by the catheter 2750 and the push rod 2850. Examples of radio transparent materials include polyether ether ketone (PEEK) or liquid crystal polymer (LCP), among others. This solution allows the catheter 2750 and the push rod 2850 to remain in the tissue 2228 and allows for electrical testing of the implantable device 2000 to be carried out while the push rod 2850 is engaged with the push rod interface 2016. This solution further allows adjusting the implant position (e.g., location, orientation, or the like) of the implantable device 2000 using the push rod 2850, the suture 2852, the catheter 2750, or a combination thereof.

Figure 40:
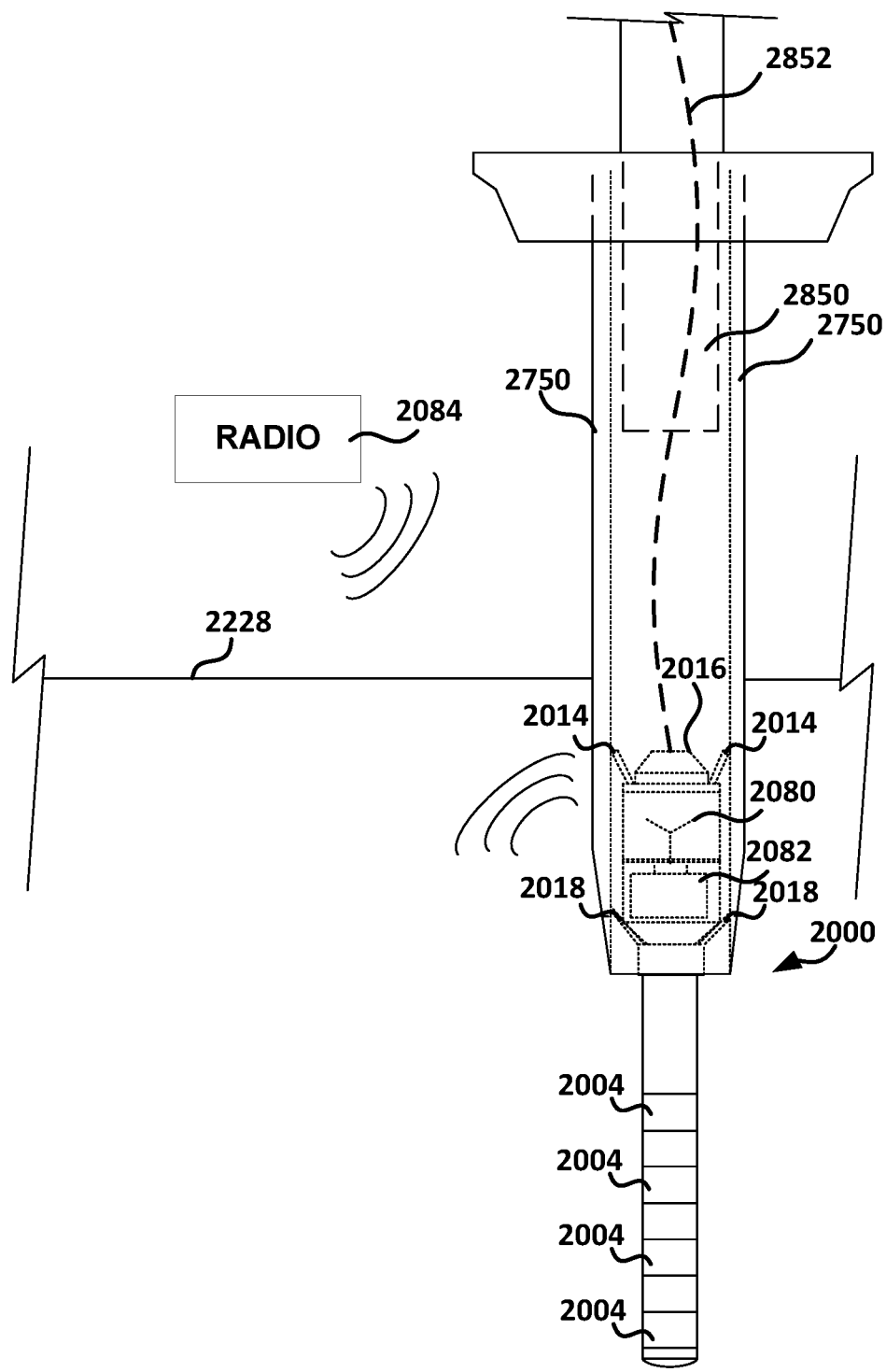
FIG. 40 illustrates, by way of example, a diagram of an embodiment of a system for improved electrical testing of an implantable device in situ.

FIG. 40 illustrates, by way of example, a diagram of an embodiment of a system for improved electrical testing of the implantable device 2000 in situ. Another solution to the aforementioned radio interference issue includes using a catheter 2750 formed of radio transparent materials and pulling the push rod 2850, made of non-radio transparent materials, away from the implantable device 2000, such as before the tines 2014, 2018 are deployed in the tissue 2228. The push rod 2850 can be completely removed from the catheter 2750 or partially situated in the catheter 2750. This solution allows the catheter 2750 to remain in the tissue 2228 and allows for electrical testing of the implantable device 2000 to be carried out. This solution further allows adjusting the implant position of the implantable device 2000 using the push rod 2850, the suture 2852, the catheter 2750, or a combination thereof. For example, after testing, the push rod 2850 can be re-inserted in the catheter 2750 and mechanically re-coupled with the push rod interface 2016 of the implantable device 2000. The push rod 2850 can then be used to differently situate the implantable device 2000 in the tissue 2228, such as deeper in the tissue 2228 or with a different orientation in the tissue 2228. The catheter 2750 can be pushed deeper in the tissue 2228. The catheter 2750 can be pulled further out of the tissue 2228, such as simultaneously with pulling on the suture 2852, to move the implantable device 2000 closer to the tissue 2228. In some cases, the implantable device 2000 can be extracted from the tissue 2228 to better position the implantable device 2000 at a therapy target. To do this, a user can simultaneously pull out the catheter 2750 while pulling on the suture 2852. By pulling out the implantable device 2000 before the tines 2014, 2018 are deployed, disruptions to the tissue 2228 can be minimized.

Various hardware and procedural considerations can be provided to ensure the suture 2852 is not pulled through the push rod 2850, such as when performing the process illustrated in FIG. 40. Some solutions are proposed, for example, as illustrated in FIGS. 41, 42, 43, 44, 45, and 46.

Figure 41:
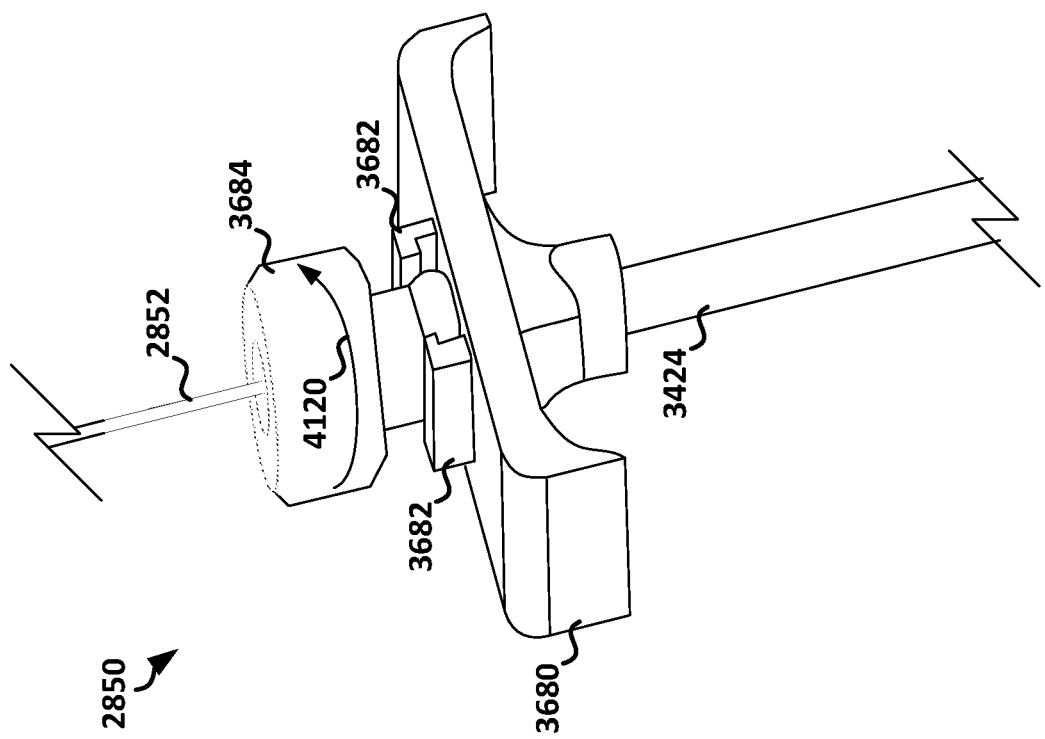
FIG. 41 illustrates, by way of example, a diagram of an embodiment of a portion of a push rod external to tissue.

FIG. 41 illustrates, by way of example, a diagram of an embodiment of a portion of the push rod 2850 external to the tissue 2228. The push rod 2850, as discussed regarding FIG. 36, can include a luer cap 3684. In some embodiments, a different connection feature can be used in place of a luer cap. Examples of different connection features include, for example, a different screw and thread, a tab and detent, or the like.

Figure 42:
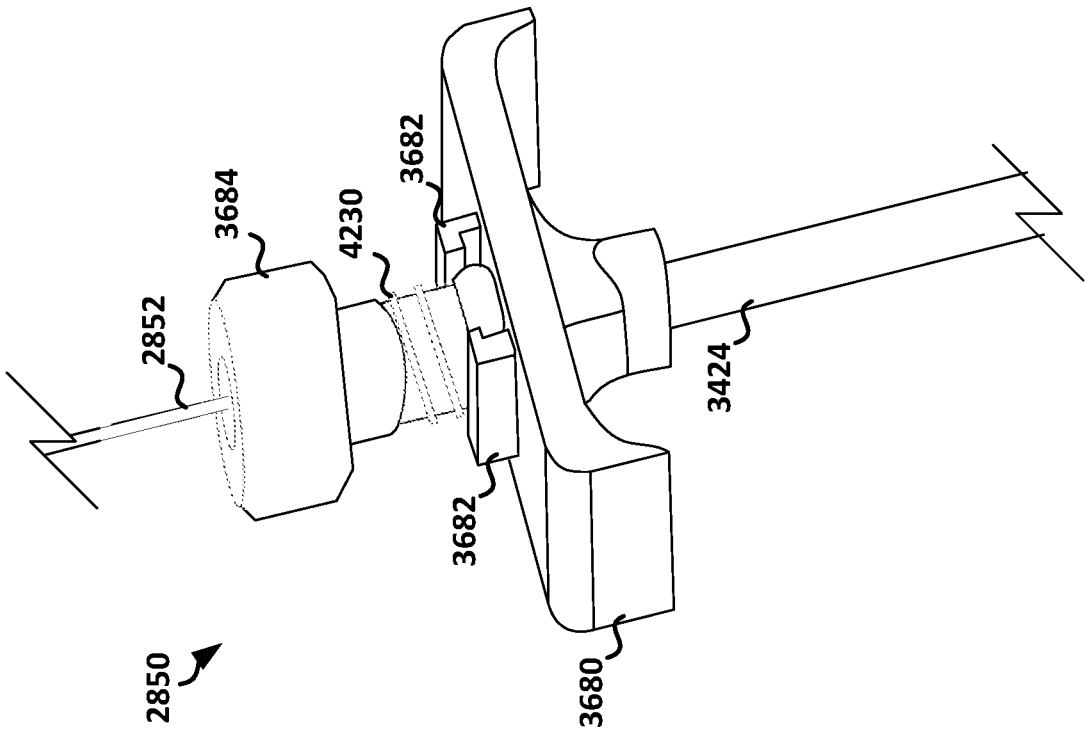
FIG. 42 illustrates, by way of example, a diagram of an embodiment of a push rod after a luer cap is rotated to displace the luer cap away from an elongated body portion of the push rod.

The luer cap 3684 can be rotated, as indicated by arrow 4120, to displace the luer cap 3684 away from threads 4230. FIG. 42 illustrates, by way of example, a diagram of an embodiment of the push rod 2850 after the luer cap 3684 is rotated to displace the luer cap 3684 away from the elongated body portion 3424 of the push rod 2850.

Figure 44:
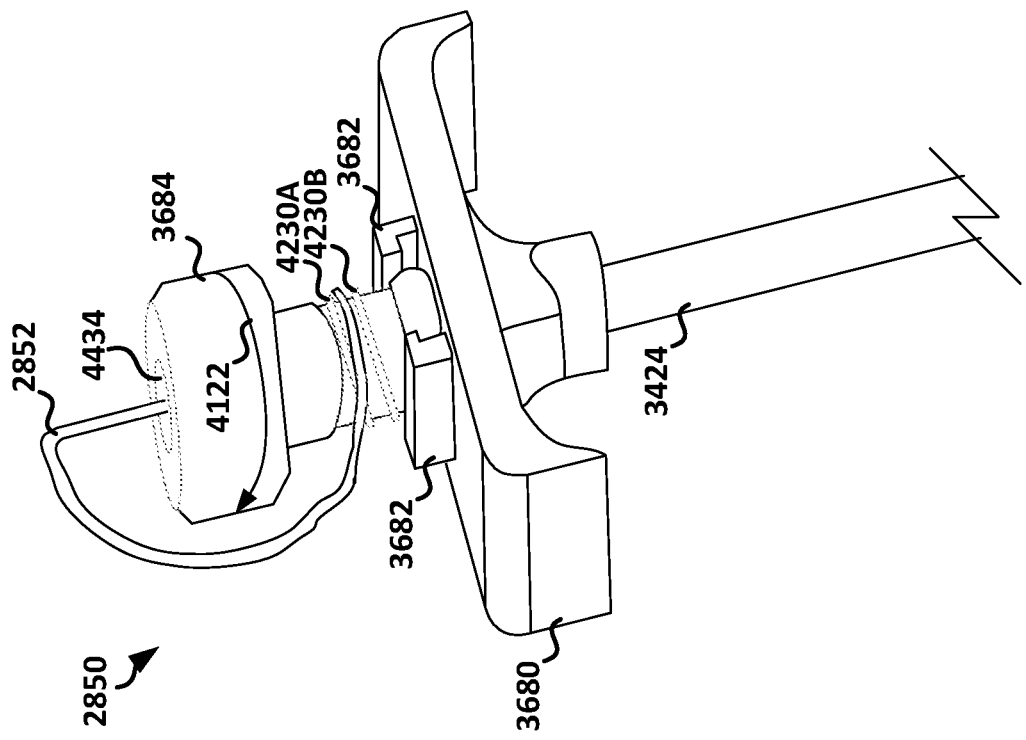
FIG. 44 illustrates, by way of example, a diagram of an embodiment of a push rod with a suture wound around threads on the push rod and the luer cap tightening to secure the suture.
Figure 43:
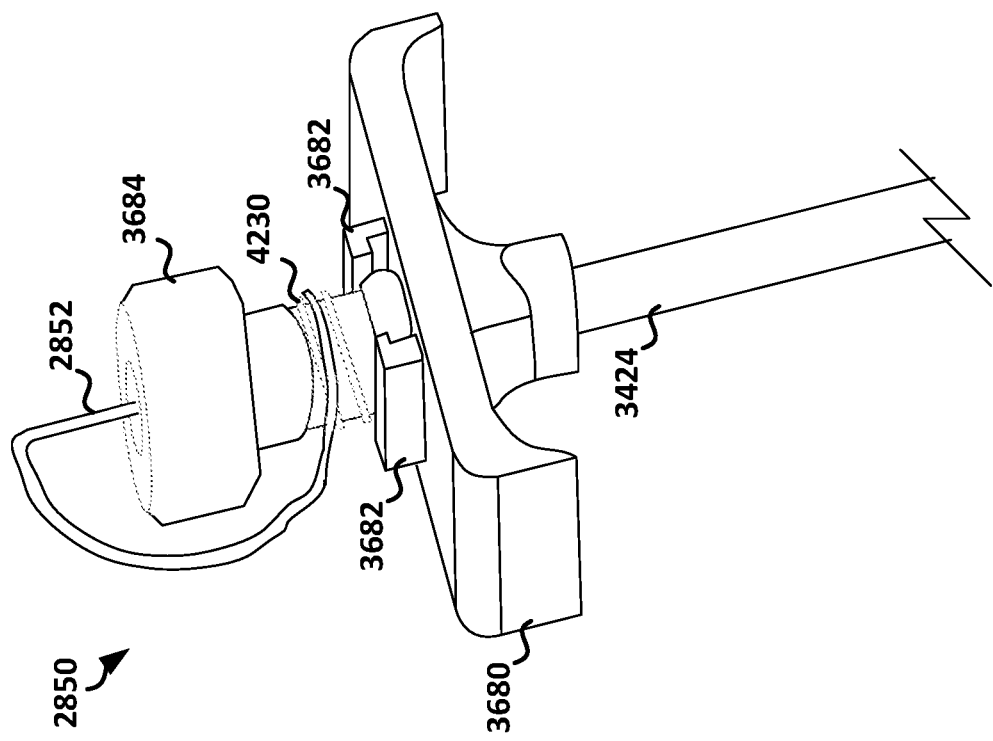
FIG. 43 illustrates, by way of example, a diagram of an embodiment of a push rod after a suture is wound around threads on the push rod.

FIG. 43 illustrates, by way of example, a diagram of an embodiment of the push rod 2850 after the suture 2852 is wound around the threads 4230. After the suture 2852 is wound around the threads 4230, the luer cap 3684 can be rotated to secure the luer cap 3684 to the threads 4230. FIG. 44 illustrates, by way of example, a diagram of an embodiment of the push rod 2850 with the suture 2852 wound around the threads 4230A, 4230B. An arrow 4122 indicates a direction to rotate the luer cap 3684 to tighten the luer cap 3684 over the threads 4230A, 4230B. By tightening the luer cap 3684, the suture 2852 is secured to the push rod 2850 and prevented from being pulled through the lumen 3534 in the push rod 2850. The suture 2852 can be wound around the threads 4230 at a position that allows the push rod 2850 to be displaced away from the implantable device 2000 but not completely removed from the catheter 2750. This allows an entity testing the position and operation of the implantable device 2000 to move the implantable device 2000 for testing and verification while giving the entity flexibility to move the implantable device 2000 using the push rod 2850 without extracting the implantable device and re-implanting the implantable device 2000.

In some embodiments, the luer cap 3684 and threads 4230A, 4230B can have multiple suture 2852 securing points. For example, a first portion of the suture 2852 can be wound around the thread 4230B and a second portion of the suture 2852 (a portion of the suture 2852 closer to an end of the suture 2852 than the first portion) can be wound around the thread 4230A. Then, after the luer cap 3684 is wound away from the elongated body portion 3424, the first portion of the suture 2852 can be released from the threads 4230B, giving the entity more freedom to move the push rod 2850 further out of the tissue 2228, while still retaining the suture 2852 in the luer cap 3684 by the second portion wound about the threads 4230A. To fully remove the push rod 2850 from the tissue 2228, the luer cap 3684 can be further displaced away from the elongated body portion 3424, and the suture 2852 can be unwound from the threads 4230A. The push rod 2850 can then be pulled until the suture 2852 is completely out of the lumen 3534.

FIG. 45 illustrates, by way of example, a diagram of an embodiment of the push rod 2850 with the suture 2852 secured thereto. FIG. 45 illustrates the push rod 2850 after the suture 2852 is wound about the thread 4230 and the luer cap 3684 is tightened around the suture 2852.

Figure 46:
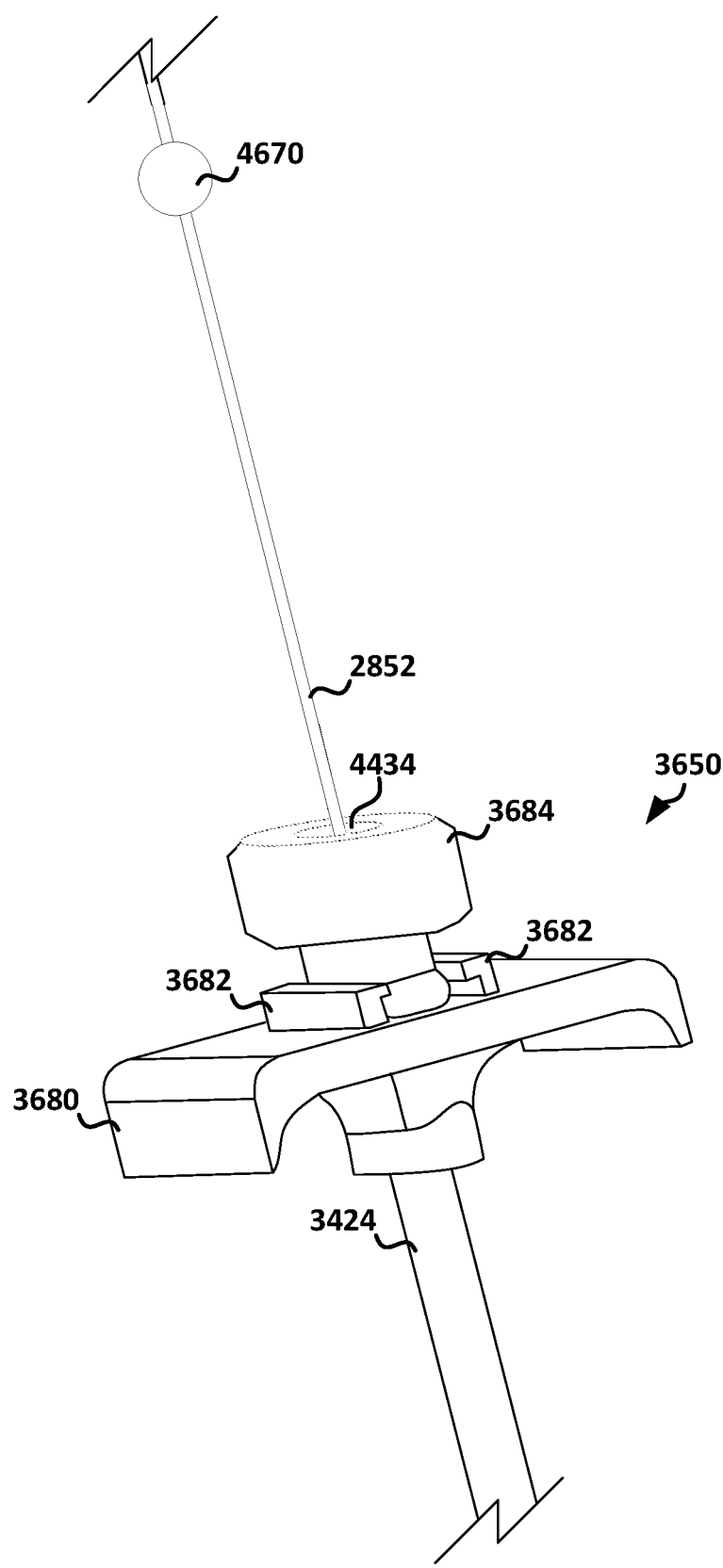
FIG. 46 illustrates, by way of example, a diagram of an embodiment of a push rod and a retention mechanism.

FIG. 46 illustrates, by way of example, a diagram of an embodiment of the push rod 2850 that provides an alternative to securing techniques discussed. The suture 2852 of FIG. 46 includes a retention mechanism 4670 attached thereto. The retention mechanism 4670 can be an attachable/detachable object. The retention mechanism 4670 can be sized or shaped such that it does not fit through the lumen 3534. Thus, when the retention mechanism 4670 is attached to the suture 2852, the suture 2852 will remain in the lumen 3534. The position of the retention mechanism 4670 can be altered such as by detaching it from the suture 2852 and re-attaching it to the suture 2852 at a different position.

In some embodiments, the retention mechanism 4670 can be attached or detached in a manner similar to a sinker used for fishing. A sinker is made of a material that expands in response to pressure put on opposing tabs. In some embodiments, the retention mechanism 4670 can be a knot in the suture 2852, a hemostat or other clamping device. These are just a few non-limiting examples of embodiments of the retention mechanism 4670.

Figure 47:
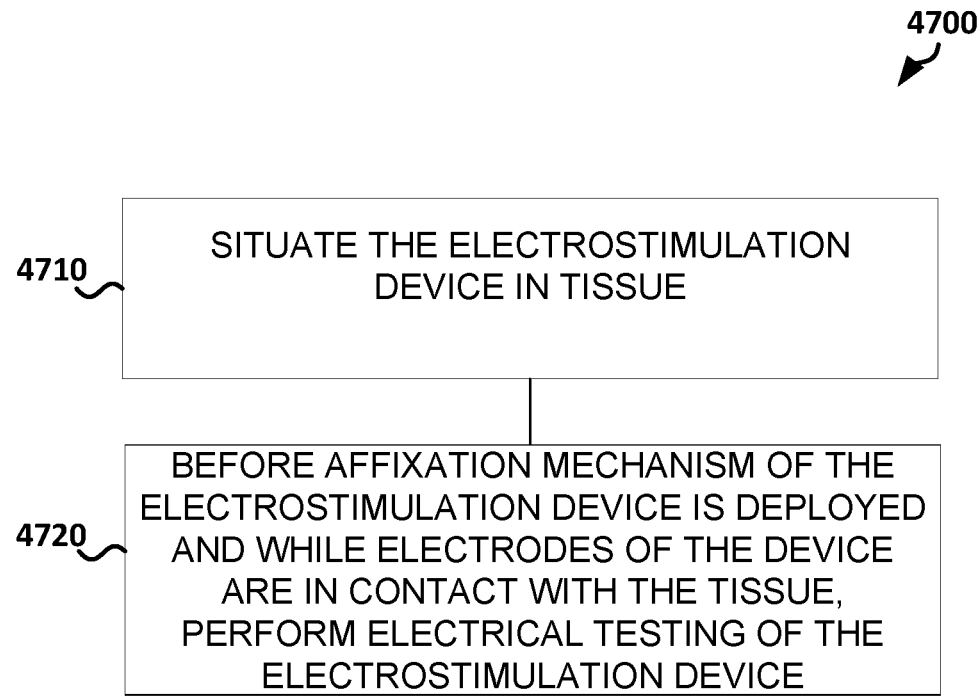
FIG. 47 illustrates, by way of example, a diagram of an embodiment of a method for testing and verification of an implantable device position.

FIG. 47 illustrates, by way of example, a diagram of an embodiment of a method 4700 for testing and verification of an implantable device position. The method 4700 can validate a position of a wirelessly powered electrostimulation device when the device is implanted in body tissue. The method 4700 can include situating (e.g., using a catheter and a push rod) the electrostimulation device in tissue, at operation 4710. The method 4700 can further include, before an affixation mechanism of the electrostimulation device is deployed (e.g., to maintain an implanted position of the device), and while electrodes of the device are in contact with the tissue, performing electrical testing of the device (e.g., to determine whether the device is situated at a desired position in the tissue), at operation 4720. The method 4700 can further include, wherein, the tine of the device is situated in the catheter, the catheter is at least partially inside the tissue, and the catheter and the push rod comprise a radio transparent material. The method 4700 can further include, wherein performing the electrical testing includes while the push rod is engaged with a push rod interface of the implantable device. The method 4700 can further include, before performing the electrical testing of the electrostimulation device, and before a tine is in contact with the tissue, and while the electrodes of the device are in contact with the tissue, pulling the push rod away from the implantable device.

The method 4700 can further include situating the electrostimulation device in the tissue by inserting the device in a catheter that is partially in the tissue so the electrodes extend out of the catheter into the tissue and the tine remains in the catheter. The method 4700 can further include using a catheter comprised of radio transparent material. The method 4700 can further include ensuring a suture extending through a lumen of the push rod and mechanically connected to a proximal portion of the implantable device remains in the lumen when the push rod is pulled away from the device.

The method 4700 can further include ensuring the suture remains in the lumen by wrapping the suture around a thread of the push rod and tightening a cap around the thread. The method 4700 can further include the thread being one of a plurality of threads and the wrapping includes a first wrapping of a first portion of the suture around a first thread of the plurality of threads, and wrapping a second, different portion of the suture around a second thread of the plurality of threads, such that loosening the cap releases the first portion during the loosening while retaining the second portion. The method 4700 can further include ensuring the suture remains in the lumen by situating a retention mechanism on the suture, the retention mechanism sized or shaped so that it cannot travel through the lumen.

Wireless Deep Brain Stimulation

This section generally relates to electro-stimulation therapy devices for stimulation of a brain. Generally discussed in this section are implantable devices and other systems, devices, and methods for installing or using implantable devices such as for neural tissue stimulation, or neural activity monitoring or recording. In an example, the systems and methods discussed herein can be used for brain stimulation, or deep brain stimulation, such as using one or more implanted, or partially implanted, electrodes, such as in, on, or near a brain, brain tissue, or other concentration of neurons or neural tissue.

In an example, the systems and devices and method discussed herein can include one or more implanted or partially implanted devices such as can be used for concurrent or nearly-concurrent sensing and therapy delivery. For example, for some movement disorders, it can be important to monitor neural activity and respond to it, such as with electrostimulation, substantially in real-time. A response to sensed neural activity can include adjusting or updating one or more electrostimulation parameters for use by an electrostimulation device. Electrostimulation parameters can include a stimulation pulse amplitude, pulse shape, pulse frequency, or therapy duration, among other things.

FIG. 48 illustrates, by way of example, a diagram of an embodiment of an implantable device 4800. The implantable device 4800 can include an elongated, distal body portion 4802. The body portion 4802 can include a plurality of electrodes 4804, such as can be embedded at least partially therein or affixed thereto. In an example, the implantable device 4800 can be configured for implantation in a patient body, such as in neural tissue or in a brain. In an example, the implantable device 4800 can include or comprise one of, or can comprise one or more components of, the various other implantable devices discussed herein. The electrodes 4804 can comprise ring electrodes or can comprise one or more other types of electrodes. For example, one or more of the electrodes 4804 can be provided on or around one side of the implantable device 4800, such as to help steer electrostimulation energy in a particular direction, such as can be defined during implantation of the implantable device 4800 in a body. In some embodiments, the electrodes 4804 can be flat. A flat electrode 4804 can be exposed on a printed circuit board, such as can include a polyimide substrate.

The body portion 4802 can include a distal end 4806 or tip and an opposing proximal end 4808. The proximal end 4808 can be affixed to a circuitry housing 4810. The circuitry housing 4810 can comprise or can be affixed to an antenna housing 4812.

The body portion 4802, electrodes 4804, circuitry housing 4810, and antenna housing 4812 are illustrated as being generally cylindrical, however, other shapes can be used. For example, the body portion 4802 can be rectangular or cuboid, or can have a substantially flat or paddle-like shape. In an example, the body portion 4802, such as having other than a circular cross-section or cylindrical shape, can include a pointed or rounded distal end 4806. In an example, a body portion 4802 that is substantially rectangular can have or include a width that is the same or similar to a diameter of a cylindrical body portion 4802. In an example, the distal end 4806 can comprise a rigid material and a tapered or needle-like face configured to piece body tissue.

In an example, an implantable device, such as the implantable device 4800, can disrupt neural tissue or brain tissue during an implantation or installation procedure. Smaller devices can thus be desirable so that a minimum amount of tissue is disrupted. In an example, a device with a substantially flat, planar, or rectangular body portion 4802 can have less surface area than a cylindrical device, and thus may affect less tissue (e.g., in the brain) during implantation.

The implantable device 4800 can be configured to be powered wirelessly. For example, the implantable device 4800 can be configured to receive power using electromagnetic waves incident on an antenna 4818, the waves originating from a location that is external to the body in which the implantable device 4800 is implanted. The implantable device 4800 can be configured to provide neurostimulation to a therapy site within a patient (e.g., a human or other animal patient). In an example, the implantable device 4800 can be configured for implantation within a patient such as using a specialized fixture such as a stereotactic device (see FIG. 55).

The body portion 4802 can include a material, such as polyurethane, silicone, polyimide, or epoxy. A material 4814 internal to the body portion 4802 can be used to make the body portion 4802 relatively more stiff or rigid than it would be otherwise without the material 4814. The material 4814 can include a metal, ceramic, Polyether Ether Ketone (PEEK), or other more rigid (more rigid than the body portion 4802) biocompatible material. In an example, the material 4814 can help facilitate implantation, for example into the brain. In an example, a body portion 4802 having its rigidity enhanced can allow the implantable device 4800 to burrow into the brain, such as without requiring a cannula, delivery catheter, or the like. That is, in an example, no secondary structural support may be used to maintain an orientation or integrity of the body portion 4802 (e.g., comprising the electrodes) during implantation in the body, such as including deeply within a brain.

The electrodes 4804 illustrated include an electrode array of four stimulation electrodes 4804 along the body portion 4802. The electrodes 4804, in one or more embodiments, include platinum, iridium, stainless steel, titanium, titanium nitride, gold, or other conductive material. In one or more embodiments, the electrodes include a platinum and iridium alloy, such as a combination that is 90% platinum and 10% iridium. In one or more embodiments, the electrodes 4804 are electrically separated from one another, such as by one or more electrical switches. In one or more embodiments, the electrodes 4804 can be about 3 mm long (e.g., along the elongated or axial dimension of the body portion 4802). In one or more embodiments, the electrodes 4804 can be separated by about 3 mm. In one or more embodiments, the diameter of the electrodes is about 1.3 mm or less. The electrodes 4804 can be respectively, electrically connected to circuitry 4816 that can be hermetically enclosed in the circuitry housing 4810. An electrical interconnect 4820 can be provided to couple the electrodes 4804 to the circuitry 4816.

The circuitry housing 4810 can provide a hermetic enclosure for the circuitry 4816. The circuitry housing 4810 can include titanium (e.g., commercially pure, 6Al/4V or other alloy), stainless steel, or a ceramic material (such as zirconia or alumina, for example), or other hermetic, biocompatible material. The circuitry housing 4810 provides an airtight space for the circuitry 4816. If a conductive material is used for the circuitry housing 4810, then the circuitry housing 4810 can be used as an electrode or as a component or part of the electrode array, thereby increasing a number of selectable electrodes for stimulation.

An antenna house 4812 can be coupled to a proximal end 4811 of the circuitry housing 4810. An antenna 4818 can be provided in the antenna housing 4812 and the antenna 4818 can be used for power and/or communication signals such as to and/or from the implantable device 4800, such as from a device external to the patient. For example, an external power unit can provide wireless power signals that can be received using the antenna 4818.

In an example, such as additionally or alternatively to being hermetic, the circuitry housing 4810 can be backfilled to prevent ingress of moisture. The backfill material can include a non-conductive, waterproof material, such as an epoxy, parylene, tecothane, or another material.

Figure 53:
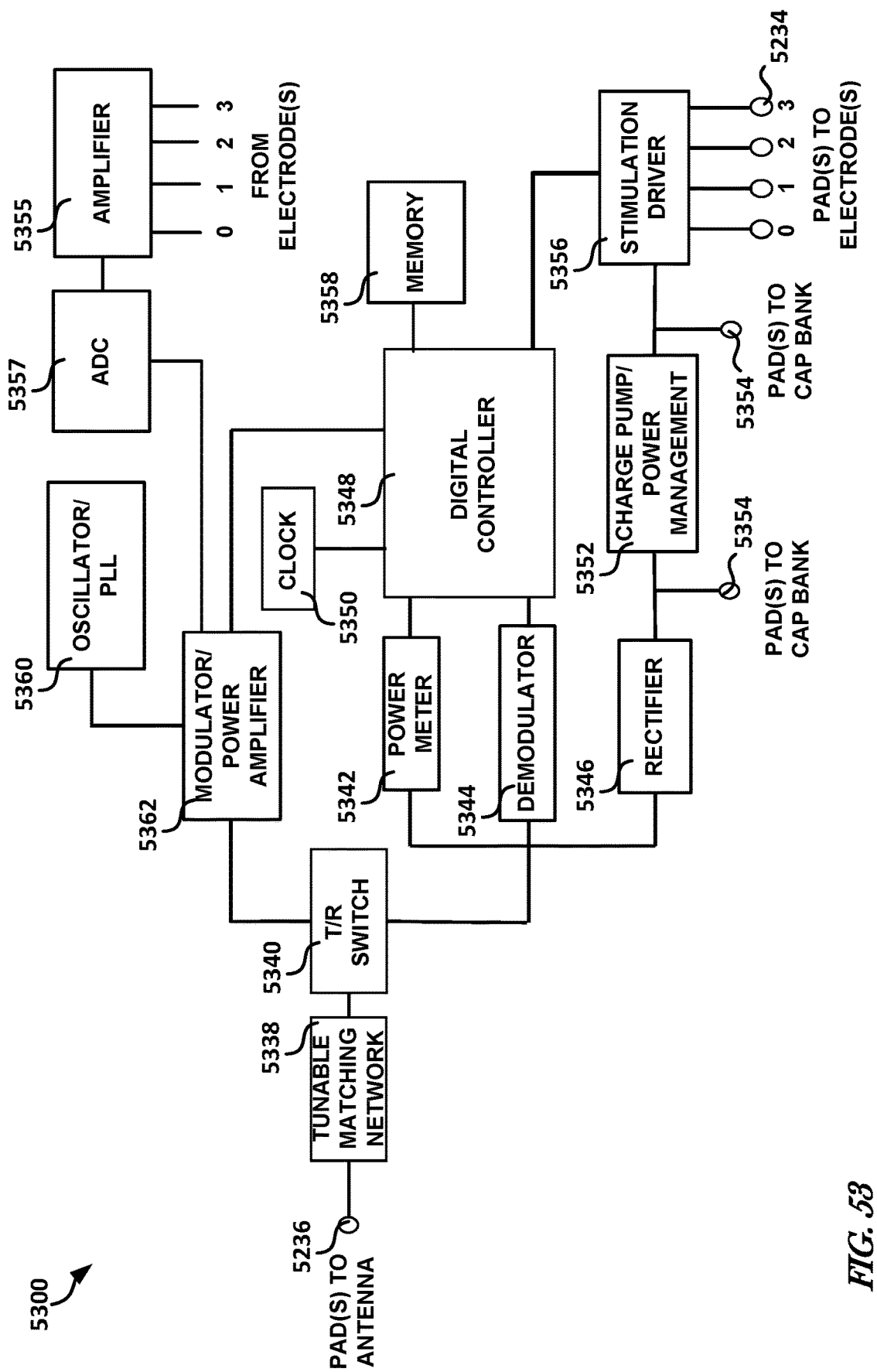
FIG. 53 illustrates generally a block diagram of circuitry for an implantable device.

The circuitry 4816 provides a programmable control for each electrode 4804 in the electrode array. Any of the electrodes 4804 along the array can be programmed, using signals from the external device received at the circuitry 4816, as a current source or sink. Each of the electrodes 4804 can be independently addressed for current or voltage amplitude in generally the same manner. For example, to reach further into the patient, a most distal electrode can be programmed as a current source. Any of the other electrodes, in this example, can be programmed as a current sink. FIG. 53 illustrates generally an example of the circuitry 4816.

In FIG. 48, the circuitry 4816 is shown housed within the circuitry housing 4810. The circuitry 4816 is connected to the electrode array 4804, such as at the distal portion of the circuitry housing 4810 by respective electrical connections 4820. The circuitry 4816 is electrically coupled to the antenna 4818, such as through an inductive coupling or a wired connection (e.g., electrical interconnect 4822 is shown in FIG. 48). The antenna 4818 and/or electrodes 4804 can be encapsulated in a non-hermetic material and connected to the circuitry 4816, such as by using one or more feedthrough connections, such as discussed with regard to FIGS. 51A, 51B, 52.

In an example, an extension structure 4817 can be attached at a proximal end 4811 of the antenna housing 4812. The extension structure 4817, or a portion thereof, can be removable or severable. In an example, the extension structure 4817 comprises a plastic, polymer, or other biocompatible material. The extension structure 4817 can have a rigidity that is the same or greater than a rigidity of the body portion 4802. The extension structure 4817, or a proximal portion of the extension structure 4817, can be used to receive a push force on the implantable device 4800 to thereby implant the implantable device 4800 into an implanted position in a body or brain. The extension structure 4817 can have structural characteristics, such that the structure will not collapse or bend under force of insertion and resistance or density of the tissue.

In an example, a method can include implanting the implantable device 4800 inside a patient, such as inside a patient's brain. A portion of a patient's skull can be removed, and the implantable device 4800 can be located within the brain. In an example, the implantable device 4800 can be positioned or installed using a stereotactic device (see FIG. 55). A depth at which the implantable device 4800 is installed can be determined at the time of implantation, such as during an implant procedure. For example, an optimal location can be determined using patient feedback during an implant procedure. In an example, after implantation at a desired location, the extension structure 4817 can extend outside of the skull of the patient. That is, a length of the implantable device 4800 can be such that the body portion 4802 can be installed in an appropriate or desired location to reach various neurostimulation targets and the proximal portion of the implantable device 4800, such as including the extension structure 4817, can be located at or near the skull opening. A portion of the extension structure 4817 can be cut or removed so that no portion of the implantable device 4800 extends beyond the brain or the skull. The skull can then be repaired and re-sealed.

FIG. 49 illustrates, by way of example, a diagram of an embodiment of the implantable device 4800 of FIG. 48 after a retaining structure 4830 is mechanically coupled to the extension structure 4817. The retaining structure 4830 can be made of a biocompatible material. The retaining structure 4830 can help maintain the implantable device 4800 in its original or intended position, such as without migrating or wandering into the brain. The retaining structure 4830, when implanted, can be provided closer to the patient skull than the antenna housing 4812 or other more distal structures of the implantable device 4800.

FIG. 50 illustrates, by way of example, a diagram of an embodiment of the implantable device 4800 of FIG. 49, such as after the extension structure 4817 is cut, so as to shorten the extension structure 4817. Shortening the extension structure 4817 allows the implantable device 4800 to be situated completely within the skull of the patient.

In an example, the retaining structure 4830 is friction-fit to the extension structure 4817. In an example, the retaining structure 4830 and/or the extension structure 4817 can be threaded, knurled, or otherwise textured such that the retaining structure 4830 can be maintained in a particular, user-selectable location along a length of the extension structure 4817. In an example, the retaining structure 4830 can be adhered to the extension structure 4817 using an adhesive or other coupling member, such as during an implantation procedure.

FIG. 51A illustrates, by way of example, a perspective view diagram of an embodiment of a circuitry housing 4810A. The circuitry housing 4810A as illustrated includes a wall 5120, proximal feedthroughs 5122, and distal feedthroughs 5124. A wall thickness 5121 can be 125 μm or less, such as can be dependent on the material(s) used to create the circuitry housing 4810A. In an example, an outer diameter 5123 of the circuitry housing 4810A, in one or more embodiments, can be about 1-2 mm. The circuitry housing 4810A can be created using a machining process or can be drawn or molded.

The proximal feedthroughs 5122 and the distal feedthroughs 5124 provide a space through which a wire (e.g., an electrically conductive wire or non-conductive wire) can be passed from inside the circuitry housing 4810A to outside the circuitry housing 4810A. The feedthroughs 5122 pass through a proximal portion 4825 of the circuitry housing 4810A, such as to provide a wire to an antenna 4818 in the antenna housing 4812 or other proximal destination, such as external to the patient's body. The feedthroughs 5124 pass through a distal portion 5127 of the circuitry housing 4810A, such as to provide a wire to a respective electrode 4804 or a distal portion of the body portion 4802, such as the distal end 4806. FIG. 51A illustrates the circuitry housing 5110A as including a bipolar proximal feedthrough 5122 (e.g., two feedthroughs through the proximal portion 5125) and a quadripolar distal feedthrough 5124 (e.g., four feedthroughs through the distal portion 5127). The circuitry housing 4810A can be used in embodiments that includes a wired connection between the antenna 4818 and the circuit 4817.

FIG. 51B illustrates, by way of example, a perspective view diagram of another embodiment of the circuitry housing 4810B. The circuitry housing 4810B includes the distal feedthroughs 5124 and omits the proximal feedthroughs 5122. Note that while the number of distal feedthroughs 5124 is illustrated as four, the number of distal feedthroughs 5124 can be any number of one or more. The number of distal feedthroughs 5124 and proximal feedthroughs 5122 can be limited by the diameter 5123 and a diameter of the feedthroughs 5124/5122.

The circuitry housing 4810B can be used in an embodiment in which there is an inductive (e.g., near field) coupling between the circuit 4816 and the antenna 4818. The feedthroughs 4824 can be used for electrical connections to the electrodes 4804, or a mechanical connection to a distal portion of the body portion 4802, such as the distal end 4806.

FIG. 51A illustrates, by way of example, a perspective view diagram of the embodiment of the circuitry housing 4810A that shows the circuit 4816 internal thereto. The circuit 4816, as illustrated, includes an Application Specific Integrated Circuit (ASIC) 5128, a printed circuit board (PCB) 5130, and discrete components (inductors, capacitors, resistors, diodes, transistors, switches, or the like). The ASIC 5128 can be designed as a System-on-Chip (SoC) package. The substrate for the SoC can be thinned to 125 μm or less. The ASIC 5128 can be attached to the PCB 5130 board using a flip-chip attachment. The material for the PCB board can be FR4, aluminum nitride, polyimide, or the like. The thickness of the PCB board can be less than 125 um, in one or more embodiments. The discrete components 5132 can be surface mount components.

Pads 5134 can be used for electrical connections to wires that are fed through the feedthroughs 5124. Pads 5136 can be used for electrical connections to wires that are fed through the feedthroughs 5122. The connections to the pads 5234/5236 can include wire bonds, magnet wire, extension of the feedthrough wires, flat ribbon wires, or soldered connections to a flexible board substrate, among others.

Figure 52:
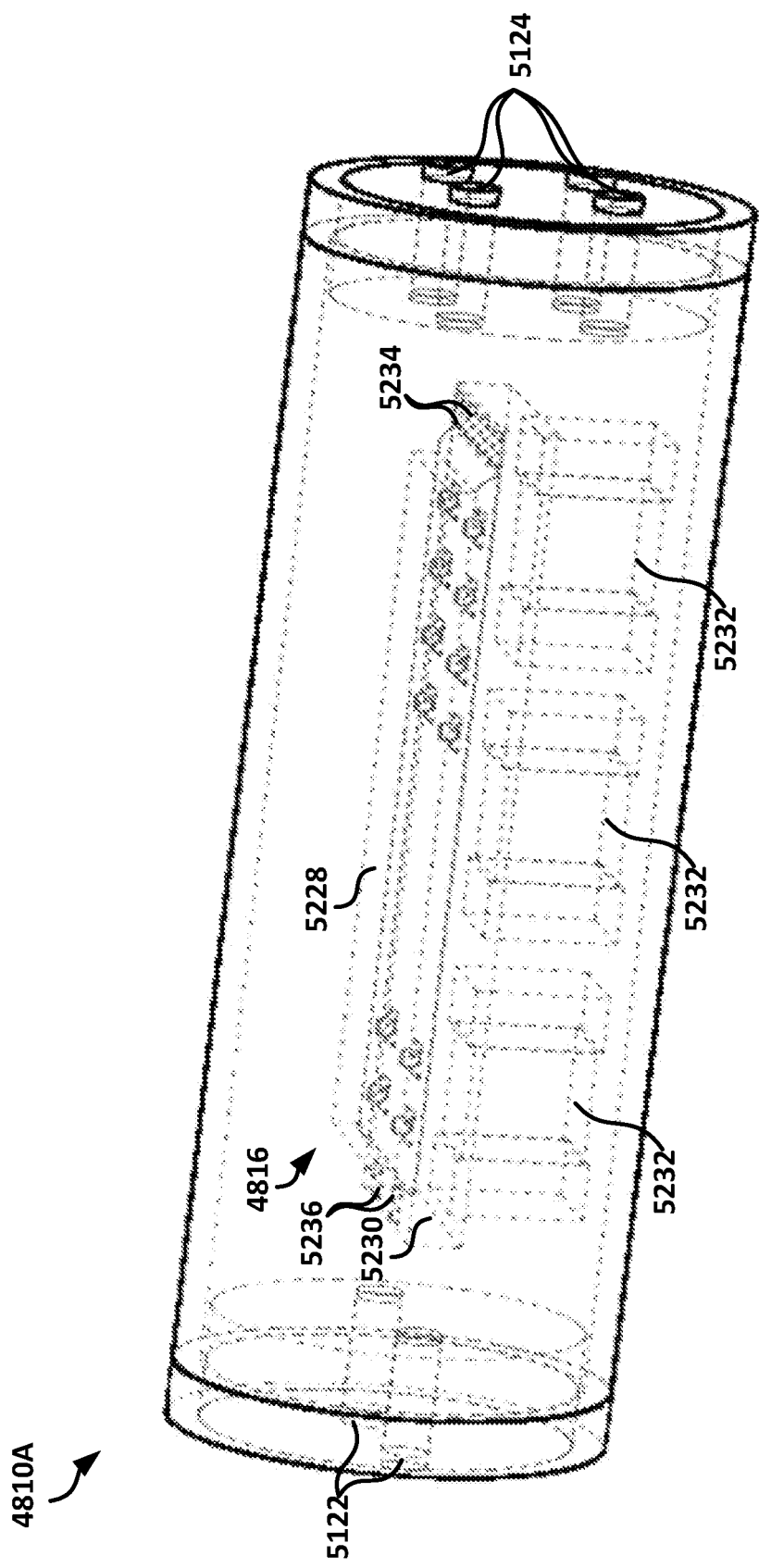

FIG. 53 illustrates, by way of example, a circuit diagram of an embodiment of a circuit 5300 to be housed by the circuitry housing 4810, such as can include the ASIC 5228, the PCB 5230, or other components of FIG. 52. The ASIC 5228 can be a SoC integrating functions for wireless RF power harvesting, RF communications, digital control, and therapy delivery. The ASIC can 5228 be manufactured using (complementary metal-oxide semiconductor) CMOS technology, such as can use a 0.18 um process.

The circuit 5300 as illustrated include the pad(s) 5236, such as can be electrically connected to the antenna 4818. The ASIC 5228 can include a tunable matching network 5338 to more closely match the impedance of the receive antenna 218 to the input impedance of the circuit 5300. The impedance of the antenna 4818 can change due to a change in the surrounding internal environment of the patient. The tunable matching network 5338 can adjust the input impedance of the circuit 5300 to more closely match this varying impedance of the antenna 4818.

A transmit-receive (T/R) switch 5340 can be used to switch the circuit 5300 from a receive mode (allowing reception of power and/or data) to transmit mode (to transfer data to an external device (e.g., a device external to the patient's body). An active transmitter can operate at an Industrial, Scientific, and Medical (ISM) band of 2.45 GHZ or 915 MHz, or the 402 MHz Medical Implant Communication Service (MICS) band for transferring data from the implant. Alternatively, data can be transmitted using a Surface Wave Acoustic (SAW) device which backscatters incident radio frequency (RF) energy to the external device.

The circuit 5300 can include a power meter 5342 for detecting an amount of received power. A signal that indicates power from the power meter 5342 can be used by a digital controller 5348 in determining if received power is sufficient (e.g., above a specified threshold). A relative value of a signal produced by the power meter 5342 can be used to help indicate to a user whether an external device used to power the implantable device 4800 is in a proper location for transferring power to the implantable device 4800.

The circuit 5300 can include a demodulator 5344 for demodulating received data. Demodulation includes trying to extract an original information-bearing signal from a modulated carrier wave.

The circuit 5300 can include a rectifier 5346 for rectifying received power. Rectifying includes converting an alternating current (AC) signal to a direct current (DC) signal. Note that a rectifier is distinct from an analog to digital converter (ADC). An ADC converts an analog signal to a digital number, while a rectifier converts an AC signal to a DC signal, sort of like an absolute value function on a current.

Circuitry (e.g., state logic, Boolean logic, or the like) can be integrated into the digital controller 5348. The digital controller 5348 control functions of the implantable device 4800 based on the input(s) from the power meter 5342, demodulator 5344, and/or the clock 5350. The digital controller 5348 can control which electrode(s) 104 are a current sink and which electrode(s) 4804 are a current source. The digital controller 5348 can control a magnitude of a stimulation pulse produced through the electrode(s) 4804.

A charge pump 5352 can be used to increase the rectified voltage to a higher voltage level, such as can be suitable for stimulation of the nervous system. The charge pump 5352 can use one or more of the discrete components 5232 to store charge for increasing the rectified voltage. In one or more embodiments, the discrete components include an on-chip bank of capacitors, such as can be coupled to pad(s) 5354 on the PCB 430.

A stimulation driver 5356 allows for programmable stimulation through the electrode array. The stimulation driver 5356 can include an impedance measurement circuit, such as can be used to test for correct positioning of the electrodes 4804. The stimulation driver 5356 can be programmed by the digital controller to make an electrode a current source, a current sink, or on a shorted path. The stimulation driver 5356 can be a voltage or a current driver.

The discrete components 5232 can include one or more off-chip capacitors. These capacitors can be used for charge balancing during stimulation, such as to help avoid tissue damage.

The circuit 5300 can also include a memory 5358, including non-volatile memory. The memory 5358 can include storage of a device identification, neural recordings, and/or programming parameters.

The circuit 5300 can include an amplifier 5355 and analog digital converter (ADC) 5357 to receive signals form the electrodes 4804. The electrodes 4804 can sense electricity from nerve signals within the body. The nerve signals can be amplified by the amplifier 5355. These amplified signals can be converted to digital signals by the ADC 5357. These digital signals can be communicated to an external device. The amplifier 5355, in one or more embodiments, is a trans-impedance amplifier.

The digital controller 5348 provides data to a modulator/power amplifier 5362. The modulator/power amplifier 5362 modulates the data onto a carrier wave. The power amplifier 5362 increases the magnitude of the modulated waveform to be transmitted.

The modulator/power amplifier 5362 is driven by an oscillator/phase locked loop (PLL) 5360. The PLL disciplines the oscillator so that it remains more precise. The oscillator is generally a different clock from the clock 5350. The oscillator generates an RF signal used to transmit data to an external device. A typical frequency range for the oscillator is about 400 MHz to about 2600 MHz. Other frequencies can be used depending on the application. The clock 5350 is used for timing of the digital controller 5348.

A typical frequency of the clock 5350 is between about one kilohertz and about one megahertz. Other frequencies can be used depending on the application. A faster clock generally uses more power than a slower clock.

Figure 54:
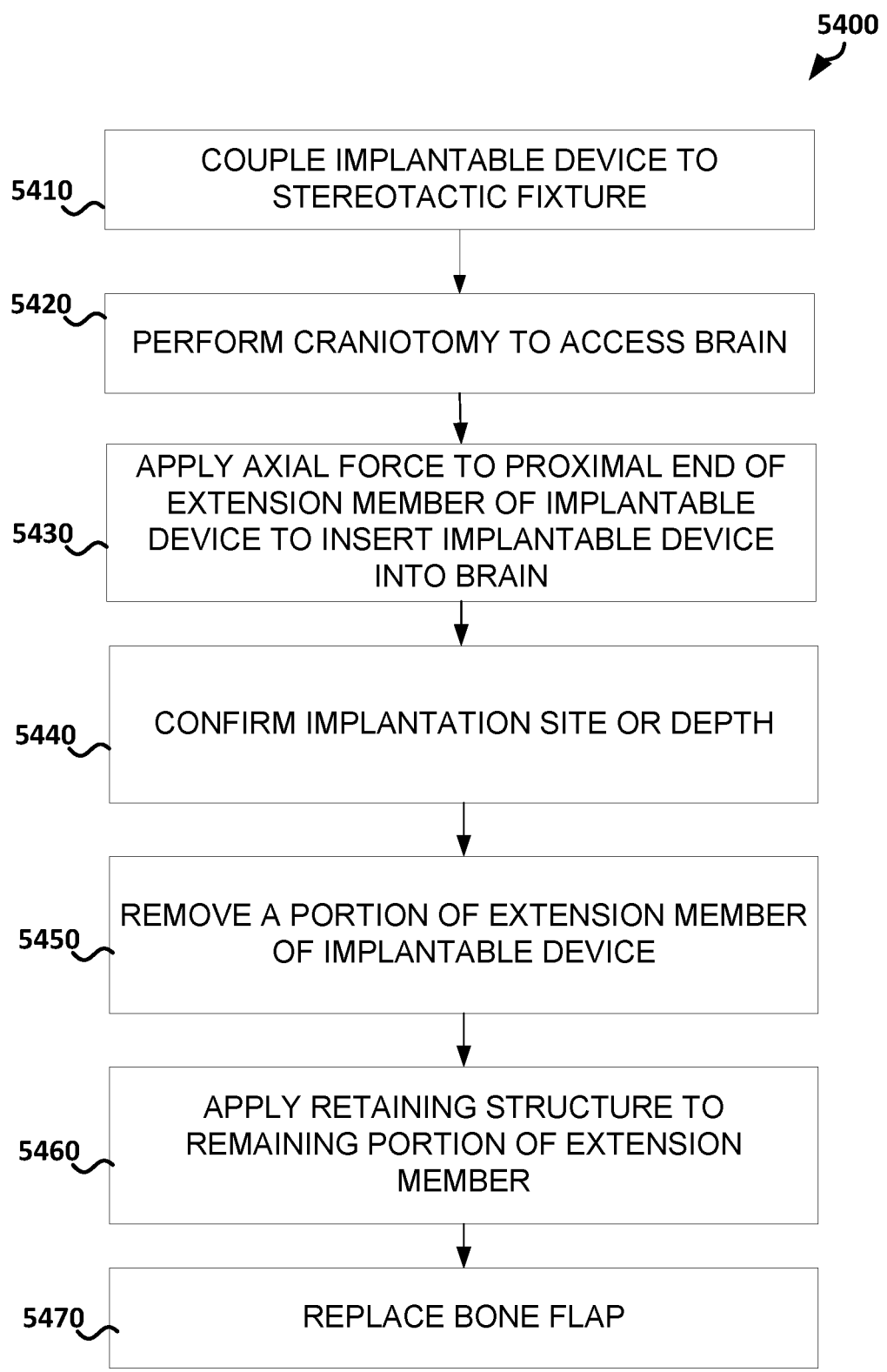
FIG. 54 illustrates generally an example of a method that can include implanting a wireless device in brain tissue.
Figure 55:
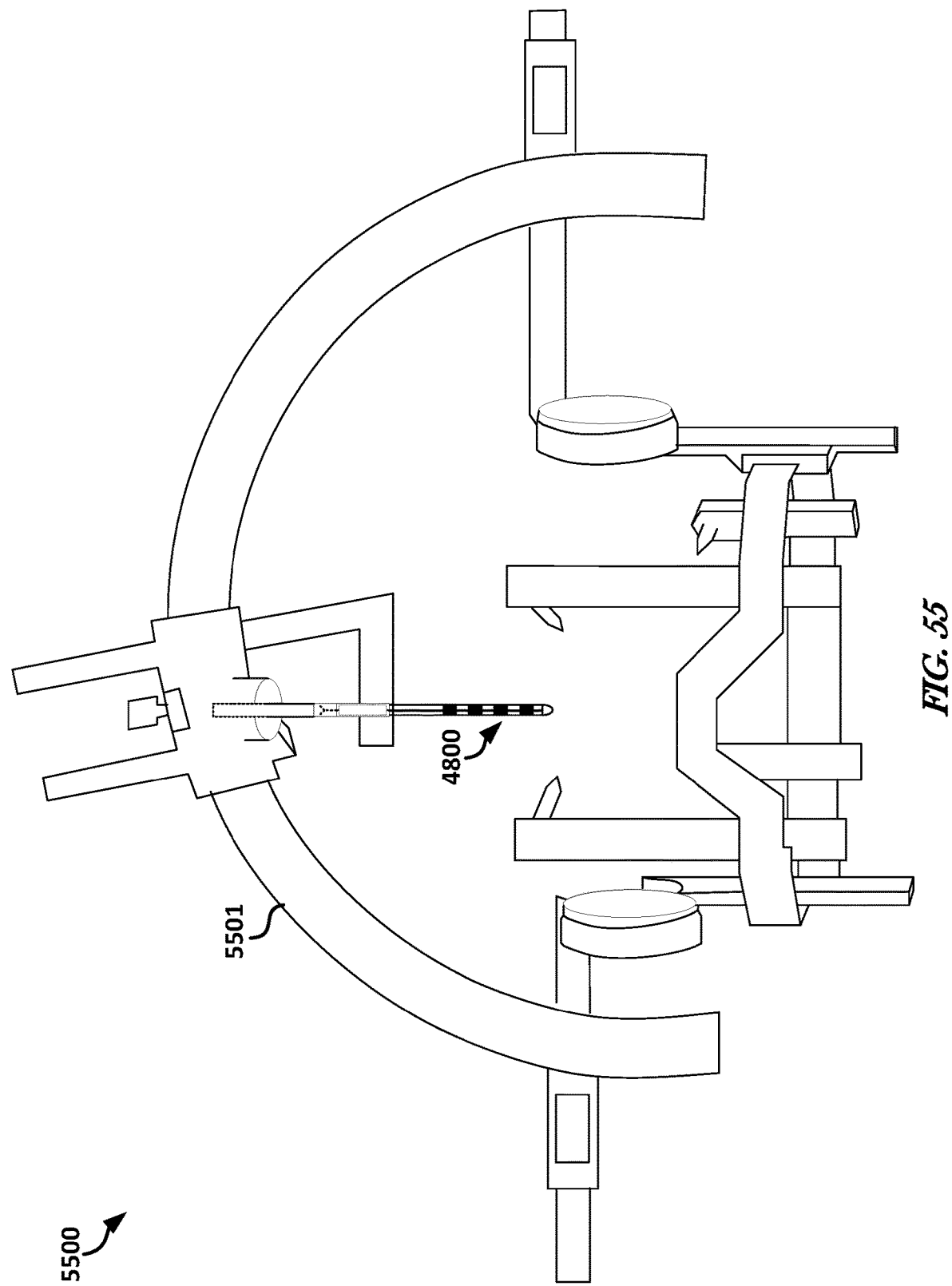
FIG. 55 illustrates generally an example of a stereotactic fixture for use in installation or implantation of a device in a brain.
Figure 56:
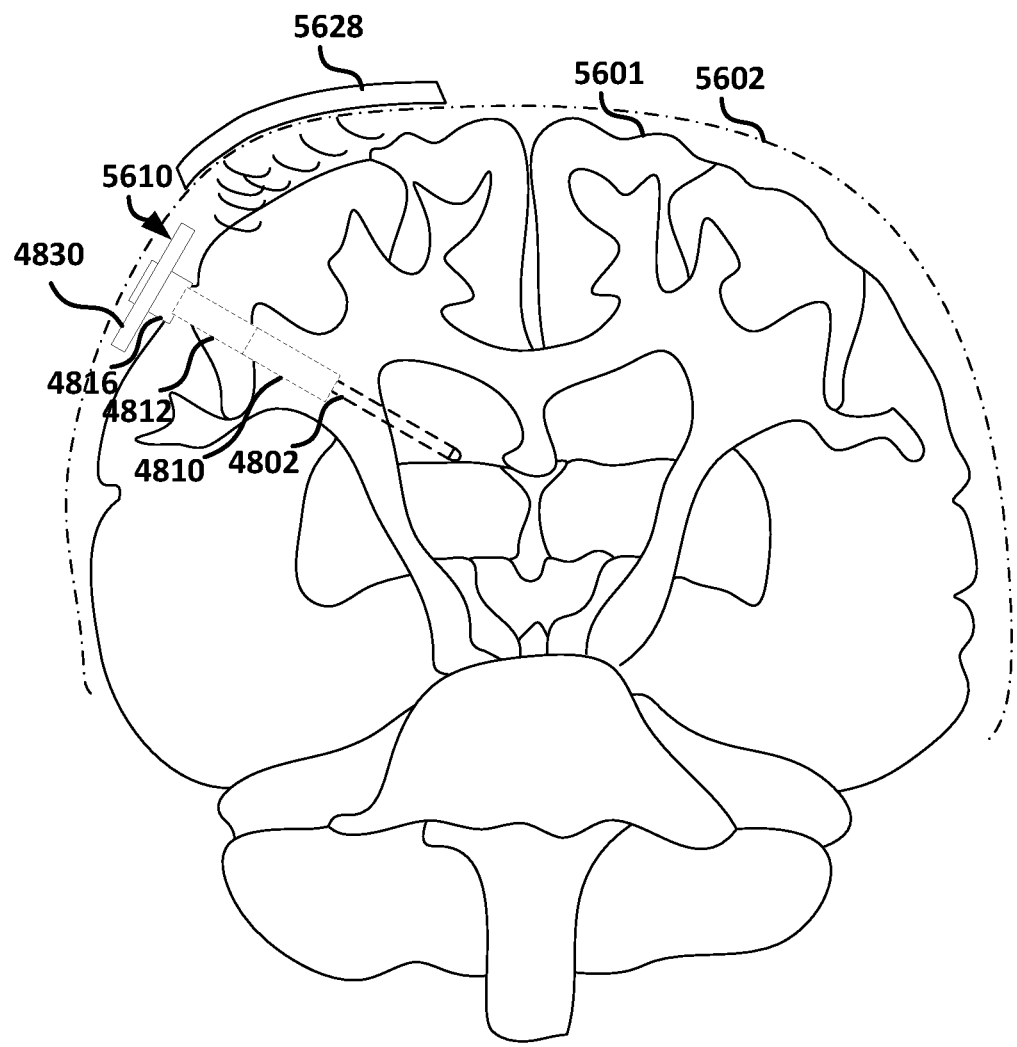
FIG. 56 illustrates generally an example of a human brain and implanted wireless device.

FIG. 54 illustrates generally an example of a method 5400 that can include implanting a wireless device, such as the implantable device 4800, in brain tissue. In the following discussion of the method 5400, reference is made to FIG. 55 and FIG. 56. FIG. 55 illustrates generally an example 5500 of a stereotactic fixture 5501 for use in installation or implantation of a device, such as the implantable device 4800, in a brain. FIG. 56 illustrates generally an example of a human brain 5601 and implanted wireless device 5610.

In the example of FIG. 54, at step 5410, the method 5400 can include coupling the implantable device 4800 to the stereotactic fixture 5501. FIG. 55 shows an example of the implantable device 4800 coupled to the stereotactic fixture 5501. The implantable device 4800 can be coupled to the stereotactic fixture 801 before or after aligning or installing the fixture to a patient.

At step 5420, the method 5400 can include performing a craniotomy to access a patient brain. The type of craniotomy or location at which the craniotomy is to be performed can be determined based on the desired implantation site. In an example, the craniotomy is one of a frontotemporal, parietal, temporal, or suboccipital craniotomy. The craniotomy can include a burr hole or keyhole craniotomy.

At step 5430, the method 5400 can include applying an axial force to the implantable device 4800 to insert the device into the brain 5601. In an example, step 5430 includes applying the axial force at a proximal end or proximal side of the extension member 4817 of the implantable device 4800.

At step 5440, the method 5400 can include confirming the implantation site or location of the implantable device. Confirming the site can include using feedback or information from an awake patient or can include sensing electrical activity of the brain (e.g., using one or more of the electrodes 4804), or can include using diagnostic imaging, or can include one or more other techniques.

In an example, step 5440 can include wirelessly powering the implantable device and, in response, at least one of delivering test electrostimulation pulses to the brain or sensing electrical property information from the brain. Sensing the electrical property information can include sensing electric neural activity or measuring an impedance characteristic of the tissue by the implantable device 4800.

At step 5450, the method 5400 can include removing a portion of the extension member 4817 of the implantable device 4800. The portion to be removed can be cut or torn away from any other portion of the extension member 4817 that is to remain attached to the body portion 4802 of the implantable device 4800. In other words, a portion of the extension member 4817 can remain implanted in the patient body, while another portion of the extension member 4817 can be removed before the implant procedure is completed. In an example, step 5450 may not be performed if a full length of the extension member is used to insert the implantable device 4800 to the target location.

At step 5460, the method 5400 can include applying the retaining structure 4830 to the portion of the extension member 4817 that remains coupled to the patient following step 5450. Applying the retaining structure 4830 can include screwing the retaining structure 4830 on to a shaft portion of the extension member 4817 or applying an adhesive to affix the retaining structure 4830 to the shaft portion, or can include providing a friction fit between the retaining structure 4830 and the shaft portion.

At step 5470, the method 5400 can include replacing a bone flap to complete the craniotomy.

FIG. 56 illustrates generally an example of a system that include an implanted device 5610 in a patient brain 5601. The implanted device 5610 includes a portion of the implantable device 4800. For example, the implanted device 5610 can include the body portion 4802, a portion of the extension member 4817, the circuitry housing 4810, and the antenna housing 4812. The implanted device 5610 can further include the retaining structure 4830 coupled to the extension member 4817. As show in the example of FIG. 56, the distal body portion 4802 is installed at a target depth in the brain 5601, such as to provide deep brain stimulation therapy. The proximal portion of the implanted device 5610 can include the retaining structure 4830 which can help maintain the implanted device 5610 at the desired or target depth or location. In an example, the retaining structure 4830 is provided adjacent to both the brain 5601 and an inner surface of the cranium 5602.

A powering device 5628 (e.g., a midfield powering device) can be proximate a surface of skin the patient, such as directly on the skin or with some fabric, adhesive, hair, dielectric material (e.g., silicone, among others), among others between the skin and the midfield powering device 5628. The powering device 5628 provides electrical power to the stimulation device 4800 from outside the body. The power from the powering device 5628 can at least partially be used by the circuitry 4816 the circuitry housing 4810 to provide stimulation therapy to the brain 5601. The powering device 5628 can include multiple ports that transmit electromagnetic energy that constructively interferes to penetrate through the skull and to the device 5610.

The powering device 5628 can include one or more flexible substrate materials, such as polyimide, glass (ultra-thin glass), metal foil, polymer, polydimethylsiloxane (PDMS), or the like. Traces on the flexible substrate can be meandering, such as to allow them to bend without breaking. Some components on the flexible substrate may not be flexible, which can cause portions of the powering device 5618 to be inflexible. The flexible substrate can allow the powering device 5628 to conform to a surface of the skull, hair, another structure on the skull of the patient, or a combination thereof.

A system of the powering device 5628 and the implantable device 5610 can be used for intermittent stimulation. Intermittent stimulation means that electrostimulation is applied for a period of time followed by a period of no stimulation, and possibly repeating with further electrostimulation. Such intermittent stimulation can be helpful for treating side effects or directly treating a movement disorder while a patient is awake, an addiction, pain, headache, dementia, depression, stroke recovery, Huntington's disease, dystonia, epilepsy, essential tremor, obsessive-compulsive disorder, Parkinson's disease, Tourette syndrome, traumatic brain injury, or the like.

Improved Thermal Management in Wireless Power Unit

Generally discussed herein are power devices that provide power to implantable devices and other systems, devices, and methods for thermal management of the power devices.

In an example, the systems and devices and method discussed herein can include an external power unit (EPU) (sometimes referred to herein as a "power device" or "source", among things). The EPU can be configured to communicate power and/or data signals to a device implanted in tissue. The EPU can be provided outside of a patient body and adjacent to a patient's skin. In an example, an airgap or other separation can be provided between the EPU and the patient body. The EPU can be configured to provide midfield power signals to one or more devices inside the patient, for example, by providing evanescent waves at or near the tissue interface that give rise to propagating fields inside the patient body. In an example, the EPU can provide programming or control signals to an implanted device, and in response, the implanted device can excite one or more electrodes that in turn produce electrostimulation therapy for the patient.

The power device can include an electromagnetic wave transmission side and an opposing thermal conducting side. An antenna, circuitry, and a circuit board can be on the electromagnetic wave transmission side. A thermal management device can be on the circuitry, circuit board, or the like. The thermal conducting side can be on or in contact with the thermal management device.

The electromagnetic wave transmission side, when in proper use, faces the skin of the patient. The thermal conducting side, when in proper use, faces away from the skin of the patient. A phase change material can be used as part of the thermal management device. The phase change material can undergo a change of phase (e.g., go from a solid to a liquid, a first solid to a different second solid, a solid to a gas, or from a liquid to a gas, or the like) at a specified temperature. The specified temperature can be lower than a maximum skin temperature for which the comfort of the patient is retained. Solid to liquid transitions can be more practical than other phase transitions because they store a relatively large quantity of heat at a narrow temperature range, with small volume changes. Solid to solid transitions, in contrast to solid to liquid transitions and liquid or solid to gas transitions, have smaller latent heat absorption. Solid to gas or liquid to gas transitions have high latent heat absorption, as compared to solid to liquid transitions or solid to solid transitions, but the large volumes required to store the gas tend to make the phase change systems complex.

A phase change material at its transition temperature, or temperature at which it changes phase, absorbs more heat per degree of increase in temperature than other, non-transition temperatures. An amount (e.g., mass) of phase change material can be used so that it undergoes a phase change during normal operation of the power device. For example, if a first patient requires or uses two hours of stimulation, an EPU associated with the first patient can include a relatively greater amount of phase change material than may be used in an EPU associated with a second patient who requires or uses less stimulation, such as a half hour or less of continuous stimulation. In some embodiments, the power devices of the aforementioned patients can include different phase change materials. The different phase change materials can have different phase change temperatures, so as to help the power device manage heat. The phase change material for the device associated with the first patient who uses more stimulation can, in an example, have a higher transition temperature than the phase change material for device associated with the second patient who uses less stimulation.

In some embodiments, an amount of a phase change material that has changed phase can be monitored by circuitry of the power device. The power device can use the data from monitoring the phase change material to determine whether to continue or stop stimulation, such as to help enhance or preserve the comfort of the patient receiving stimulation. Please see FIG. 2 and the corresponding description thereof for a description of an implantable device and power source (e.g., "EPU") system that can include or use a phase change material.

Figure 57:
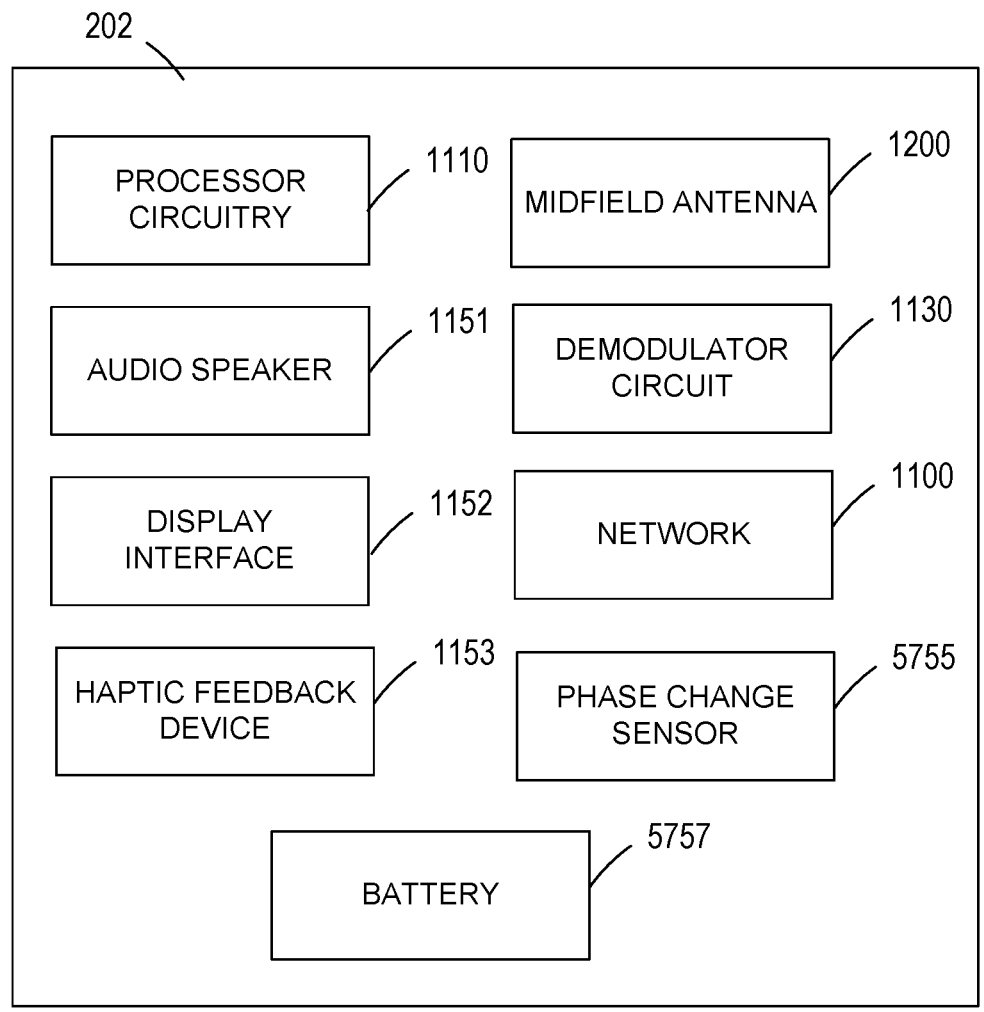
FIG. 57 illustrates generally a block diagram of an embodiment of a midfield source device.

FIG. 57 illustrates, by way of example, a block diagram of and embodiment of a midfield source device, such as the external source 202 (sometimes called an external power unit (EPU), power source, power unit, or source). FIG. 57 is similar to FIG. 11A, with FIG. 57 including a battery 5757, phase change sensor 5755, and not including the sensor electrodes 1120. The external source 202 can include various components, circuitry, or functional elements that are in data communication with one another. In the example of FIG. 57, the external source 202 includes components, such as processor circuitry 1110, demodulator circuitry 1130, a phase-matching or amplitude-matching network circuitry 1100, a midfield antenna 1200, a battery 5757 or other power device, and/or one or more feedback devices, such as can include or use an audio speaker 1151, a display interface 1152, and/or a haptic feedback device 1153. The midfield antenna 1200 is further described in the embodiment of FIG. 12, and the network circuitry 1100 is further described below in the embodiment of FIG. 58. For a discussion of some of the structure and operations of the processor circuitry 1110, the midfield antenna 1200, the audio speaker 1151, the display interface 1152, the network circuitry 1100, and the haptic feedback device 1153 please see FIG. 11 and the corresponding description thereof.

The battery 5757 can include a lithium-ion battery, nickel cadmium battery, alkaline, silver oxide, or other battery. The battery 5757 can be rechargeable, replaceable or a combination thereof. The battery 5757 can provide electrical power to the circuitry of the power unit 202. The battery 5757 can have a specified power rating that indicates a maximum amount of electrical power (typically specified in amp-hours, milliamp-hours, or the like) that can be provided by the battery 5757. The power rating can inform how much phase change material 5962 can be included in the power unit 202, discussed regarding FIG. 59.

Figure 58:
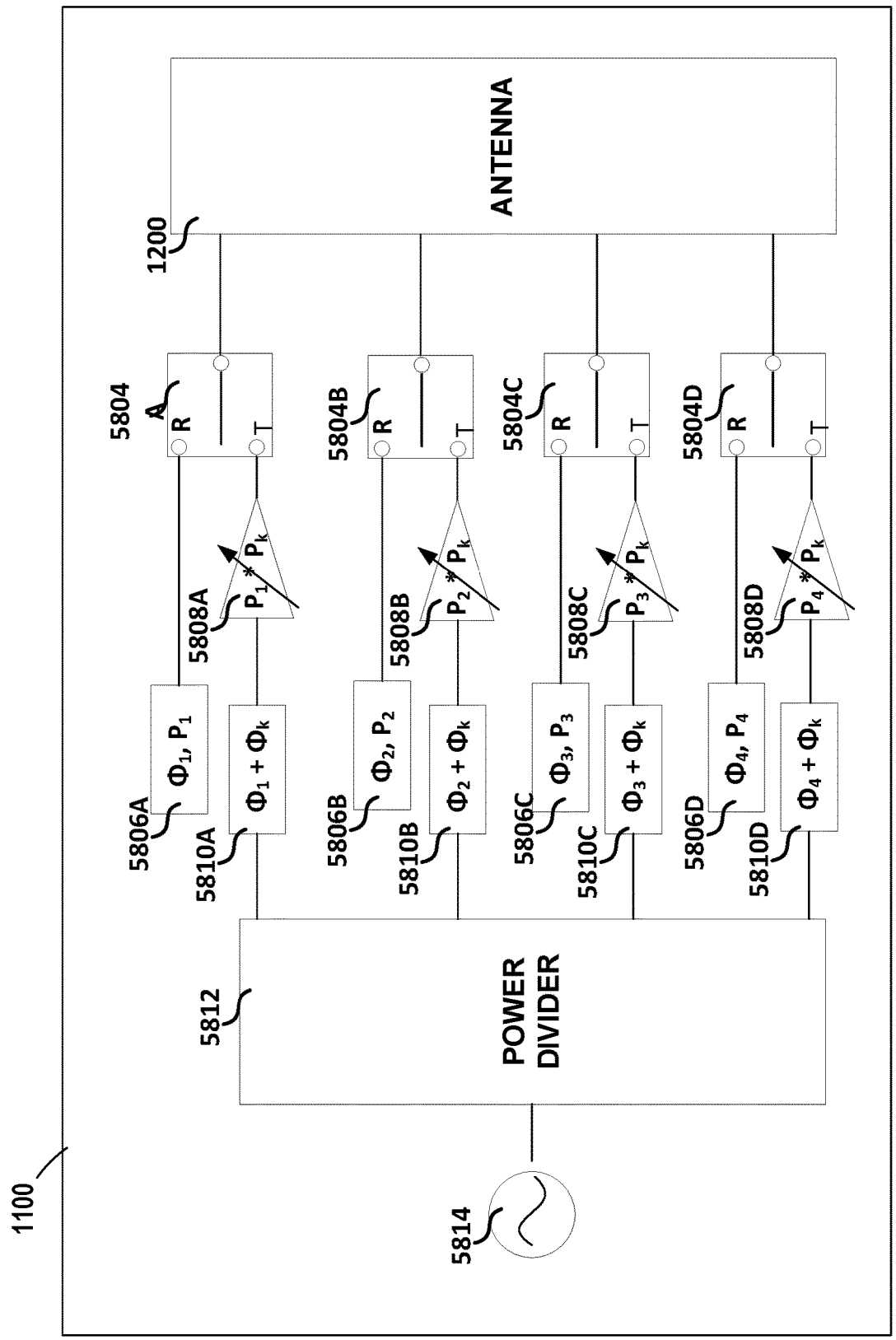
FIG. 58 illustrates generally a diagram of an embodiment of a phase-matching and/or amplitude-matching network for a midfield source device.

FIG. 58 illustrates generally the phase-matching or amplitude-matching network circuitry 1100. In an example, the network 5800 can include the antenna 1200. The antenna 1200 can be electrically coupled to a plurality of switches 5804A, 5804B, 5804C, and 5804D, for example, via the first through fourth RF ports 1211, 1212, 1213, and 1214 illustrated in FIG. 12. The switches 5804A-D are each electrically coupled to a respective phase and/or amplitude detector 5806A, 5806B, 5806C, and 5806D, and a respective variable gain amplifier 5808A, 5808B, 5808C, and 5808D. Each amplifier 5808A-D is electrically coupled to a respective phase shifter 5810A, 5810B, 5810C, and 5810D, and each phase shifter 5810A-D is electrically coupled to a common power divider 5812 that receives an RF input signal 5814 to be transmitted using the external source 202.

In one or more examples, the switches 5804A-D can be configured to select either a receive line ("R") or a transmit line ("T"). A number of switches 5804A-D of the network circuitry 1100 can be equal to a number of ports of the midfield source 5802. In the example of the network 5800, the midfield source 5802 includes four ports (e.g., corresponding to the four subwavelength structures in the antenna 1200 of the example of FIG. 12), however any number of ports (and switches), such as one, two, three, four, five, six, seven, eight or more, can be used.

The phase and/or amplitude detectors 5806A-D are configured to detect a phase ($\Phi 1$, $\Phi 2$, $\Phi 3$, $\Phi 4$) and/or power (P1, P2, P3, P4) of a signal received at each respective port of the midfield source 5802. In one or more examples, the phase and/or amplitude detectors 5806A-D can be implemented in one or more modules (hardware modules that can include electric or electronic components arranged to perform an operation, such as determining a phase or amplitude of a signal), such as including a phase detector module and/or an amplitude detector module. The detectors 5806A-D can include analog and/or digital components arranged to produce one or more signals representative of a phase and/or amplitude of a signal received at the external source 202.

The amplifiers 5808A-D can receive respective inputs from the phase shifters 5810A-D (e.g., Pk phase shifted by $\Phi k$, $\Phi 1+\Phi k$, $\Phi 2+\Phi k$, $\Phi 3+\Phi k$, or $\Phi 4+\Phi k$). The output of the amplifier, O, is generally the output of the power divider, M when the RF signal 5814 has an amplitude of 4*M (in the embodiment of FIG. 58), multiplied by the gain of the amplifier Pi*Pk. Pk can be set dynamically as the values for P1, P2, P3, and/or P4 change. $\Phi k$ can be a constant. In one or more examples, the phase shifters 5810A-D can dynamically or responsively configure the relative phases of the ports based on phase information received from the detectors 5806A-D.

In one or more examples, a transmit power requirement from the midfield source 202 is Ptt. The RF signal provided to the power divider 5812 has a power of 4*M. The output of the amplifier 5808A is about M*P1*Pk. Thus, the power transmitted from the midfield coupler is M*(P1*Pk+P2*Pk+P3*Pk+P4*Pk)=Ptt. Solving for Pk yields Pk=Ptt/(M*(P1+P2+P3+P4)).

The amplitude of a signal at each RF port can be transmitted with the same relative (scaled) amplitude as the signal received at the respective port of the midfield coupler coupled thereto. The gain of the amplifiers 5808A-D can be further refined to account for any losses between the transmission and reception of the signal from the midfield coupler. Consider a reception efficiency of $\eta$=Pir/Ptt, where Pir is the power received at the implanted receiver. An efficiency (e.g., a maximum efficiency), given a specified phase and amplitude tuning, can be estimated from an amplitude received at the external midfield source from the implantable source. This estimation can be given as $\eta \approx$(P1+P2+P3+P4)/Pit, where Pit is an original power of a signal from the implanted source. Information about a magnitude of the power transmitted from the implantable device 210 can be communicated as a data signal to the external source 202. In one or more examples, an amplitude of a signal received at an amplifier 5808A-D can be scaled according to the determined efficiency, such as to ensure that the implantable device receives power to perform one or more programmed operation(s). Given the estimated link efficiency, and an implant power (e.g., amplitude) requirement of Pir', Pk can be scaled as Pk=Pir'/[$\eta$(P1+P2+P3+P4)], such as to help ensure that the implant receives adequate power to perform the programmed functions.

Control signals for the phase shifters 5810A-D and the amplifiers 5808A-D, such as the phase input and gain input, respectively, can be provided by processing circuitry that is not shown in FIG. 58. The circuitry is omitted to not overly complicate or obscure the view provided in FIG. 58. The same or different processing circuitry can be used to update a status of one or more of the switches 5804A-D between receive and transmit configurations. See the processor circuitry 1110 of FIG. 57 or 11 and its associated description for an example of processing circuitry.

Figure 59:
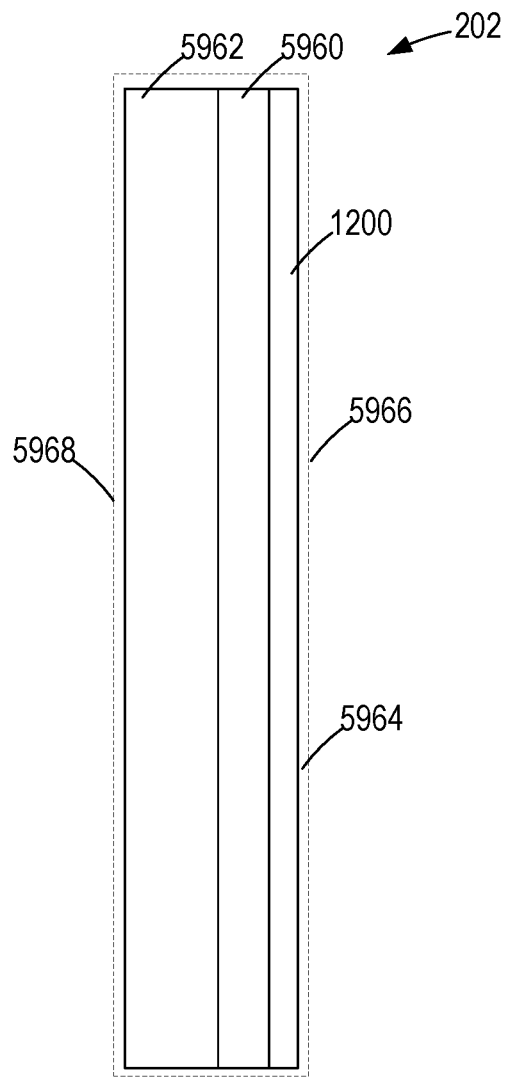
FIG. 59 illustrates generally a diagram of an embodiment of the wireless power unit with improved thermal management.

FIG. 59 illustrates, by way of example, a diagram of an embodiment of the external power unit 202. The external power unit 202 can have stringent requirements for operating while still keeping a patient comfortable. Typical thermal management components, such as heat sinks, fans, or the like, can be insufficient to reduce the heat produced by the power unit 202 or uncomfortable due to form factor. This is due, at least in part, to the continuous duration of time that the power unit 202 operates to provide electromagnetic power to the implantable device 210. For many neurostimulation treatments, the power unit 202 provides electromagnetic energy to the implantable device 210 continuously for more than fifteen (15) minutes. Some treatments are provided for twenty (20) minutes, thirty (30) minutes, forty-five (45) minutes, an hour, even two or more hours continuously.

A volume of a phase change material 5962 can be based on the power rating of the battery 5757 of the power unit 202. The volume of the phase change material 5962 can be larger for a battery 5757 with a larger capacity and lesser for a battery 5757 with a lesser capacity. Using a volume of phase change material 5962 that can absorb a maximum amount of thermal energy that can be produced by the power unit can help ensure that the patient remains comfortable. A comfortable temperature for the power unit 202 can be below fifty-five (55), fifty-three (53), fifty (50), forty-five (45), forty (40) degrees centigrade, some temperature therebetween, or a greater or lesser temperature.

Unless the heat dissipation components remove more thermal energy than is generated by the power unit 202, then the temperature of the power unit 202 will increase. This will eventually cause the power unit 202 to reach an uncomfortable temperature. The power unit 202 illustrated in FIG. 59 has improved thermal dissipation performance over other power units.

The external power unit 202 as illustrated includes the antenna 1200, circuitry 5960, a phase change material 5962, and a case 5964. The antenna 1200 is described previously. The circuitry 5960 can include any of the processor circuitry 1110, speaker 1151, haptic feedback device 1153, demodulator circuitry 1130, network circuitry 1100, or phase change sensor 5755, among other electric or electronic circuitry. The circuitry can be mounted on a first side of a circuit board, and the antenna 1200 can be mounted on a second, opposite side of the circuit board. A portion of the heat generated by the power unit 202 is generated by the circuitry 5960. The heat generated by the circuitry 5960 can be, at least partially, incident on the phase change material 5962.

The phase change material 5962 can include a formulated paraffin wax, a hydrated salt, or the like. Paraffins are high-molecular-mass hydrocarbons with a waxy consistency at room temperature. Paraffins are made up of straight chain hydrocarbons. The melting point of paraffin is directly related to the number of carbon atoms within the material structure. The paraffins possess melting points between about 6 and 80 degrees centigrade. These are termed 'pure paraffins' and should not be confused with paraffin waxes. Paraffin waxes contain a mixture of hydrocarbon molecules with various carbon numbers with lower melting points and poorer latent heats than pure paraffins. Paraffin waxes are often considered a low-grade phase change material (PCM). These are sometimes called paraffin wax formulations or formulated paraffin waxes.

Paraffin waxes in particular have been of interest due their promising properties as a PCM. Paraffin wax is safe, reliable, predictable, inexpensive, and non-corrosive. Parrafin waxes are chemically inert, show little volume change during melting and have low vapor in the melt. Favorable properties of paraffin waxes include congruent melting and self-nucleating properties.

There are different ways in which the phase change material 5962 can be stored, such as direct incorporation of wax into the polymer and encapsulation of wax by micro-encapsulation that can reduce leakage or other issues. Paraffins form a good PCM candidate for certain applications and certain select temperature ranges. Paraffins have good thermal storage capacity plus the materials are proven to freeze without supercooling. Paraffins also have the advantages of chemical stability over many heating and freezing cycles, high heat of fusion, and can be compatible with most all materials and non-reactive to most materials of encapsulation.

The phase change material 5962 can be situated in contact with or proximate a second surface 5968 of the container 5964. The second surface 5968 opposes a first surface 5966 of the container 5964. The first surface 5966 faces skin of the patient using the power unit 202 (in proper usage).

The phase change material 5962 can absorb heat and transfer to the surface 5968. The surface 5968 can transfer the heat to the surrounding environment. The phase change material 5962, at/near the transition temperature (the temperature at which the phase change material 5962 changes phase), can absorb more heat energy without increasing temperature than at other temperatures. The phase change material 5962 can have a larger surface area in contact with the surface 5968 than a typical heat sink. This is because the phase change material 5962 can be pliable, moldable, or the like. The shape of the of the phase change material 5962 can conform to the internal surface of the case 5964.

The volume of the phase change material 5962 can substantially fill the case 5964 between the circuit board and the surface 5968. The volume or chemical makeup of the phase change material 5962 can be chosen based on the duration of the neurostimulation to be applied to the patient. For example, a larger volume of the phase change material 5962, a phase change material 5962 with a higher transition temperature or a combination thereof, can be used for a power unit or EPU such as the source 202 that is to provide stimulation for a longer, continuous duration. In another example, a smaller volume of the phase change material 5962, a phase change material 5962 with a lower transition temperature, or a combination thereof can be used for an EPU that is to provide stimulation for a shorter, continuous duration.

The formulation of the phase change material 5962 can be chosen such that it includes a transition temperature below a temperature at which the patient can become uncomfortable (e.g., 53 degrees Centigrade or other temperature discussed). The formulation of the phase change material 5962 can be chosen to keep the battery 5757 within a recommended operating range. Li-ion batteries, for example, have a discharge rate that increases substantially when the temperature is above 52 degrees C. The phase change material 5962 can help keep the battery 5757 below this temperature (a safe operating temperature). The formulation of the phase change material 5962 can help ensure that the battery 5757 remains in a safe operating temperature.

The state of the phase change material 5962 can indicate a rate at which heat is dissipated from the EPU. For example, a phase change material 5962 with thermal energy added can increase temperature more in solid phase than in liquid phase. In another example, a phase change material in liquid phase can absorb heat faster than a phase change material in gas phase.

The phase change sensor 5755 (see FIG. 57) can monitor the state of the phase change material 5962, such as to indicate how much thermal energy the EPU can dissipate. The thermal energy the EPU can dissipate can inform how much stimulation can be provided while retaining the comfort of the user (e.g., without making the user uncomfortable). The phase change sensor 5755 can include a resistivity sensor, a moisture sensor, a capacitance sensor, a temperature sensor, an optical sensor, or the like. The phase change sensor 5755 can provide data indicating the phase of the phase change material 5962. The data from the phase change material 5962 can indicate an amount of the phase change material 5962 in a particular phase.

The processor circuitry 1110 can receive the data from the phase change sensor 5755. The processor circuitry 1110 can determine the amount of thermal energy the EPU can dissipate based on the data from the phase change sensor 5755. The processor circuitry 1110 can determine the amount of the phase change material 5962 in a particular phase. The processor circuitry 1110 can cause the EPU to refrain from providing additional stimulation in response to determining the EPU cannot dissipate the thermal energy produced and thus is likely to make the user uncomfortable (e.g., within a specified period of time). Determining the user will be uncomfortable can include determining a temperature of the EPU will be greater than (or equal to) a specified threshold.

FIGS. 60 and 61 illustrate, by way of example, diagrams of an embodiment of a top cover 6022 of the EPU that includes fins 6038. The fins 6038 can help conduct heat away from the user's body (away from the circuitry of the power unit 202). The fins 6038 can be touching or near a heat conducting top layer. The top layer can comprise a portion of a pocket or sleeve in which the EPU is situated). The fins 6038 can be in contact with the phase change material 5962, such as to dissipate thermal energy of the phase change material 5962 external to the EPU. The fins 6038 can extend from within the top cover 6022 beyond an outer surface of the top cover 6022. The fins 6038 can be made of a heat conductive material, such as can include a metal, carbon, or the like. Examples of materials that conduct heat well include gold, copper, silver, graphite, tungsten, aluminum, zinc, diamond, and silicon carbide. One or more flat or planar heat sinks can additionally, or alternatively, be included, such as to dissipate heat.

Intravenous Ultrasound Neuromodulation

FIG. 62A illustrates generally a block diagram of an embodiment of a portion of an implantable device (e.g., of the implantable device 210) configured to provide ultrasonic therapy signals to tissue targets. The example of FIG. 62A includes an antenna 6201, an implant power and data management circuit 6202, an ultrasonic signal generator 6271, an ultrasonic signal driver array 6272, and an ultrasonic transducer array 6273. The example of FIG. 62A illustrates four transducers in the array 6273, however, fewer or additional transducers can be used.

In an example, the antenna 6201 and the implant power and data management circuit 6202 are configured to receive wireless power and/or data signals from an external device and provide power signals and control signals to the signal generator 6271. In response to the power and/or data signals, the signal generator 6271 can provide signals to the driver array 6272 and, in turn, the driver array 6272 can drive one or more of the transducers in the transducer array 6273. In an example, the signal generator 6271 causes the ultrasound transducers in the transducer array 6273 to produce ultrasound signals having the same or different magnitude, phase, or frequency, to thereby provide an ultrasound therapy signal.

Figure 62B:
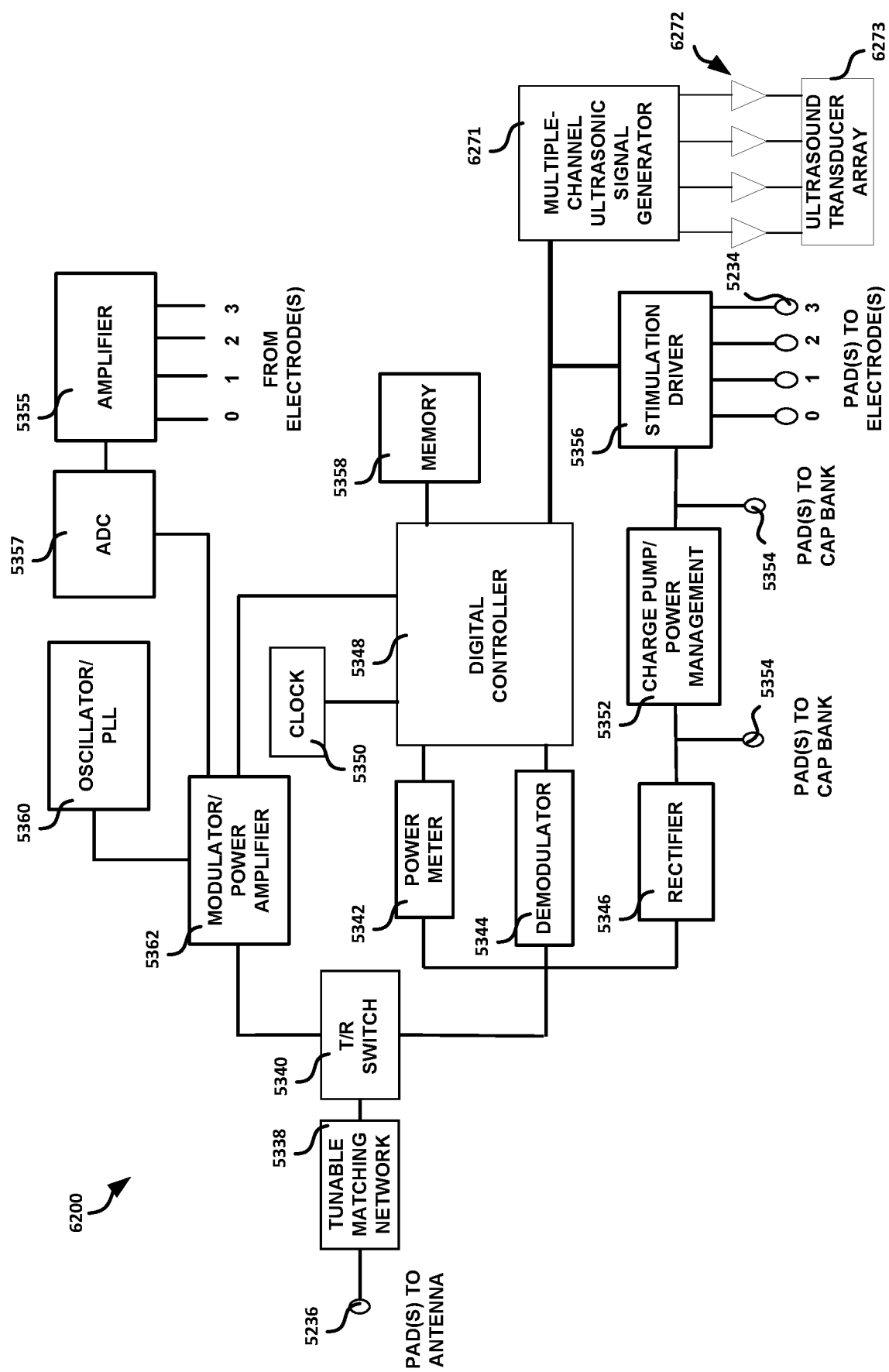
FIG. 62B illustrates generally a diagram of an embodiment of circuitry of an implantable device.

FIG. 62B illustrates generally a diagram of an embodiment of circuitry 6200 of the implantable device 210, or target device, such as can include an elongate device and such as can optionally be deployed inside a blood vessel, according to one or more of the embodiments discussed herein. The circuitry 6200 includes the components of FIG. 53 and the signal generator 6271, driver array 6272, and the transducer array 6273.

In one or more examples, the digital controller 5348, the amplifier 5355, and/or the stimulation driver circuitry 5356, among other components of the circuitry 6200, can comprise portions of a state machine device. The state machine device can be configured to wirelessly receive power and data signals via the pad(s) 5336 and, in response, release or provide a therapy signal via one or more of the outputs 5334 or using transducers in the ultrasound transducer array 6273. In one or more examples, such a state machine device needs not retain information about available therapy settings or vectors, and instead the state machine device can carry out or provide therapy signals after, and/or in response to, receipt of instructions from the source 202.

For example, the state machine device can be configured to receive an instruction to deliver a neural therapy signal, such as at a specified time or having some specified signal characteristic (e.g., amplitude, duration, etc.), and the state machine device can respond by initiating or delivering the therapy signal at the specified time and/or with the specified signal characteristic(s). At a subsequent time, the device can receive a subsequent instruction to terminate the therapy, to change a signal characteristic, or to perform some other task. Thus, the device can optionally be configured to be substantially passive or can be configured to be responsive to received instructions (e.g., contemporaneously received instructions).

Vascular Deployments

Solutions to the various problems discussed herein and associated with traditional electrostimulation-based devices and implant procedures can be addressed using miniature or injectable devices and assemblies. In an example, such an assembly can be leadless, and can be wirelessly coupled with one or more other devices using midfield wireless communication techniques, such as to transfer power or data. Midfield powering technology, including transmitters, transceivers, implantable devices, circuitry, and other details are discussed generally herein.

Various advantages come with midfield-powered devices. For example, a wirelessly-powered device does not require implantation of a relatively large, battery-powered pulse generator and the leads that are required to connect it electrically to stimulation electrodes or transducers. This enables a simpler implant procedure at a lower cost and a lower risk of chronic infection and other complications. A second advantage includes that the battery power source can be external to the patient and thus traditional design constraints (e.g., ultra-low power and ultra-high circuit efficiency requirements) can be less critical. Third, a midfield implant device can be substantially smaller than traditional devices. Smaller devices can be better tolerated by and more comfortable to patients. In some examples, midfield devices can also be less costly to manufacture and implant or install inside of a patient.

In an example, a midfield device can be implanted or installed and configured to deliver therapy, such as electrostimulation or ultrasound signals, to a renal nerve target. In an example, the midfield device can be implanted or installed at least partially in the vascular system of a patient. For example, the midfield device can be implanted or installed in an artery, vein, or other blood vessel. In an example, a midfield device can be implanted or installed in a jugular vein and configured to deliver therapy signals to a vagal nerve target. Examples of various implantable device configurations are discussed below.

In an example, a midfield-based implantable device can be used to deliver therapy to renal targets. In recent years, there has been a significant amount of pre-clinical and clinical investigation into the denervation of the renal nerves to modulate blood pressure in the treatment hypertension. The size of the hypertension patient population is significant and there is a subset of that patient population that are refractory or non-responsive to conventional medical management including pharmaceuticals such as diuretics, ace inhibitors and other stronger pharmaceutical agents that are intended to lower blood pressure.

Although an acute procedure known as renal denervation showed promise in early clinical studies in reducing systolic and diastolic blood pressures in these refractory uncontrolled patients, the present inventors have recognized that a clinical need remains for a medical device that can treat patients with hypertension. In an example, an alternative to denervation can include providing therapy to renal nerve targets, such as using neuromodulation techniques. In an example, such therapy signal can be delivered through the large renal arteries with an implantable stimulation device. Other, non-renal tissue areas can be similarly targeted from within the arteries.

The renal nerves are part of the sympathetic nervous system. In an example, neuromodulation (e.g., delivery of electrostimulation and/or ultrasound signal therapy) at the renal nerves can result in a similar effect that is achieved in the acute renal denervation procedure. In an example, such renal stimulation can be used in the treatment of uncontrolled hypertension. Other potential therapeutic benefits include the modulation of sympathetic-parasympathetic balance and modulation of the inflammatory response which is central in several serious diseases including heart failure and inflammatory bowel syndrome.

In an example, systems and methods according to the present disclosure can include or use a midfield-powered device that is implanted, installed, fixated, coupled, or otherwise disposed in a renal (or other) artery or another portion of a patient's vasculature. The device can be powered by an external powering unit that can be located at or near the kidney region where the device is implanted.

In an example, a therapy signal delivered by the implanted midfield device can create a therapy field that emanates from the artery and travels through the artery wall to the renal nerve(s) (or another neural target) located nearby. In an example, the implanted midfield device can be implanted using tools that are substantially the same or similar to tools used in balloon catheter angioplasty, as discussed above. In an example, a proximal end of the device includes a fixation mechanism that is deployed at implant and is configured to minimally impede and not block blood flow through the artery. The fixation mechanism can have varied and different configurations, some of which are described herein.

Figure 63:
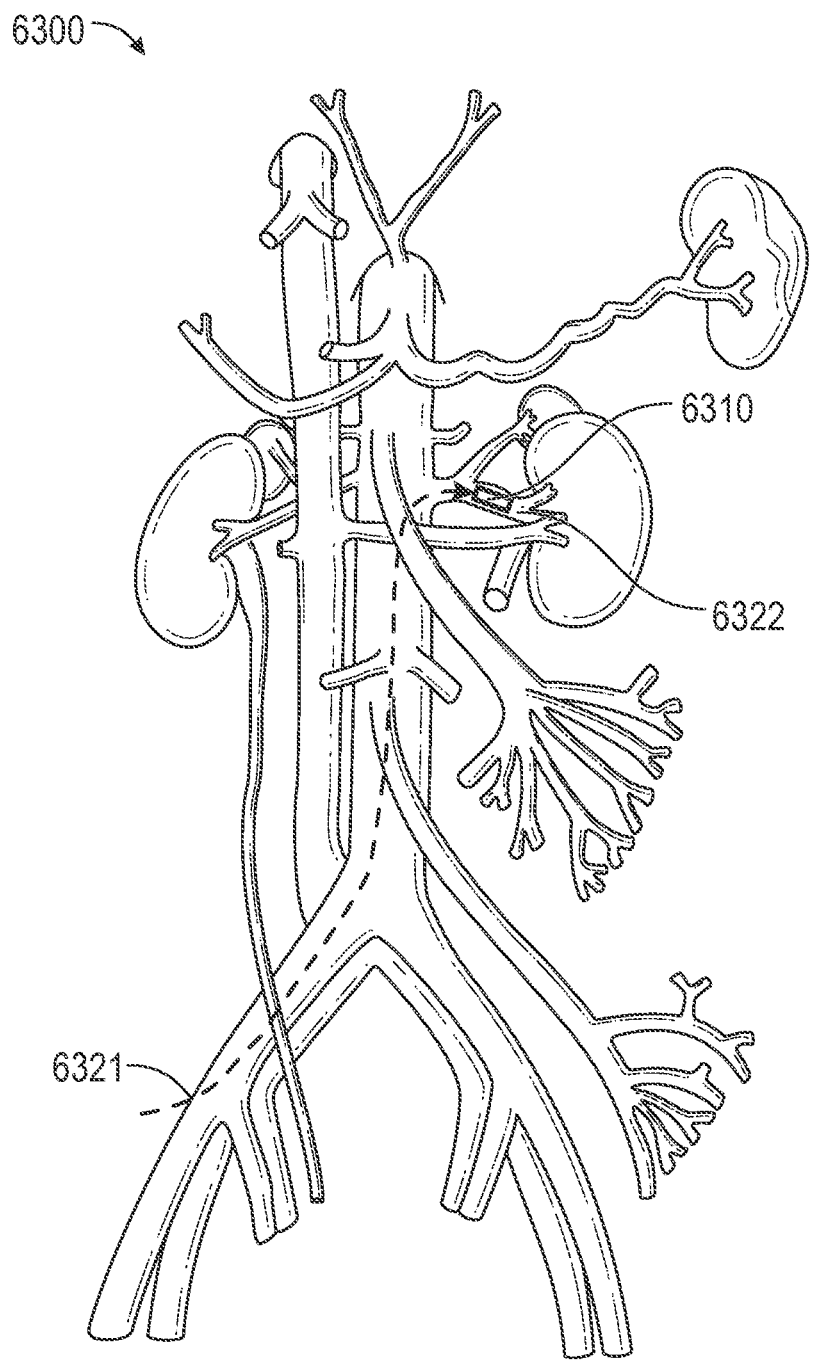
FIG. 63 illustrates generally an example of an implant location for a midfield device with respect to vasculature in a torso.

FIG. 63 illustrates generally an example 6300 of an implant location for a midfield device 6310 with respect to vasculature in the torso. In an example, an implant procedure can begin with an introduction of a delivery catheter or cannula through the Right Femoral Artery and to the Right External Iliac Artery 6321. The dashed line in FIG. 63 shows a path by which the midfield device 6310 can be introduced and located into position near or in the renal artery 6322. Other paths or destination locations can similarly be reached by the midfield device. In the example of FIG. 63, the midfield device 6310 comprises two (or more) ultrasound transducers that, when the midfield device 6310 is positioned inside the artery, are disposed or maintained adjacent to an inner sidewall of the artery to help facilitate energy transfer (e.g., ultrasound energy) from the transducers to a tissue target outside of the artery.

Figure 64:
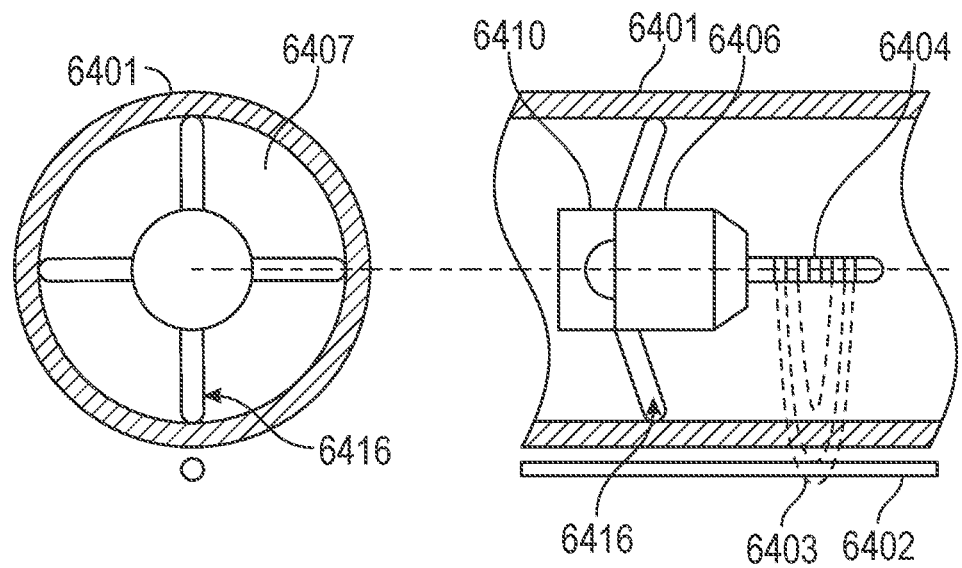
FIG. 64 illustrates generally an example that includes side and cross-section views of a midfield device configured for installation and fixation inside a blood vessel.

FIG. 64 illustrates generally an example that includes side and cross-section views of a midfield device 6410 configured for installation and fixation inside a blood vessel. Fixation of the device can be important to secure its chronic positioning for optimal nerve stimulation (e.g., at a renal target or elsewhere) and to allow substantially unrestricted blood flow through the vessel. In an example, the midfield device 6410 is 7 French (2.33 mm) or less at its largest diameter on the proximal end. Devices with other dimensions can similarly be used.

In an example, the implantable device does not block blood flow through the vessel when deployed because the vessel's inner diameter is larger than a cross-sectional area of the midfield device 6410 itself. The measured mean diameter of an artery can differ depending on the imaging method used. In an example, a representative diameter was found to be 5.04±0.74 mm using ultrasound, but 5.68±1.19 mm using angiography.

At right in the example of FIG. 64, the midfield device 6410 is deployed and affixed inside a first vessel having vessel wall 6401. The location of the midfield device 6410 can be near or adjacent to a renal nerve 6402 or another neural target. In an example, the midfield device 6410 includes a proximal housing assembly 6406 and a distal energy delivery assembly 6404. Drive circuitry, such as inside the proximal housing assembly 6406, can be used to provide signals that drive the energy delivery assembly 6404 to provide a therapy field 6403, and such field can be configured to influence or affect activity at the neural target. In an example, the therapy field 6403 comprises an electrical field and/or an ultrasonic emission.

In the example of FIG. 64, the midfield device 6410 includes various fixation features 6416. For example, the midfield device 6410 as shown can include multiple tines that extend away from the device's body portion, and the tines impinge on the inner surface of the vessel wall 6401 to locate and affix the device relative to the vessel, such as coaxially with the vessel. At least a portion of the midfield device 6410 is spaced apart from the vessel wall 6401 by the tines or fixation features 6416 such that one or more regions 6407 of unrestricted blood flow exist around the midfield device 6410. Although the example of FIG. 64 shows four discrete tines as the fixation features 6416, additional or fewer tines can be used as long as the number of tines is sufficient to affix the midfield device 6410 in a specified location relative to the vessel.

Figure 65:
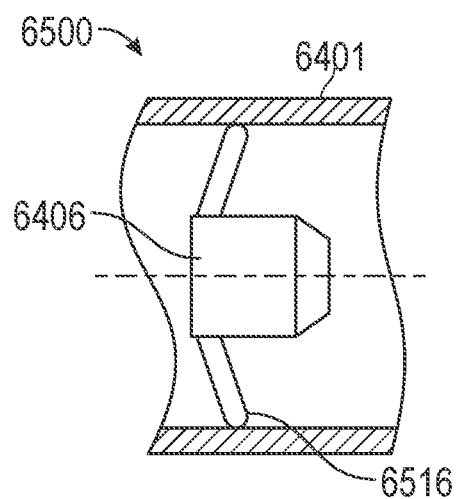
FIG. 65 illustrates generally a first example of a midfield device with multiple passive elements that project laterally away from the midfield device's housing assembly.
Figure 66:
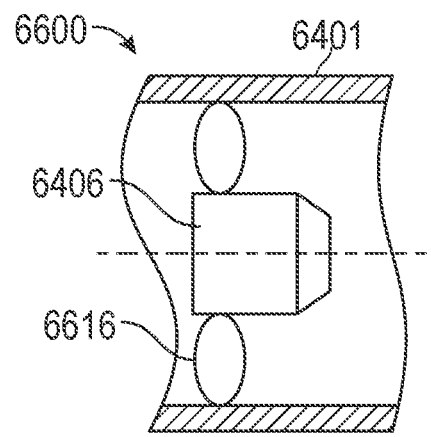
FIG. 66 illustrates generally a second example of a midfield device with multiple inflatable elements that project laterally away from the midfield device's housing assembly.
Figure 67:
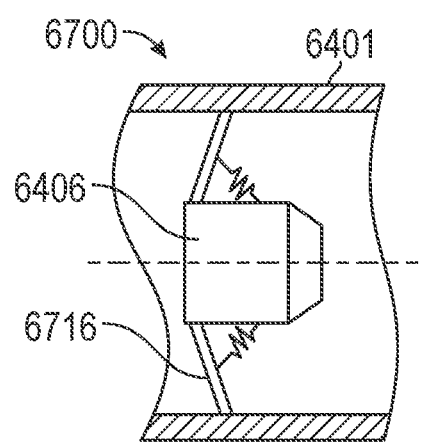
FIG. 67 illustrates generally a third example of a midfield device with multiple active elements that project laterally away from the midfield device's housing assembly.

FIGS. 65-67 illustrate generally partial views of examples of different embodiments of the fixation features 6416 as applied to the midfield device 6410. FIG. 65 illustrates generally a first example 6500 of a midfield device with multiple passive elements 6516 that project laterally away from the midfield device's housing assembly 6406. The passive elements 6516 can comprise silicone or other non-reactive material, and can be configured to hold the implantable midfield device 6410 in position with respect to the vessel wall 6401. In an example, the passive elements 6516 provide a friction-fit with the vessel wall 6401 at a location where an inner diameter of the vessel becomes small enough, or tapers, to create an interference fit. In other words, an outer dimension of the passive elements 6516 can be about the same as the vessel inner cross-section dimension (e.g., at a location where the vessel tapers), while the body of the midfield device 6410 (e.g., comprising one or more electrodes or transducers) has a smaller outer dimension so as not to restrict blood flow around the device.

FIG. 66 illustrates generally a second example 6600 of a midfield device with multiple inflatable elements 6616 that project laterally away from the midfield device's housing assembly 6406. The inflatable elements 6616 can include one or more inflatable balloons (e.g., using gas or a liquid) that are configured to hold the implantable midfield device 6410 in position with respect to the vessel wall 6401, such as when inflated to an inner diameter of the vessel wall 6401 and thereby provide an interference fit. In an example, total occlusion of the vessel by, e.g., the inflatable elements 6616, can be acceptable under some circumstances. For example, occlusion of some small veins can be tolerated, or temporary occlusion can be permitted during placement procedures, such as for intraoperative testing.

FIG. 67 illustrates generally a third example 6700 of a midfield device with multiple active elements 6716 that project laterally away from the midfield device's housing assembly 6406. In an example, the active elements 6716 include one or more spring-loaded elements that can be deployed by the implanting clinician at the time of the implant procedure. In an example, the active elements 6716 can be retracted or constrained to a minimal diameter as the device is inserted or implanted. Once located in position, the clinician can deploy the active elements 6716 (e.g., using a mechanism on the cannula or push rod) and cause the active elements 6716 to expand to the inner diameter of the vessel wall 6401 thereby providing an interference fit and fixating the midfield device 6410 in a specified location. In an example, one or more electrodes or ultrasound transducers can be coupled to or integrated with the active elements 6716 to thereby position a therapy delivery source closer to a vessel wall.

Figure 68:
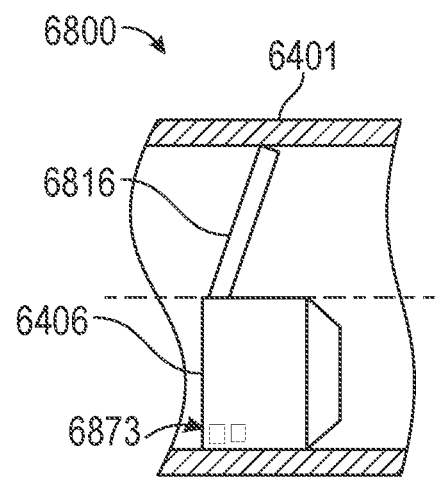
FIG. 68 illustrates generally a fourth example of a midfield device with a fixation element that projects laterally away from the midfield device's housing assembly.

FIG. 68 illustrates generally a fourth example 6800 of a midfield device with a fixation element 6816 that projects laterally away from the midfield device's housing assembly 6406. The fixation element 6816 can be configured to hold the implantable midfield device 6410 in position against the vessel wall 6401. That is, while the examples of FIGS. 64-67 generally show fixation elements that are configured to locate the midfield device 6410 centrally or coaxially with respect to the vessel, the fourth example 6800 is configured to be offset from the center or axis of the vessel. That is, the fourth example 6800 includes a fixation element 6816 that biases the midfield device's housing assembly 6406 toward one side of the blood vessel. Similar to various other embodiments, the fourth example 6800 has a smaller outer dimension than an interior diameter of the vessel wall 6401 so as not to restrict blood flow around the device.

In the example of FIG. 68, the midfield device can include an ultrasound transducer array 6873 comprising one or more ultrasound transducers. The array 6873 can be coupled to or comprise a portion of the housing assembly 6406. When the midfield device is installed in the vessel, the array 6873 can be positioned adjacent to an inner surface of the vessel wall 6401, for example to help facilitate maximum energy transfer (e.g., ultrasound energy) from the transducers to a tissue target outside of the artery. In an example, one or more of the transducers in the array 6873 can include an ultrasound energy emission surface that is directly coupled to the vessel wall 6401 when the device is installed.

Figure 69:
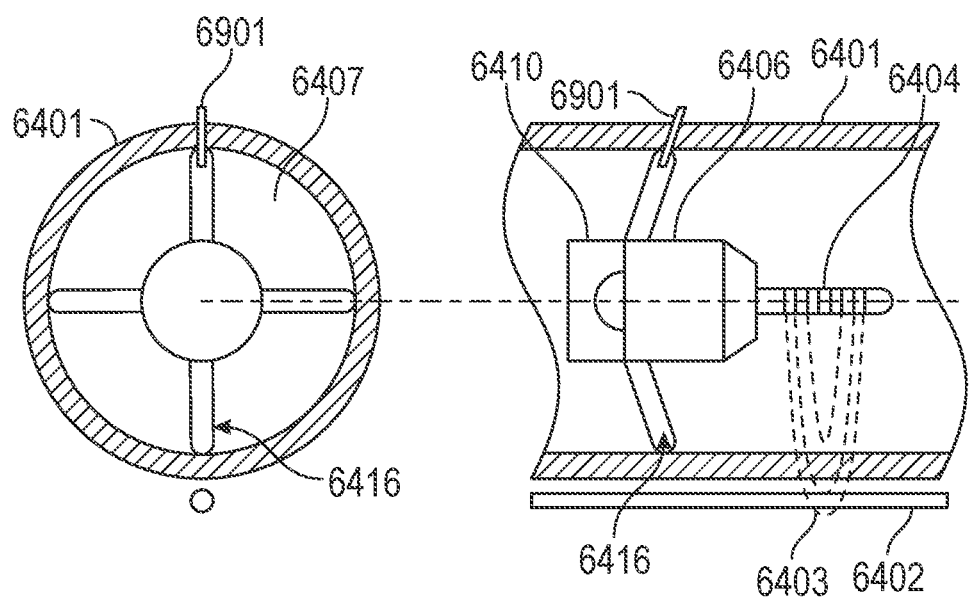
FIG. 69 illustrates generally a variation of the example midfield device from FIG. 64.

FIG. 69 illustrates generally a variation of the example device 6410 from FIG. 64. In the example 6900 of FIG. 69, at least one of the fixation features 6416 includes an electrode 6901 that is configured to penetrate the vessel wall 6401. That is, in an example, the electrode 6901 is integrated with one or more of the fixation features 6416. In another example, the electrode 6901 is a discrete electrode that is separate from the fixation features 6416. The electrode 6901 can be deployable after the device is located in position in the arterial system. In an example, the electrode 4801 includes a portion of an electrode array (e.g., a radially-extending array) provided along a portion of the midfield device 6410. In an example, the electrode 6901 can be replaced with an ultrasound transducer.

In an example, various other embodiments can include stent-based and/or spring-based systems for locating a midfield device inside a vessel. Such embodiments can have a low profile, can be constructed using biocompatible materials, and can be compatible with existing catheter-based tools and techniques.

Figure 70:
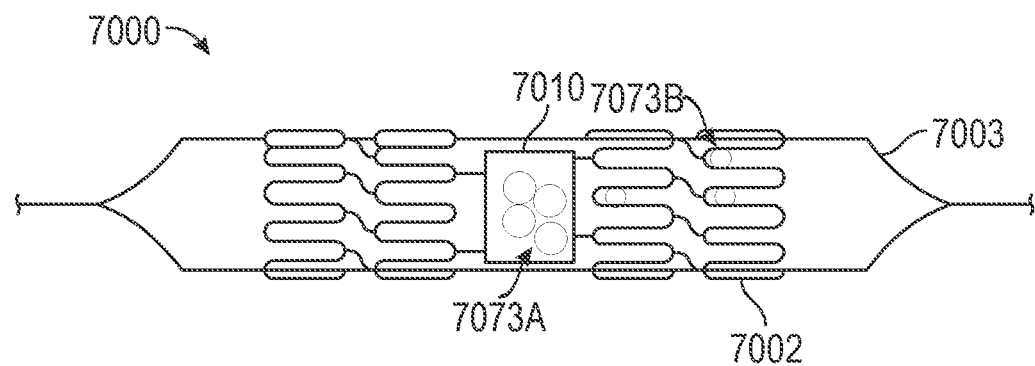
FIG. 70 illustrates generally an example of a stent-based system that can include a midfield device coupled to an expandable scaffold.

FIG. 70 illustrates generally an example of a stent-based system 7000 that can include a midfield device 7010 coupled to an expandable scaffold 7002. Although illustrated schematically in the figure by a rectangle, the midfield device 7010 can have any suitable size and shape for deployment inside a vessel. Generally, an outer hermetic housing of the midfield device 7010 has a minimal or low profile to minimize obstruction of fluid flow around or over the device, as described elsewhere herein.

The midfield device 7010 includes, or is coupled to, an antenna to receive midfield signals, such as from another implant or from a device provided externally to the patient. The midfield device 7010 can further include an energy storage element, and one or more sensors (e.g., to sense a physiologic characteristic from within the vasculature) or therapy delivery sources (e.g., to provide an electrostimulation therapy or ultrasound therapy from within, or at least partially within, the vasculature).

The system 7000 can be configured for delivery to an intravascular location using a cannula. That is, the expandable scaffold 7002 and midfield device 7010 can be configured to be pushed through a lumen of a cannula toward a distal open end of the cannula for installation inside of a vessel. After exiting the lumen, the system 7000 can be expanded, using the expandable scaffold 7002, to thereby hold the midfield device 7010 inside of the vessel, and preferably toward one side wall of the vessel, to reduce obstruction of flow through the vessel. In an example, the delivery system includes or uses a balloon 7003 to expand the scaffold 7002 after deployment from the cannula.

In an example, the expandable scaffold 7002 comprises a spring material or spring construction. In this example, the scaffold 7002 is contracted or compressed inside of the delivery lumen of the cannula but the scaffold 7002 recoils or expands automatically, such as due to shape memory of the material, upon deployment from the lumen. In an example, one or more electrodes or ultrasound transducers can be coupled to the midfield device 7010 or to the scaffold 7002.

The example of FIG. 70 includes a first ultrasound transducer array 7073A coupled to the midfield device 7010, and a second ultrasound transducer array 7073B coupled to the scaffold 7002. In an example, the transducers in the arrays 7073A and/or 7073B can be electrically coupled to drive circuitry inside the midfield device 7010. Although two arrays are illustrated, embodiments can include a single array (e.g., comprising as few as one transducer) or can include more than two arrays (e.g., comprising one or more transducers in each array). When the system 7000 is deployed inside a blood vessel, the transducers in the arrays can be positioned adjacent to, or can be coupled with, an inner surface of a wall of the blood vessel. In an example, ultrasound signals from different arrays can be used together (e.g., via constructive or destructive interference) to apply therapy to specific target tissue sites.

Figure 71:
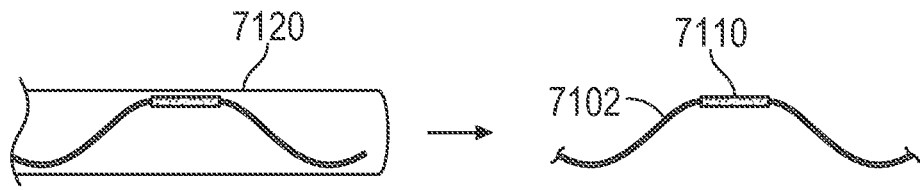
FIG. 71 illustrates generally an example of a stent-based or spring-based system that can include or use a midfield device.
Figure 72:
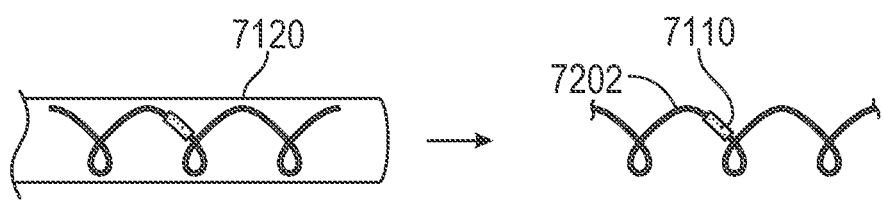
FIG. 72 illustrates generally an example of a spring-based support member coupled to a midfield device.
Figure 73:
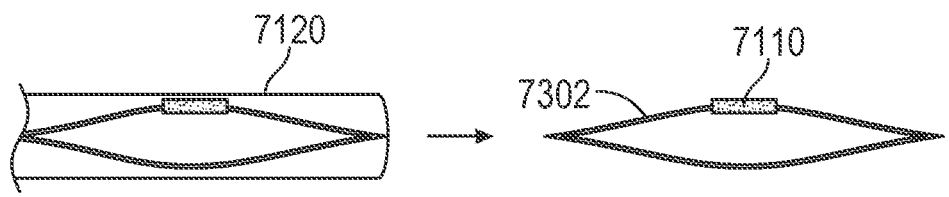
FIG. 73 illustrates generally an example of a spring-based support member coupled to a midfield device.

FIGS. 71-73 illustrate generally examples of stent-based or spring-based systems that can include or use a midfield device 7110. In the example of FIG. 71, the midfield device 7110 is coupled to a first spring support 7102. The first spring support 7102 can include at least one elongate member having a curved or wave-type shape. The midfield device 7110 can be coupled at various locations along the elongate member. In the example of FIG. 71, the midfield device 7110 is coupled at a substantially central location of the elongate member, such as near one of the member's maximum (or minimum) extents.

At left in FIG. 71, the first spring support 7102 is illustrated inside of a cannula 7120, and at right, FIG. 71 shows the first spring support 7102 deployed outside of the cannula 7120. The first spring support 7102 is compressed or contracted before deployment when it is inside of the cannula 7120. After deployment from a distal end of the cannula 7120 into a vessel, e.g., by a clinician using a push rod to slide the first spring support 7102 through the lumen of the cannula 7120, the first spring support 7102 can expand inside of the vessel and thereby force the midfield device 7110, and one or more electrodes or transducers therein, toward or against a sidewall of the vessel. Placing the midfield device 7110 toward one sidewall of the vessel can help minimize restriction of blood flow through the vessel, can help reduce blood flow turbulence around the device, and can help improve efficacy and efficiency of neural modulation.

FIGS. 72 and 73 illustrate generally other examples of spring-based support members coupled to the same or different midfield device 7110. Like the example of FIG. 71, second and third spring-based supports 7202 and 7302 in FIGS. 72 and 73, respectively, can be compressed during a deployment procedure, such as when each member is disposed inside of the cannula 7120, and can be expanded after deployment from a delivery cannula.

In the example of FIG. 72, the second spring-based support 7202 includes at least one elongate member have a coil shape. The midfield device 7110 can be coupled at various locations along the elongate member. In the example of FIG. 72, the midfield device 7110 is coupled at a substantially central location of the elongate member.

In the example of FIG. 73, the third spring-based support 7302 includes a pair of wire members arranged to form an elongated, compressible oval-shaped assembly. The midfield device 7110 can be coupled at various locations along the assembly. In the example of FIG. 73, the midfield device 7110 is coupled at a substantially central location of the assembly such that the device is pushed toward one sidewall of the vessel when the third spring-based support 7302 expands inside of a vessel.

Figure 74:
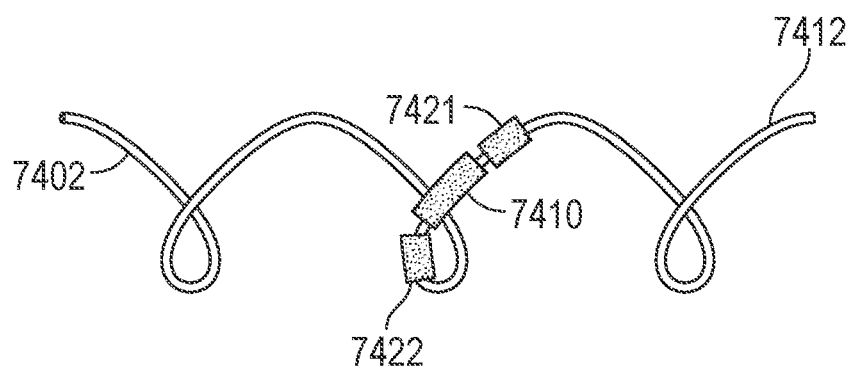
FIG. 74 illustrates generally an example of a spring-based support that includes an elongate member having a coil shape.

FIG. 74 illustrates generally an example of a fourth spring-based support 7402 that includes an elongate member having a coil shape. In the example of FIG. 74, a midfield device 7410 is coupled to the support 7402. In an example, the midfield device 7410 includes or is coupled to a portion of the support 7402 that comprises a portion of an antenna 7412 for the midfield device 7410. That is, the antenna 7412 for the midfield device 7410 can be integrated with the support 7402 or formed at least in part from the same material as the support 7402. In an example, the midfield device 7410 includes integrated electrodes, ultrasound transducers, or sensors, and in other examples, one or more therapy sources or sensors is coupled to, and located remotely from, a main housing of the midfield device 7410. In the example of FIG. 74, the midfield device 7410 includes first and second therapy signal sources 7421 and 7422 coupled to the support 7402 and spaced apart from the main housing of the midfield device 7410. The therapy signal sources can be provided in fixed locations along the support 7402 or, in some examples, their positions can be adjusted by a clinician such as before or during implantation in a vessel.

In an example, a method of using the midfield device 7410 includes receiving energy at the midfield device 7410 using the antenna 7412. At least a portion of the received energy can be used in an electrostimulation therapy or ultrasound therapy provided using the first and second therapy signal sources 7421 and 7422. In an example, one or more physiologic sensors can be coupled to the midfield device 7410, and at least a portion of the received energy can be used to power the sensor(s) and/or to process information from the sensor(s) and/or to transmit information from the sensor(s) to a remote device, such as to another implant or to an external device.

In the examples of at least FIGS. 71-74, at least some portion of the respective support members can have a helical shape configured to encourage the support members to reside near or against a vessel wall when the device is deployed. Providing the support members against a vessel wall can help promote endothelialization and minimize blood flow obstruction.

Figure 75:
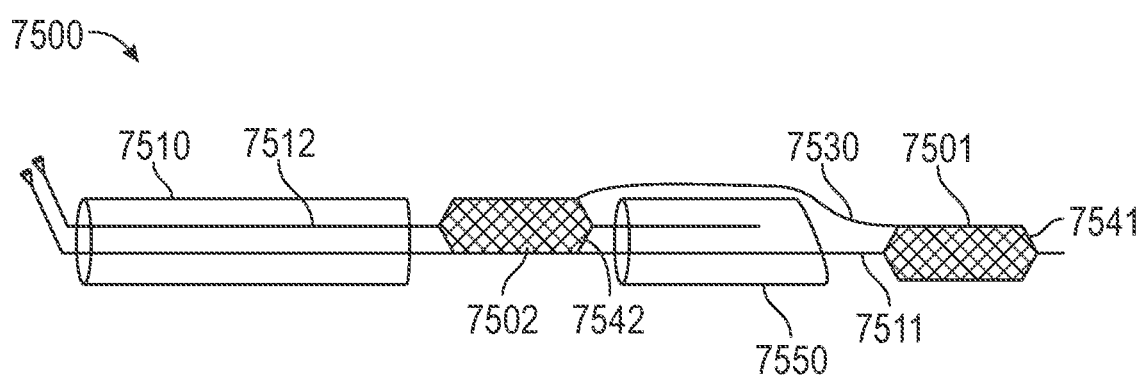
FIG. 75 illustrates generally an example of a system that can include multiple structures that are each configured for intravascular placement during a single implant procedure.

FIG. 75 illustrates generally an example of a system 7500 that can include multiple structures that are each configured for intravascular placement during a single implant procedure. The system 7500 includes a distal structure 7501 and a proximal structure 7502, and each of the distal and proximal structures 7501 and 7502, respectively, can be deployed using a common cannula 7510. In an example, the distal and proximal structures 7501 and 7502, respectively, are coupled to a common push rod. In the example of FIG. 75, the distal and proximal structures 7501 and 7502, respectively, are coupled to respective first and second push rods 7511 and 7512. In an example, each of the distal and proximal structures 7501 and 7502, respectively, includes a respective deployment device, such as a balloon.

In an example, the distal and proximal structures 7501 and 7502, respectively, are communicatively coupled, such as to provide a transmission channel for one or both of power and data between the structures. In the example of FIG. 75, the structures are coupled using a conductive lead 7530. In an example, the distal and proximal structures 7501 and 7502, respectively, are additionally or alternatively coupled using a wireless communication link.

In an example, at least one of the distal and proximal structures 7501 and 7502, respectively, includes or uses a midfield device that is coupled to a stent-based or spring-based support, such as described above in the examples of FIGS. 70-74. In an example, one of the distal and proximal structures 7501 and 7502, respectively, includes a midfield receiver, and the other of the structures includes at least one sensor or therapy signal source configured to deliver a therapy signal.

In an example, the distal and proximal structures 7501 and 7502, respectively, are expandable outside of the cannula 7510. The distal structure 7501 can have a dedicated first balloon 7541 configured to inflate and expand the distal structure 7501 when the structure is deployed from the cannula 7510. The proximal structure 7502 can similarly have a corresponding dedicated second balloon 7542. In an example, the system 7500 includes a sleeve 7550 provided between the distal and proximal structures 7501 and 7502, respectively. The sleeve 7550 can be configured to buttress or support the vessel between the structures. In an example, one or more active or passive elements (e.g., sensors and/or electrodes and/or ultrasound transducers) can be disposed on the sleeve 7550 and coupled to one or both of the distal and proximal structures 7501 and 7502, respectively.

In an example, the sleeve 7550 diameter is selected such that the assembly comprising the sleeve 7550 and distal structure 7501 advanced by the first push rod 7511 can be held firmly against the cannula 7510. In an example, as the cannula 7510 advances through vasculature (e.g., over a wire, such as is used for coronary artery stent placement), it also carries the sleeve 7550 and the distal structure 7501. The sleeve 7550 and distal structure 7501 can be deployed from the cannula 7510 using, e.g., the first push rod 7511 and the first balloon 7541. In an example, after the distal structure 7501 is deployed and the first balloon 7541 is deflated, the first push rod 7511 can be further advanced (e.g., up to several additional inches) to release the proximal structure 7502 from a sleeve of the main cannula 7510. Following this deployment, the first push rod 7511 can be withdrawn from the body entirely, and one or more sleeve portions of the main cannula 7510 can be withdrawn with it. Next, the proximal balloon 7542 can be expanded to deploy the proximal structure 7502. In another example, the first and second balloons 7541 and 7542 can be provided on a single catheter and push rod assembly, such as with separate lumens to independently inflate the balloons.

In examples that include a spring-based or stent-based support or member, the members can be configured to expand automatically after deployment from a cannula. In other examples, a balloon or other inflation or expansion device can be used together with the various members to expand them into a configuration that can chronically reside in a specified vessel location.

In an example, an implantable device is configured for deployment using a cannula lumen that extends through the vasculature. In some examples, the same or similar intraluminal delivery systems, such as used for vascular stent deployment, can be used to deploy an implantable neural stimulator as described herein.

Figure 76:
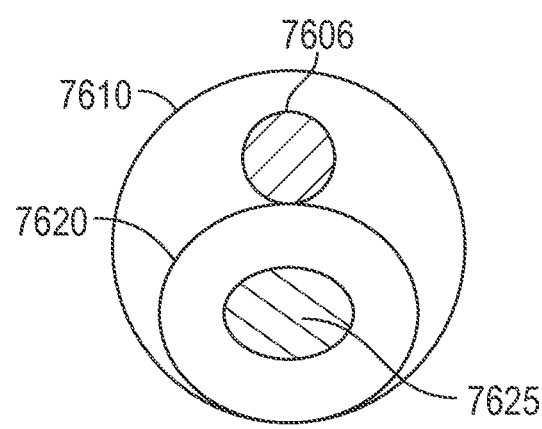
FIG. 76 illustrates generally a cross section view of a lumen that can enclose an implantable midfield device, a deployment structure, and an inflatable balloon.

FIG. 76 illustrates generally a cross section view of a lumen 7610 that can enclose an implantable device 7606 such as can include or use a midfield device, a deployment structure 7620, and an inflatable balloon 7625. The implantable device 7606 can be configured for intravascular deployment using the lumen 7610. In an example, the implantable device 7606 can be coupled to, or provided adjacent to, the deployment structure 7620 inside of the lumen 7610. The implantable device 7606 can be configured to ride on an outside portion of the deployment structure 7620 as it slides inside of the lumen 7610. In other examples, the implantable device 7606 can be configured to ride within the deployment structure 7620 (e.g., encircled or enclosed at least partially by the deployment structure 7620), such as displacing a portion of the balloon 7625.

Figure 77:
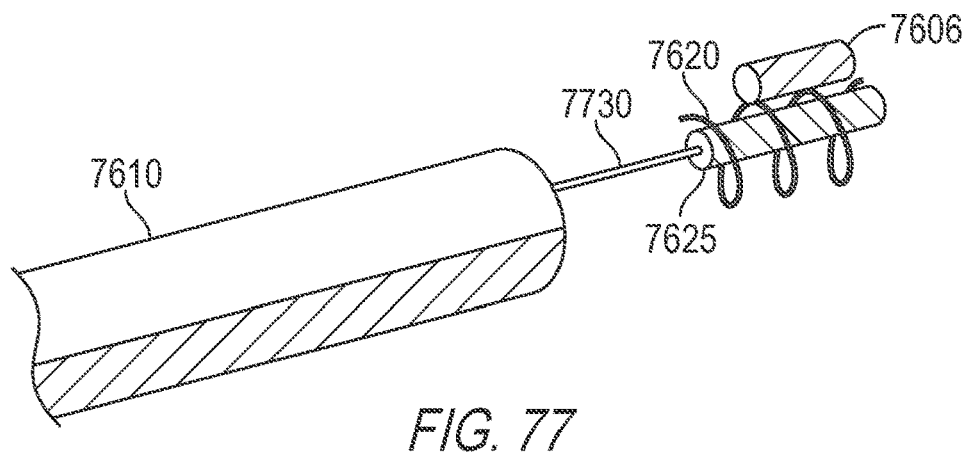
FIG. 77 illustrates generally a perspective view of an implantable device and deployment structure provided outside of a distal end of a lumen.

FIG. 77 illustrates generally a perspective view of the implantable device 7606 and deployment structure 7620 provided outside of a distal end of the lumen 7610. In an example, a push rod 7730 operable by a clinician can be used to adjust a location of the implantable device 7606 and deployment structure 7620 in the vasculature at implant. Although illustrated in FIG. 77 as having a coil or spring shape, the deployment structure 7620 can be any biocompatible structure configured to retain the implantable device 7606 in a substantially chronic position within a vessel.

Figure 78:
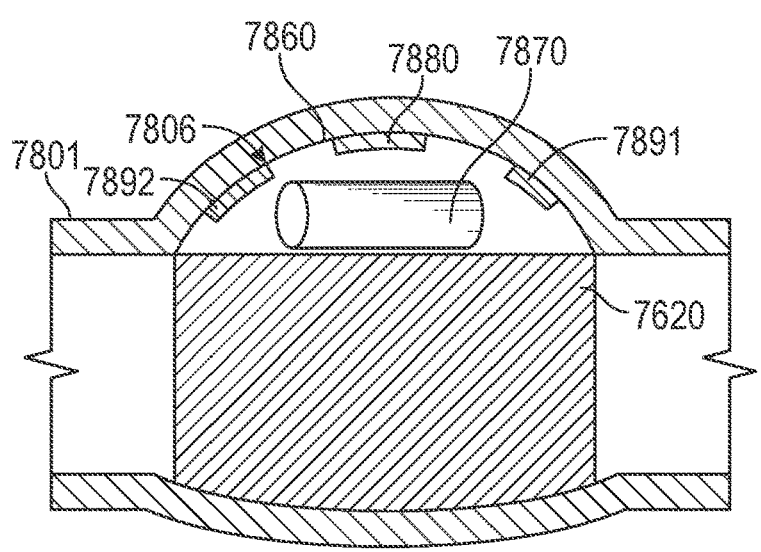
FIG. 78 illustrates generally an example of an implantable device installed in a vessel.

FIG. 78 illustrates generally an example of an implantable device 7806 installed in a vessel having a vessel wall 7801. The deployment structure 7620 is represented schematically and can have any suitable construction or configuration to encourage chronic placement of the implantable device 7806 against the vessel wall 7801.

In an example, the implantable device 7806 is a midfield device configured to receive and use energy received wirelessly using midfield signals. For example, the midfield device can include an antenna configured to receive energy from a propagating field inside of body tissue. The implantable device 7806 can include a device housing 7860, such as can include a hermetic or otherwise sealed housing structure, and various circuitry, or a hermetically sealed electronics module 7870, disposed inside of the device housing 7860. In an example, the electronics module 7870 includes one or more of a power storage circuit, a processor circuit, a memory circuit, or other circuit, as similarly described elsewhere. In an example, the electronics module 7870 comprises a hermetic, cylindrical electronics housing to minimize its cross-sectional area. The cylindrical housing can be mounted or suspended in a biocompatible resin or epoxy with smoothed outer edges, such as to make the implantable package more streamlined and to reduce irritation to adjacent vessel walls. Other hermetic and non-cylindrical housing shapes can similarly be used.

In an example, the implantable device 7806 includes an antenna 7880 provided inside of the device housing 7860 but outside of the hermetically sealed electronics module 7870. In an example, the implantable device 7806 includes at least one and preferably at least two therapy signal sources 7891 and 7892 provided at or near an outer-facing surface of the device housing 7860. That is, the therapy signal sources 7891 and 7892 can be configured to face outward toward the vessel wall 7801 when the implantable device 7806 is installed using the deployment structure 7620. When properly installed, the therapy signal sources 7891 and 7892 can contact the vessel wall 7801 to minimize signal transmission or shorting that can occur through the blood inside the vessel. Various features can be incorporated with the implantable device 7806 and/or therapy signal sources 7891 and 7892 to help encourage the sources to maintain contact with (or maintain a specified separation distance from) the vessel walls. Some examples are shown in FIGS. 80 and 81 and are discussed below.

In the example of FIG. 78, the implantable device 7806 and deployment structure 7620 are configured to expand at least a portion of the vessel wall 7801, such as on one side of the vessel, and thus cause the vessel wall to distend or bulge slightly. By providing the implantable device 7806 in a bulged portion of the vessel, a central open area of the vessel can be provided to maintain blood flow therethrough.

Figure 79:
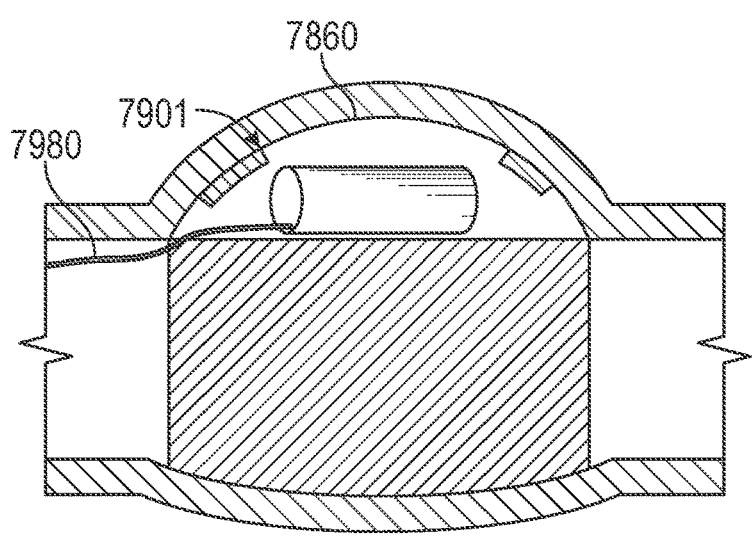
FIG. 79 illustrates generally an example of an implantable device that includes a device housing and an antenna that can extend outside of the housing.

FIG. 79 illustrates generally an example of a second implantable device 7901 configured similarly to the implantable device 7606 and/or 7806 but including an antenna 7980 that can extend outside of the device housing 7860. For example, the antenna 7980 can be a rigid or flexible structure that can reside inside the vessel after implant. Since the antenna 7980 is not constrained to being inside of, or contained within the device housing 7860, the antenna 7980 can be substantially longer or larger than the housing portion of the implant.

Figure 80:
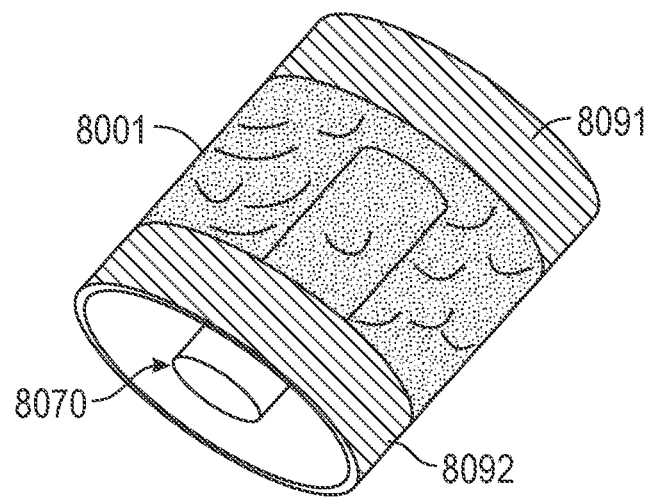
FIG. 80 illustrates generally a perspective view of an example of a first therapy signal source assembly coupled to an electronics module for an intravascular implantable device.
Figure 81:
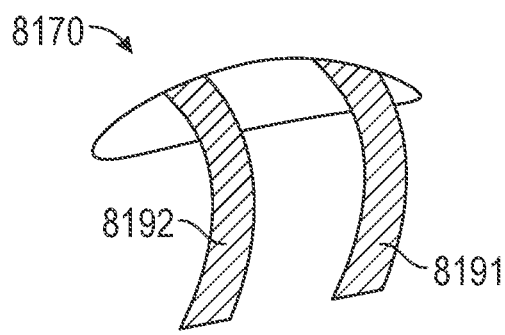
FIG. 81 illustrates generally a perspective view of an example of a second therapy signal source assembly coupled to an electronics module for an intravascular implantable device.

FIG. 80 illustrates generally a perspective view of an example of a first therapy signal source assembly coupled to a hermetically sealed electronics module 8070 for an intravascular implantable device. The therapy signal source assembly is configured to encourage contact between a vessel wall and one or more electrodes or transducers. In an example, the therapy signal source assembly includes a curved surface with one or more transducers or discrete conductive areas or electrodes coupled thereto. In an example, the curved surface can be selected to match a curvature of an interior vessel wall, or the surface can be flexible and can conform to a wall curvature. In examples with two or more signal sources, a non-conductive portion of the curved surface can be provided between the electrodes. In the example of FIG. 80, first and second therapy signal sources 8091 and 8092 can be provided at opposite sides of a membrane 8001 that separates the sources. The membrane 8001 can comprise various biocompatible materials and can be solid, barbed, or perforated. In an example, the membrane 8001 has a regular or irregular honeycomb configuration that helps the implant maintain chronic placement in a vessel and can, in some examples, integrate itself with the vessel wall. The membrane 8001 can help reduce or minimize signal shunting between the first and second sources 8091 and 8092, such as by redirecting energy through the adjacent vessel wall and toward a neural target.

FIG. 81 illustrates generally a perspective view of an example of a second therapy signal source assembly coupled to a hermetically sealed electronics module 8170 for an intravascular implantable device. The electronics module 8170 is coupled to first and second therapy signal sources 8191 and 8192 that have an arcuate shape and extend laterally relative to a body portion of the electronics module 8170. The example of FIG. 81 is similar to that of FIG. 80 but without the membrane 8001 between the electrodes 8191 and 8192.

Figure 82:
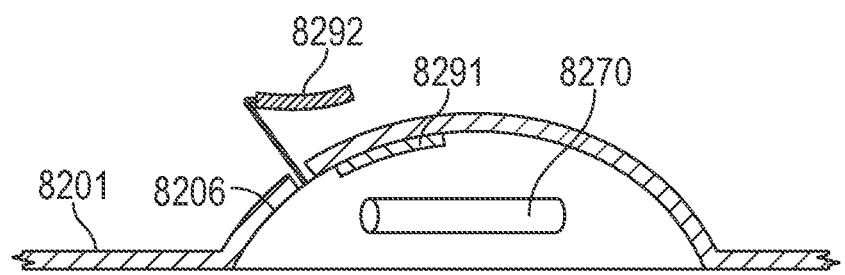
FIG. 82 illustrates generally an example of an intravascular implantable device.

FIG. 82 illustrates generally an example of an intravascular implantable device 8206. The example of FIG. 82 includes a hermetic device housing that encapsulates a hermetically sealed electronics module 8270. The implantable device 8206 can include a first therapy signal source 8291 coupled to the electronics module 8270 and disposed on an outer-facing surface of the housing. In an example, the implantable device 8206 includes a second therapy signal source 8292 provided on a deployment mechanism that can be configured to pierce a vessel wall. In an example, the second therapy signal source 8292 is located outside of the vessel and therefore can be provided closer to a therapy target, and can thus be used to deliver a therapy (or sense a physiologic parameter) such as without adverse effects such as due to a vessel wall being between the signal source and the target.

Figure 83:
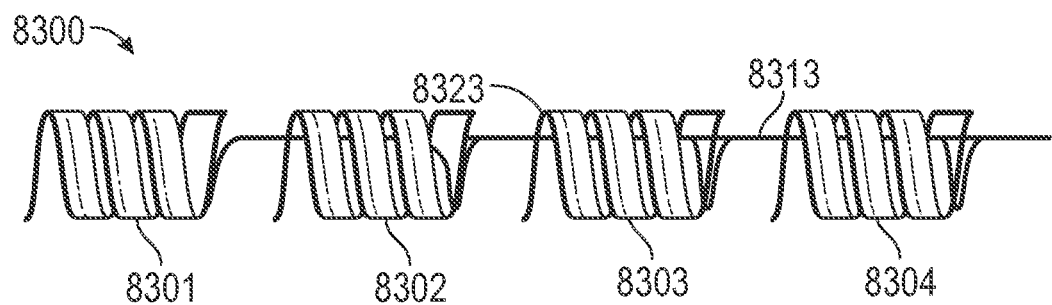
FIG. 83 illustrates generally a side view of an intravascular implantable device.

FIG. 83 illustrates generally a side view of an intravascular implantable device 8300. In an example, a midfield device can be implanted or installed and configured to deliver electrostimulation to a neural target using one or more portions of the device 8300. In an example, the device 8300 can be implanted or installed at least partially in the vascular system of a patient. For example, the device 8300 can be implanted or installed in an artery. The device 8300 can include one or more discrete therapy signal source and/or support portions. In the example of FIG. 83, the device 8300 includes first, second, third, and fourth portions 8301, 8302, 8303, and 8304, respectively. Each of the first through fourth portions 8301-8304 can include or use an electrode, an ultrasound transducer, and/or a support for a portion of a midfield device.

In the example of FIG. 83, the third portion 8303 includes a coiled support. The coiled support can include an elongated, substantially flat and optionally continuous material that is wound or coiled to a specified diameter. One or more portions of the coiled support can be conductive and can be coupled to a midfield device for use in physiologic parameter sensing or stimulation. That is, one or more portions of the coiled support can include or use an electrode or an ultrasound transducer. The coil diameter can be adjusted, such as at a time of implant or explant. The coil stiffness or material can be selected based on the particular application of the device 8300. For example, different materials can be used for renal applications and cardiac applications. The third portion 8303 can include a first therapy signal source 8323 that can be coupled to or supported by the coiled support. The first therapy signal source 8323 can be coupled to a midfield device and can be used for electrostimulation or ultrasound stimulation or physiologic parameter sensing together with drive or sense electronics included in the midfield device.

The example of FIG. 83 as illustrated includes four discrete portions; additional or fewer portions can be used, such as to provide a multi-polar stimulation or sensing device. A coupling wire 8313 can be used to couple adjacent ones of the portions of the implantable device 8300. In an example, the coupling wire 8313 is a series connection between adjacent portions of the device, and in other examples, different coupling wires can extend in parallel from each of the first through fourth portions 8301-8304 to another portion of a midfield device.

Figure 84:
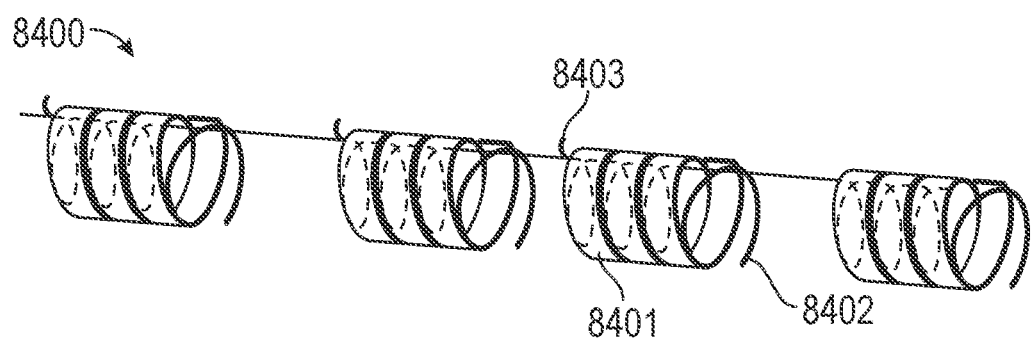
FIG. 84 illustrates generally a perspective view of a second intravascular implantable device.

FIG. 84 illustrates generally a perspective view of a second intravascular implantable device 8400. The second intravascular implantable device 8400 can include a coiled portion and one or more discrete support and/or therapy signal source portions as similarly described above in the example of FIG. 83.

The second intravascular implantable device 8400 includes a first portion 6301 with a coiled support, and one or more portions of the support can be conductive and/or configured for use as an electrode or transducer. In an example, the first portion 8401 includes a discrete electrode extension 8402. The electrode extension 8402 can be curved to follow an inner wall shape of a vessel in which the device 8400 is installed. In an example, the first portion 8401 includes one or more tines, such as a first tine 8403. The first tine 8403 can extend orthogonally to a longitudinal axis of the coiled support. In an example, the first tine 8403 is configured to impinge on or pierce an interior vessel wall. The first tine 8403 can thus be used to anchor or fixate the implantable device 8400 at a particular specified location within a patient's vasculature. In an example, the first tine 8403 includes one or more conductive portions and can be used as an electrode when coupled to a midfield device.

Figure 85:
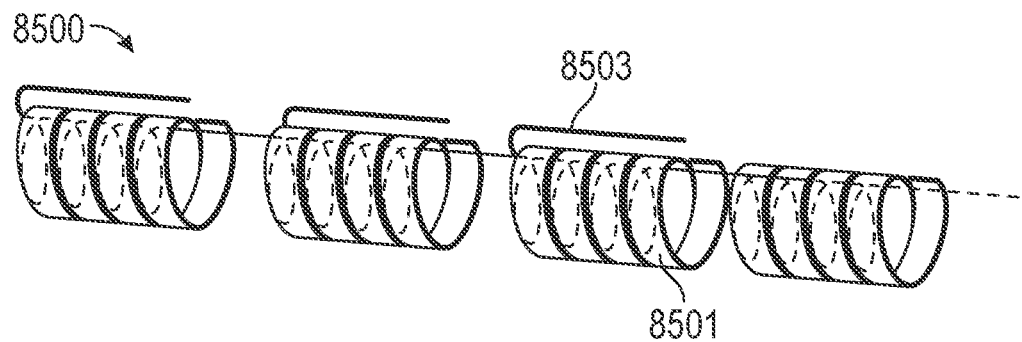
FIG. 85 illustrates generally a perspective view of a third intravascular implantable device.

FIG. 85 illustrates generally a perspective view of a third intravascular implantable device 8500. The third intravascular implantable device 8500 can include a coiled portion and one or more discrete support and/or therapy signal source portions as similarly described above in the examples of FIGS. 84 and/or 85. In the example of FIG. 85, a first portion 8501 of the device 8500 includes an extension member 8503. In an example, the extension member 8503 extends substantially parallel to an axis of the third device's coiled support. The extension member 8503 can be configured to be deployed outside of a vessel wall, such as adjacent to the first portion 8501 of the device 8500. The extension member 8503 can help anchor or fixate the implantable device 8500 at a particular specified location within a patient's vasculature. In an example, the extension member 8503 includes one or more conductive portions and can be used as an electrode when coupled to a midfield device.

Figure 86:
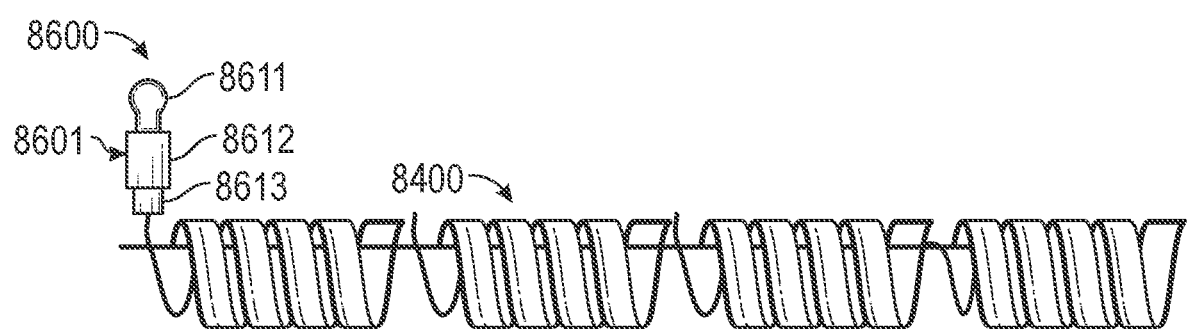
FIG. 86 illustrates generally an example of a midfield device coupled to an intravascular implantable device.

FIG. 86 illustrates generally an example 8600 of a midfield device 8601 coupled to the intravascular implantable device 8400. The midfield device 8601 can include an antenna 8611 configured to receive wireless midfield power and/or data signals, and a body portion 8612 that encloses telemetry, processing, and drive circuits, as similarly described elsewhere herein for implantable midfield devices.

The midfield device 8601 can further include an interconnect portion 8613 configured to be coupled to one or more electrodes or transducers deployed in a vessel. The midfield device 8601 can, in an example, receive a wireless power signal and, in response, use one or more therapy signal sources on the implantable device 8400 to provide a therapy or to sense a physiologic parameter from a patient. In the example of FIG. 86, the midfield device 8601 is coupled to each portion of the implantable device 8400 using a serial connection. That is, a common conductor couples each portion of the four illustrated portions of the device 8400 to the midfield device 8601. In other examples, a parallel connection can be used, such as to provide separate signals from the midfield device 8601 to the different discrete portions of the device 8400.

Figure 87:
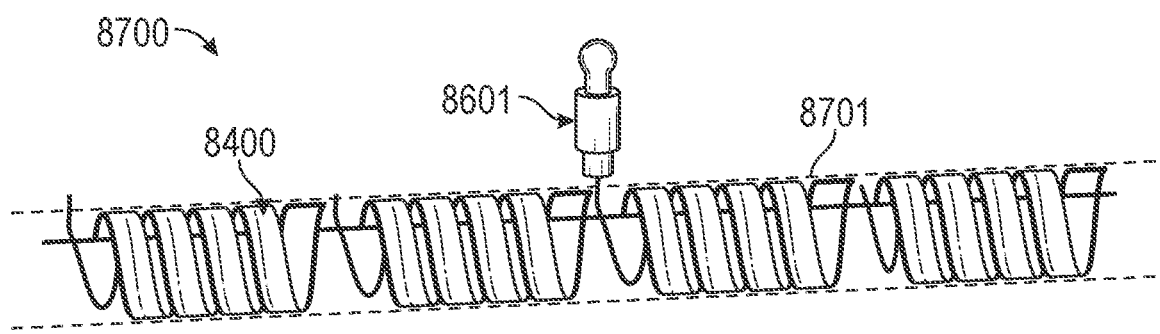
FIG. 87 illustrates generally an example of a midfield device coupled to the intravascular implantable device inside of a vessel.

FIG. 87 illustrates generally an example 8700 of the midfield device 8601 coupled to the intravascular implantable device 6300 inside of a vessel. The vessel walls 8701 are indicated by dashed lines. The coiled portions of the device 8400 abut or contact the vessel walls 8701. In the example of FIG. 87, tines from the device 8400 pierce the vessel walls 8701 at each of the different discrete coiled portions of the device 8400. As explained above, the tines can be used to fixate the device 8400 inside of the vessel, and/or the tines can include one or more conductive portions or electrodes for sensing a physiologic parameter or providing an electrostimulation to the patient. The various electrodes or other therapy signal sources can be separately or commonly addressed by drive circuitry inside the midfield device 8601. In the example of FIG. 87, the midfield device 8601 is coupled to a central portion of the intravascular implantable device 8400, with conductors extending from the central portion of the device 8400 to the distal portions of the device 8400 to either side of the midfield device 8601.

Any one or more of the fixation features described herein can include a contingency (device, feature, mechanism, etc.) to pull backwards, to deflate, or to contract the device to a smaller diameter to allow for retrieval, explant (e.g., through the same vessel implant path), and/or adjustment of a placement of the various intravascular devices described herein.

Although the preceding discussion was generally directed to midfield-powered therapy delivery devices that are configured for renal nerve stimulation, the midfield-powered therapy delivery devices and features discussed herein can be deployed in other blood vessels or body locations. That is, the systems and methods discussed herein can be used to provide electrostimulation or ultrasound-based therapy to targets throughout the body, such as by locating chronically placed implantable devices in the vasculature at or near a particular target. In addition to renal system targets, other targets accessible from the vasculature can include a patient's phrenic nerves, splanchnic nerves, genital nerves, vagus nerve, or various receptors or targets in the gastrointestinal tract.

In an example, a midfield device can be deployed in a vessel that is in or near a patient's brain. Such a device can be configured to deliver electrostimulation to a neural brain target or can be configured to sense brain activity. In an example, a midfield sensor device can record or archive measured neural activity information and report the information, in real-time or otherwise, to an external device, such as using midfield or other communication techniques.

Neuromodulation for Pain and Inflammation

This section generally relates to neuromodulation for pain and inflammation management. Conventional waveforms for pain operate to treat an indicator of pain, but do not help to treat the underlying cause of the pain. Conventional therapy for pain indications follow typical spinal-cord stimulation paradigms. These conventional pain treatment waveforms can include (a) continuous, tonic stimulation, (b) continuous, high frequency stimulation, or (c) continuous, burst stimulation. The primary mechanisms of action for the conventional waveforms include blocking afferent sensory pain activity or a central nervous system mediated adjustment of pain thresholds.

Embodiments can include devices, methods, and systems for pain and inflammation management. Inflammation management can be provided through stimulation of a dorsal root, or other part of a nerve. The devices, systems, and methods can include neuromodulation of a nerve target. A waveform of the neuromodulation signal can be improved relative to conventional or other prior neuromodulation waveforms. The waveform of neuromodulation can include a portion that reduces or eliminates pain and another portion of the waveform can reduce or eliminate inflammation. By reducing inflammation, a cause of the pain can be reduced for a longer-term solution to the pain. This longer-term solution can help a user no longer need neuromodulation therapy.

Midfield powering technology can provide power to an implanted electrostimulation device from an external power source located on or near a tissue surface, such as at an external surface of a user's skin. The user can be a clinical patient or other user. The midfield powering technology can have one or more advantages over implantable pulse generators. For example, a pulse generator can have one or more relatively large, implanted batteries and/or one or more lead systems. Midfield devices, in contrast, can include relatively small battery cells that can be configured to receive and store relatively small amounts of power. A midfield device can include one or more electrodes integrated in a unitary implantable package. The midfield devices thus do not include a lead that extends from its implant site in the body external to the body. Thus, in some examples, a midfield-powered device can provide a simpler implant procedure over other conventional devices, which can lead to a lower cost and a lower risk of infection or other implant complications. One or more of the advantages can be from an amount of power transferred to the implanted device. The ability to focus the energy from the midfield device can allow for an increase in the amount of power transferred to the implanted device. Implant procedures discussed herein can be used with lead devices, leadless devices, near field stimulation devices, far field stimulation devices, or midfield stimulation devices.

Figure 88:
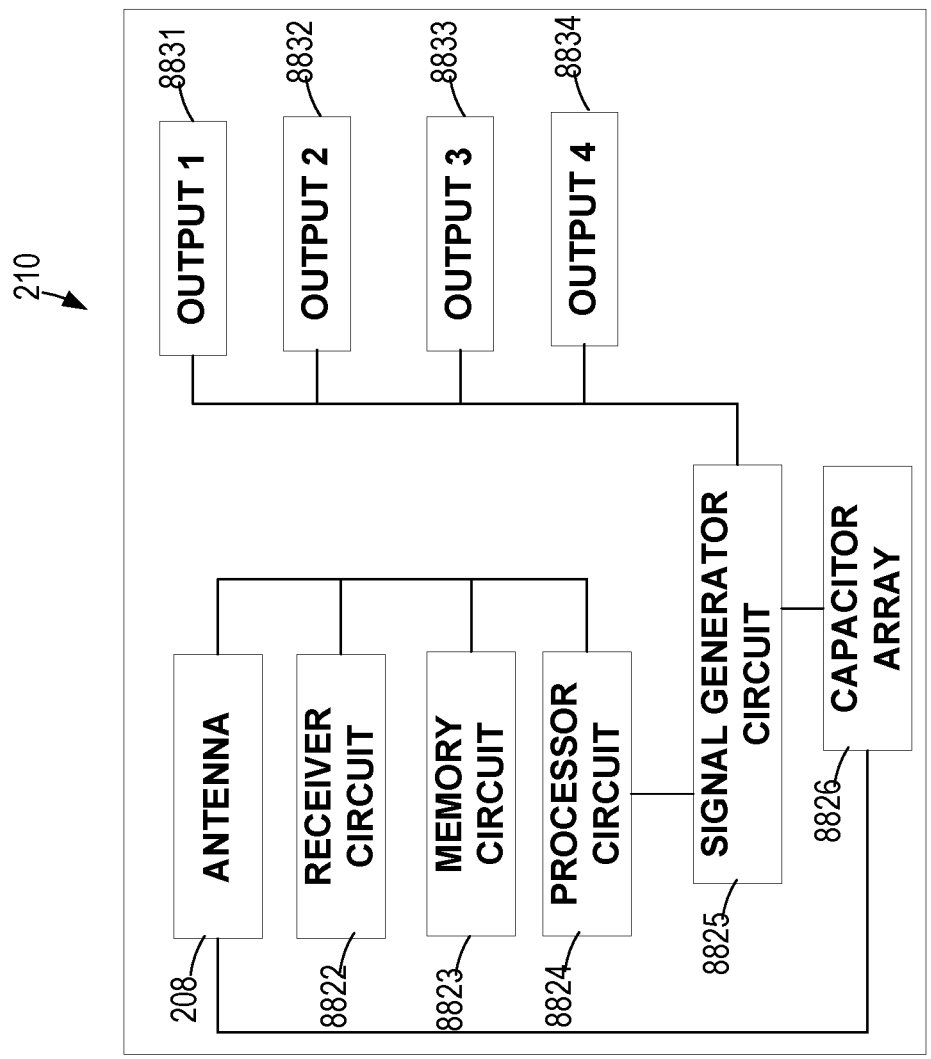
FIG. 88 illustrates, by way of example, a schematic of a multi-polar therapy delivery device.

FIG. 2, as previously discussed, illustrates a schematic of an embodiment of a system 200 using wireless communication paths. The following discussion makes reference to components of FIG. 2. FIG. 88 illustrates, by way of example, a schematic of a multi-polar therapy delivery device, such as the device 210 of FIG. 2. In an example, the device 210 includes an antenna 208, such as a dipole antenna, such as can be configured to receive power or data communication signals from the source 202. The device 210 can include a receiver circuit 8822, such as coupled to the antenna 208. The receiver circuit 8822 can receive or interpret one or more signals received via the antenna 208.

In an example, the device 210 includes a processor circuit 8824 and a memory circuit 8823. The processor circuit 8824 can be configured to act in coordination with the receiver circuit 8822 to receive power or data signals from the source 202 and direct the signals to one or more of the memory circuit 8823, a signal generator circuit 8825, or a capacitor array 8826.

In an example, the signal generator circuit 8825 is configured to use power signals wirelessly received via the antenna 208 to generate a therapy signal, such as a neural electrostimulation or modulation signal. The therapy signal can include an AC signal having one or more adjustable characteristics. The one or more adjustable characteristics can include a waveform morphology shape, amplitude, phase, frequency, pulse width, timing, or other characteristic. In an example, the signal generator circuit 8825 is coupled to the capacitor array 8826, and the capacitor array 8826 stores electrostimulation energy from the signal generator circuit 8825, and one or more of the signal generator circuit 8825 or the processor circuit 8824 can selectively discharge stored electrostimulation energy, for example, to provide a therapy via one or more outputs of the device 210.

The device 210, as illustrated, includes multiple outputs. Each output can include output circuitry or other hardware configured to provide an electrostimulation signal to a target. In an example, the device 210 includes a first output 8831 that includes, among other things, an output stage of a therapy signal amplifier or a hardware coupler for coupling the first output 8831 to a therapy delivery electrode. The device 210 in the example of FIG. 88 includes second, third, and fourth outputs 8832, 8833, and 8834, such as can each be similarly configured to the first output 8831.

In an example, the signal generator circuit 8825 can provide time delivery of electrostimulation signals via one or more of the first, second, third, and fourth outputs 8831-8834. For example, the signal generator circuit 8825 can provide different electrostimulation signals to one or more of the outputs 8831-8834 in a serial or parallel manner. That is, in an example, the signal generator circuit 8825 can be configured to provide different, discrete electrostimulation signals from each of at least two of the first through fourth outputs 8831-8834 in turn, such as one following another in time. In an example, the signal generator circuit 8825 can be configured to provide different, discrete electrostimulation signals from each of at least two of the first through fourth outputs 8831-8834 concurrently, such as at least partially overlapping in time.

In an example, the processor circuit 8824 and/or signal generator circuit 8825 comprise portions of a state machine device. The state machine device can be configured to wirelessly receive power and data signals via the antenna 208 and, in response, release or provide an electrostimulation signal via one or more of the first-fourth outputs 8831-8834. In an example, such a state machine device needs not retain information about available electrostimulation settings or vectors, and instead the state machine device carries out or provides electrostimulation events substantially immediately after, and in response to, receipt of instructions from the wireless transmitter.

For example, the state machine device can be configured to receive an instruction to deliver a neural electrostimulation therapy signal, such as at a specified time or having some specified signal characteristic (e.g., amplitude, duration, etc.), and the state machine device can respond by initiating or delivering the therapy signal. At a subsequent time, the device can receive a subsequent instruction to terminate the therapy, to change a signal characteristic, or to perform some other task. Thus, the device 210 can optionally be configured to be substantially passive, or responsive to contemporaneously-received instructions.

The midfield antenna 208 can be configured to provide a midfield excitation signal, such as can include RF signals having a non-negligible H-field component that is substantially parallel to an external tissue surface. In one or more embodiments, the RF signals can be adapted or selected to manipulate an evanescent field at or near a tissue surface, such as to transmit a power and/or data signal to respective different target devices (e.g., the implantable device 210) implanted in tissue.

Figure 89:
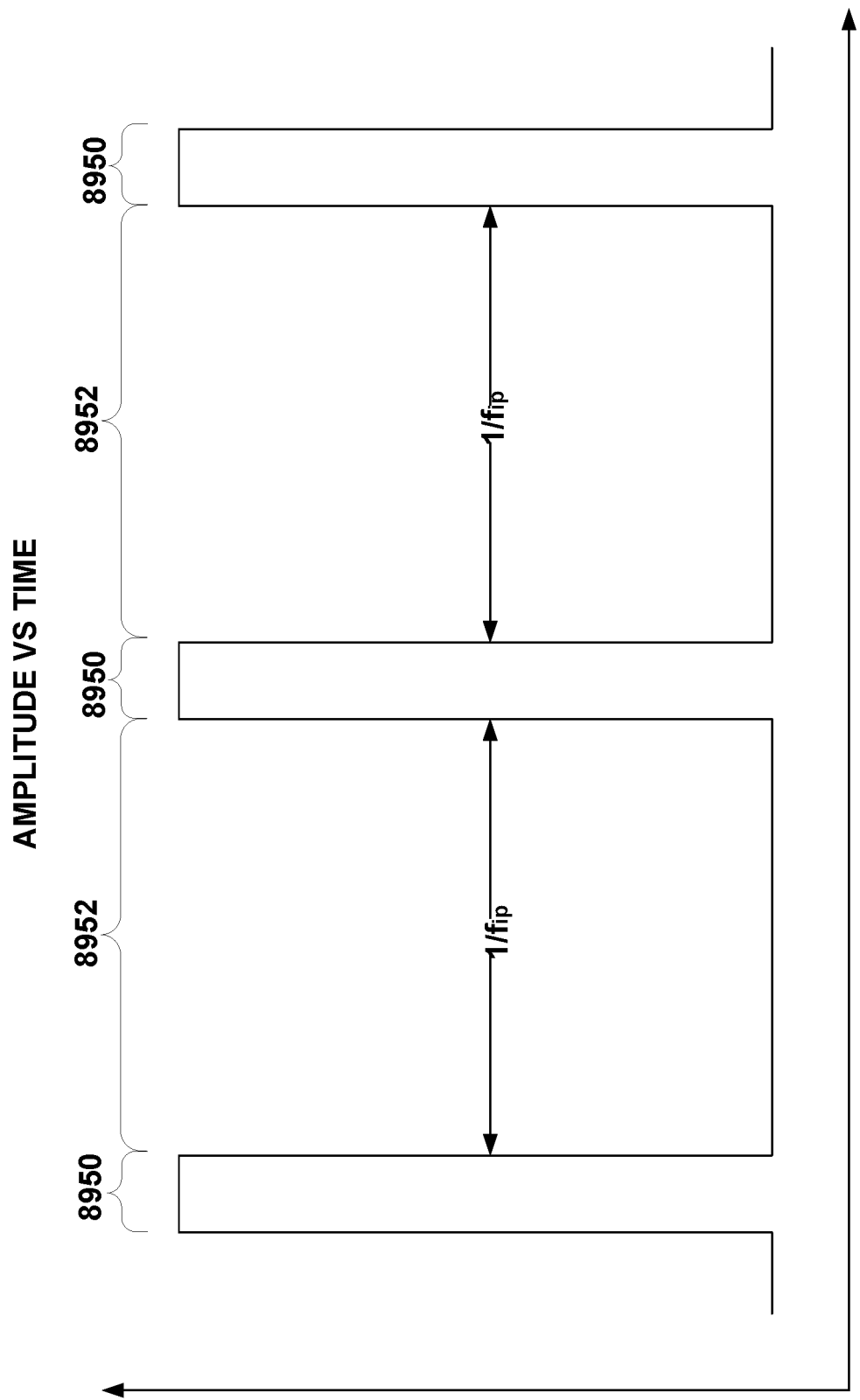
FIG. 89 illustrates an example of a stimulation waveform generated by an implantable device to control pain.

FIG. 89 illustrates an example of a common waveform generated by an implantable device to control pain. The waveform of FIG. 89 is a conventional waveform for controlling pain. The waveform includes periods of stimulation 8950 and inter-stimulation rests 8952. The time between stimulation 8950 is defined by a frequency at which the stimulation 8950 is performed. The time between stimulations can be determined as 1/f where f is the frequency of the stimulation 8950. The frequency in this context, is different from the frequency of the stimulation 8950 itself. Herein, $f_{ip}$, will be used as the interpulse frequency, and $f_{stim}$, will be used as the frequency of the stimulation 8950. Thus, $1/f_{ip}$ is the duration of the inter-stimulation rests of the stimulation 8950 and the pulse duration of a pulse of the stimulation 8950.

In some conventional stimulation therapy, $f_{ip}$ is less than 100 Hertz (Hz). Such therapy is called low frequency tonic stimulation. In other conventional stimulation therapy, $f_{ip}$ is greater than 2 kHz and less than 10 kHz. Such therapy is called high frequency tonic stimulation. In yet other conventional stimulation therapy, $f_{ip}$ is about 10 kHz. Such therapy is called high frequency stimulation.

The stimulation 8950 can include a burst of pulses for a specified duration of time. The number of pulses in the burst is variable and depends on the application or treatment.

The waveform of FIG. 89 can be useful for treating pain. As discussed elsewhere herein, pain treatment waveforms can include continuous, tonic stimulation, continuous, high frequency stimulation, or continuous, burst stimulation. The primary mechanisms of action for stimulation according to such waveforms can include blocking afferent sensory pain activity or a central nervous system mediated adjustment of pain thresholds.

Figure 90:
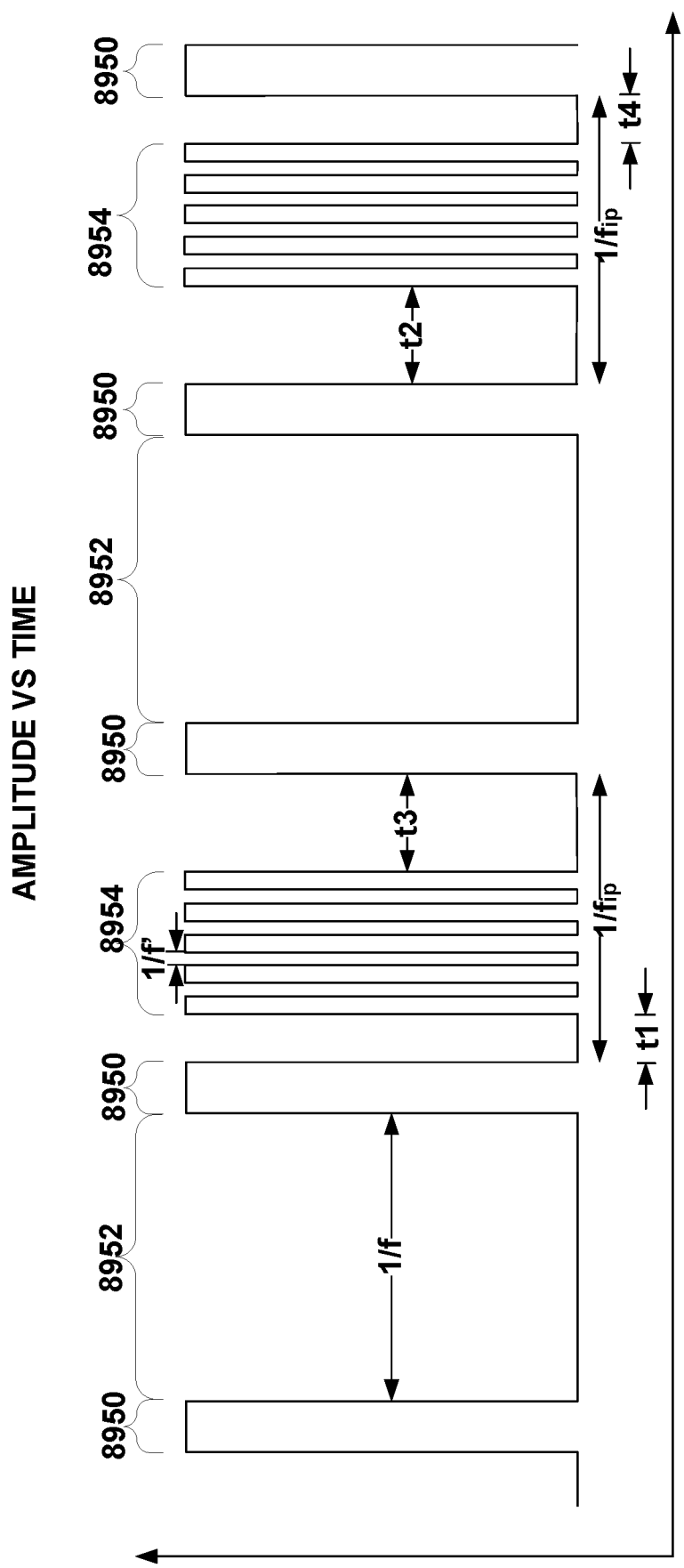
FIG. 90 illustrates an example of a stimulation waveform for treating pain and/or inflammation.

FIG. 90 illustrates an example of a waveform for treating pain and inflammation. The waveform of FIG. 90 includes the typical waveform discussed with additional neurostimulation in one or more of the inter-stimulation rests 8952 that would normally not include neurostimulation (see FIG. 89). This additional neurostimulation is called inflammation stimulation 8954. The time, t1, t2, before the inflammation stimulation 8954 starts (and after the stimulation 8950 ends) can be variable. In some embodiments, the time before the inflammation stimulation 8954 starts can be determined using a pseudorandom number generator (PNG) (e.g., implemented by the processor circuit 8824).

The number of pulses provided in the inflammation stimulation 8954 can be variable or static. The number of pulses can include be determined based on the inter-stimulation time (1/f) and a frequency of the inflammation stimulation 8954. For example, with a pain stimulation frequency, f, of about 0.5 Hz to about 30 Hz, the inflammation stimulation 8954 can include a neurostimulation pulses from about 250 Hz to about 500 Hz. In some embodiments, the number of pulses can be a pseudorandom number within a range of integers (for integers greater than one). In some embodiments, an amplitude of a pulse can be varied based on a pseudorandom number within a range of values (continuous values, as opposed to integer values).

A pseudorandom number can be generated using a pseudorandom number generator (PNG). The pseudorandom number can be mapped to a value within the range of values. In this way, the pseudorandom number can be used to determine an amplitude, frequency, number of pulses, time between pulses, time between tonic and inflammation stimulation, or the like.

Note that the inflammation stimulation 8954 does not have to occur in every inter-stimulation rest 8952. The inflammation stimulation 8954 can occur in every inter-stimulation rest 8952, every other inter-stimulation rest 8952, every third inter-stimulation rest 8952, every fourth inter-stimulation rest 8952, etc., or can occur randomly. A first inflammation stimulation 8954 can occur after one or more inter-stimulation rests 8952, called a first number of inter-stimulation rests 8952 (e.g., including one or more rests or blanking periods), and a second, immediately subsequent inflammation stimulation 8954 can occur after a second number of inter-stimulation rests 8952 that is different than the first number of inter-stimulation rests (e.g., including one or more rests or blanking periods). The number of inter-stimulation rests 8952 between inflammation stimulations 8954 can be determined by a PNG.

A user can have an option to request the inflammation stimulation 8954, such as by toggling or selecting a control of the source 202, providing a communication to the source 202 such as by a user device, or the like. The source 202 can then cause the device 210 to generate inflammation stimulation 8954 in the next or another subsequent inter-stimulation rest 8952.

Figure 91:
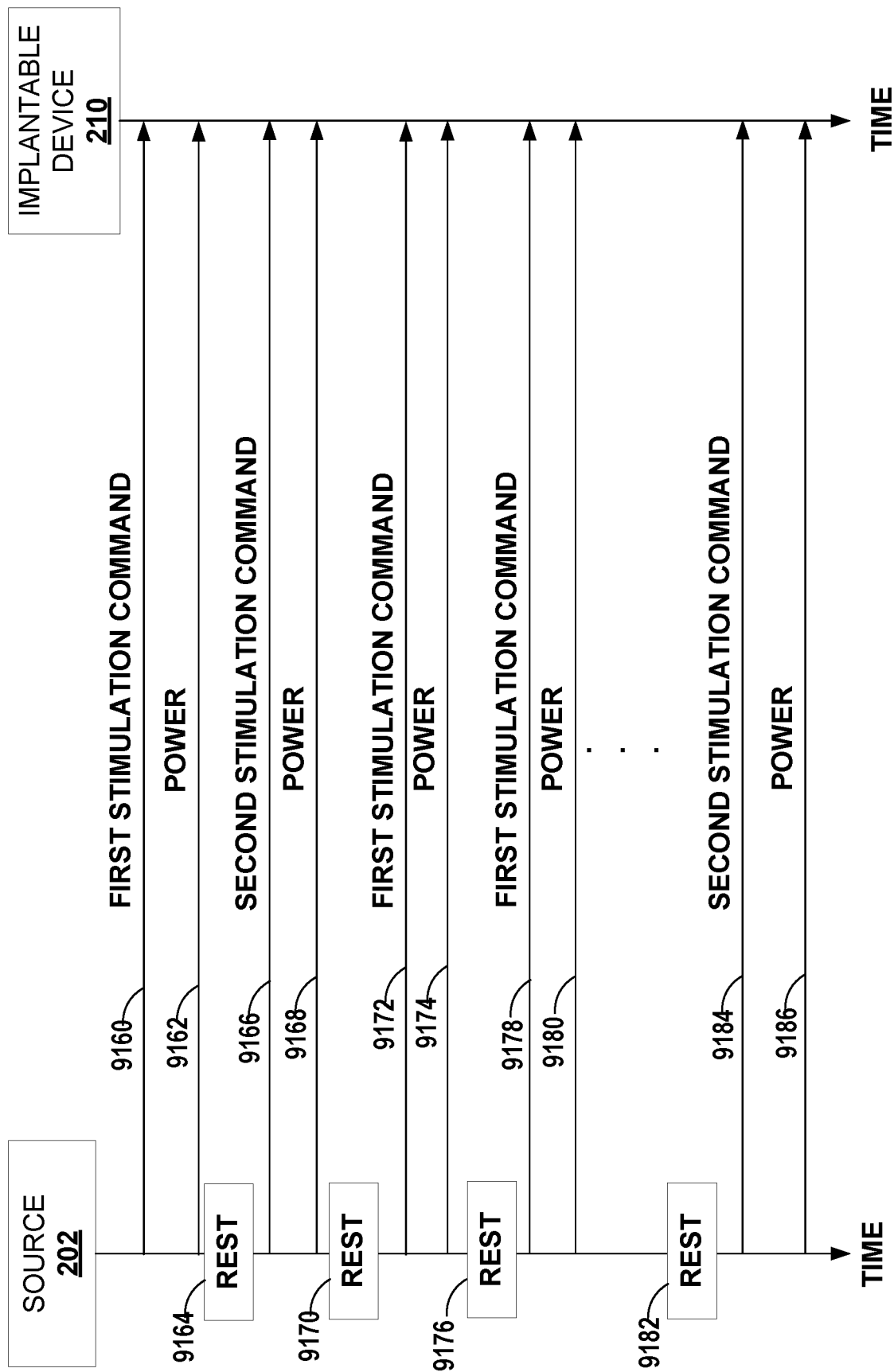
FIG. 91 illustrates, by way of example, a communication diagram to implement a pain and/or inflammation management stimulation waveform.

FIG. 91 illustrates, by way of example, a communication diagram to implement a pain and inflammation management waveform, such as that illustrated in and discussed regarding FIG. 90. In the implementation of FIG. 91 the source 202 transmits communications to the implantable device 210. The implantable device 210, in the example of FIG. 91, does not provide any communications to the source 202. This does not mean that the source 202 does not get any useful information from the implantable device 210; in this example, the implantable device 210 may not actively transmit information to the source 202. Backscatter signals from normal operation of the implantable device 210 can be used by the source 202 to determine parameters (e.g., angle, phase, power, frequency, or the like) of transmissions to the implantable device 210. In this way, the source 202 can act as a primary or controller device and the implantable device 210 can act as a secondary or responsive device. Since the implantable device 210, when in use, is implanted, a user can alter the stimulation provided by programming the source 202 (re-programming the source 202) or replacing the source 202 with a different, pre-programmed source 202.

The source 202 can be responsible for configuring the implantable device 210 for neuro-stimulation delivery. The implantable device 210 may have limited persistent memory and may, in some examples, not be configured to store stimulation parameters. The source 202 can configure the implantable device 210 by issuing commands that cause the implantable device 210 to generate neurostimulation with specified parameters. The commands issued by the source 202 can be interpreted by the processor circuit 8824. The processor circuit 8824 can, in response, issue commands that configure one or more parameters of a signal generated by the signal generator circuit 8825 or the output 8831-8834. For example, the processor circuit 8824 can cause the signal generator circuit 8825 to adjust an amplitude, frequency, phase, or the like, of a generated signal.

The communication in FIG. 91 includes only communications from the source 202 to the implantable device 210. Some of the communications include power communications 9162, 9168, 9174, 9180, 9186. The power communications 9162, 9168, 9174, 9180, 9186 provide the implantable device 210 with electrical energy required to provide the neurostimulation indicated in stimulation commands 9160, 9166, 9172, 9178, 9184. Power from the power communications 9162, 9168, 9174, 9180, 9186 can charge the capacitor array 8826. The stimulation commands 9160, 9166, 9172, 9178, 9184 can include data configured to alter a configuration of the signal generator circuit 8825. The stimulation commands 9160, 9166, 9172, 9178, 9184 can configure one or more of a frequency, amplitude, phase, or the like, of a signal generated by the signal generator circuit 8825, such as in response to a particular one or more of the stimulation commands. For example, the stimulation commands 9160, 9166, 9172, 9178, 9184 can configure the output 8831-8834 as an anode or cathode or neutral.

In the example of FIG. 91, the source 202 can issue a first stimulation command 9160 to the implantable device to configure the signal generator circuit 8825 to generate a signal at a first frequency, first amplitude, and first phase, and using the output 8831-8834 as an anode, cathode, or neutral, or the like. The first frequency can include a frequency between about 0.5 to about 30 Hz, or a larger frequency. The source 202 can (e.g., after issuing the first stimulation command 9160) provide a power communication 9162 to the implantable device 210. After the first stimulation is provided or after power sufficient to charge the capacitor array 8826 has been communicated to the implantable device 210, the source 202 can rest 9164. The source 202 can rest 9164 until another signal or stimulation command is communicated to the implantable device 210. The rest 9164 can mean no communications take place between the source 202 and the implantable device 210, and the rest 9164 does not necessarily mean that the source 202 and/or the implantable device 210 is not performing any operations. An operation during the rest 9164, 9170, 9176, 9182 can include operating an oscillator or timer to determine when to provide a subsequent command to the implantable device 210. The duration of the rest 9164, 9170, 9176, 9182 can be different in various circumstances, for example: (a) between a first stimulation command 9160, 9172, 9178 and an immediately subsequent second stimulation command 9166, 9184, (b) between a second stimulation command 9166, 9184 and an immediately subsequent first stimulation command 9160, 9172, 9178, and (c) between a first stimulation command 9160, 9172, 9178 and an immediately subsequent first stimulation command 9172, 9178. The duration of the rest between the first stimulation command 9160, 9172, 9178 and the immediately subsequent second stimulation command 9166, 9184 can be pre-determined, variable, or determined based on a value generated by a PNG. The duration of the rest between a second stimulation command 9166, 9178, 9184 and the immediately subsequent first stimulation command 9172, 9178 can be pre-determined, variable, or determined based on the value generated by the PNG. The duration of the rest between a first stimulation command 9160, 9172, 9178 and the immediately subsequent first stimulation command 9172, 9178 can be pre-determined.

The first stimulation command 9160, 9172, 9178 can configure the implantable device 210 to provide pain relief neurostimulation or what is sometimes called tonic stimulation. Tonic stimulation frequencies are discussed previously. In some embodiments, the tonic stimulation can be between about 0.5 Hz and 30 Hz. The second stimulation command 9166, 9184 can configure the implantable device 210 to provide anti-inflammation stimulation. The frequency of the anti-inflammation stimulation can be between about 250 Hz to about 5 kHz. The second stimulation command 9166, 9184 can be provided to the implantable device 210 to provide the inflammation stimulation 8954 (see FIG. 89). A duration of the rest 9176 can be about the same as the duration of the inter-stimulation rest 8952 (see FIG. 89). A duration of the rest 9164 can be about the same as the duration of t1 or t2 from FIG. 89. A duration of the rest 9170, 9182 can be about the same as the duration of t3, t4. The inflammation stimulation can include a burst of pulses, such as a burst of two or more pulses (e.g., bursts of 3-5 pulses). The intermittency of the bursts can be determined based on the PNG, or the like.

Prior to receiving a power communication, the capacitor array 8826 may not have sufficient charge to operate the processor circuit 8824, signal generator circuit 8825, or the like. The source 202 can provide another power communication before transmitting the stimulation command 9160, 9166, 9172, 9178, 9184. The power provided in the power communication 9162, 9168, 9174, 9180, 9186 can be sufficient to carry out the stimulation indicated by the stimulation command and to receive a next stimulation command.

In some examples, the implantable device 210 can provide stimulation as long as it has sufficient power, such as from the power communication 9162, 9168, 9174, 9180, 9186 or in the capacitor array 8826. In some examples, a stimulation command is not needed unless there is a change in the stimulation configuration of the implantable device 210. In such examples, the first stimulation command 9178 is not required as the implantable device is already configured to provide stimulation in accord with the first stimulation command 9160, 9172, 9178.

In providing the stimulation, an implantable device can be situated five centimeters or more below a tissue interface, that is, below a surface of the skin. In one or more examples, an implantable device can be situated between about 2 centimeters and 4 centimeters, about 3 centimeters, between about 1 centimeter and five centimeters, less than 1 centimeter, about two centimeters, or other distance below the surface of the skin. The depth of implantation can depend on the use of the implanted device. For example, to treat depression, hypertension, epilepsy, and/or PTSD the implantable device can situated between about 2 centimeters and about four centimeters below the surface of the skin. In another example, to treat sleep apnea, arrhythmia (e.g., bradycardia), obesity, gastroesophageal reflux, and/or gastroparesis the implantable device can be situated at greater than about 3 centimeters below the surface of the skin. In yet another example, to treat Parkinson's, essential tremors, and/or dystonia the implantable device can be situated between about 1 centimeter and about 5 centimeters below the surface of the skin. Yet other examples include situating the implantable device between about 1 centimeter and about 2 centimeters below the surface of the skin, such as to treat fibromyalgia, stroke, and/or migraine, at about 2 centimeters to treat asthma, and at about one centimeter or less to treat dry eyes.

Although many embodiments included herein describe devices or methods for providing stimulation (e.g., electrostimulation), the embodiments may be adapted to provide other forms of modulation (e.g., denervation) in addition to or instead of stimulation. In addition, although many embodiments included herein refer to the use of electrodes to deliver therapy, other energy delivery members (e.g., ultrasound transducers or other ultrasound energy delivery members) or other therapeutic members or substances (e.g., fluid delivery devices or members to deliver chemicals, drugs, cryogenic fluid, hot fluid or steam, or other fluids) may be used or delivered in other embodiments.

Embodiments of Computer Hardware and/or Architecture

Figure 92:
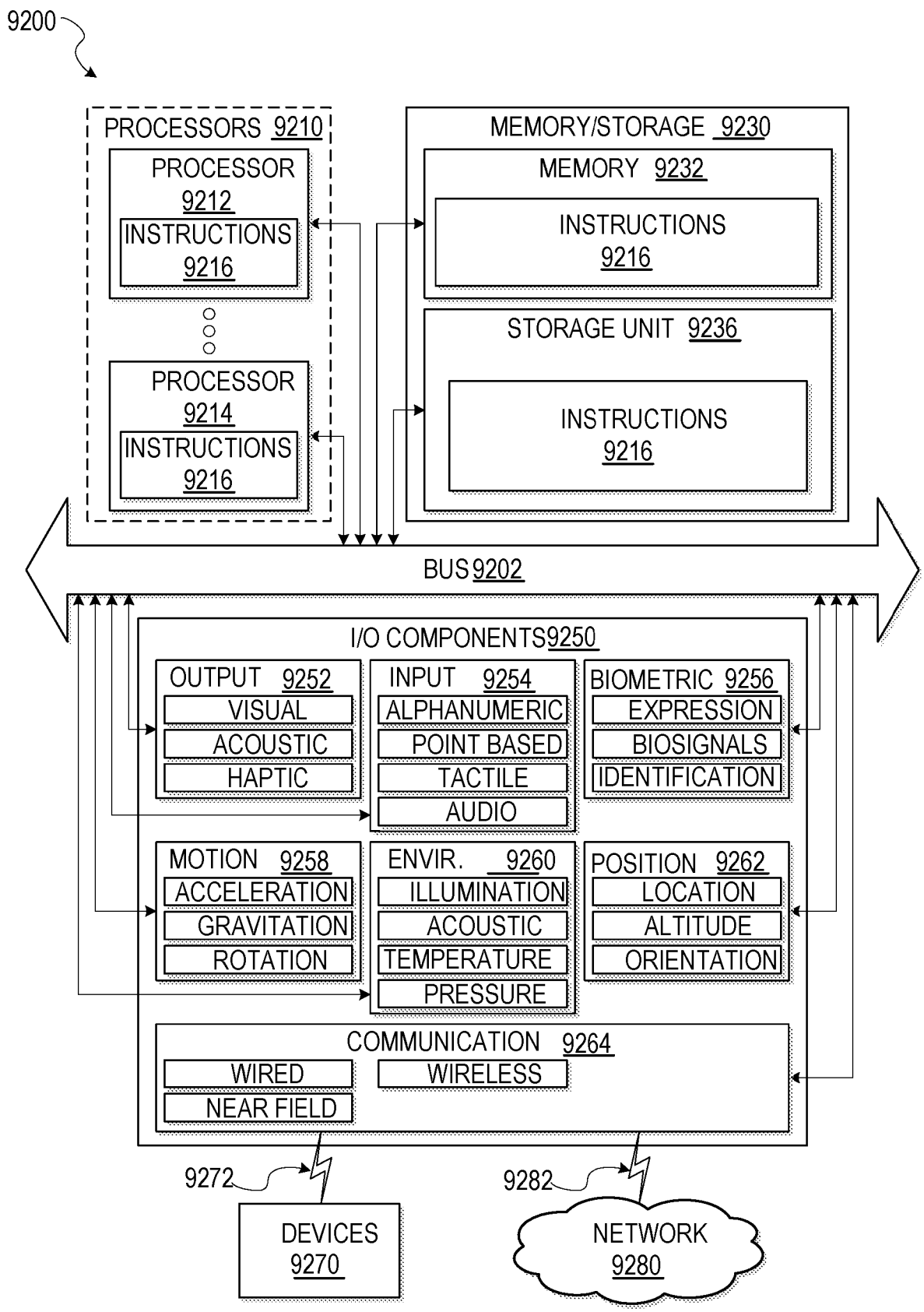
FIG. 92 illustrates, by way of example, a system with which one or more methods discussed herein can be performed.

FIG. 92 illustrates, by way of example, a block diagram of an embodiment of a machine 9200 upon which one or more methods discussed herein can be performed or in conjunction with one or more systems or devices described herein may be used. FIG. 92 includes reference to structural components that are discussed and described in connection with several of the embodiments and figures above. In one or more embodiments, the implantable device (sometimes called an electrostimulation device or a neurostimulation device) 100, 210, 300, 1000, 1300, 2000, 4800, 6410, 8206, 8300, 8400, 8500, the source (sometimes called a midfield powering device) 202, 5628, the sensor 230, circuitry 1416, electronics module 7870, 8170, 8270, or other components, can include one or more of the items of the machine 9200. The machine 9200, according to some example embodiments, is able to read instructions from a machine-readable medium (e.g., a machine-readable storage medium) and to perform any one or more of the methodologies, one or more operations of the methodologies, or one or more circuitry functions discussed herein, such as the methods described with regard to FIGS. 1-91. For example, FIG. 92 shows a diagrammatic representation of the machine 9200 in the example form of a computer system, within which instructions 9216 (e.g., software, a program, an application, an applet, an app, or other executable code) for causing the machine 9200 to perform any one or more of the methodologies discussed herein can be executed. The instructions transform the general, non-programmed machine into a particular machine programmed to carry out the described and illustrated functions in the manner described. In alternative embodiments, the machine 9200 operates as a standalone device or can be coupled (e.g., networked) to other machines. In a networked deployment, the machine 9200 can operate in the capacity of a server machine or a client machine in a server-client network environment, or as a peer machine in a peer-to-peer (or distributed) network environment.

In one or more embodiments, the machine 9200 can comprise, but is not limited to, a server computer, a client computer, a personal computer (PC), a tablet computer, a laptop computer, a cellular telephone, a smart phone, a mobile device, a wearable device (e.g., a smart watch), a smart home device (e.g., a smart appliance), other smart devices, a web appliance, a network router, a network switch, a network bridge, or any machine capable of executing the instructions 9216, sequentially or otherwise, that specify actions to be taken by machine 9200. Further, while only a single machine 9200 is illustrated, the term "machine" shall also be taken to include a collection of machines 9200 that individually or jointly execute the instructions 9216 to perform any one or more of the methodologies discussed herein.

The machine 9200 can include processors 9210, memory 9230, or I/O components 9250, which can be configured to communicate with each other such as via a bus 9202. In one or more embodiments embodiment, the processors 9210

(e.g., a Central Processing Unit (CPU), a Reduced Instruction Set Computing (RISC) processor, a Complex Instruction Set Computing (CISC) processor, a Graphics Processing Unit (GPU), a Digital Signal Processor (DSP), an Application Specific Integrated Circuitry (ASIC), a Radio-Frequency Integrated Circuitry (RFIC), another processor, or any suitable combination thereof) can include, for example, processor 9212 and processor 9214 that can execute instructions 9216. The term "processor" is intended to include multi-core processors that can include two or more independent processors (sometimes referred to as "cores") that can execute instructions contemporaneously. Although FIG. 92 shows multiple processors, the machine 9200 can include a single processor with a single core, a single processor with multiple cores (e.g., a multi-core process), multiple processors with a single core, multiple processors with multiples cores, or any combination thereof.

The memory/storage 9230 can include a memory 9232, such as a main memory, or other memory storage, and a storage unit 9236, both accessible to the processors 9210 such as via the bus 9202. The storage unit 9236 and memory 9232 store the instructions 9216 embodying any one or more of the methodologies or functions described herein. The instructions 9216 can also reside, completely or partially, within the memory 9232, within the storage unit 9236, within at least one of the processors 9210 (e.g., within the processor's cache memory), or any suitable combination thereof, during execution thereof by the machine 9200. Accordingly, the memory 9232, the storage unit 9236, and the memory of processors 9210 are examples of machine-readable media.

As used herein, "machine-readable medium" means a device able to store instructions and data temporarily or permanently and can include, but is not be limited to, random-access memory (RAM), read-only memory (ROM), buffer memory, flash memory, optical media, magnetic media, cache memory, other types of storage (e.g., Erasable Programmable Read-Only Memory (EEPROM)) and/or any suitable combination thereof. The term "machine-readable medium" should be taken to include a single medium or multiple media (e.g., a centralized or distributed database, or associated caches and servers) able to store instructions 9216. The term "machine-readable medium" shall also be taken to include any medium, or combination of multiple media, that is capable of storing instructions (e.g., instructions 9216) for execution by a machine (e.g., machine 9200), such that the instructions, when executed by one or more processors of the machine 9200 (e.g., processors 9210), cause the machine 9200 to perform any one or more of the methodologies described herein. Accordingly, a "machine-readable medium" refers to a single storage apparatus or device, as well as "cloud-based" storage systems or storage networks that include multiple storage apparatus or devices. The term "machine-readable medium" excludes signals per se.

The I/O components 9250 can include a wide variety of components to receive input, provide output, produce output, transmit information, exchange information, capture measurements, and so on. The specific I/O components 9250 that are included in a particular machine will depend on the type of machine. For example, portable machines such as mobile phones will likely include a touch input device or other such input mechanisms, while a headless server machine will likely not include such a touch input device. It will be appreciated that the I/O components 9250 can include many other components that are not shown in FIG. 92. The I/O components 9250 are grouped according to functionality merely for simplifying the following discussion and the grouping is in no way limiting. In various example embodiments, the I/O components 9250 can include output components 9252 and input components 9254. The output components 9252 can include visual components (e.g., a display such as a plasma display panel (PDP), a light emitting diode (LED) display, a liquid crystal display (LCD), a projector, or a cathode ray tube (CRT)), acoustic components (e.g., speakers), haptic components (e.g., a vibratory motor, resistance mechanisms), other signal generators, and so forth. The input components 9254 can include alphanumeric input components (e.g., a keyboard, a touch screen configured to receive alphanumeric input, a photo-optical keyboard, or other alphanumeric input components), point based input components (e.g., a mouse, a touchpad, a trackball, a joystick, a motion sensor, or other pointing instrument), tactile input components (e.g., a physical button, a touch screen that provides location and/or force of touches or touch gestures, or other tactile input components), audio input components (e.g., a microphone), and the like.

In further example embodiments, the I/O components 9250 can include biometric components 9256, motion components 9258, environmental components 9260, or position components 9262 among a wide array of other components. For example, the biometric components 9256 can include components to detect expressions (e.g., hand expressions, facial expressions, vocal expressions, body gestures, or eye tracking), measure physiologic signals (e.g., blood pressure, heart rate, body temperature, perspiration, or brain waves, neural activity, or muscle activity), identify a person (e.g., voice identification, retinal identification, facial identification, fingerprint identification, or electroencephalogram based identification), and the like.

The motion components 9258 can include acceleration sensor components (e.g., accelerometer), gravitation sensor components, rotation sensor components (e.g., gyroscope), and so forth. In one or more embodiments, one or more of the motion components 9258 can be incorporated with the external source 202 or the implantable device 210 and can be configured to detect motion or a physical activity level of a patient. Information about the patient's motion can be used in various ways, for example, to adjust a signal transmission characteristic (e.g., amplitude, frequency, etc.) when a physical relationship between the external source 202 and the implantable device 210 changes or shifts.

The environmental components 9260 can include, for example, illumination sensor components (e.g., photometer), temperature sensor components (e.g., one or more thermometer that detect ambient temperature), humidity sensor components, pressure sensor components (e.g., barometer), acoustic sensor components (e.g., one or more microphones that detect background noise), proximity sensor components (e.g., infrared sensors that detect nearby objects), gas sensors (e.g., gas detection sensors to detection concentrations of hazardous gases for safety or to measure pollutants in the atmosphere), or other components that can provide indications, measurements, or signals corresponding to a surrounding physical environment. The position components 9262 can include location sensor components (e.g., a Global Position System (GPS) receiver component), altitude sensor components (e.g., altimeters or barometers that detect air pressure from which altitude can be derived), orientation sensor components (e.g., magnetometers), and the like. In one or more embodiments, the I/O component(s) 9250 can be a part of the implantable device 210 and/or the external source 202.

Communication can be implemented using a wide variety of technologies. The I/O components 9250 can include communication components 9264 operable to couple the machine 9200 to a network 9280 or devices 9270 via coupling 9282 and coupling 9272 respectively. For example, the communication components 9264 can include a network interface component or other suitable device to interface with the network 9280. In further examples, communication components 9264 can include wired communication components, wireless communication components, cellular communication components, Near Field (nearfield) Communication (NFC) components, midfield communication components, farfield communication components, and other communication components to provide communication via other modalities. The devices 9270 can be another machine or any of a wide variety of peripheral devices.

Moreover, the communication components 9264 can detect identifiers or include components operable to detect identifiers. For example, the communication components 9264 can include Radio Frequency Identification (RFID) tag reader components, NFC smart tag detection components, optical reader components (e.g., an optical sensor to detect one-dimensional bar codes such as Universal Product Code (UPC) bar code, multi-dimensional bar codes such as Quick Response (QR) code, Aztec code, Data Matrix, Dataglyph, MaxiCode, PDF417, Ultra Code, UCC RSS-2D bar code, and other optical codes), or acoustic detection components (e.g., microphones to identify tagged audio signals). In addition, a variety of information can be derived via the communication components 9264, such as, location via Internet Protocol (IP) geo-location, location via Wi-Fi® signal triangulation, location via detecting a NFC beacon signal that can indicate a particular location, and so forth.

In some embodiments, the systems comprise various features that are present as single features (as opposed to multiple features). For example, in one embodiment, the system includes a single external source and a single implantable device or stimulation device with a single antenna. Multiple features or components are provided in alternate embodiments.

In some embodiments, the system comprises one or more of the following: means for tissue stimulation (e.g., an implantable stimulation device), means for powering (e.g., a midfield powering device or midfield coupler), means for receiving (e.g., a receiver), means for transmitting (e.g., a transmitter), means for controlling (e.g., a processor or control unit), etc.

To better illustrate the methods, systems, devices, and apparatuses disclosed herein, a non-limiting list of examples is provided here. Each of these Examples can be used alone or combined in various combinations and permutations.

Although various general and specific embodiments are described herein, it will be evident that various modifications and changes can be made to these embodiments without departing from the broader scope of the present disclosure. Accordingly, the specification and drawings are to be regarded in an illustrative rather than a restrictive sense. The accompanying drawings that form a part of this application show, by way of illustration, and not of limitation, specific embodiments in which the subject matter can be practiced. The embodiments illustrated are described in sufficient detail to enable those skilled in the art to practice the teachings disclosed herein. Other embodiments can be used or derived therefrom, such that structural and logical substitutions and changes can be made without departing from the scope of this disclosure. This Detailed Description, therefore, is not to be taken in a limiting sense, and the scope of various embodiments is defined only by the appended claims, along with the full range of equivalents to which such claims are entitled. Specific embodiments or examples are illustrated and described herein, however, it should be appreciated that any arrangement calculated to achieve the same purpose can be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The ranges disclosed herein also encompass any and all overlap, sub-ranges, and combinations thereof. Language such as "up to," "at least," "greater than," "less than," "between," and the like includes the number recited. Numbers preceded by a term such as "about" or "approximately" include the recited numbers. For example, "about 10 kHz" includes "10 kHz." Terms or phrases preceded by a term such as "substantially" or "generally" include the recited term or phrase. For example, "substantially parallel" includes "parallel" and "generally cylindrical" includes cylindrical.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention(s) and embodiments should be determined with reference to the appended claims, along with the full scope of equivalents to which such claims are entitled.

What is claimed is:

1. A method of validating a position of a wirelessly powered electrostimulation device while the device is implanted in body tissue, the method comprising:

situating, using a catheter and a push rod configured to travel inside the catheter, the electrostimulation device in tissue;

pulling the push rod away from the electrostimulation device while electrodes of the device are in contact with the tissue; and before an affixation mechanism of the electrostimulation device is deployed to maintain an implanted position of the electrostimulation device, after pulling the push rod away from the electrostimulation device, and while electrodes of the device are in contact with the tissue, performing electrical testing of the electrostimulation device to determine whether the electrostimulation from the electrostimulation device evokes a specified response from the body that contains the tissue.

2. The method of claim 1, wherein performing electrical testing of the electrostimulation device occurs while:

the affixation mechanism of the device is situated in the catheter, and the catheter is at least partially inside the tissue.

3. The method of claim 1, wherein the catheter comprises a radio transparent material.

4. The method of claim 1, wherein situating the electrostimulation device in the tissue includes translating the device axially inside the catheter while the catheter is partially in the tissue so the electrodes extend out of the catheter into the tissue and the affixation mechanism remains in the catheter.

5. The method of claim 1, wherein the catheter comprises a radio transparent material and the method further comprises pulling the push rod away from the electrostimulation device while maintaining a suture in a lumen of the push rod, the suture extending through the lumen of the push rod and mechanically connected to a proximal portion of the electrostimulation device.

6. The method of claim 5, wherein maintaining the suture in the lumen includes wrapping a proximal portion of the suture around a thread of the push rod and securing the thread.

7. The method of claim 6, wherein securing the thread further includes tightening a luer cap around the thread of the push rod.

8. The method of claim 7, wherein:

the thread is one of a plurality of threads;

the wrapping is a first wrapping of a first portion of the suture around a first thread of the plurality of threads; and the method further comprises further wrapping a second, different portion of the suture around a second thread of the plurality of threads, such that loosening the cap releases the first portion during the loosening while retaining the second portion.

9. The method of claim 5, wherein maintaining the suture in the lumen includes situating a retention mechanism on the suture at a location more proximal than the lumen, the retention mechanism configured such that it cannot travel through the lumen.

10. The method of claim 1, wherein performing the electrical testing includes, performing operations by an external device in wireless communication with the electrostimulation device, the operations comprising:

providing a first configuration signal to the electrostimulation device to cause the electrostimulation device to configure a particular first one of its multiple electrodes as an anode electrode and a particular second one of its multiple electrodes as a cathode electrode;

providing one or more first operation signals to the electrostimulation device to cause the electrostimulation device to provide a first electrostimulation output at a specified first voltage or current level;

in response to a determination that the first electrostimulation output did not evoke a response from the patient, providing one or more second operation signals to the electrostimulation device to cause the electrostimulation device to provide a second electrostimulation output at a specified second voltage or current level that is greater than the first voltage or current level;

in response to a determination that the first or the second electrostimulation output did evoke a response from the patient, providing one or more signals to the electrostimulation device that cause the electrode configuration to change and the electrode configuration to be recorded, at the external device, along with the voltage or current that caused the response; and providing one or more signals to the electrostimulation device that cause the electrostimulation device to produce third electrostimulation at a voltage or current for which the electrostimulation evoked a response.

11. The method of claim 10, wherein the operations further comprise, in response to a determination that voltage or current is at or above a specified threshold, providing one or more signals to the electrostimulation device that cause the electrode configuration to change.

12. The method of claim 10, wherein the determination of whether the electrostimulation produced a response includes receiving data from an electromyography sensor situated on the patient indicating the response was detected.

13. The method of claim 10, wherein the determination of whether the electrostimulation produced a response includes receiving data from an accelerometer situated on the patient indicating the response was detected.

14. The method of claim 10, wherein the operations further comprise alerting an operator to adjust a position of the electrostimulation device within the patient when the first or second voltage or current level meets or exceeds a specified threshold level.

15. The method of claim 14, wherein alerting the operator to adjust the position of the electrostimulation device includes providing instructions to re-position the electrostimulation device without requiring removal of the electrostimulation device from a deployment catheter.

\* \* \* \* \*